US006955717B2

(12) United States Patent
Johnson et al.

(10) Patent No.: US 6,955,717 B2
(45) Date of Patent: Oct. 18, 2005

(54) CRYSTALS AND STRUCTURE OF SYNAGIS FAB

(75) Inventors: Leslie S. Johnson, Darnestown, MD (US); Bradford Braden, Baltimore, MD (US)

(73) Assignees: Medimmune Inc., Gaithersburg, MD (US); Bowie State University, Bowie, MD (US)

( * ) Notice: Subject to any disclaimer, the term of this patent is extended or adjusted under 35 U.S.C. 154(b) by 129 days.

(21) Appl. No.: 10/135,636

(22) Filed: Apr. 29, 2002

(65) Prior Publication Data

US 2003/0097974 A1 May 29, 2003

Related U.S. Application Data

(60) Provisional application No. 60/288,005, filed on May 1, 2001.

(51) Int. Cl.[7] ............................................... C30B 29/58
(52) U.S. Cl. ..................... 117/2; 117/925; 117/926; 117/927; 424/133.1; 424/136.1; 435/70.21; 530/387.7; 530/388.1; 530/388.75; 530/388.85
(58) Field of Search ............................. 117/2, 925, 926, 117/927; 424/133.1, 136.1; 435/70.21; 530/387.7, 388.1, 388.75, 388.85

(56) References Cited

U.S. PATENT DOCUMENTS

| 5,994,511 A | 11/1999 | Lowman et al. |
| 6,113,898 A | 9/2000 | Anderson et al. |
| 6,129,914 A | 10/2000 | Weiner et al. |

FOREIGN PATENT DOCUMENTS

| WO | WO 96/40252 | 12/1996 |
| WO | WO 00/61618 | 10/2000 |
| WO | PCT/US 02/13583 | 4/2003 |

OTHER PUBLICATIONS

Hampton Research, "Crystal Screen Users Guide," (1991).
Johnson et al., "Development of a Humanized Monoclonal Antibody (MEDI–493) With Potent In Vitro and In Vivo Activity Against Respiratory Syncytial Virus," The Journal of Infectious Diseases (1997) 176:1215–24.
Meissner et al., "Immunoprophylaxis With Palivizumab, A Humanized Respiratory Syncytial Virus Monoclonal Antibody, For Prevention of Respiratory Syncytial Virus Infection In High Risk Infants: A Consensus Opinion," Pediatr Infect Dis. J, (1999) 18:223–31.

*Primary Examiner*—Robert Kunemund
(74) *Attorney, Agent, or Firm*—Jones Day

(57) ABSTRACT

The present invention provides machine readable media embedded with the three-dimensional atomic structure coordinates of Synagis Fab, and subsets thereof, and methods of using them.

17 Claims, 13 Drawing Sheets

Figure 1:
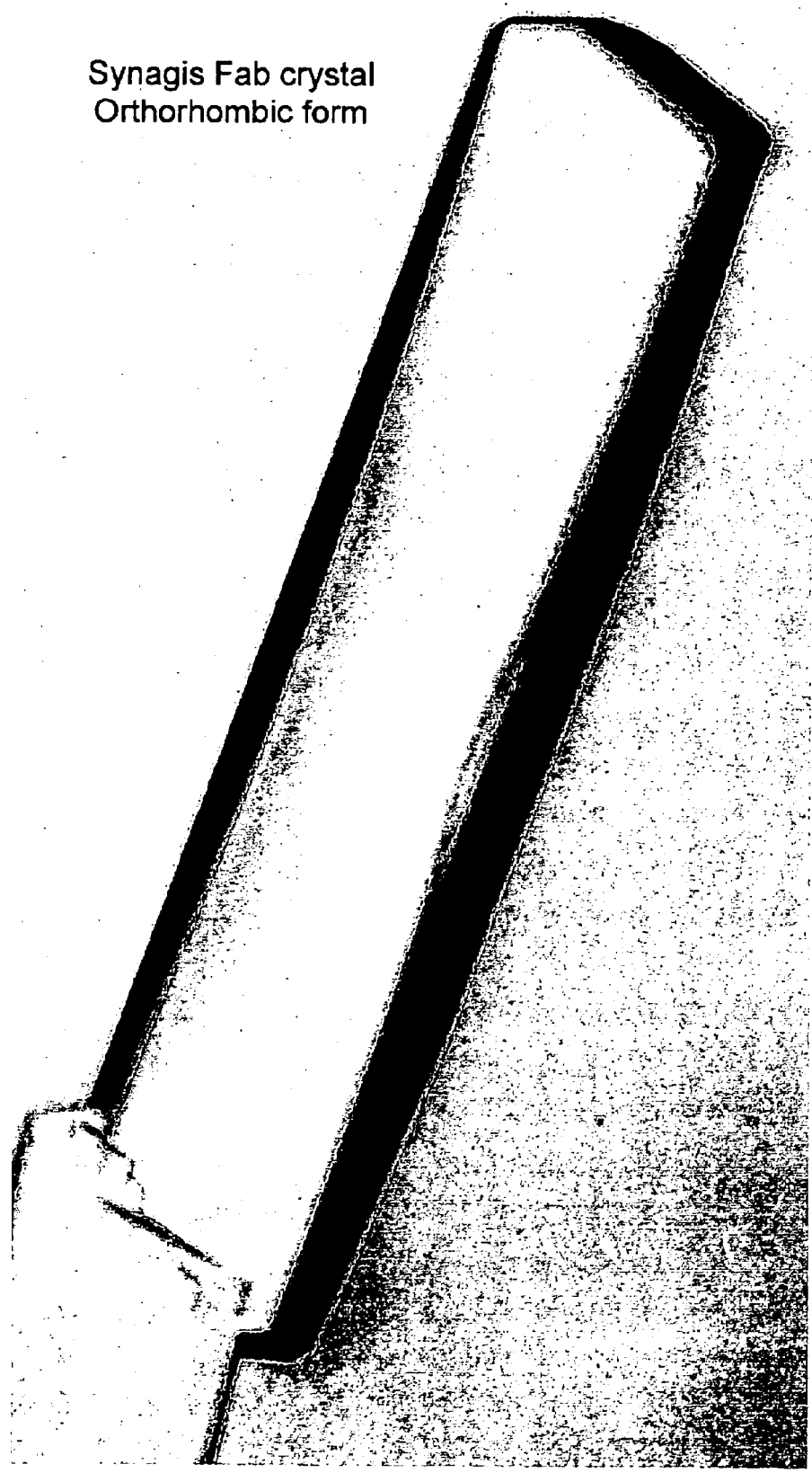

Synagis Fab crystal
Orthorhombic form

Sequence ID No. 1
Synagis Heavy Chain Sequence (KABAT Numbering Scheme)

```
         10        20        30        40
QVTLRESGPALVKPTQTLTLTCTFSGFSLSTSGMSVGWIRQPPGKALEWL 50        60        70        80        90
ADIWWDDKKDYNPSLKSRLTISKDTSKNQVVLKVTNMDPADTATYYCARS 110       120       130       140
MITNWYFDVWGAGTTVTVSSASTKGPSVFPLAPSSKSTSGGTAALGCLVK
         150       160       170       180       190
DYFPEPVTVSWNSGALTSGVHTFPAVLQSSGLYSLSSVVTVPSSSLGTQT
         200       210       220       230       240
YICNVNHKPSNTKVDKRVEPKSCDKTHTCPPCPAPELLGGPSVFLFPPKP
         250       260       270       280       290
KDTLMISRTPEVTCVVVDVSHEDPEVKFNWYVDGVEVHNAKTKPREEQYN
         300       310       320       330       340
STYRVVSVLTVLHQDWLNGKEYKCKVSNKALPAPIEKTISKAKGQPREPQ
         350       360       370       380       390
VYTLPPSREEMTKNQVSLTCLVKGFYPSDIAVEWESNGQPENNYKTTPPV
         400       410       420       430       440
LDSDGSFFLYSKLTVDKSRWQQGNVFSCSVMHEALHNHYTQKSLSLSPGK
```

Sequence ID No. 2
Synagis FAB Heavy Chain

```
         10        20        30        40
QVTLRESGPALVKPTQTLTLTCTFSGFSLSTSGMSVGWIRQPPGKALEWL 50        60        70        80        90
ADIWWDDKKDYNPSLKSRLTISKDTSKNQVVLKVTNMDPADTATYYCARS 110       120       130       140
MITNWYFDVWGAGTTVTVSSASTKGPSVFPLAPSSKSTSGGTAALGCLVK
         150       160       170       180       190
DYFPEPVTVSWNSGALTSGVHTFPAVLQSSGLYSLSSVVTVPSSSLGTQT
         200       210       220
YICNVNHKPSNTKVDKRVEPKSCDKTH
```

FIG.3A-1

Sequence ID No. 3
Synagis FC

```
          230         240         250         260         270
    TCPPCPAPELLGGPSVFLFPPKPKDTLMISRTPEVTCVVVDVSHEDPEVKFNWY
          280         290         300         310         320
    VDGVEVHNAKTKPREEQYNSTYRVVSVLTVLHQDWLNGKEYKCKVSNKALPAPI
    330         340         350         360         370         380
    EKTISKAKGQPREPQVYTLPPSREEMTKNQVSLTCLVKGFYPSDIAVEWESNGQ
          390         400         410         420         430
    PENNYKTTPPVLDSDGSFFLYSKLTVDKSRWQQGNVFSCSVMHEALHNHYTQKS
    440
    LSLSPGK
```

Sequence ID No. 4
Synagis CDR H1

```
    26  27  28  29  30  31  32  33  34  35  35a  35b
    G   F   S   L   S   T   S   G   M   S   V    G
```

FIG. 3A-2

Sequence ID No. 5
Synagis CDR H2

```
50 51 52  52a 52b 52c 53 54 55 56 57 58 59 60 61 62
 D  I  W   W   D   D   K  K  D  Y  N  P  S  L  K  S
```

Sequence ID No. 6
Synagis CDR H3

```
95 96 97 98 99 100 100A 100B 101 102
 S  M  I  T  N  W    Y    F    D   V
```

Sequence ID No. 7
Synagis Light Chain Sequence

```
            10         20         30         40         50
DIQMTQSPSTLSASVGDRVTITCKCQLSVGYMHWYQQKPGKAPKLLIYDT 60         70         80         90        100
SKLASGVPSRFSGSGSGTEFTLTISSLQPDDFATYYCFQGSGYPFTFGGG 110        120        130        140        150
TKLEIKRTVAAPSVFIFPPSDEQLKSGTASVVCLLNNFYPREAKVQWKVD 160        170        180        190        200
NALQSGNSQESVTEQDSKDSTYSLSSTLTLSKADYEKHKVYACEVTHQGL

210
SSPVTKSFNRGEC
```

Sequence ID No. 8
CDR L1
```
24 25 26 28 29 30 31 32 33 34
 K  C  Q  L  S  V  G  Y  M  H
```

Sequence ID No. 9
CDR L2

```
50 51 52 53 54 55 56
 D  T  S  K  L  A  S
```

Sequence ID No. 10
CDR L3

```
89 90 91 92 93 94 95 96 97
 F  Q  G  S  G  Y  P  F  T
```

FIG.3B

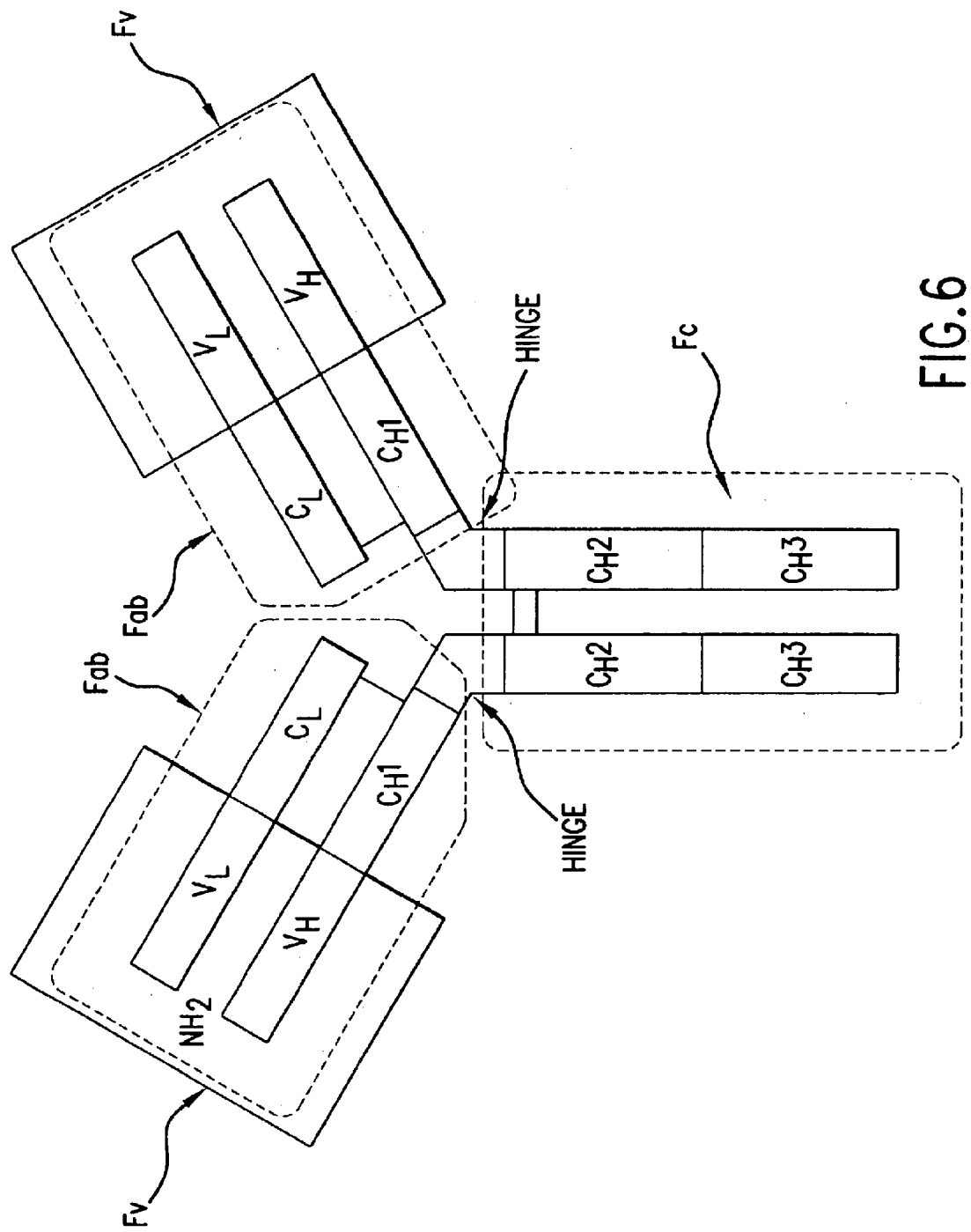

CRYSTALS AND STRUCTURE OF SYNAGIS FAB

1. CROSS-REFERENCE TO RELATED APPLICATIONS

This application claims the benefit under 35 U.S.C. § 119 of copending provisional application No. 60/288,005, filed May 1, 2001, the content of which is hereby incorporated by reference in its entirety.

2. INTRODUCTION

The present invention concerns crystalline forms of polypeptides that correspond to Synagis (palivizumab) or a fragment thereof such as Synagis Fab, methods of obtaining such crystals and the high-resolution X-ray diffraction structures and atomic structure coordinates obtained therefrom. The crystals of the invention and the atomic structural information obtained therefrom are useful for solving the crystal and solution structures of related and unrelated proteins, and for screening for, identifying and/or designing compounds that bind and/or modulate a biological activity of respiratory syncytial virus.

3. BACKGROUND OF THE INVENTION

Respiratory Syncytial Virus ("RSV") is the most important respiratory pathogen in infancy and early childhood. Studies estimate that RSV causes up to 90% of brochiolitis and approximately 90% of all pneumonia in infancy. These conditions result in over 90,000 hospitalizations and 4500 deaths annually in the United States alone (Hall, 1998, Textbook of Pediatric Infectious Diseases, 2084-2111). RSV infection in early childhood might be an important risk factor for subsequent development of recurrent wheezing and asthma (Eigen, 1999, J. Pediatr. 135:S1–S50; Stein et al., 1999, Lancet 354:541–545).

Current methods for treatment and prevention of RSV infection are limited. For instance, vaccination against RSV has not been successful to date. Vaccination of infants with an inactivated RSV actually increased the severity of RSV infection and pulmonary pathology when vaccinated infants were later challenged with RSV (Groothius, 1994, Antiviral Res 23:1–10; Hall et al., 1995, Principles and Practice of Infectious Disease, 1501–1519; Wyde, 1998, Antiviral Res. 39:63–79).

Direct administration of antibodies against RSV has had some prophylactic effect. A human immunoglobulin against RSV ("RSVIG") was approved in 1996 for the prevention of serious lower respiratory tract disease caused by RSV in premature infants and infants with bronchopulmonary dysplasia (PREVENT study group, 1999, Pediatrics 99:93–99). Recently, Synagis (or palivizumab), a humanized monoclonal antibody against the surface fusion glycoprotein ("F protein") of RSV, was approved for similar indications (Meissner et al., 1999, Pediatrics 18:223–31; Johnson et al., 1997, J. Infect. Dis. 176:1215–1224; Impact-RSV Study Group, 1998, Pediatrics 102:531–537). In studies on test animals, Synagis was twice as potent as RSVIG in inhibiting the RSV-induced potentiation of inflammation when administered before or in the early phase of RSV infection (Piedimonte et al., 2000, Pediatric Research 47:351–356).

Although Synagis provides safe and effective prevention of RSV infection, improved therapeutics, such as small molecule therapeutics, are needed to treat and/or prevent RSV infection. Small molecule therapeutics are easier and less expensive to manufacture and also easier to administer orally. In addition, a small molecule therapeutic such as an antigen that mimics the epitope recognized by Synagis could be administered to generate an immune response against RSV. A composition comprising an antigen that mimics RSV would provide a safer method of preventing RSV infection. An effective antigen mimic of RSV could be administered, to persons with a functioning immune system, as an immunoprophylactic to raise an immune response against the virus with minimal or no danger of infection caused by the immunoprophylactic itself.

The three-dimensional structure coordinates of crystalline Synagis would enable the design or selection of such an antigen mimic. Synagis is effective in preventing RSV infection in vivo, and a mimic of an antigen bound specifically by Synagis could raise an immune response that is as effective or even more effective than Synagis in preventing infection. The structure coordinates of the antigen binding region of crystalline Synagis and/or the structure coordinates of a co-crystal complex of Synagis and an antigen would elucidate the atomic requirements of binding between Synagis and the antigen. This atomic resolution information could then be used to design and/or select a mimic of the antigen to be used as an immunoprophylactic against RSV.

Furthermore, the atomic structure coordinates of crystalline Synagis would enable the design of an antibody with improved virus binding and/or neutralizing properties. The atomic structure coordinates of crystalline Synagis would identify those residues of Synagis that are involved in antigen-antibody binding. These residues could then be selectively altered to generate mutant Synagis molecules that could be screened for binding and/or virus neutralizing effects. These improved Synagis molecules would provide more and perhaps improved options for prevention of RSV infection.

Until the present invention, the ability to obtain the atomic structure coordinates of Synagis has not been realized.

4. SUMMARY OF THE INVENTION

In one aspect, the invention provides compositions comprising crystalline forms of polypeptides corresponding to Synagis (palivizumab), a humanized monoclonal antibody with specificity for the F protein of respiratory syncytial virus ("RSV"), or a fragment thereof such as an Fab fragment of Synagis ("Synagis Fab"). The amino acid sequences of the crystalline polypeptides may correspond to the sequence of wild-type Synagis Fab, or mutants thereof. The crystals of the invention include native crystals, in which the crystalline Synagis Fab is substantially pure; heavy-atom atom derivative crystals, in which the crystallizine Synagis Fab is in association with one or more heavy-metal atoms; and co-crystals, in which the crystalline Synagis Fab is in association with one or more binding compounds, including but not limited to, antigens, eptiopes, epitope analogs, inhibitors, etc. to form a crystalline co-complex. Preferably, such binding compounds bind the antigen binding site of Synagis Fab. The co-crystals may be native co-crystals, in which the co-complex is substantially pure, or they may be heavy-atom derivative co-crystals, in which the co-complex is in association with one or more heavy-metal atoms.

The Synagis Fab crystals (FIG. 1) of the invention are characterized by space group symmetry $P2_12_12_1$ and an orthorhombic unit cell (i.e., a unit cell wherein $a \neq b \neq c$; and $\alpha = \beta = \gamma = 90°$) with dimensions of $a = 77.36 \pm 0.2$ Å, $b = 103.92 \pm 0.2$ Å and $c = 68.87 \pm 0.2$ Å and are preferably of diffraction quality. A typical diffraction pattern is illustrated in FIG. 2. In more preferred embodiments, the crystals of the invention are of sufficient quality to permit the determination of the three-dimensional X-ray diffraction structure of the crystalline polypeptide to high resolution, preferably to a resolution of greater than about 3 Å, typically greater than about 2.5 Å, and more usually to a resolution of about 2 Å, 1.9 Å, 1.8 Å or even greater. The three-dimensional structural information may be used in a variety of methods to design and screen for compounds that bind Synagis Fab, as described in more detail below.

In another aspect, the invention provides methods of making the crystals of the invention. Generally, native crystals of the invention are grown by dissolving substantially pure Synagis Fab polypeptide in an aqueous buffer that includes a precipitant at a concentration just below that necessary to precipitate the polypeptide. Water is then removed by controlled evaporation to produce precipitating conditions, which are maintained until crystal growth ceases.

Co-crystals of the invention are prepared by soaking a native crystal prepared according to the above method in a liquor comprising the binding compound of the desired co-complex. Alternatively, the co-crystals may be prepared by co-crystallizing the polypeptide in the presence of the compound according to the method discussed above or by forming a co-complex comprising the polypeptide and the binding compound and crystallizing the co-complex.

Heavy-atom derivative crystals of the invention may be prepared by soaking native crystals or co-crystals prepared according to the above method in a liquor comprising a salt of a heavy atom or an organometallic compound. Alternatively, heavy-atom derivative crystals may be prepared by crystallizing a polypeptide comprising selenomethionine and/or selenocysteine residues according to the methods described previously for preparing native crystals.

In another aspect, the invention provides machine and/or computer-readable media embedded with the three-dimensional structural information obtained from the crystals of the invention, or portions or subsets thereof. Such three-dimensional structural information will typically include the atomic structure coordinates of the crystalline Synagis Fab polypeptides, either alone or in a co-complex with a binding compound, or the atomic structure coordinates of a portion thereof such as, for example, the atomic structure coordinates of residues comprising an antigen binding site, but may include other structural information, such as vector representations of the atomic structures coordinates, etc. The types of machine- or computer-readable media into which the structural information is embedded typically include magnetic tape, floppy discs, hard disc storage media, optical discs, CD-ROM, electrical storage media such as RAM or ROM, and hybrids of any of these storage media. Such media further include paper on which is recorded the structural information that can be read by a scanning device and converted into a three-dimensional structure with an OCR and also include stereo diagrams of three-dimensional structures from which coordinates can be derived. The machine readable media of the invention may further comprise additional information that is useful for representing the three-dimensional structure, including, but not limited to, thermal parameters, chain identifiers, and connectivity information.

The atomic structure coordinates and machine readable media of the invention have a variety of uses. For example, the coordinates are useful for solving the three-dimensional X-ray diffraction and/or solution structures of other proteins, including mutated Synagis Fab, co-complexes comprising Synagis Fab, and unrelated proteins, to high resolution. Structural information may also be used in a variety of molecular modeling and computer-based screening applications to, for example, intelligently design mutants of the crystallized Synagis that have altered biological activity and to computationally design and identify compounds that bind the antibody or a portion or fragment of the antibody, such as the antigen binding site. Such compounds may be used as lead compounds in pharmaceutical efforts to identify compounds that mimic the epitope of the RSV F protein recognized by Synagis as a therapeutic approach toward the development of, e.g., an anti-idiotypic vaccine for the treatment of respiratory infections caused by RSV.

Accordingly, the invention further includes methods of designing or identifying compounds that bind Synagis Fab as an approach to developing new therapeutic agents. In one method, the three-dimensional structure of Synagis Fab can be used to design molecules which bind the antigen binding site of Synagis Fab. For instance, a binding molecule can be synthesized computationally from a series of chemical groups or fragments that bind Synagis Fab. Alternatively, the three-dimensional structure of can be used to screen a plurality of molecules to identify those that bind Synagis Fab at binding sites including, for example, the antigen binding site of Synagis Fab. The potential inhibitory or binding effect of molecules can be analyzed by actual synthesis and testing or by the use of modeling techniques. The compounds can be optimized by further modeling and/or testing.

4.1 Abbreviations

The amino acid notations used herein for the twenty genetically encoded L-amino acids are conventional and are as follows:

| Amino Acid | One-Letter Symbol | Three-Letter Symbol |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

As used herein, unless specifically delineated otherwise, the three-letter amino acid abbreviations designate amino acids in either the D- or L-configuration. Specific enantiomers are preceded with a "D-" or "L-", depending upon the enantiomer. The capital one-letter abbreviations refer to amino acids in the L-configuration. Lower-case one-letter abbreviations designate amino acids in the D-configuration. For example, "R" and "L-Arg" designate L-arginine, and "r" and "D-Arg" designate D-arginine.

Unless noted otherwise, when polypeptide sequences are presented as a series of one-letter and/or three-letter abbreviations, the sequences are presented in the N→C direction, in accordance with common practice.

4.2 Definitions

As used herein, the following terms shall have the following meanings:

"Genetically Encoded Amino Acid" refers to L-isomers of the twenty amino acids that are defined by genetic codons. The genetically encoded amino acids are the L-isomers of glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine and lysine.

"Genetically Non-Encoded Amino Acid" refers to amino acids that are not defined by genetic codons. Genetically non-encoded amino acids include derivatives or analogs of the genetically-encoded amino acids that are capable of being enzymatically incorporated into nascent polypeptides using conventional expression systems, such as selenomethionine (SeMet) and selenocysteine (SeCys); isomers of the genetically-encoded amino acids that are not capable of being enzymatically incorporated into nascent polypeptides using conventional expression systems, such as D-isomers of the genetically-encoded amino acids; L- and D-isomers of naturally occurring or synthetic α-amino acids that are not defined by genetic codons, such as α-aminoisobutyric acid (Aib); and other amino acids that are not encoded by genetic codons such as β-amino acids, γ-amino acids, etc. In addition to the D-isomers of the genetically-encoded amino acids, common genetically non-encoded amino acids include, but are not limited to norleucine (Nle), penicillamine (Pen), N-methylvaline (MeVal), homocysteine (hCys), homoserine (hSer), 2,3-diaminobutyric acid (Dab) and ornithine (Orn). Additional exemplary genetically non-encoded amino acids are found, for example, in *Practical Handbook of Biochemistry and Molecular Biology*, 1989, Fasman, Ed., CRC Press, Inc., Boca Raton, Fla., pp. 3–76 and the various references cited therein.

"Hydrophilic Amino Acid" refers to an amino acid having a side chain exhibiting a hydrophobicity of less than zero according to the normalized consensus hydrophobicity scale of Eisenberg et al., 1984, J. Mol. Biol. 179:125–142. Genetically encoded hydrophilic amino acids include, but are not limited to, L-Thr (T), L-Ser (S), L-His (H), L-Glu (E), L-Asn (N), L-Gln (Q), L-Asp (D), L-Lys (K) and L-Arg (R). Genetically non-encoded hydrophilic amino acids include the D-isomers of the above-listed genetically-encoded amino acids, ornithine (Orn), 2,3-diaminobutyric acid (Dab) and homoserine (hSer).

"Acidic Amino Acid" refers to a hydrophilic amino acid having a side chain pK value of less than 7 under physiological conditions. Acidic amino acids typically have negatively charged side chains at physiological pH due to loss of a hydrogen ion. Genetically encoded acidic amino acids include, but are not limited to, L-Glu (E) and L-Asp (D). Genetically non-encoded acidic amino acids include, but are not limited to, D-Glu (e) and D-Asp (d).

"Basic Amino Acid" refers to a hydrophilic amino acid having a side chain pK value of greater than about 7 under physiological conditions. Basic amino acids typically have positively charged side chains at physiological pH due to association with hydronium ion. Genetically encoded basic amino acids include, but are not limited to, L-His (H), L-Arg (R) and L-Lys (K). Although L-His might have a pK value slightly less than 7.0 when included in a polypeptide, L-His residues are generally classified as basic amino acids.

Genetically non-encoded basic amino acids include, but are not limited to, the D-isomers of the above-listed genetically-encoded amino acids, ornithine (Orn) and 2,3-diaminobutyric acid (Dab).

"Polar Amino Acid" refers to a hydrophilic amino acid having a side chain that is uncharged at physiological pH, but which comprises at least one covalent bond in which the pair of electrons shared in common by two atoms is held more closely by one of the atoms and is thus capable of participating in a hydrogen bond. Genetically encoded polar amino acids include, but are not limited to, L-Asn (N), L-Gln (Q), LSer (S) and L-Thr (T). Genetically non-encoded polar amino acids include, but are not limited to, the D-isomers of the above-listed genetically-encoded amino acids and homoserine (hSer).

"Hydrophobic Amino Acid" refers to an amino acid having a side chain exhibiting a hydrophobicity of greater than zero according to the normalized consensus hydrophobicity scale of Eisenberg et al., 1984, J. Mol. Biol. 179:125–142. Genetically encoded hydrophobic amino acids include, but are not limited to, L-Pro (P), L-Ile (I), L-Phe (F), L-Val (V), L-Leu (L), L-Trp (W), L-Met (M), L-Ala (A), L-Gly (G) and L-Tyr (Y). Genetically non-encoded hydrophobic amino acids include, but are note limited to, the D-isomers of the above-listed genetically-encoded amino acids, norleucine (Nle) and N-methyl valine (MeVal).

"Aromatic Amino Acid" refers to a hydrophobic amino acid having a side chain comprising at least one aromatic or heteroaromatic ring. The aromatic or heteroaromatic ring may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently (C$_1$–C$_6$) alkyl, (C$_2$–C$_6$) alkenyl, or (C$_2$–C$_6$) alkynyl. Genetically encoded aromatic amino acids include, but are not limited to, L-Phe (F), L-Tyr (Y), L-Trp (W) and L-His (H). Genetically non-encoded aromatic amino acids include, but are not limited to, the D-isomers of the above-listed genetically-encoded amino acids.

"Apolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include, but are not limited to, L-Leu (L), L-Val (V), L-Ile (I), L-Met (M), L-Gly (G) and L-Ala (A). Genetically non-encoded apolar amino acids include, but are not limited to, the D-isomers of the above-listed genetically-encoded amino acids, norleucine (Nle) and N-methyl valine (MeVal).

"Aliphatic Amino Acid" refers to a hydrophobic amino acid having an aliphatic hydrocarbon side chain. Genetically encoded aliphatic amino acids include, but are not limited to, L-Ala (A), L-Val (V), L-Leu (L) and L-Ile (1). Genetically non-encoded aliphatic amino acids include, but are not limited to, the D-isomers of the above-listed genetically-encoded amino acids, norleucine (Nle) and N-methyl valine (MeVal).

"Helix-Breaking Amino Acid" refers to those amino acids that have a propensity to disrupt the structure of α-helices when contained at internal positions within the helix.

Amino acid residues exhibiting helix-breaking properties are well-known in the art (see, e.g., Chou & Fasman, 1978, Ann. Rev. Biochem. 47:251–276) and include, but are not limited to L-Pro (P), D-Pro (p), L-Gly (G) and potentially all D-amino acids (when contained in an L-polypeptide; conversely, L-amino acids disrupt helical structure when contained in a D-polypeptide).

"Cysteine-like Amino Acid" refers to an amino acid having a side chain capable of participating in a disulfide linkage. Thus, cysteine-like amino acids generally have a side chain containing at least one thiol (—SH) group. Cysteine-like amino acids are unusual in that they can form disulfide bridges with other cysteine-like amino acids. The ability of L-Cys (C) -residues and other cysteine-like amino acids to exist in a polypeptide in either the reduced free —SH or oxidized disulfide-bridged form affects whether they contribute net hydrophobic or hydrophilic character to a polypeptide. Thus, while L-Cys (C) exhibits a hydrophobicity of 0.29 according to the consensus scale of Eisenberg (Eisenberg, 1984, supra), it is to be understood that for purposes of the present invention L-Cys (C) is categorized as a polar hydrophilic amino acid, notwithstanding the general classifications defined above. Other cysteine-like amino acids are similarly categorized as polar hydrophilic amino acids. Typical cysteine-like residues include, but are not limited to, penicillamine (Pen), homocysteine (hCys), etc.

As will be appreciated by those of skill in the art, the above-defined classes or categories are not mutually exclusive. Thus, amino acids having side chains exhibiting two or more physico-chemical properties can be included in multiple categories. For example, amino acid side chains having aromatic groups that are have a side chain pKa that is ionizable above or below pH 7.0, such as His (H), may exhibit both aromatic hydrophobic properties and basic or acidic hydrophilic properties, and could therefore be included in both the aromatic and basic or acidic categories. Typically, amino acids will be categorized in the class or classes that most closely define their net physico-chemical properties. The appropriate categorization of any amino acid will be apparent to those of skill in the art.

The classifications of the genetically encoded and common non-encoded amino acids according to the categories defined above are summarized in Table 1, below. It is to be understood that Table 1 is for illustrative purposes only and does not purport to be an exhaustive list of the amino acid residues belonging to each class. Other amino acid residues not specifically mentioned herein can be readily categorized based on their observed physical and chemical properties in light of the definitions provided herein.

TABLE 1

CLASSIFICATIONS OF COMMONLY ENCOUNTERED AMINO ACIDS

| Classification | Genetically Encoded | Genetically Non-Encoded |
| --- | --- | --- |
| Hydrophobic | | |
| Aromatic | F, Y, W | f, y, w |
| Apolar | L, V, I, M, G, A, P | l, v, i, m, a, p, Nle, MeVal |
| Aliphatic | A, V, L, I | a, v, l, i, Nle, MeVal |
| Hydrophilic | | |
| Acidic | D, E | d, e |
| Basic | H, K, R | h, k, r, Orn, Dab |
| Polar | C, Q, N, S, T | c, q, n, s, t, hSer |
| Helix-Breaking | P, G | p |

"Synagis" or "palivizumab" refers to the humanized monoclonal antibody that is sold under the tradename SYNAGIS (MedImmune), or that is known by the name palivizumab. Synagis comprises an immunoglobulin complex of a Synagis heavy chain and a Synagis light chain that specifically binds the F protein of respiratory syncytial virus ("RSV"), as defined herein.

"Synagis heavy chain" refers to a polypeptide having an amino acid sequence that corresponds identically to the amino acid sequence of SEQ ID NO:1 (FIG. 3A).

"Synagis light chain" refers to a polypeptide having an amino acid sequence that corresponds identically to the amino acid sequence of SEQ ID NO:7 (FIG. 3B).

"Smagis Fab" refers to the antigen binding fragment of Synagis which can be obtained by digesting Synagis with papain. Synagis Fab includes the antigen binding region of Synagis and comprises a complex of Synagis light chain (SEQ ID NO:7) and N-terminal fragment (residues 1 to 220) of Synagis heavy chain (SEQ ID NO:2) linked by a disulfide bridge between Cys 216 of SEQ ID NO:2 and Cys 214 of Synagis light chain (SEQ ID NO:7). Unless stated otherwise, "Synagis Fab" includes either wild-type Syangis Fab and mutant Synagis Fab as defined herein.

"Synagis Fc" refers to a fragment of Synagis which can be obtained by digesting Synagis with papain. Synagis Fc does not include the antigen binding region of Synagis and comprises a complex of two C-terminal fragments of Synagis heavy chain (SEQ ID NO:3) linked by at least two disulfide bridges, one between the Cys 222 residues of the two chains and the other between the Cys 225 residues of the two chains.

"Synagis Fv" refers to a complex comprising the N-terminal variable segment residues 1 to 105 of Synagis heavy chain (SEQ ID NO:1) and the N-terminal sequence residues 1 to 109 of Synagis light chain (SEQ. ID NO:7). Synagis Fv includes the complementarity determining regions ("CDRs") of Synagis heavy chain, H1 (SEQ ID NO:4), H2 (SEQ ID NO:5) and H3 (SEQ ID NO:6), and the CDRs of Synagis light chain, L1 (SEQ ID NO:8), L2 (SEQ ID NO:9) and L3 (SEQ ID NO:10).

"Association" refers to a condition of proximity between a chemical entity or compound, or portions or fragments thereof, and a polypeptide such as Synagis Fab, or portions or fragments thereof. The association may be non-covalent, i.e., where the juxtaposition is energetically favored by, e.g., hydrogen-bonding, van der Waals, electrostatic or hydrophobic interactions, or it may be covalent.

"Co-Complex" refers to a complex between Synagis, Synagis Fab, Synagis Fv or another binding fragment of Synagis and another compound, for example, an antigen, an epitope, a hapten or an analog, a mimic or a fragment thereof or an inhibitor of Synagis.

"Antibody" or "Immunoglobulin" refers to a glycoprotein produced by B leukocyte cells in response to stimulation with an immunogen, or a synthetic or recombinant version or analog of such a glycoprotein. Antibodies comprise heavy chains and light chains linked together by disulfide bonds. IgG type antibodies typically comprise two antigen binding sites.

"Complementarity Determining Region" or "CDR" refers to the hypervariable regions of an antibody that form the three-dimensional cavity or surface where an antigen or an epitope binds to the antibody. Typically, heavy chains and light chains contribute three CDRs to the antigen binding region of an antibody.

"Antigen" refers to a substance that specifically binds with antibody CDRs.

"Epitope" refers to the smallest structural area on an antigen molecule that binds an antibody.

"Antigen binding site" or "antibody binding site" refers to the location on an antibody molecule where the antigen or eptiope binds. The antigen binding site is located at the molecular surface define by the N-terminal CDRs and/or in a cleft bordered by the N-terminal CDRs of the heavy and light chains of the Fab region of an antibody molecule.

"Crystallized Synagis" refers to Synagis which is in crystalline form.

"Crystallized Synagis Fab" refers to a Synagis Fab complex which is in the crystalline form.

"Wild-type" refers to a Synagis molecule, that comprises Synagis heavy chain corresponding identically to SEQ ID NO:1 and/or Synagis light chain corresponding identically to SEQ ID NO:7, or fragments thereof. Although Synagis is a humanized antibody not derived from a natural source, for convenience the phrase "wild-type" is used to refer to a molecule which corresponds identically to Synagis, or a fragment thereof, and the phrase "mutant" is used as defined below.

"Mutant" refers to a polypeptide or complex of polypeptides characterized by an amino acid sequence that differs from the wild-type Synagis heavy chain and/or light chain sequence by the substitution of at least one amino acid residue of the wild-type Synagis sequence with a different amino acid residue and/or by the addition and/or deletion of one or more amino acid residues to or from the wild-type Synagis sequence. The additions and/or deletions can be from an internal region of the wild-type Synagis sequence and/or at either or both of the N- or C-termini. A mutant may have, but need not have, Synagis activity. Preferably, a mutant displays biological activity that is substantially similar to that of Synagis.

"Conservative Mutant" refers to a mutant in which at least one amino acid residue from the wild-type Synagis heavy chain and/or light chain sequence is substituted with a different amino acid residue that has similar physical and chemical properties, i.e., an amino acid residue that is a member of the same class or category, as defined above. For example, a conservative mutant may be a polypeptide that differs in amino acid sequence from the wild-type Synagis sequence by the substitution of a specific aromatic Phe (F) residue with an aromatic Tyr (Y) or Trp (W) residue.

"Non-Conservative Mutant" refers to a mutant in which at least one amino acid residue from the wild-type Synagis heavy chain and/or light chain sequence is substituted with a different amino acid residue that has dissimilar physical and/or chemical properties, i.e., an amino acid residue that is a member of a different class or category, as defined above. For example, a non-conservative mutant may be a polypeptide that differs in amino acid sequence from the wild-type Synagis sequence by the substitution of an acidic Glu (E) residue with a basic Arg (R), Lys (K) or Orn residue.

"Deletion Mutant" refers to a mutant having an amino acid sequence that differs from the wild-type Synagis heavy chain and/or light chain sequence by the deletion of one or more amino acid residues from the wild-type sequence. The residues may be deleted from internal regions of the wild-type Synagis sequence and/or from one or both termini.

"Truncated Mutant" refers to a deletion mutant in which the deleted residues are from the N- and/or C-terminus of the wild-type Synagis sequence.

"Extended Mutant" refers to a mutant in which additional residues are added to the N- and/or C-terminus of the wild-type Synagis sequence.

"Methionine mutant" refers to (1) a mutant in which at least one methionine residue of the wild-type Synagis heavy chain and/or light chain sequence is replaced with another residue, preferably with an aliphatic residue, most preferably with a Leu (L) or Ile (I) residue; or (2) a mutant in which a non-methionine residue, preferably an aliphatic residue, most preferably a Leu (L) or Ile (I) residue, of the wild-type Synagis sequence is replaced with a methionine residue.

"Selenomethionine mutant" refers to (1) a mutant which includes at least one selenomethionine (SeMet) residue, typically by substitution of one or more Met residues of the wild-type Synagis heavy chain and/or light chain sequence with a SeMet residue, or by addition of one or more SeMet residues at one or more termini, or (2) a methionine mutant in which at least one Met residue is substituted with a SeMet residue. Preferred SeMet mutants are those in which each Met residue is substituted with a SeMet residue.

"Cysteine mutant" refers to (1) a mutant in which at least one cysteine residue of the wild-type Synagis heavy chain and/or light chain sequence is replaced with another residue, preferably with a Ser (S) residue; or (2) a mutant in which a non-cysteine residue, preferably a Ser (S) residue, of the wild-type Synagis sequence is replaced with a cysteine residue.

"Selenocysteine mutant" refers to (1) a mutant which includes at least one selenocysteine (SeCys) residue, typically by substitution of one or more Cys residues of the wild-type Synagis heavy chain and/or light chain sequence with a SeCys residue, or by addition of one or more SeCys residues at one or more termini, or (2) a cysteine mutant in which at least one Cys residue is substituted with a SeCys residue. Preferred SeCys mutants are those in which each Cys residue or selected Cys residues of Synagis not typically involved in disulfide bonding under physiological conditions is substituted with a SeCys residue. One such Cys residue in the Synagis Fab fragment that may be substituted with selenocysteine is Cys 25 in the light chain (SEQ. ID NO: 7).

"Homologue" refers to a polypeptide having at least 70%, 80%, 90%, 95% or 99% amino acid sequence identity or having a BLAST score of $1 \times 10^{-6}$ over at least 100 amino acids (Altschul et al., 1997, Nucleic Acids Res. 25:3389–402) with wild-type Synagis, Synagis heavy chain and/or Synagis light chain, or any functional domain of Synagis, Synagis heavy chain and/or Synagis light chain, as defined herein.

"Crystal" refers to a composition comprising a polypeptide and/or polypeptides in crystalline form. The term "crystal" includes native crystals, heavy-atom derivative crystals and co-crystals, as defined herein.

"Native Crystal" refers to a crystal wherein the polypeptide and/or polypeptides are substantially pure. As used herein, native crystals do not include crystals of polypeptides comprising amino acids that are modified with heavy atoms, such as crystals of selenomethionine mutants, selenocysteine mutants, etc.

"Heavy-atom Derivative Crystal" refers to a crystal wherein the polypeptide and/or polypeptides are in association with one or more heavy-metal atoms. As used herein, heavy-atom derivative crystals include native crystals into which a heavy metal atom is soaked, as well as crystals of selenomethionine mutants and selenocysteine mutants.

"Co-Crystal" refers to a composition comprising a co-complex, as defined above, in crystalline form. Co-crystals include native co-crystals and heavy-atom derivative co-crystals.

"Diffraction Quality Crystal" refers to a crystal that is well-ordered and of a sufficient size, i.e., at least 10 µm, preferably at least 50 μm, and most preferably at least 100 μm in its smallest dimension such that it produces measurable diffraction to at least 3 Å resolution, preferably to at least 2 Å resolution, and most preferably to at least 1.5 Å resolution or lower. Diffraction quality crystals include native crystals, heavy-atom derivative crystals, and co-crystals.

"Unit Cell" refers to the smallest and simplest volume element (i.e., parallelpiped-shaped block) of a crystal that is completely representative of the unit or pattern of the crystal, such that the entire crystal can be generated by translation of the unit cell. The dimensions of the unit cell are defined by six numbers: dimensions a, b and c and angles α, β and γ (Blundel et al., 1976, Protein Crystallography, Academic Press.). A crystal is an efficiently packed array of many unit cells.

"Triclinic Unit Cell" refers to a unit cell in which a≠b≠c and α≠β≠γ.

"Monoclinic Unit Cell" refers to a unit cell in which a≠b≠c; α=γ=90°; and β≠90°, defined to be ≧90°.

"Orthorhombic Unit Cell" refers to a unit cell in which a≠b≠c; and α=β=γ=90°.

"Tetragonal Unit Cell" refers to a unit cell in which a=b≠c; and α=β=γ=90°.

"Trigonal/Rhombohedral Unit Cell" refers to a unit cell in which a=b=c; and α=β=γ≠90°.

"Trigonal/Hexagonal Unit Cell" refers to a unit cell in which a=b≠c; α=β=90°; and γ=120°.

"Cubic Unit Cell" refers to a unit cell in which a=b=c; and α=β=γ=90°.

"Crystal Lattice" refers to the array of points defined by the vertices of packed unit cells.

"Space Group" refers to the set of symmetry operations of a unit cell. In a space group designation (e.g., C2) the capital letter indicates the lattice type and the other symbols represent symmetry operations that can be carried out on the unit cell without changing its appearance.

"Asymmetric Unit" refers to the largest aggregate of molecules in the unit cell that possesses no symmetry elements that are part of the space group symmetry, but that can be juxtaposed on other identical entities by symmetry operations.

"Crystallographically-Related Dimer" refers to a dimer of two molecules wherein the symmetry axes or planes that relate the two molecules comprising the dimer coincide with the symmetry axes or planes of the crystal lattice.

"Non-Crystallographically-Related Dimer" refers to a dimer of two molecules wherein the symmetry axes or planes that relate the two molecules comprising the dimer do not coincide with the symmetry axes or planes of the crystal lattice.

"Isomorphous Replacement" refers to the method of using heavy-atom derivative crystals to obtain the phase information necessary to elucidate the three-dimensional structure of a crystallized polypeptide (Blundel et al., 1976, Protein Crystallography, Academic Press.).

"Multi-Wavelength Anomalous Dispersion or MAD" refers to a crystallographic technique in which X-ray diffraction data are collected at several different wavelengths from a single heavy-atom derivative crystal, wherein the heavy atom has absorption edges near the energy of incoming X-ray radiation. The resonance between X-rays and electron orbitals leads to differences in X-ray scattering from absorption of the X-rays (known as anomalous scattering) and permits the locations of the heavy atoms to be identified, which in turn provides phase information for a crystal of a polypeptide. A detailed discussion of MAD analysis can be found in Hendrickson, 1985, Trans. Am. Crystallogr. Assoc., 21:11; Hendrickson et al, 1990, EMBO J. 9:1665; and Hendrickson, 1991, Science 4:91.

"Single Wavelength Anomalous Dispersion or SAD" refers to a crystallographic technique in which X-ray diffraction data are collected at a single wavelength from a single native or heavy-atom derivative crystal, and phase information is extracted using anomalous scattering information from atoms such as sulfur or chlorine in the native crystal or from the heavy atoms in the heavy-atom derivative crystal. The wavelength of X-rays used to collect data for this phasing technique need not be close to the absorption edge of the anomalous scatterer. A detailed discussion of SAD analysis can be found in Brodersen et al., 2000, Acta Cryst., D56:431–441.

"Single Isomorphous Replacement With Anomalous Scattering or SIRAS" refers to a crystallographic technique that combines isomorphous replacement and anomalous scattering techniques to provide phase information for a crystal of a polypeptide. X-ray diffraction data are collected at a single wavelength, usually from a single heavy-atom derivative crystal. Phase information obtained only from the location of the heavy atoms in a single heavy-atom derivative crystal leads to an ambiguity in the phase angle, which is resolved using anomalous scattering from the heavy atoms. Phase information is therefore extracted from both the location of the heavy atoms and from anomalous scattering of the heavy atoms. A detailed discussion of SIRAS analysis can be found in North, 1965, Acta Cryst. 18:212–216; Matthews, 1966, Acta Cryst. 20:82–86.

"Molecular Replacement" refers to the method of calculating initial phases for a new crystal of a polypeptide whose structure coordinates are unknown by orienting and positioning a polypeptide whose structure coordinates are known within the unit cell of the new crystal so as to best account for the observed diffraction pattern of the new crystal. Phases are then calculated from the oriented and positioned polypeptide and combined with observed amplitudes to provide an approximate Fourier synthesis of the structure of the polypeptides comprising the new crystal. This, in turn, is subject to any of several methods of refinement to provide a final, accurate set of structure coordinates for the new crystal (Lattman, 1985, Methods in Enzymology 115:55–77; Rossmann, 1972, "The Molecular Replacement Method," Int. Sci. Rev. Ser. No. 13, Gordon & Breach, New York; Brünger et al, 1991, Acta Crystallogr A. 47:195–204).

"Having Substantially the Same Three-dimensional Structure" refers to a polypeptide that is characterized by a set of atomic structure coordinates that have a root mean square deviation (r.m.s.d.) of less than or equal to about 2 Å when superimposed onto the atomic structure coordinates of Table 2, or a subset thereof such as individual CDRs, individual secondary structure elements or grouped secondary structure elements such as β-sheets, when at least about 50% to 100% of the Cα atoms of the coordinates are included in the superposition.

"Cα:" As used herein, "Cα" refers to the alpha carbon of an amino acid residue.

5. BRIEF DESCRIPTION OF THE FIGURES

Figure 2:
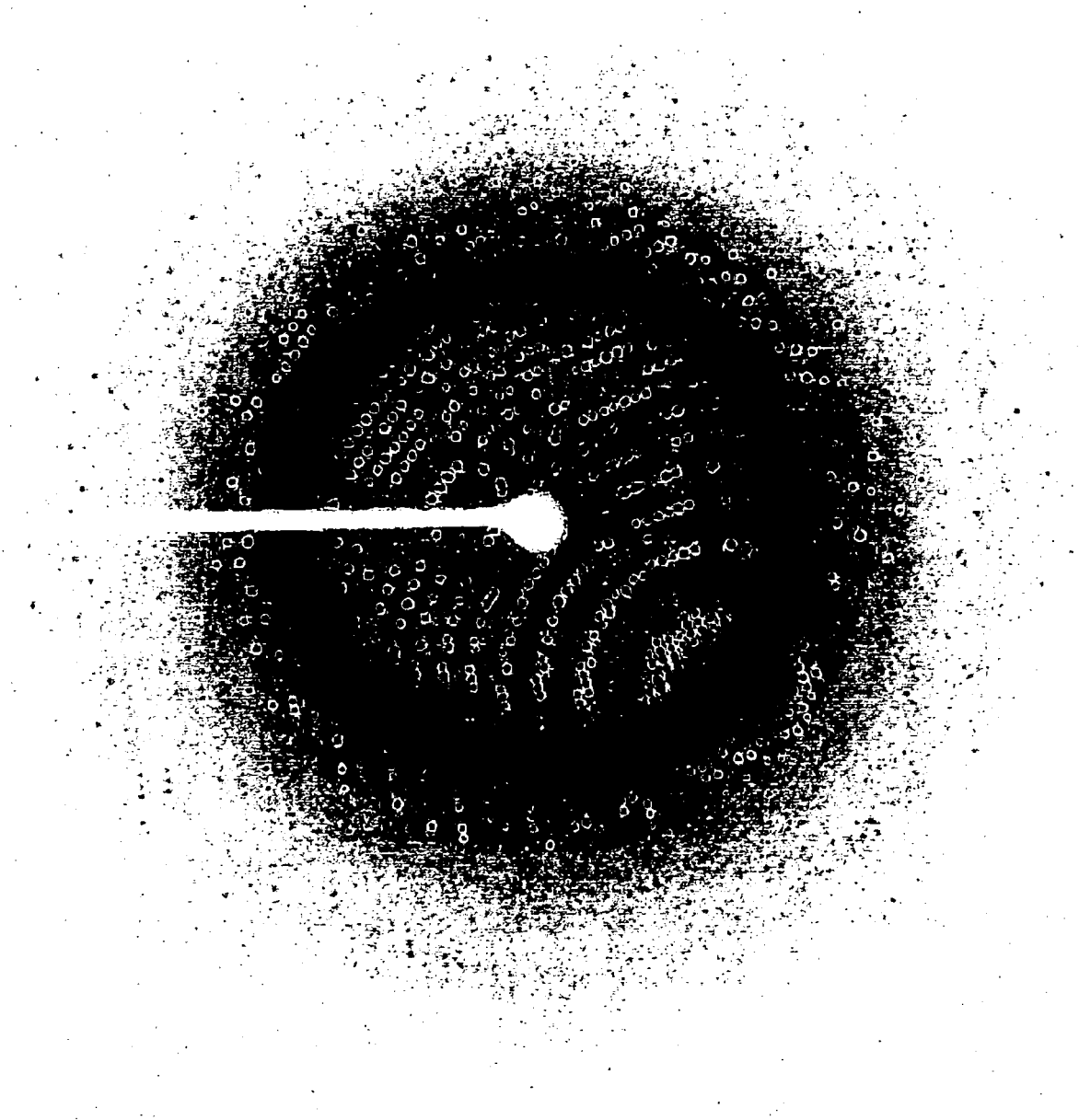

FIG. 1 provides a photograph of an orthorhombic crystal of Synagis Fab;

FIG. 2 provides a diffraction pattern (1° oscillation) of Synagis Fab prepared as described in the Examples;

FIG. 3A provides the amino acid sequences of Synagis heavy chain (SEQ ID NO:1), Synagis heavy chain Fab fragment (SEQ ID NO:2), Synagis heavy chain Fc fragment (SEQ ID NO:3), Synagis heavy chain variable region H1 (SEQ ID NO:4), heavy chain variable region H2 (SEQ ID NO:5) and Synagis heavy chain variable region H3 (SEQ ID NO:6).

FIG. 3B provides the amino acid sequences of Synagis light chain (SEQ ID NO:7), Synagis light chain variable region L1 (SEQ ID NO:8), Synagis light chain variable region L2 (SEQ ID NO:9) and Synagis light chain variable region L3 (SEQ ID NO:10).

Figure 4:
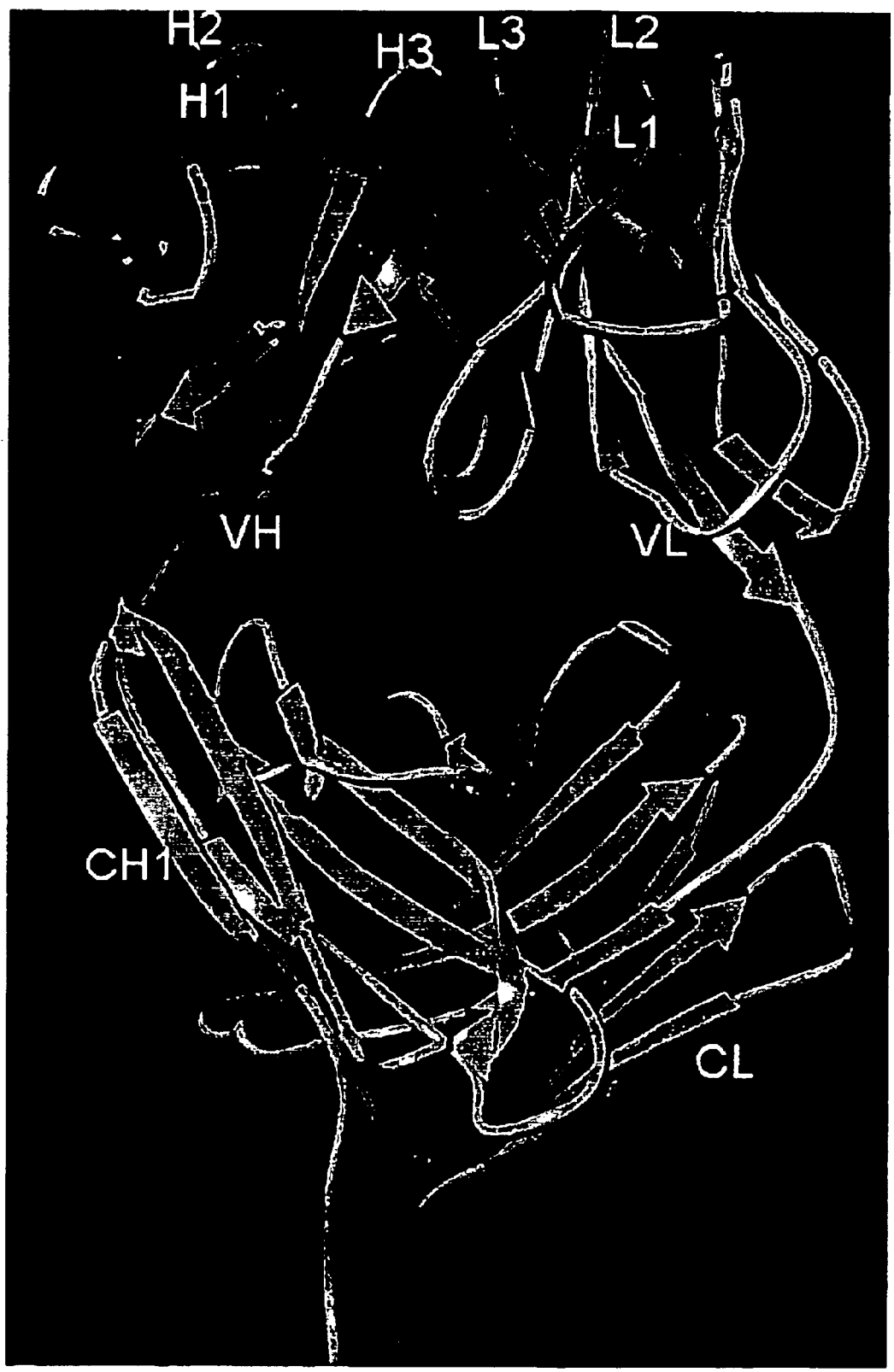
Figure 5:
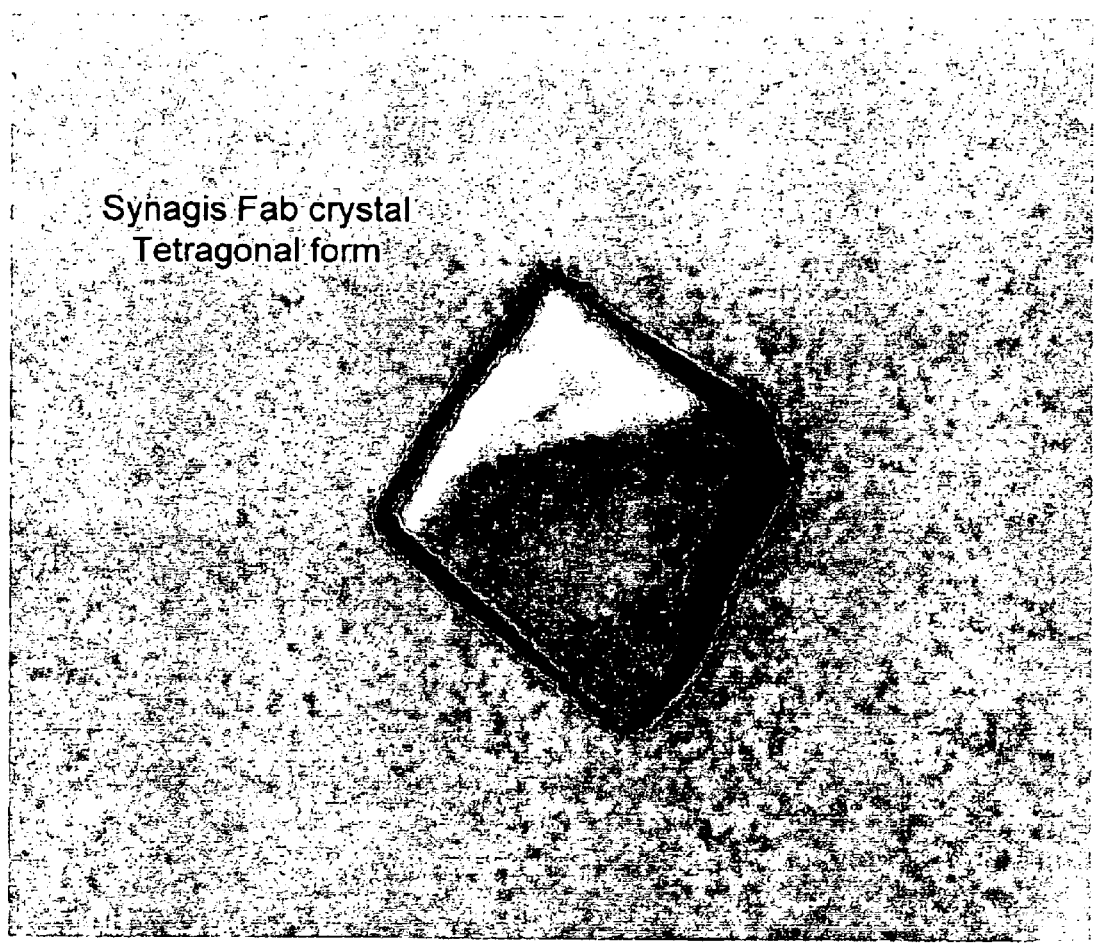
Figure 7A:
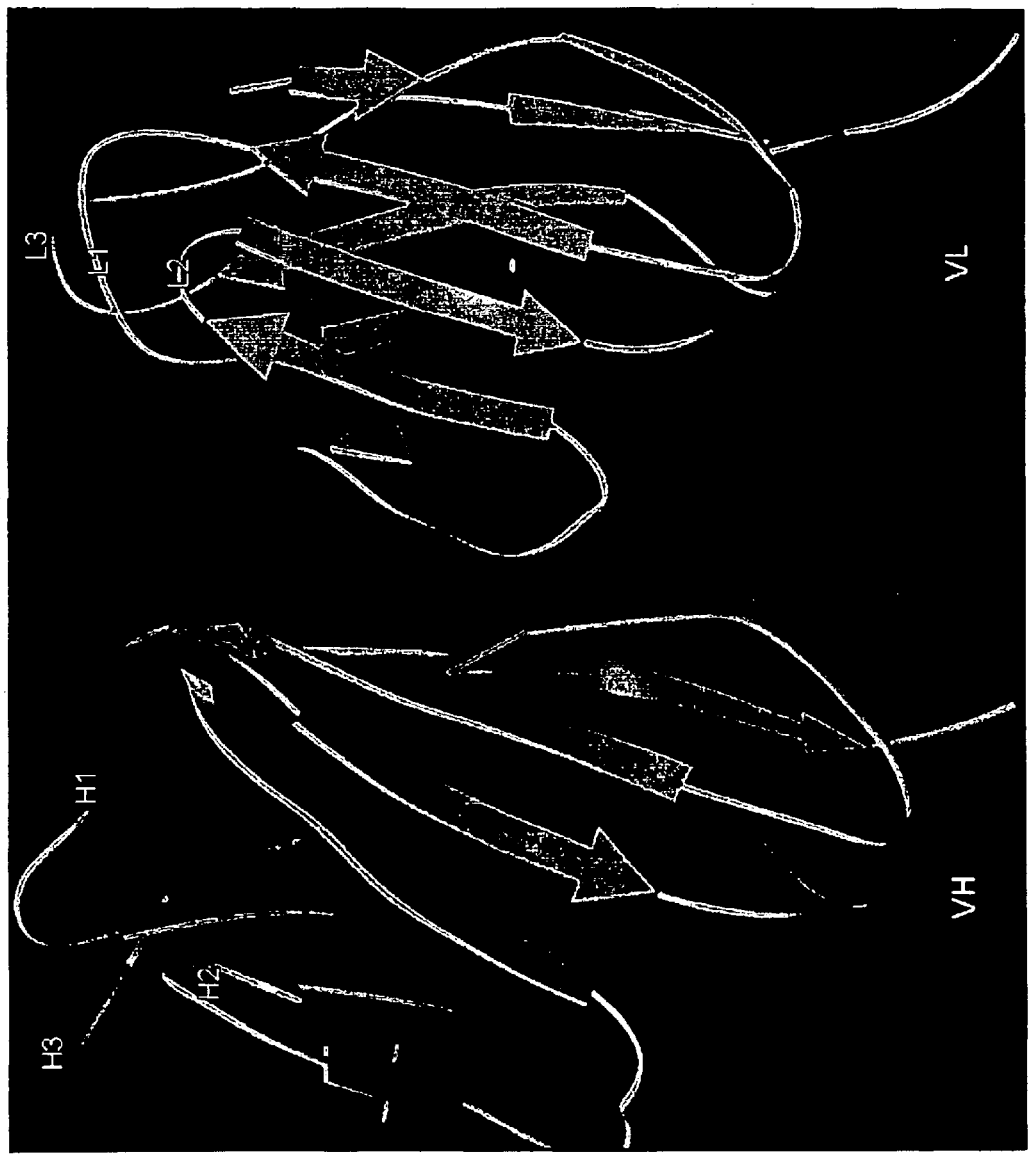
Figure 7B:
Figure 8:
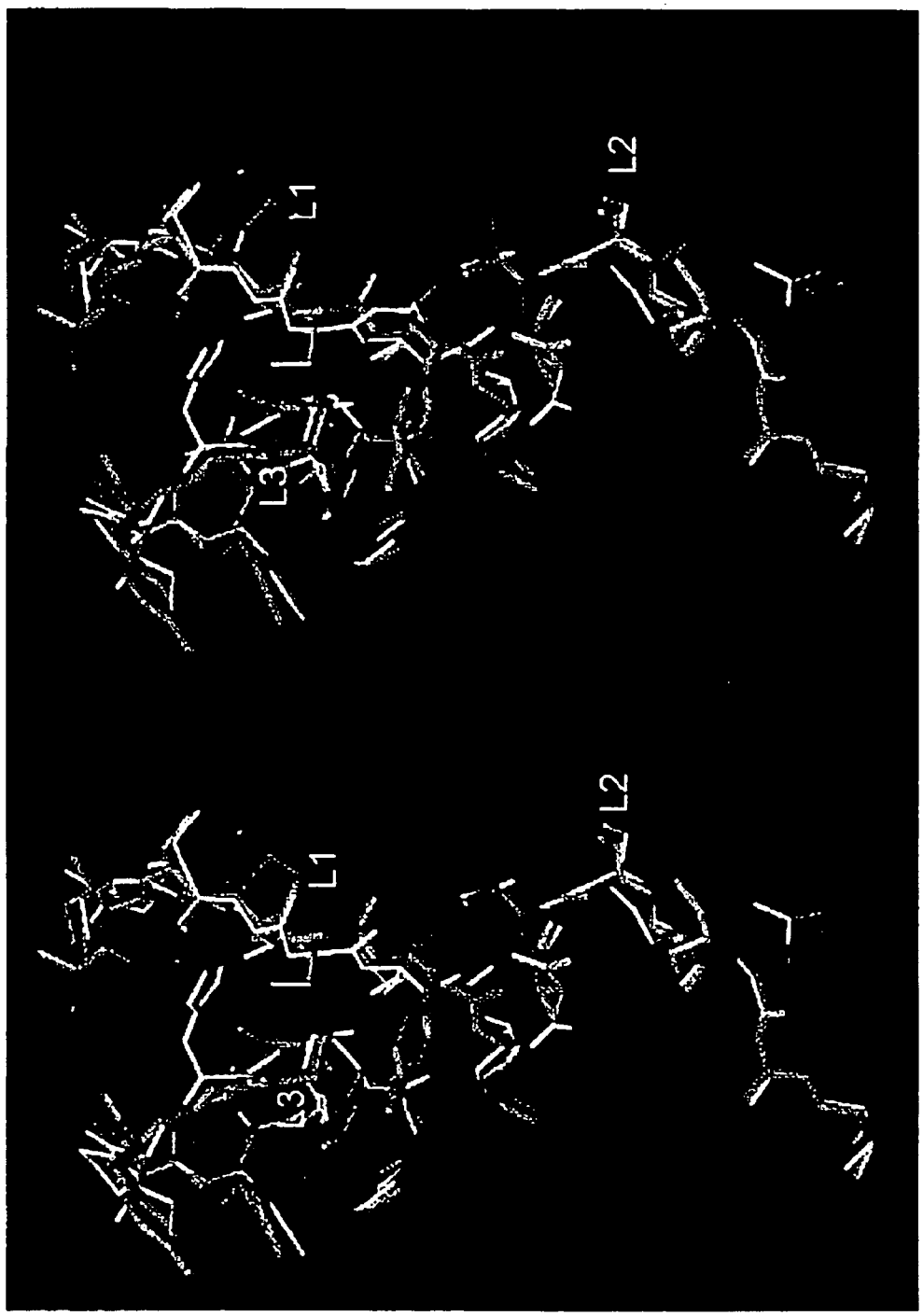
Figure 9:
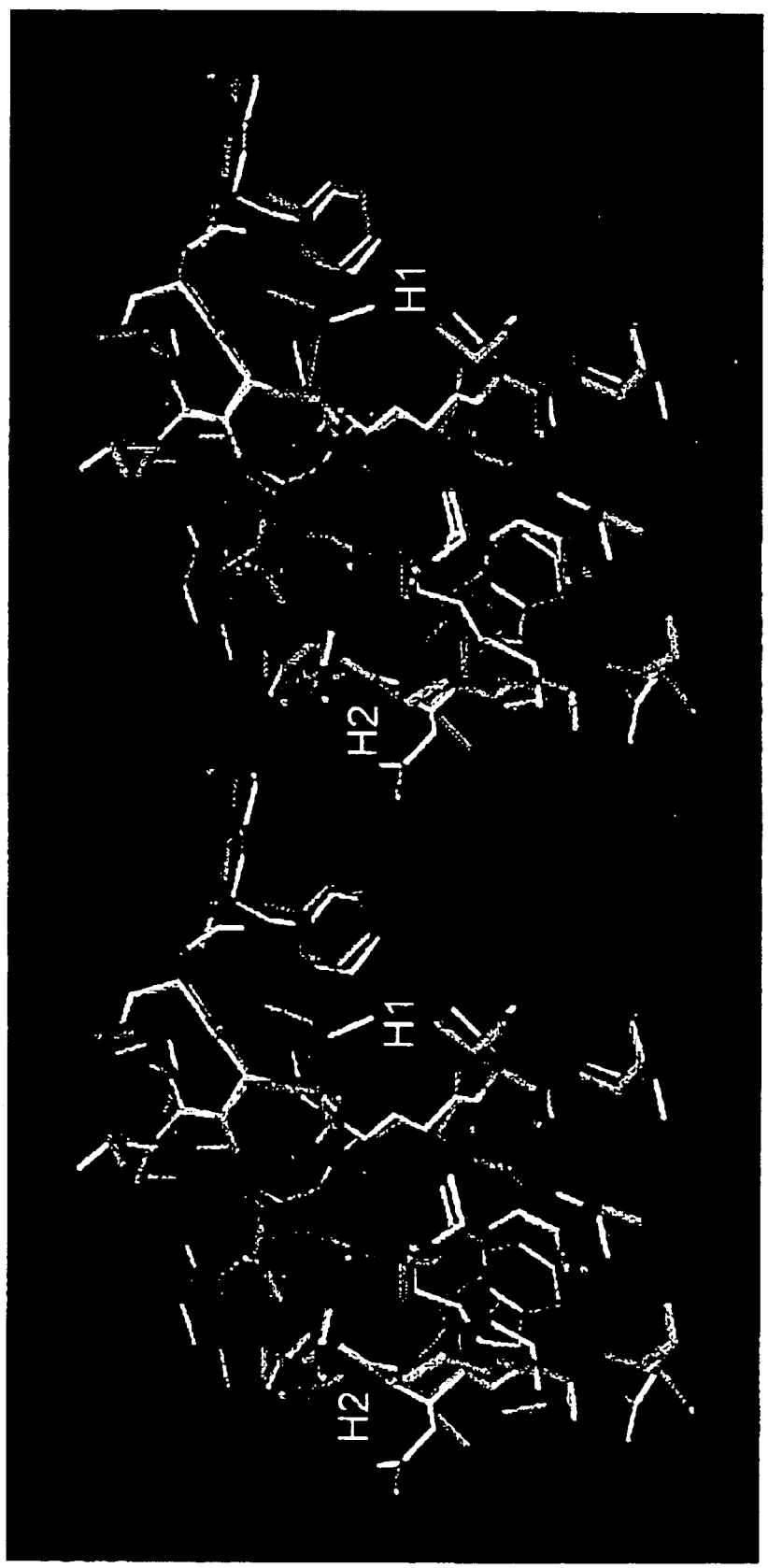
Figure 10:
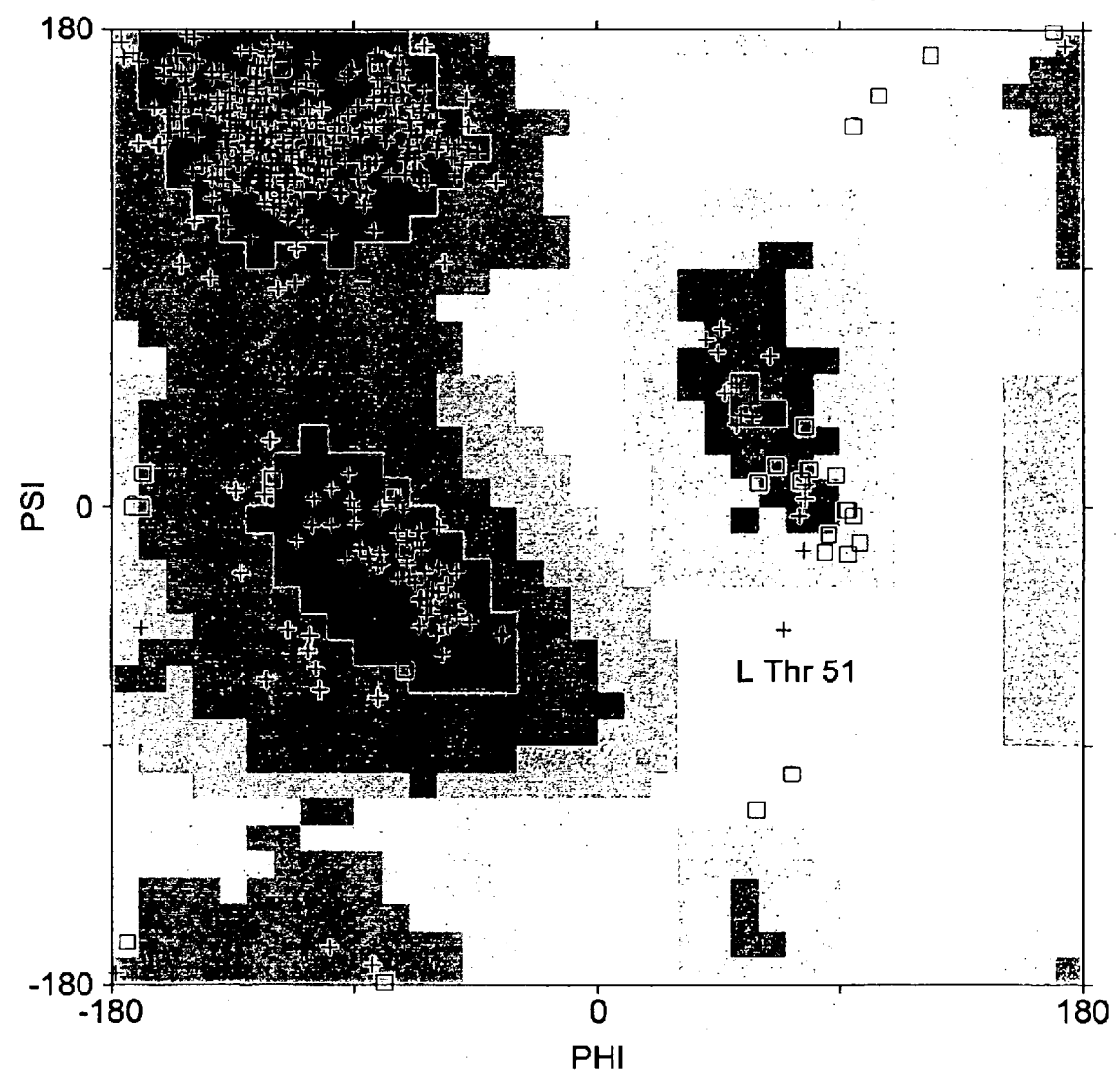

FIG. 4 provides a ribbon diagram of the three-dimensional X-ray diffraction structure of Synagis Fab;

FIG. 5 provides a photograph of a tetragonal crystal form of Synagis Fab;

FIG. 6 provides a schematic representation of a generalized IgG type antibody showing the relative positions of the light chain VL and CL domains and the heavy chain VH, CH1, CH2 and CH3 domains;

FIG. 7A provides a ribbon diagram of the three-dimensional structure of Synagis VH and VL domains;

FIG. 7B provides a ribbon diagram of the three-dimensional structure of Synagis Fab CL and CH1 domains;

FIG. 8 provides a stereo view of a superposition of Synagis light chain CDRs L1, L2 & L3 with representative canonical structures;

FIG. 9 provides a stereo view of a superposition of Synagis heavy chain CDRs H1 & H2 with representative canonical structures; and FIG. 10 provides a Ramachandran plot of the model Synagis Fab crystal structure.

5.1. BRIEF DESCRIPTION OF THE TABLES

Table 1 Classifications of Commonly Encountered Amino Acids;

Table 2 Coordinates of Synagis Fab;

Table 3 Description and Comparison of Synagis Light Chain CDR Canonical Structure;

Table 4 Description and Comparison of Synagis Heavy Chain CDR Canonical Structure;

Table 5 Data Collection Summary;

Table 6 Refinement Parameters.

6. DETAILED DESCRIPTION OF THE INVENTION

6.1 Crystalline Synagis Fab

The crystals of the invention may be obtained include native crystals and heavy-atom derivative crystals. Native crystals generally comprise substantially pure polypeptides corresponding to Synagis Fab in crystalline form.

It is to be understood that the crystalline Synagis Fab of the invention that can be obtained is not limited to wild-type Synagis Fab. Indeed, the crystals may comprise mutants of wild-type Synagis Fab. Mutants of wild-type Synagis Fab are obtained by replacing at least one amino acid residue in the sequence of the wild-type Synagis Fab with a different amino acid residue, or by adding or deleting one or more amino acid residues within the wild-type sequence and/or at the N- and/or C-terminus of the wild-type Synagis Fab. Such mutants should crystallize under crystallization conditions that are substantially similar to those used to crystallize the wild-type Synagis Fab.

The types of mutants contemplated by this invention include conservative mutants, non-conservative mutants, deletion mutants, truncated mutants, extended mutants, methionine mutants, selenomethionine mutants, cysteine mutants and selenocysteine mutants. A mutant or a fragment may have, but need not have, Synagis activity. Preferably, a mutant or a fragment displays biological activity that is substantially similar to that of the wild-type Synagis. Methionine, selenomethione, cysteine, and selenocysteine mutants are particularly useful for producing heavy-atom derivative crystals, as described in detail, below.

It will be recognized by one of skill in the art that the types of mutants contemplated herein are not mutually exclusive; that is, for example, a polypeptide having a conservative mutation in one amino acid may in addition have a truncation of residues at the N-terminus, and several Leu or Ile→Met mutations.

Sequence alignments of polypeptides in a protein family or of homologous polypeptide domains can be used to identify potential amino acid residues in the polypeptide sequence that are candidates for mutation. Identifying mutations that do not significantly interfere with the three-dimensional structure of Synagis and/or that do not deleteriously affect, and that may even enhance, the activity of Synagis will depend, in part, on the region where the mutation occurs. In the CDR regions of the molecule, such as those shown in FIG. 4, non-conservative substitutions as well as conservative substitutions may be tolerated without significantly disrupting the three-dimensional structure and/or biological activity of the molecule. In framework regions, or regions containing significant secondary structure, such as those regions shown in FIG. 4, conservative amino acid substitutions are preferred.

Conservative amino acid substitutions are well-known in the art, and include substitutions made on the basis of a similarity in polarity, charge, solubility, size, hydrophobicity and/or the hydrophilicity of the amino acid residues involved. Typical conservative substitutions are those in which the amino acid is substituted with a different amino acid that is a member of the same class or category, as those classes are defined herein. Thus, typical conservative substitutions include aromatic to aromatic, apolar to apolar, aliphatic to aliphatic, acidic to acidic, basic to basic, polar to polar, etc. Other conservative amino acid substitutions are well known in the art. It will be recognized by those of skill in the art that generally, a total of about 20% or fewer, typically about 10% or fewer, most usually about 5% or fewer, of the amino acids in the wild-type polypeptide sequence can be conservatively substituted with other amino acids without deleteriously affecting the biological activity and/or three-dimensional structure of the molecule, provided that such substitutions do not involve residues that are critical for structure or activity, as discussed above. There has been no complete examination of the effect of conservative mutations of the closely conserved amino acids in immunoglobulin framework regions.

In some embodiments, it may be desirable to make mutations in the active site of a protein or in the antigen binding site of an antibody, e.g., to reduce or completely eliminate antibody activity. While in most instances the amino acids of Synagis will be substituted with genetically-encoded amino acids, in certain circumstances mutants may include genetically non-encoded amino acids. For example, non-encoded derivatives of certain encoded amino acids, such as SeMet and/or SeCys, may be incorporated into the polypeptide chain using biological expression systems (such SeMet and SeCys mutants are described in more detail, infra).

Alternatively, in instances where the mutant will be prepared in whole or in part by chemical synthesis, virtually any non-encoded amino acids may be used, ranging from D-isomers of the genetically encoded amino acids to non-encoded naturally-occurring natural and synthetic amino acids.

Conservative amino acid substitutions for many of the commonly known non-genetically encoded amino acids are well known in the art. Conservative substitutions for other non-encoded amino acids can be determined based on their physical properties as compared to the properties of the genetically encoded amino acids.

In some instances, it may be particularly advantageous or convenient to substitute, delete from and/or add amino acid residues to Synagis in order to provide convenient cloning sites in cDNA encoding the polypeptide, to aid in purification of the polypeptide, etc. Such substitutions, deletions and/or additions that do not substantially alter the three dimensional structure of the native Synagis will be apparent to those having skills in the art. These substitutions, deletions and/or additions include, but are not limited to, His tags, intein-containing self-cleaving tags, maltose binding protein fusions, glutathione S-transferase protein fusions, antibody fusions, green fluorescent protein fusions, signal peptide fusions, biotin accepting peptide fusions, and the like.

Mutations may also be introduced into a polypeptide sequence where there are residues, e.g., cysteine residues, that interfere with crystallization. Such cysteine residues can be substituted with an appropriate amino acid that does not readily form covalent bonds with other amino acid residues under crystallization conditions; e.g., by substituting the cysteine with Ala, Ser or Gly. Any cysteine residue that does not form disulfide bonds either between a heavy chain and a light chain or between two heavy chains of Synagis is a good candidate for replacement. Preferably, Cys residues that are known to participate in disulfide bridges are not substituted or are conservatively substituted with other cysteine-like amino acids so that the residue can participate in a disulfide bridge. In addition, other cysteine residues located in a non-helical or non-β-stranded segment, based on secondary structure assignments, are good candidates for replacement. One such Cys residue in the Synagis Fab crystal structure is at light chain position 25 (SEQ. ID NO: 7).

It should be noted that the mutants contemplated herein need not exhibit Synagis activity. Indeed, amino acid substitutions, additions or deletions that interfere with the activity of Synagis are specifically contemplated by the invention. Such crystalline polypeptides, or the atomic structure coordinates obtained therefrom, can be used to provide phase information to aid the determination of the three-dimensional X-ray structures of other related or non-related crystalline polypeptides.

The heavy-atom derivative crystals from which the atomic structure coordinates of the invention can be obtained generally comprise a crystalline Synagis Fab complex in association with one or more heavy metal atoms. The complex may correspond to a wild-type or a mutant Synagis Fab, which may optionally be in co-complex with one or more molecules, as previously described. The complex may also correspond to another Synagis fragment or to a mutated form thereof. There are two types of heavy-atom derivatives of polypeptides: heavy-atom derivatives resulting from exposure of the protein to a heavy metal in solution, wherein crystals are grown in medium comprising the heavy metal, or in crystalline form, wherein the heavy metal diffuses into the crystal, and heavy-atom derivatives wherein the polypeptide comprises heavy-atom containing amino acids, e.g., selenomethionine and/or selenocysteine mutants.

In practice, heavy-atom derivatives of the first type can be formed by soaking a native crystal in a solution comprising heavy metal atom salts, or organometallic compounds, e.g., lead chloride, gold thiomalate, ethylmercurithiosalicylic acid-sodium salt (thimerosal), uranyl acetate, platinum tetrachloride, osmium tetraoxide, zinc sulfate, and cobalt hexamine, which can diffuse through the crystal and bind to the crystalline polypeptide.

Heavy-atom derivatives of this type can also be formed by adding to a crystallization solution comprising the polypeptide to be crystallized an amount of a heavy metal atom salt, which may associate with the protein and be incorporated into the crystal. The location(s) of the bound heavy metal atom(s) can be determined by X-ray diffraction analysis of the crystal. This information, in turn, is used to generate the phase information needed to construct the three-dimensional structure of the protein.

Heavy-atom derivative crystals may also be prepared from polypeptides that include one or more SeMet and/or SeCys residues (SeMet and/or SeCys mutants). Such selenocysteine or selenomethionine mutants may be made from wild-type or mutant Synagis Fab by expression of Synagis Fab-encoding cDNAs in auxotrophic *E. coli* strains. Hendrickson et al., 1990, EMBO J. 9(5):1665–1672. The selenocysteine or selenomethionine mutants may also be made from intact Synagis, other fragments of Synagis, or mutated forms thereof. In this method, a cDNA encoding a wild-type or mutant Synagis polypeptide may be expressed in a host organism on a growth medium depleted of either natural cysteine or methionine (or both) but enriched in selenocysteine or selenomethionine (or both). Alternatively, selenocysteine or selenomethionine mutants may be made using nonauxotrophic *E. coli* strains, e.g., by inhibiting methionine biosynthesis in these strains with high concentrations of Ile, Lys, Thr, Phe, Leu or Val and then providing selenomethionine in the medium (Doublié, 1997, Methods in Enzymology 276:523–530). Furthermore, selenocysteine can be selectively incorporated into polypeptides by exploiting the prokaryotic and eukaryotic mechanisms for selenocysteine incorporation into certain classes of proteins in vivo, as described in U.S. Pat. No. 5,700,660 to Leonard et al. (filed Jun. 7, 1995). One of skill in the art will recognize that selenocysteine is preferably not incorporated in place of cysteine residues that form disulfide bridges, as these may be important for maintaining the three-dimensional structure of the protein and are preferably not to be eliminated. One of skill in the art will further recognize that, in order to obtain accurate phase information, approximately one selenium atom should be incorporated for every 140 amino acid residues of the polypeptide chain. The number of selenium atoms incorporated into the polypeptide chain can be conveniently controlled by designing a Met or Cys mutant having an appropriate number of Met and/or Cys residues, as described more fully below.

In some instances, a polypeptide to be crystallized may not contain cysteine or methionine residues. Therefore, if selenomethionine and/or selenocysteine mutants are to be used to obtain heavy-atom derivative crystals, methionine and/or cysteine residues must be introduced into the polypeptide chain. Likewise, Cys residues may be introduced into the polypeptide chain if the use of a cysteine-binding heavy metal, such as mercury, is contemplated for production of a heavy-atom derivative crystal.

Such mutations are preferably introduced into the polypeptide sequence at sites that will not disturb the overall protein fold. For example, a residue that is conserved among many members of the protein family or that is thought to be involved in maintaining its activity or structural integrity, as determined by, e.g., sequence alignments, should not be mutated to a Met or Cys. In addition, conservative mutations, such as Ser to Cys, or Leu or Ile to Met, are preferably introduced. One additional consideration is that, in order for a heavy-atom derivative crystal to provide phase information for structure determination, the location of the heavy atom(s) in the crystal unit cell must be determinable and provide phase information. Therefore, a mutation is preferably not introduced into a portion of the protein that is likely to be mobile, e.g., at, or within about 1–5 residues of, the N- and C-termini.

Conversely, if there are too many methionine and/or cysteine residues in a polypeptide sequence, over-incorporation of the selenium-containing side chains can lead to the inability of the polypeptide to fold and/or crystallize, as well as to complications in solving the crystal structure. In this case, methionine and/or cysteine mutants are prepared by substituting one or more of these Met and/or Cys residues with another residue. The considerations for these substitutions are the same as those discussed above for mutations that introduce methionine and/or cysteine residues into the polypeptide. Specifically, the Met and/or Cys residues are preferably conservatively substituted with Leu/Ile and Ser, respectively.

As DNA encoding cysteine and methionine mutants can be used in the methods described above for obtaining SeCys and SeMet heavy-atom derivative crystals, the preferred Cys or Met mutant will have one Cys or Met residue for every 140 amino acids.

6.2 Production of Polypeptides

The native and mutated Synagis polypeptides described herein may be chemically synthesized in whole or part using techniques that are well-known in the art (see, e.g., Creighton, 1983, Proteins: Structures and Molecular Principles, W. H. Freeman & Co., NY.). Alternatively, methods that are well known to those skilled in the art can be used to construct expression vectors containing a native or mutated Synagis polypeptide coding sequence and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning: A Laboratory Manual, Cold Spring Harbor Laboratory, NY and Ausubel et al., 1989, Current Protocols in Molecular Biology, Greene Publishing Associates and Wiley Interscience, NY.

A variety of host-expression vector systems may be utilized to express Synagis coding sequences. These include but are not limited to microorganisms such as bacteria transformed with recombinant bacteriophage DNA, plasmid DNA or cosmid DNA expression vectors containing the Synagis coding sequences; yeast transformed with recombinant yeast expression vectors containing the Synagis coding sequences; insect cell systems infected with recombinant virus expression vectors (e.g., baculovirus) containing the Synagis coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the Synagis coding sequences; or animal cell systems. The expression elements of these systems vary in their strength and specificities.

Specifically designed vectors allow the shuttling of DNA between hosts such as bacteria-yeast or bacteria-animal cells. An appropriately constructed expression vector may contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency.

Depending on the host/vector system utilized, any of a number of suitable transcription and translation elements, including constitutive and inducible promoters, may be used in the expression vector. For example, when cloning in bacterial systems, inducible promoters such as the T7 promoter, pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the tyrosine kinase domain DNA, SV40-, BPV- and EBV-based vectors may be used with an appropriate selectable marker.

The expression vector may be introduced into host cells via any one of a number of techniques including but not limited to transformation, transfection, infection, protoplast fusion, and electroporation. The expression vector-containing cells are clonally propagated and individually analyzed to determine whether they produce Synagis. Identification of Synagis expressing host cell clones may be done by several means, including but not limited to immunological reactivity with anti-Synagis antibodies, and the presence of host cell-associated Synagis activity.

Expression of Synagis cDNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes.

To determine the Synagis cDNA sequence(s) that yields optimal levels of Synagis activity and/or Synagis protein, modified Synagis cDNA molecules are constructed. Host cells are transformed with the cDNA molecules and the levels of Synagis RNA and/or protein are measured.

Levels of Synagis protein in host cells are quantitated by a variety of methods such as immunoaffinity and/or ligand affinity techniques, Synagis-specific affinity beads or Synagis-specific antibodies are used to isolate $^{35}$S-methionine labeled or unlabeled Synagis protein. Labeled or unlabeled Synagis protein is analyzed by SDS-PAGE. Unlabeled Synagis is detected by Western blotting, ELISA or RIA employing Synagis-specific antibodies.

Following expression of a Synagis polypeptide in a recombinant host cell, the Synagis polypeptide may be recovered to provide Synagis Fab in active form. Several Synagis purification procedures are available and suitable for use. Recombinant Synagis may be purified from cell lysates or from conditioned culture media, by various combinations of, or individual application of, fractionation, or chromatography steps that are known in the art.

In addition, a recombinant Synagis polypeptide can be separated from other cellular proteins by use of an immunoaffinity column made with monoclonal or polyclonal antibodies specific for full length nascent Synagis or polypeptide fragments thereof.

Alternatively, a Synagis polypeptide may be recovered from a host cell in an unfolded, inactive form, e.g., from inclusion bodies of bacteria. Proteins recovered in this form may be solublized using a denaturant, e.g., guanidinium hydrochloride, and then refolded into an active form using methods known to those skilled in the art, such as dialysis (Rudolph & Lee, FASEB J., 10:49–56).

6.3 Crystallization of Polypeptides and Characterization of Crystal

The native crystalline Synagis Fab from which the atomic structure coordinates of the invention are obtained can be obtained by conventional means and are well-known in the art of protein crystallography, including batch, liquid bridge, dialysis, and vapor diffusion methods (see, e.g., McPherson, 1982, Preparation and Analysis of Protein Crystals, John Wiley, New York; McPherson, 1990, Eur. J. Biochem. 189:1–23.; Weber, 1991, Adv. Protein Chem. 41:1–36.).

Generally, native crystals are grown by dissolving substantially pure Synagis Fab in an aqueous buffer containing a precipitant at a concentration just below that necessary to precipitate the protein. Examples of precipitants include, but are not limited to, polyethylene glycol, ammonium sulfate, 2-methyl-2,4-pentanediol, sodium citrate, sodium chloride, glycerol, isopropanol, lithium sulfate, sodium acetate, sodium formate, potassium sodium tartrate, ethanol, hexanediol, ethylene glycol, dioxane, t-butanol and combinations thereof. Water is removed by controlled evaporation to produce precipitating conditions, which are maintained until crystal growth ceases.

In a preferred embodiment, native crystals are grown by vapor diffusion in hanging drops (McPherson, 1982, Preparation and Analysis of Protein Crystals, John Wiley, New York; McPherson, 1990, Eur. J. Biochem. 189:1–23.). In this method, the polypeptide/precipitant solution is allowed to equilibrate in a closed container with a larger aqueous reservoir having a precipitant concentration optimal for producing crystals. Generally, less than about 25 μL of substantially pure polypeptide solution is mixed with an equal volume of reservoir solution, giving a precipitant concentration about half that required for crystallization. This solution is suspended as a droplet underneath a coverslip, which is sealed onto the top of the reservoir. The sealed container is allowed to stand, usually for about 2–6 weeks, until crystals grow.

For native crystals from which the atomic structure coordinates of the invention are obtained, it has been found that hanging drops or sitting drops containing about 2 μL of Synagis Fab (15 mg/mL in 1 mM Tris, pH 7.6) and 2 μL reservoir solution (15% w/v PEG 4000, 10% 2-propanol, 0.2 M ammonium sulfate and 100 mM Tris, pH 8.5) suspended over 500 μL reservoir solution for about 10 to 14 days at 22° C. provide diffraction quality crystals.

Of course, those having skill in the art will recognize that the above-described crystallization conditions can be varied. Such variations may be used alone or in combination, and include polypeptide solutions containing Synagis Fab concentrations between 3 mg/mL and 10 mg/mL, Tris concentrations between 50 mM and 100 mM, 2-propanol concentrations between 7% and 20%, pH ranges between 6.4 and 11, PEG concentrations of 7% to 10%, PEG molecular weights of 3350 to 8000; and equilibrated with reservoir solutions containing PEG 4000 concentrations between 14% and 20% (w/v), polyethylene glycol molecular weights between 3350 and 8000, 2-propanol concentrations between 7% and 20% (v/v). Other buffer solutions may be used such as sodium cacodylate, HEPES, CAPS, CAPSO, bicine and glycine buffer, so long as the desired pH range is maintained.

Synagis Fab has also been crystallized using ammonium sulfate as the precipitant. These crystals (FIG. 5) are grown from a solution of 15 mg/ml Synagis Fab with equal volume of 1.8 to 2.1 M ammounium sulfate, pH 9.0, equilibrated against 1.8 to 2.1 M ammonium sulfate. The crystals are tetragonal, space group R32 with a=b=92.63 Å, c=179.02 Å, $\alpha=\beta=\gamma=90°$. These Synagis Fab crystals diffract to 3.5 Å or better.

Heavy-atom derivative crystals can be obtained by soaking native crystals in mother liquor containing salts of heavy metal atoms. It has been found that soaking a native crystal in a solution identical to the crystallization solution and additionally containing 1 mM to about 100 mM of a molecule containing the desired heavy atom (Hg, Ur, Pt, Sm, Cd, W, Os, Ir, Pb, ect.) for about 1 hour to several months. One to two day soakings of the crystal in the heavy atom containing solution should be sufficient to provide derivative crystals suitable for use as isomorphous replacements in determining the X-ray crystal structure of the Synagis Fab polypeptide.

Heavy-atom derivative crystals can also be obtained from SeMet and/or SeCys mutants, as described above for native crystals.

Mutant proteins may crystallize under slightly different crystallization conditions than wild-type protein, or under very different crystallization conditions, depending on the nature of the mutation, and its location in the protein. For example, a non-conservative mutation may result in alteration of the hydrophilicity of the mutant, which may in turn make the mutant protein either more soluble or less soluble than the wild-type protein. Typically, if a protein becomes more hydrophilic as a result of a mutation, it will be more soluble than the wild-type protein in an aqueous solution and a higher precipitant concentration will be needed to cause it to crystallize. Conversely, if a protein becomes less hydrophilic as a result of a mutation, it will be less soluble in an aqueous solution and a lower precipitant concentration will be needed to cause it to crystallize. If the mutation happens to be in a region of the protein involved in crystal lattice contacts, crystallization conditions may be affected in more unpredictable ways.

Co-crystals can be obtained by soaking a native crystal in mother liquor containing compound that binds Synagis Fab such as an antigen or an analog thereof, or by co-crystallizing Synagis Fab in the presence of one or more binding compounds.

6.4 Characterization of Crystals

The dimensions of a unit cell of a crystal are defined by six numbers, the lengths of three unique edges, a, b, and c, and three unique angles, $\alpha$, $\beta$, and $\gamma$. The type of unit cell that comprises a crystal is dependent on the values of these variables, as discussed above in Section 3.2.

When a crystal is placed in an X-ray beam, the incident X-rays interact with the electron cloud of the molecules that make up the crystal, resulting in X-ray scatter. The combination of X-ray scatter with the lattice of the crystal gives rise to nonuniformity of the scatter; areas of high intensity are called diffracted X-rays. The angle at which diffracted beams emerge from the crystal can be computed by treating diffraction as if it were reflection from sets of equivalent, parallel planes of atoms in a crystal (Bragg's Law). The most obvious sets of planes in a crystal lattice are those that are parallel to the faces of the unit cell. These and other sets of planes can be drawn through the lattice points. Each set of planes is identified by three indices, hkl. The h index gives the number of parts into which the a edge of the unit cell is cut, the k index gives the number of parts into which the b edge of the unit cell is cut, and the l index gives the number of parts into which the c edge of the unit cell is cut by the set of hkl planes. Thus, for example, the 235 planes cut the a edge of each unit cell into halves, the b edge of each unit cell into thirds, and the c edge of each unit cell into fifths. Planes that are parallel to the bc face of the unit cell are the 100 planes; planes that are parallel to the ac face of the unit cell are the 010 planes; and planes that are parallel to the ab face of the unit cell are the 001 planes.

When a detector is placed in the path of the diffracted X-rays, in effect cutting into the sphere of diffraction, a series of spots, or reflections, are recorded to produce a "still" diffraction pattern. Each reflection is the result of X-rays reflecting off one set of parallel planes, and is characterized by an intensity, which is related to the distribution of molecules in the unit cell, and hkl indices, which correspond to the parallel planes from which the beam producing that spot was reflected. If the crystal is rotated about an axis perpendicular to the X-ray beam, a large number of reflections is recorded on the detector, resulting in a diffraction pattern as shown in FIG. 2.

The unit cell dimensions and space group of a crystal can be determined from its diffraction pattern. First, the spacing of reflections is inversely proportional to the lengths of the edges of the unit cell. Therefore, if a diffraction pattern is recorded when the X-ray beam is perpendicular to a face of the unit cell, two of the unit cell dimensions may be deduced from the spacing of the reflections in the x and y directions of the detector, the crystal-to-detector distance, and the wavelength of the X-rays. Those of skill in the art will appreciate that, in order to obtain all three unit cell dimensions, the crystal must be rotated such that the X-ray beam is perpendicular to another face of the unit cell. Second, the angles of a unit cell can be determined by the angles between lines of spots on the diffraction pattern. Third, the absence of certain reflections and the repetitive nature of the diffraction pattern, which may be evident by visual inspection, indicate the internal symmetry, or space group, of the crystal. Therefore, a crystal may be characterized by its unit cell and space group, as well as by its diffraction pattern. Because the lengths of the unit cell axes in a protein crystal are large and the concomitant reciprocal cell lengths are very short, the unit cell dimensions and space group of a protein crystal can be determined from one reciprocal space photograph if the crystal is rotated through approximately one degree. A digital representative of such a photograph is shown in FIG. 2 for the orthorhombic Synagis Fab crystal.

Once the dimensions of the unit cell are determined, the likely number of polypeptides in the asymmetric unit can be deduced from the size of the polypeptide, the density of the average protein, and the typical solvent content of a protein crystal, which is usually in the range of 30–70% of the unit cell volume (Matthews, 1968. J. Mol. Biol. 33:491–497).

The Synagis Fab crystals of the present invention are generally characterized by a diffraction pattern, as shown in FIG. 2. The crystals are further characterized by unit cell dimensions and space group symmetry information obtained from the diffraction patterns, as described above. The crystals, which may be native crystals, heavy-atom derivative crystals or co-crystals, have an a orthorhombic unit cell (i.e., unit cells wherein a≠b≠c; and $\alpha=\beta=\gamma=90°$) and space group symmetry $P2_12_12_1$.

In one form of crystalline Synagis Fab, the unit cell has dimensions of a=77.36+/−0.2 Å, b=103.92+/−0.2 Å, c=68.87+/−0.2 Å. There is one Synagis Fab complex in the asymmetric unit.

6.5 Collection of Data and Determination of Structure Solutions

The diffraction pattern is related to the three-dimensional shape of the molecule by a Fourier transform. The process of determining the solution is in essence a re-focusing of the diffracted X-rays to produce a three-dimensional image of the molecule in the crystal. Since re-focusing of X-rays cannot be done with a lens at this time, it is done via mathematical operations.

The sphere of diffraction has symmetry that depends on the internal symmetry of the crystal, which means that certain orientations of the crystal will produce the same set of reflections. Thus, a crystal with high symmetry has a more repetitive diffraction pattern, and there are fewer unique reflections that need to be recorded in order to have a complete representation of the diffraction. The goal of data collection, a dataset, is a set of consistently measured, indexed intensities for as many reflections as possible. A complete dataset is collected if at least 80%, preferably at least 90%, most preferably at least 95% of unique reflections are recorded. In one embodiment, a complete dataset is collected using one crystal. In another embodiment, a complete dataset is collected using more than one crystal of the same type.

Sources of X-rays include, but are not limited to, a rotating anode X-ray generator such as a Rigaku RU-200 or a beamline at a synchrotron light source, such as the Advanced Photon Source at Argonne National Laboratory. Suitable detectors for recording diffraction patterns include, but are not limited to, X-ray sensitive film, multiwire area detectors, image plates coated with phosphorus, and CCD cameras. Typically, the detector and the X-ray beam remain stationary, so that, in order to record diffraction from different parts of the crystal's sphere of diffraction, the crystal itself is moved via an automated system of moveable circles called a goniostat.

One of the biggest problems in data collection, particularly from macromolecular crystals having a high solvent content, is the rapid degradation of the crystal in the X-ray beam. In order to slow the degradation, data is often collected from a crystal at liquid nitrogen temperatures. In order for a crystal to survive the initial exposure to liquid nitrogen, the formation of ice within the crystal must be prevented by the use of a cryoprotectant. Suitable cryoprotectants include, but are not limited to, low molecular weight polyethylene glycols, ethylene glycol, sucrose, glycerol, xylitol, and combinations thereof. Crystals may be soaked in a solution comprising the one or more cryoprotectants prior to exposure to liquid nitrogen, or the one or more cryoprotectants may be added to the crystallization solution. Data collection at liquid nitrogen temperatures may allow the collection of an entire dataset from one crystal.

Once a dataset is collected, the information is used to determine the three-dimensional structure of the molecule in the crystal. However, this cannot be done from a single measurement of reflection intensities because certain information, known as phase information, is lost between the three-dimensional shape of the molecule and its Fourier transform, the diffraction pattern. This phase information must be acquired by methods described below in order to perform a Fourier transform on the diffraction pattern to obtain the three-dimensional structure of the molecule in the crystal. It is the determination of phase information that in effect refocuses X-rays to produce the image of the molecule.

One method of obtaining phase information is by isomorphous replacement, in which heavy-atom derivative crystals are used. In this method, the positions of heavy atoms bound to the molecules in the heavy-atom derivative crystal are determined, and this information is then used to obtain the phase information necessary to elucidate the three-dimensional structure of a native crystal. (Blundel et al., 1976, Protein Crystallography, Academic Press).

Another method of obtaining phase information is by molecular replacement, which is a method of calculating initial phases for a new crystal of a polypeptide whose structure coordinates are unknown by orienting and positioning a polypeptide whose structure coordinates are known, and believed to be similar to the polypeptide of unknown structure, within the unit cell of the new crystal so as to best account for the observed diffraction pattern of the new crystal. Phases are then calculated from the oriented and positioned polypeptide and combined with observed amplitudes to provide an approximate Fourier synthesis of the structure of the molecules comprising the new crystal. (Lattman, 1985, Methods in Enzymology 115:55–77; Rossmann, 1972, "The Molecular Replacement Method," Int. Sci. Rev. Ser. No. 13, Gordon & Breach, New York; Brünger et al., 1991, Acta Crystallogr A. 47:195–204).

A third method of phase determination is multi-wavelength anomalous diffraction or MAD. In this method, X-ray diffraction data are collected at several different wavelengths from a single crystal containing at least one heavy atom with absorption edges near the energy of incoming X-ray radiation. The resonance between X-rays and electron orbitals leads to differences in X-ray scattering that permits the locations of the heavy atoms to be identified, which in turn provides phase information for a crystal of a polypeptide. A detailed discussion of MAD analysis can be found in Hendrickson, 1985, Trans. Am. Crystallogr. Assoc., 21:11; Hendrickson et al., 1990, EMBO J. 9:1665; and Hendrickson, 1991, Science 4:91.

A fourth method of determining phase information is single wavelength anomalous dispersion or SAD. In this technique, X-ray diffraction data are collected at a single wavelength from a single native or heavy-atom derivative crystal, and phase information is extracted using anomalous scattering information from atoms such as sulfur or chlorine in the native crystal or from the heavy atoms in the heavy-atom derivative crystal. The wavelength of X-rays used to collect data for this phasing technique need not be close to the absorption edge of the anomalous scatterer. A detailed discussion of SAD analysis can be found in Brodersen et al., 2000, Acta Cryst., D56:431–441.

A fifth method of determining phase information is single isomorphous replacement with anomalous scattering or SIRAS. This technique combines isomorphous replacement and anomalous scattering techniques to provide phase information for a crystal of a polypeptide. X-ray diffraction data are collected at a single wavelength, usually from a single heavy-atom derivative crystal. Phase information obtained only from the location of the heavy atoms in a single heavy-atom derivative crystal leads to an ambiguity in the phase angle, which is resolved using anomalous scattering from the heavy atoms. Phase information is therefore extracted from both the location of the heavy atoms and from anomalous scattering of the heavy atoms. A detailed discussion of SIRAS analysis can be found in North, 1965, Acta Cryst. 18:212–216; Matthews, 1966, Acta Cryst. 20:82–86.

Once phase information is obtained, it is combined with the diffraction data to produce an electron density map, an image of the electron clouds that surround the atoms of the molecule(s) in the unit cell. The higher the resolution of the data, the more distinguishable are the features of the electron density map, e.g., amino acid side chains and the positions of carbonyl oxygen atoms in the peptide backbones, because atoms that are closer together are resolvable. A model of the macromolecule is then built into the electron density map with the aid of a computer, using as a guide all available information, such as the polypeptide sequence and the established rules of molecular structure and stereochemistry. Interpreting the electron density map is a process of finding the chemically realistic conformation that fits the map precisely.

After a model is generated, a structure is refined. Refinement is the process of minimizing the function $$R-\text{factor} = \frac{\sum_{(h,k,l)} ||F_{obs}(h,k,l)|-|F_{calc}(h,k,l)||}{\sum_{(h,k,l)} |F_{obs}(h,k,l)|}$$

which is an average of the differences between observed structure factors (square-root of intensity) and calculated structure factors which are a function of the position, temperature factor and occupancy of each non-hydrogen atom in the model. This usually involves alternate cycles of real space refinement, i.e., calculation of electron density maps and model building, and reciprocal space refinement, i.e., computational attempts to improve the agreement between the original intensity data and intensity data generated from each successive model. Refinement ends when the R-factor converges on a minimum wherein the model fits the electron density map and is stereochemically and conformationally reasonable. During refinement, ordered solvent molecules are added to the structure.

6.6.1 Structures of Synagis Fab

The present invention provides, for the first time, the high-resolution three-dimensional structures and atomic structure coordinates of crystalline Synagis Fab as determined by X-ray crystallography. The specific methods used to obtain the structure coordinates are provided in the examples, infra. The atomic structure coordinates of crystalline Synagis Fab, obtained from the $P2_12_12_1$ form of the crystal to 1.8 Å resolution, are listed in Table 2.

Those having skill in the art will recognize that atomic structure coordinates as determined by X-ray crystallography are not without error. Thus, it is to be understood that any set of structure coordinates obtained for crystals of Synagis Fab, whether native crystals, heavy-atom derivative crystals or co-crystals, that have a root mean square deviation ("r.m.s.d.") of less than or equal to about 2 Å when superimposed, using backbone atoms (N, Cα, C and O), on the structure coordinates listed in Table 2 are considered to be identical with the structure coordinates listed in the Table when at least about 50% to 100% of the backbone atoms of Synagis Fab are included in the superposition.

All IgG-type antibodies have a common structure of two identical light chains of about 25 kilodaltons and two identical heavy chains of about 50 kilodaltons. Each light chain is attached to a heavy chain by disulfide bridges and the two heavy chains are likewise attached by disulfide bridges (FIG. 6). Both the light and heavy chains contain a series of repeating, homologous units, each about 110 amino acids residues in length and a characteristic molecular weight of 12 kDa. Each of these homologous units or domains fold independently into a common structural motif call an immunoglobulin fold (FIG. 7A; FIG. 7B). The amino acid sequences of the amino terminal domains of the heavy and light chains are called variable regions ($V_H$ and $V_L$) due to sequence diversity between antibodies at the variable domain CDRs. The remaining domains, $C_L$ of the light chain and $C_{H1}$, $C_{H2}$ and $C_{H3}$ of the heavy chain differ less among antibodies and are thus classified as constant regions.

In IgG-type antibodies light chains fall into one of two so-called isotypes, κ and λ. Each member of a light-chain isotype shares amino acid sequence identity of the carboxy terminus with all other members of that isotype. As for IgG light chains, IgG heavy chain polypeptides contain a series of segments, each approximately 110 amino acid residues in length. The segments are likewise homologous to each other and all fold into characteristic 12 kilodalton domains. As in the light chains, the amino terminal variable domain ($V_H$) displays the greatest sequence variation among heavy chains, and the most variable residues are concentrated into three stretches of amino acids called CDR1, CDR2 and CDR3.

The association between light and heavy chains involves both covalent and non-covalent interactions. Covalent interactions are in the form of disulfide bonds between the carboxy terminus of the light chain and the $C_{H1}$ domain of the heavy chain. Non-covalent interactions arise primarily from hydrophobic interactions between $V_L$ and $V_H$ domains and between the $C_L$ and $C_{H1}$ domains.

Immunoglobulin V and C domains consists of sequence discontinuous antiparallel β-strands forming two β-pleated sheets linked by an intrachain disulfide bond. In the V domains, nine such β-strands form the β-sheets (FIG. 7A) while in the C domains seven strands form the β-sheets (FIG. 7B). The β strands of the V domains, comprising the 'framework' regions support the hypervariable loops or complementary determining regions that form the antigen binding site. As the β-strands are tightly packed in the formation of the β-sheets through hydrogen bonding to main-chain atoms and by side chain interactions, non-conservative mutants of the framework amino acids may be deleterious to the proper formation of these so-called "immunoglobulin folds" (Poljak et al., 1973, Proc. Natl. Acad. Sci. USA 70:3305–3310). Additionally, the quaternary structure of immunoglobulins requires the association of the domains of the heavy and light immunoglobulin chains. As such, amino acids involved in the associations of the β-strands forming the β-pleated sheets and of the β-pleated sheets of individual domains in the formation of immunoglobulin quaternary structure are assumed to be strongly conserved, or replaceable by closely conserved amino acids. The solvent exposed amino acids on the exterior of the $V_L$-$V_H$ complex and $C_L$-$C_{H1}$ complex, are assumed to be subject to less restriction in the substitution of amino acids.

The antigen binding fragment Fab, composed of the four domains $V_H$, $V_L$, $C_{H1}$ and $C_L$, has been the subject of numerous X-ray crystallographic structure determinations (reviewed in Padlan, 1994, Mol. Immunol. 31:169–217). Each immunoglobulin domain is paired with a second (i.e. $V_H$-$V_L$, $C_{H1}$-$C_L$) with the components of each of these pairs related by a pseudo two-fold rotation axis (FIG. 4). Moreover, each antibody domain is joined to a subsequent domain (i.e. $V_H$-$C_{H1}$, $V_L$-$C_L$) by a short segment of polypeptide sometimes refered to as the "switch". This sequence of extended polypeptide permits intersegmental flexiblity of the Fab and, as such, allows for differing relative orientations of the $V_H$, $V_L$ (i.e. the Fv fragment) and the $C_{H1}$ and $C_L$ domains. The relative disposition of the variable and constant domains (the so-called elbow angle) of an Fab is defined as the angle between the pseudo two-fold rotation axes of the Fv and $C_{H1}$-$C_L$ domains. Thus, an elbow angle of 180° specifies that the pseudo two-fold axes of the Fv and $C_{H1}$-$C_L$ domains are colinear and angles greater or less than 180° specifly an Fab which is asymmetric.

The structure of the Fv fragment consists of the two immunoglobulin variable domains ($V_H$ and $V_L$) which, as stated previously, are related by a pseudo two-fold rotation axis. Six hypervariable segments, or complementarity-determining-regions (CDRs), three each from the $V_H$ (H1, H2 and H3; FIG. 4) and $V_L$ (L1, L2 and L3; FIG. 4) domains, are formed from loops which connect beta strands in the immunoglobulin variable domains. The conformation of the CDR loops are generally determined by the length of the loop, the distance between the invariant (framework) residues which anchor the loop and the primary sequence of amino acids. By comparing the sequences and lengths of CDR loops of known structure, Chothia et al., 1989, Nature 342:877–833 discovered that each CDR loop, with the exception of the third hypervariable loop of the heavy chain (CDR H3), generally comformed to one of a few structural posibilities (i.e. canonical models). Thus, while there may be an extremely large repertoire of primary sequences of hypervariable loops, there appears to be some limit to the number of tertiary structures into which the backbone polypeptide chain at each loop can fold. This limits the overall structural design but still provides for structural diversity at the level of the amino acid side chain. As yet, no canonical models have been suggested for CDR H3. Since the specificity of antigen binding is determined almost exclusively by the topology of the CDRs, the structure of the CDRs and the interaction of the CDR with antigen has been the primary focus in the study of antibody structure.

The hypervariable loops, or CDRs, L1, L2, L3, H1 and H2 from immunoglobulins have been noted to usually have one of a small number of main chain conformations or canonical structures. The conformation of a particular canonical structure is determined by the length of the loop and residues present at key sites that interact with the loop. The conformation of CDR H3, however, does not appear to be limited based on the length of the loop as are the other CDRs.

The canonical classification of the CDRs for the Synagis Fab crystal structure were assigned by comparing loop lengths, sequences and root-mean-square deviations to example canonical loops. Tables 3 and 4 detail the canonical conformations for the free Synagis Fab crystal structure and selected representative CDRs for each canonical loop. The average main chain atom deviations for each of the defined canonical structures are significantly less than 1.0 Å and unambiguously assign the 5 CDRs to canonical classes. It is interesting to note that CDR L1 is a member of the type 1 canonical structure which is absent in the human $V_L$ repertoire. Superpositioning of the Synagis CDRs with representative canonical loops as shown in FIGS. 8 & 9.

6.7 Structure Coordinates

The atomic structure coordinates can be used in molecular modeling and design, as described more fully below. The present invention encompasses the structure coordinates and other information, e.g., amino acid sequence, connectivity tables, vector-based representations, temperature factors, etc., used to generate the three-dimensional structure of the polypeptide for use in the software programs described below and other software programs.

The invention encompasses machine readable media embedded with the three-dimensional structure of the model described herein, or with portions thereof. As used herein, "machine readable medium" refers to any medium that can be read and accessed directly by a computer or scanner. Such media include, but are not limited to: magnetic storage media, such as floppy discs, hard disc storage medium and magnetic tape; optical storage media such as optical discs or CD-ROM; electrical storage media such as RAM or ROM; and hybrids of these categories such as magnetic/optical storage media. Such media further include paper on which is recorded a representation of the atomic structure coordinates, e.g., Cartesian coordinates, that can be read by a scanning device and converted into a three-dimensional structure with an OCR.

A variety of data storage structures are available to a skilled artisan for creating a computer readable medium having recorded thereon the atomic structure coordinates of the invention or portions thereof and/or X-ray diffraction data. The choice of the data storage structure will generally be based on the means chosen to access the stored information. In addition, a variety of data processor programs and formats can be used to store the sequence and X-ray data information on a computer readable medium. Such formats include, but are not limited to, Protein Data Bank ("PDB") format (Research Collaboratory for Structural Bioinformatics; http://www.rcsb.org/pdb/docs/format/pdbguide2.2/guide2.2_frame.html); Cambridge Crystallographic Data Centre format (http://www.ccdc.cam.ac.uk/support/csd_doc/volume3/z323.html); Structure-data ("SD") file format (MDL Information Systems, Inc.; Dalby et al., 1992, J. Chem. Inf. Comp. Sci. 32:244–255), and line-notation, e.g., as used in SMILES (Weininger, 1988, J. Chem. Inf. Comp. Sci. 28:31–36). Methods of converting between various formats read by different computer software will be readily apparent to those of skill in the art, e.g., BABEL (v. 1.06, Walters & Stahl, ©1992, 1993, 1994; http://www.brunel.ac.uk/departments/chem/babel.htm.) All format representations of the polypeptide coordinates described herein, or portions thereof, are contemplated by the present invention. By providing computer readable medium having stored thereon the atomic coordinates of the invention, one of skill in the art can routinely access the atomic coordinates of the invention, or portions thereof, and related information for use in modeling and design programs, described in detail below.

While Cartesian coordinates are important and convenient representations of the three-dimensional structure of a polypeptide, those of skill in the art will readily recognize that other representations of the structure are also useful. Therefore, the three-dimensional structure of a polypeptide, as discussed herein, includes not only the Cartesian coordinate representation, but also all alternative representations of the three-dimensional distribution of atoms. For example, atomic coordinates may be represented as a Z-matrix, wherein a first atom of the protein is chosen, a second atom is placed at a defined distance from the first atom, a third atom is placed at a defined distance from the second atom so that it makes a defined angle with the first atom. Each subsequent atom is placed at a defined distance from a previously placed atom with a specified angle with respect to the third atom, and at a specified torsion angle with respect to a fourth atom. Atomic coordinates may also be represented as a Patterson function, wherein all interatomic vectors are drawn and are then placed with their tails at the origin. This representation is particularly useful for locating heavy atoms in a unit cell. In addition, atomic coordinates may be represented as a series of vectors having magnitude and direction and drawn from a chosen origin to each atom in the polypeptide structure. Furthermore, the positions of atoms in a three-dimensional structure may be represented as fractions of the unit cell (fractional coordinates), or in spherical polar coordinates.

Additional information, such as thermal parameters, which measure the motion of each atom in the structure, chain identifiers, which identify the particular chain of a multi-chain protein in which an atom is located, and connectivity information, which indicates to which atoms a particular atom is bonded, is also useful for representing a three-dimensional molecular structure.

6.8 Uses of the Atomic Structure Coordinates

Structure information, typically in the form of the atomic structure coordinates, can be used in a variety of computational or computer-based methods to, for example, design, screen for and/or identify compounds that bind crystallized Synagis Fab or a portion or fragment thereof, or to intelligently design mutants that have altered biological properties.

In one embodiment, the crystals and structure coordinates obtained therefrom are useful for identifying and/or designing compounds that bind Synagis Fab as an approach towards developing new therapeutic agents. For example, a high resolution X-ray structure will often show the locations of ordered solvent molecules around the protein, and in particular at or near putative binding sites on the protein. This information can then be used to design molecules that bind these sites, the compounds synthesized and tested for binding in biological assays. Travis, 1993, Science 262:1374.

In another embodiment, the structure is probed with a plurality of molecules to determine their ability to bind to the Synagis Fab at various sites. Such compounds can be used as targets or leads in medicinal chemistry efforts to identify, for example, inhibitors of potential therapeutic importance.

In still another embodiment, compounds that can isomerize to short-lived reaction intermediates in the chemical reaction of a Synagis Fab-binding compound with Synagis Fab can be developed. Thus, the time-dependent analysis of structural changes in Synagis Fab during its interaction with other molecules is enabled. The reaction intermediates of Synagis Fab can also be deduced from the reaction product in co-complex with Synagis Fab. Such information is useful to design improved analogues of known Synagis Fab inhibitors or to design novel classes of inhibitors based on the reaction intermediates of Synagis Fab and Synagis Fab-inhibitor co-complexes. This provides a novel route for designing Synagis Fab inhibitors with both high specificity and stability.

In yet another embodiment, the structure can be used to computationally screen small molecule data bases for chemical entities or compounds that can bind in whole, or in part, to Synagis Fab. In this screening, the quality of fit of such entities or compounds to the binding site may be judged either by shape complementarity or by estimated interaction energy. Meng et al., 1992, J. Comp. Chem. 13:505–524.

The design of compounds that bind to or inhibit Synagis Fab according to this invention generally involves consideration of two factors. First, the compound must be capable of physically and structurally associating with Synagis Fab. This association can be covalent or non-covalent. For example, covalent interactions may be important for designing irreversible or suicide inhibitors of a protein. Non-covalent molecular interactions important in the association of Synagis Fab with its substrate include hydrogen bonding, ionic interactions and van der Waals and hydrophobic interactions. Second, the compound must be able to assume a conformation that allows it to associate with Synagis Fab. Although certain portions of the compound will not directly participate in this association with Synagis Fab, those portions may still influence the overall conformation of the molecule. This, in turn, may have a significant impact on potency. Such conformational requirements include the overall three-dimensional structure and orientation of the chemical group or compound in relation to all or a portion of the binding site, or the spacing between functional groups of a compound comprising several chemical groups that directly interact with Synagis Fab.

The potential inhibitory or binding effect of a chemical compound on Synagis Fab may be analyzed prior to its actual synthesis and testing by the use of computer modeling techniques. If the theoretical structure of the given compound suggests insufficient interaction and association between it and Synagis Fab, synthesis and testing of the compound is unnecessary. However, if computer modeling indicates a strong interaction, the molecule may then be synthesized and tested for its ability to bind to Synagis Fab and inhibit its activity. In this manner, synthesis of ineffective compounds may be avoided.

An inhibitory or other binding compound of Synagis Fab may be computationally evaluated and designed by means of a series of steps in which chemical groups or fragments are screened and selected for their ability to associate with the individual binding pockets or other areas of Synagis Fab. One skilled in the art may use one of several methods to screen chemical groups or fragments for their ability to associate with Synagis Fab. This process may begin by visual inspection of, for example, the active site on the computer screen based on the Synagis Fab coordinates. Selected fragments or chemical groups may then be positioned in a variety of orientations, or docked, within an individual binding pocket of Synagis Fab as defined supra. Docking may be accomplished using software such as QUANTA and SYBYL, followed by energy minimization and molecular dynamics with standard molecular mechanics forcefields, such as CHARMM and AMBER.

Specialized computer programs may also assist in the process of selecting fragments or chemical groups. These include:

1. GRID (Goodford, 1985, J. Med. Chem. 28:849–857). GRID is available from Oxford University, Oxford, UK;

2. MCSS (Miranker & Karplus, 1991, Proteins: Structure, Function and Genetics 11:29–34). MCSS is available from Molecular Simulations, Burlington, Mass.;

3. AUTODOCK (Goodsell & Olsen, 1990, Proteins: Structure, Function, and Genetics 8:195–202). AUTODOCK is available from Scripps Research Institute, La Jolla, Calif.; and 4. DOCK (Kuntz et al., 1982, J. Mol. Biol. 161:269–288). DOCK is available from University of California, San Francisco, Calif.

Once suitable chemical groups or fragments have been selected, they can be assembled into a single compound or inhibitor. Assembly may proceed by visual inspection of the relationship of the fragments to each other in the three-dimensional image displayed on a computer screen in relation to the structure coordinates of Synagis Fab. This would be followed by manual model building using software such as QUANTA or SYBYL.

Useful programs to aid one of skill in the art in connecting the individual chemical groups or fragments include:

1. CAVEAT (Bartlett et al., 1989, 'CAVEAT: A Program to Facilitate the Structure-Derived Design of Biologically Active Molecules'. In Molecular Recognition in Chemical and Biological Problems', Special Pub., Royal Chem. Soc. 78:182–196). CAVEAT is available from the University of California, Berkeley, Calif.;

2. 3D Database systems such as MACCS-3D (MDL Information Systems, San Leandro, Calif.). This area is reviewed in Martin, 1992, J. Med. Chem. 35:2145–2154); and 3. HOOK (available from Molecular Simulations, Burlington, Mass.).

Instead of proceeding to build a Synagis Fab inhibitor in a step-wise fashion one fragment or chemical group at a time, as described above, Synagis Fab binding compounds may be designed as a whole or 'de novo' using either an empty active site or optionally including some portion(s) of a known inhibitor(s). These methods include:

1. LUDI (Bohm, 1992, J. Comp. Aid. Molec. Design 6:61–78). LUDI is available from Molecular Simulations, Inc., San Diego, Calif.;

2. LEGEND (Nishibata & Itai, 1991, Tetrahedron 47:8985). LEGEND is available from Molecular Simulations, Burlington, Mass.; and 3. LeapFrog (available from Tripos, Inc., St. Louis, Mo.).

Other molecular modeling techniques may also be employed in accordance with this invention. See, e.g., Cohen et al, 1990, J. Med. Chem. 33:883–894. See also, Navia & Murcko, 1992, Current Opinions in Structural Biology 2:202–210.

Once a compound has been designed or selected by the above methods, the efficiency with which that compound may bind to Synagis Fab may be tested and optimized by computational evaluation. For example, a compound that has been designed or selected to function as a Synagis Fab-inhibitor must also preferably occupy a volume not overlapping the volume occupied by the active site residues when the native substrate is bound. An effective Synagis Fab inhibitor must preferably demonstrate a relatively small difference in energy between its bound and free states (i.e., it must have a small deformation energy of binding). Thus, the most efficient Synagis Fab inhibitors should preferably be designed with a deformation energy of binding of not greater than about 10 kcal/mol, preferably, not greater than 7 kcal/mol. Synagis Fab inhibitors may interact with the protein in more than one conformation that is similar in overall binding energy. In those cases, the deformation energy of binding is taken to be the difference between the energy of the free compound and the average energy of the conformations observed when the inhibitor binds to the enzyme.

A compound selected or designed for binding to Synagis Fab may be further computationally optimized so that in its bound state it would preferably lack repulsive electrostatic interaction with the target protein. Such non-complementary electrostatic interactions include repulsive charge-charge, dipole-dipole and charge-dipole interactions. Specifically, the sum of all electrostatic interactions between the inhibitor and the protein when the inhibitor is bound to it preferably make a neutral or favorable contribution to the enthalpy of binding.

Specific computer software is available in the art to evaluate compound deformation energy and electrostatic interaction. Examples of programs designed for such uses include: Gaussian 92, revision C (Frisch, Gaussian, Inc., Pittsburgh, Pa. ©1992); AMBER, version 4.0 (Kollman, University of California at San Francisco, ©1994); QUANTA/CHARMM (Molecular Simulations, Inc., Burlington, Mass., ©1994); and Insight II/Discover (Biosym Technologies Inc., San Diego, Calif., ©1994). These programs may be implemented, for instance, using a computer workstation, as are well-known in the art. Other hardware systems and software packages will be known to those skilled in the art.

Once a Synagis Fab-binding compound has been optimally selected or designed, as described above, substitutions may then be made in some of its atoms or chemical groups in order to improve or modify its binding properties. Generally, initial substitutions are conservative, i.e., the replacement group will have approximately the same size, shape, hydrophobicity and charge as the original group. One of skill in the art will understand that substitutions known in the art to alter conformation should be avoided. Such altered chemical compounds may then be analyzed for efficiency of binding to Synagis Fab by the same computer methods described in detail above.

Because Synagis Fab may crystallize in more than one crystal form, the structure coordinates of Synagis Fab, or portions thereof, are particularly useful to solve the structure of those other crystal forms of Synagis or other Synagis fragments. They may also be used to solve the structure of Synagis mutants, Synagis co-complexes, fragments thereof, or of the crystalline form of any other protein that shares significant amino acid sequence homology with a structural domain of Synagis Fab.

One method that may be employed for this purpose is molecular replacement. In this method, the unknown crystal structure, whether it is another crystal form of Synagis Fab, a Synagis Fab mutant, or a Synagis Fab co-complex, or the crystal of some other protein with significant amino acid sequence homology to any functional domain of Synagis Fab, may be determined using phase information from the Synagis Fab structure coordinates. The phase information may also be used to determine the crystal structure of full-length Synagis, fragments of Synagis other than Synagis Fab, and mutants or co-complexes thereof, and other proteins with significant homology to Synagis or fragments thereof. This method will provide an accurate three-dimensional structure for the unknown protein in the new crystal more quickly and efficiently than attempting to determine such information ab initio. In addition, in accordance with this invention, Synagis Fab mutants may be crystallized in co-complex with known Synagis Fab inhibitors. The crystal structures of a series of such complexes may then be solved by molecular replacement and compared with that of wild-type Synagis Fab. Potential sites for modification within the various binding sites of the protein may thus be identified. This information provides an additional tool for determining the most efficient binding interactions, for example, increased hydrophobic interactions, between Synagis Fab and a chemical group or compound.

If an unknown crystal form has the same space group as and similar cell dimensions to the known Synagis Fab crystal form, then the phases derived from the known crystal form can be directly applied to the unknown crystal form, and in turn, an electron density map for the unknown crystal form can be calculated. Difference electron density maps can then be used to examine the differences between the unknown crystal form and the known crystal form. A difference electron density map is a subtraction of one electron density map, e.g., that derived from the known crystal form, from another electron density map, e.g., that derived from the unknown crystal form. Therefore, all similar features of the two electron density maps are eliminated in the subtraction and only the differences between the two structures remain. For example, if the unknown crystal form is of a Synagis Fab co-complex, then a difference electron density map between this map and the map derived from the native, uncomplexed crystal will ideally show only the electron density of the ligand. Similarly, if amino acid side chains have different conformations in the two crystal forms, then those differences will be highlighted by peaks (positive electron density) and valleys (negative electron density) in the difference electron density map, making the differences between the two crystal forms easy to detect. However, if the space groups and/or cell dimensions of the two crystal forms are different, then this approach will not work and molecular replacement must be used in order to derive phases for the unknown crystal form.

All of the complexes referred to above may be studied using well-known X-ray diffraction techniques and may be refined versus 50 Å to 1.5 Å or greater resolution X-ray data to an R value of about 0.20 or less using computer software, such as X-PLOR (Yale University, (c) 1992, distributed by Molecular Simulations, Inc.). See, e.g., Blundel et al., 1976, Protein Crystallography, Academic Press.; Methods in Enzymology, vol. 114 & 115, Wyckoff et al., eds., Academic Press, 1985. This information may thus be used to optimize known classes of Synagis Fab inhibitors, and more importantly, to design and synthesize novel classes of Synagis Fab inhibitors.

The structure coordinates of Synagis Fab mutants will also facilitate the identification of related proteins or enzymes analogous to Synagis Fab in function, structure or both, thereby further leading to novel therapeutic modes for treating or preventing Synagis Fab mediated diseases.

Subsets of the atomic structure coordinates can be used in any of the above methods. Particularly useful subsets of the coordinates include, but are not limited to, coordinates of single domains, coordinates of residues lining an antigen binding site, coordinates of residues of a CDR, coordinates of residues that participate in important protein-protein contacts at an interface, and Ca coordinates. For example, the coordinates of a fragment of an antibody that contains the antigen binding site may be used to design inhibitors that bind to that site, even though the antibody is fully described by a larger set of atomic coordinates. Therefore, a set of atomic coordinates that define the entire polypeptide chain, although useful for many applications, do not necessarily need to be used for the methods described herein.

7. EXAMPLE

Preparation of Crystals of Synagis Fab

The subsections below describe the production of a polypeptide containing the Synagis Fab, and the preparation and characterization of diffraction quality crystals, heavy-atom derivative crystals.

7.1 Production and Purification of Synagis Fab

Synagis IgG was prepared as described in U.S. Pat. No. 5,824,307, which is hereby incorporated by reference in its entirety.

The Synagis Fab fragment was produced by papain digestion of Synagis IgG. In brief, 20 mg of IgG was digested in a solution of PBS buffer, 1 mM EDTA, 1 mM b-mercaptoethanol and 0.2 mg papain. Digestion was carried out for 45 minutes at 37° C. The resultant digested antibody was concentrated to 250 ul in 50 mM Tris buffer, ph 8.5. This solution was applied to a Q-2 anion exchange column (BioRad) with a flow rate of 1 ml/min. The Fab fragment eluted in the void volume. The Fab preparation was further purified by size exclusion chromatography using a Pharmacia S-200 SEC column and PBS buffer flowing at a rate of 0.5 ml/min. Pure Fab eluted as a sharp peak at the appropriate molecular weight. Finally, the Fab preparation was concentrated and buffer-exchanged with Centricon P-20 centrifugal concentrators (Spectrum).

The final concentration of Synagis Fab measured at 280 nm was 15 mg/mL in approximately 1 mM Tris, pH 7.6.

7.1.1 Preparation of Synagis Fab Native Crystals

Crystals were grown at room temperature by the hanging drop vapor diffusion method using Linbro multi-well plates. Drops containing 2 µL of the protein solution and 2 µL of precipitant buffer were equilibrated against 500 µL precipitant buffer. The precipitant buffer was 15% PEG 4000, 10% 2-propanol, 0.2 M ammonium sulfate, 0.1 M Tris, pH 8.5. Crystals shaped as long rectangular prisms appeared after 4 days and grew to a maximum size of 0.8×0.1×0.1 mm in 10 to 14 days.

7.2 Analysis and Characterization of Synagis Fab Crystals

7.2.1 Diffraction Data Collection

X-ray diffraction data were collected using graphite-monochromated Cu Kα x-rays from a Siemens rotating anode source. Intensities were measured in 1° oscillation steps using a MAR 345 imaging plate and processed with the Denzo/Scalepack suite of programs. A single crystal was used to collect the diffraction data. The crystal was cryo-protected in a solution of the crystallization buffer with the addition of glycerol. The crystal was mounted in a nylon loop and flash frozen to 100 K. Data indicate that the crystals are orthorhombic, space group $P2^1 2_1 2_1$ and cell parameters a=77.361, b=103.925, c=68.866. Data extend to 1.8 Å, the limit available by detector geometry at the crystal to detector distance of 12 cm. Statistics for the data collection and data reduction are listed in Table 5.

7.2.2 Structure Determination

Estimation of solvent content suggest one Fab molecule per asymmetric unit in the crystal. A preliminary model for the Synagis Fab structure was determined by molecular replacement techniques. The procedure was carried out using the program XPLOR (Brunger) running on a Silicon Graphics Indigo2 workstation. The procedure followed that used for the molecular replacement solution of Fab 26-10 (Brunger). For the test model, the anti-tumor Fab (CTM01, IgG1 κ, Protein Data Bank code 1AD9) was chosen. Best rotation and translation solutions were found with the model modified by a −20° change in the elbow angle. A single solution emerged from the application of rotation function, PC-refinement and translation function. Using the molecular replacement solution an initial crystallographic R-value, based on rigid body refinement of the four 1AD9 model domains ($V_L$, $C_L$, $V_H$ and $C_{H1}$), was calculated to be 0.42.

Using the model from the molecular replacement approach and the rigid body refinement, a single cycle of simulated annealing refinement (SA) followed by a cycle of grouped B-factor refinement resulted in a crystallographic residual of 0.29. Inspection of initial 2Fo-Fc and Fo-Fc electron density maps clearly indicated the differences in amino acid sequence between and model and Synagis Fab. Refinement was continued with alternate cycles of manual model building using the visualization program TURBO and simulated annealing refinement using XPLOR, and by the 5th cycle of refinement, the complete Synagis Fab sequence was fit to electron density. Refinement continued for an additional 15 cycles with improvements to stereochemistry of the polypeptide and the addition of solvent water molecules. Refinement was terminated when no peaks in an Fo-Fc difference Fourier were greater than 2.5σ. Electron density for the light chain is well resolved from residues 4 through the C-terminus residue 213. The entire heavy chain has been modeled from the N-terminus residue 1 through C-terminus residue 220. No breaks in the electron density for the modeled polypeptides are found.

TABLE 5

Data Collection Summary

| | Native |
|---|---|
| X-ray source | Cu Rotating Anode |
| Resolution limit (Å) | 1.86Å |
| $R_{sym}$[b](%) | 6.0 |
| Total observations | 425,773 |
| Unique reflections | 39,800 |
| Completeness (%) | 92 |
| Signal % > 2σ) | 83 |

[b]$R_{sym} = 100 \times \Sigma_h \Sigma_i |I_i(h) - <I(h)>|/\Sigma_h \Sigma_i I_i(h)$.

7.2.3 Structure Analyses

A Ramachandran (Φ, Ψ) plot of the final model shows only one residue in a region usually considered to be disallowed (light chain Thr 51, CDR L2, FIG. 10). This residue, at residue i+1 of a γ turn, has been noted to occur with this conformation in class 3 γ turns (Milner-White & Poet, 1987). Moreover, the conformation of this residue is in agreement with the classification of CDR L2 as a class 1 canonical loop. The errors in atomic coordinates estimated by the method of Luzzatti (1952) are 0.21 Å.

The following table summarizes the X-ray crystallography refinement parameters of the structure of crystalline Synagis Fab of the invention.

TABLE 6

Refinement Parameters
Synagis Fab: 429 residues, 357 water molecules (3664 atoms)

| | | | | R.m.s.d. | | |
|---|---|---|---|---|---|---|
| | d-spacings (Å) | Reflections (N) | R-value[a] (%) | bonds (Å) | angles (°) | B-values[b] (Å²) |
| Synagis Fab: | 1.86 | 33,300 | 19.4 (21.4)[c] | 0.01 | 1.84 | 25.6 |

[a]R-value = $100 \times \Sigma_h ||F_{obs}(h)| - |F_{calc})h)|/\Sigma_h |F_{obs}(h)|$ for reflections with $F_{obs} > 2\sigma$.
[b]For bonded protein atoms.
[c]Value in parentheses is the free R-value (Brünger, 1992, "Free R value: a novel statistical quantity for assessing the accuracy of crystal structures," Nature 355:472–475.) determined from 5% of the data.

Table 2, following this page, provides the atomic structure coordinates of Synagis Fab. The amino acid residue numbers coincide with those used in FIGS. 3A and 3B.

The following abbreviations are used in Table 2:

"Atom Type" refers to the element whose coordinates are provided. The first letter in the column defines the element.

"A.A." refers to amino acid.

"X, Y and Z" provide the Cartesian coordinates of the element.

"B" is a thermal factor that measures movement of the atom around its atomic center.

"OCC" refers to occupancy, and represents the percentage of time the atom type occupies the particular coordinate. OCC values range from 0 to 1, with 1 being 100%.

Structures coordinates for Synagis Fab according to Table 2 may be modified by mathematical manipulation. Such manipulations include, but are not limited to, crystallographic permutations of the raw structure coordinates, fractionalization of the raw structure coordinates, integer additions or subtractions to sets of the raw structure coordinates, inversion of the raw structure coordinates and any combination of the above.

The present invention is not to be limited in scope by the exemplified embodiments, which are intended as illustrations of single aspects of the invention. Indeed, various modifications of the invention in addition to those described herein will become apparent to those having skill in the art from the foregoing description and accompanying drawings. Such modifications are intended to fall with in the scope of the appended claims.

TABLE 3

Synagis VL CDR canonical structure
L1-canonical structure type 1–10 residues
Torsion Angles

| | Synagis | | | J539 (PDB code 2FBJ) | | |
|---|---|---|---|---|---|---|
| Residue | Amino Acid | Φ | Ψ | Amino Acid | Φ | Ψ |
| 24 | Lys | −114 | 123 | Ser | −123 | 143 |
| 25 | Cys | −107 | 151 | Ala | −107 | 147 |
| 26 | Gln | −73 | −26 | Ser | −71 | −16 |
| 28 | Leu | −105 | 147 | Ser | −157 | 169 |
| 29 | Ser | −61 | 145 | Ser | −59 | 133 |
| 30 | Val | −123 | 140 | Val | −113 | 151 |
| 31 | Gly | −71 | −61 | Ser | −75 | −37 |
| 32 | Tyr | −142 | 164 | Ser | −157 | 160 |
| 33 | Met | −128 | 148 | Leu | −141 | 140 |
| 34 | His | −117 | 149 | His | −136 | 156 | r.m.s. difference Cα positions = 0.297A; r.m.s. difference main-chain atoms = 0.685A L2-canonical structure type 1 Torsion Angles

| | Synagis | | | HyHel-5 (PDB code 1BQL) | | |
|---|---|---|---|---|---|---|
| Residue | Amino Acid | Φ | Ψ | Amino Acid | Φ | Ψ |
| 50 | Asp | 48 | 43 | Asp | 41 | 57 |
| 51 | Thr | 67 | −46 | Thr | 54 | −64 |
| 52 | Ser | −133 | 5 | Ser | −107 | −6 |
| 53 | Lys | −85 | 119 | Lys | −85 | 124 |
| 54 | Leu | −68 | 126 | Leu | −72 | 139 |
| 55 | Ala | −71 | 166 | Ala | −78 | 161 |
| 56 | Ser | −69 | 135 | Ser | −53 | 100 | r.m.s. difference Cα positions = 0.098A; r.m.s. difference main-chain atoms = 0.261A L3-canonical structure type 1 Torsion Angles

| | Synagis | | | TE33 (PDB code 1TET) | | |
|---|---|---|---|---|---|---|
| Residue | Amino Acid | Φ | Ψ | Amino Acid | Φ | Ψ |
| 89 | Phe | −132 | 129 | Phe | −142 | 141 |
| 90 | Gln | −107 | 106 | Gln | −117 | 135 |
| 91 | Gly | −120 | 10 | Gly | −129 | 32 |
| 92 | Ser | −80 | −21 | Ser | −97 | −35 |

TABLE 3-continued

| 93 | Gly | −152 | 167 | His | −124 | 125 |
|---|---|---|---|---|---|---|
| 94 | Tyr | −87 | 142 | Phe | −81 | 124 |
| 95 | Pro | −88 | 150 | Pro | −81 | 140 |
| 96 | Phe | −67 | 131 | Phe | −61 | 128 |
| 97 | Thr | −147 | 153 | Thr | −124 | 151 | r.m.s. difference Cα positions = 0.240A; r.m.s. difference main-chain atoms = 0.622A

TABLE 4

Synagis V$_H$ CDR canonical structure residues and torsion angles

H1-canonical structure type 1

| | Synagis | | | 50.1 (PDB code 2GGI) | | |
|---|---|---|---|---|---|---|
| Residue | Amino Acid | Φ | Ψ | Amino Acid | Φ | Ψ |
| 26 | Gly | 92 | 0 | Gly | 114 | −14 |
| 27 | Phe | −169 | 168 | Phe | −165 | 132 |
| 27A | Ser | −124 | 135 | Ser | −80 | 145 |
| 27B | Leu | −73 | 1 | Leu | −77 | 6 |
| 28 | Ser | −93 | −18 | Ser | −90 | −13 |
| 29 | Thr | −65 | 132 | Thr | −65 | 127 |
| 30 | Ser | −43 | 134 | Tyr | −60 | 124 |
| 31 | Gly | 85 | −10 | Gly | 94 | 6 |
| 32 | Met | −76 | 143 | Met | −82 | 154 |
| 33 | Ser | −150 | 151 | Gly | 179 | 159 |
| 34 | Val | −129 | 124 | Val | −132 | 135 |
| 35 | Gly | −116 | 165 | Ser | −100 | 154 | r.m.s. difference Cα positions = 0.218A; r.m.s. difference main-chain atoms = 0.390A H2-canonical structure type 1

| | Synagis | | | HC19 (PDB code 1GIG) | | |
|---|---|---|---|---|---|---|
| Residue | Amino Acid | Φ | Ψ | Amino Acid | Φ | Ψ |
| 50 | Asp | −152 | 167 | Val | −143 | 149 |
| 51 | Ile | −138 | 134 | Ile | −126 | 117 |
| 52 | Trp | −90 | 165 | Trp | −79 | 165 |
| 53 | Trp | −55 | −29 | Ala | −50 | −42 |
| 54 | Asp | −91 | 12 | Gly | −75 | −5 |
| 55 | Asp | 77 | 8 | Gly | 98 | −5 |
| 56 | Lys | −70 | 132 | Asn | −69 | 144 |
| 57 | Lys | −112 | 140 | Thr | −125 | 155 |
| 58 | Asp | −130 | 143 | Asn | −138 | 143 |
| 59 | Tyr | −135 | 149 | Tyr | −123 | 154 |
| 60 | Asn | −67 | 125 | Asn | −66 | 125 |
| 61 | Pro | −55 | 125 | Ser | −56 | −35 |
| 62 | Ser | −58 | −31 | Ala | −58 | −40 |
| 63 | Leu | −111 | −12 | Leu | −90 | −32 |
| 64 | Lys | −34 | −47 | Met | −3 | −59 |
| 65 | Ser | −53 | −34 | Ser | −66 | −44 | r.m.s. difference Cα positions = 0.106A; r.m.s. difference main-chain atoms = 0.243A

TABLE 2

| | | Atom | A.A. Type | | X | Y | Z | Occ | B |
|---|---|---|---|---|---|---|---|---|---|
| ATOM | CB | MET | L | 4 | 69.801 | 42.361 | −3.359 | 1.00 | 52.70 |
| ATOM | CG | MET | L | 4 | 70.492 | 41.405 | −4.309 | 1.00 | 51.32 |
| ATOM | SD | MET | L | 4 | 72.128 | 42.056 | −4.674 | 1.00 | 57.06 |
| ATOM | CE | MET | L | 4 | 72.891 | 41.926 | −3.102 | 1.00 | 53.48 |
| ATOM | C | MET | L | 4 | 67.468 | 42.053 | −4.233 | 1.00 | 49.95 |
| ATOM | O | MET | L | 4 | 66.690 | 41.125 | −4.478 | 1.00 | 51.62 |
| ATOM | N | MET | L | 4 | 68.326 | 40.617 | −2.404 | 1.00 | 53.46 |
| ATOM | CA | MET | L | 4 | 68.367 | 41.989 | −2.995 | 1.00 | 51.42 |
| ATOM | N | THR | L | 5 | 67.583 | 43.119 | −5.019 | 1.00 | 44.36 |
| ATOM | CA | THR | L | 5 | 66.756 | 43.254 | −6.205 | 1.00 | 40.62 |
| ATOM | CB | THR | L | 5 | 66.015 | 44.603 | −6.189 | 1.00 | 40.31 |
| ATOM | OG1 | THR | L | 5 | 65.256 | 44.692 | −4.977 | 1.00 | 42.05 |
| ATOM | CG2 | THR | L | 5 | 65.074 | 44.729 | −7.390 | 1.00 | 38.21 |
| ATOM | C | THR | L | 5 | 67.506 | 43.078 | −7.527 | 1.00 | 37.94 |
| ATOM | O | THR | L | 5 | 68.429 | 43.831 | −7.841 | 1.00 | 35.88 |
| ATOM | N | GLN | L | 6 | 67.085 | 42.085 | −8.305 | 1.00 | 33.98 |
| ATOM | CA | GLN | L | 6 | 67.696 | 41.816 | −9.598 | 1.00 | 31.54 |
| ATOM | CB | GLN | L | 6 | 68.193 | 40.367 | −9.660 | 1.00 | 29.52 |
| ATOM | CG | GLN | L | 6 | 69.005 | 40.022 | −10.899 | 1.00 | 23.42 |
| ATOM | CD | GLN | L | 6 | 69.621 | 38.625 | −10.838 | 1.00 | 23.94 |
| ATOM | OE1 | GLN | L | 6 | 70.059 | 38.085 | −11.855 | 1.00 | 25.77 |
| ATOM | NE2 | GLN | L | 6 | 69.684 | 38.048 | −9.643 | 1.00 | 17.08 |
| ATOM | C | GLN | L | 6 | 66.673 | 42.086 | −10.701 | 1.00 | 29.67 |
| ATOM | O | GLN | L | 6 | 65.479 | 41.868 | −10.530 | 1.00 | 29.35 |
| ATOM | N | SER | L | 7 | 67.141 | 42.560 | −11.838 | 1.00 | 29.10 |
| ATOM | CA | SER | L | 7 | 66.244 | 42.855 | −12.927 | 1.00 | 29.63 |
| ATOM | CB | SER | L | 7 | 65.667 | 44.273 | −12.772 | 1.00 | 33.97 |
| ATOM | OG | SER | L | 7 | 66.678 | 45.280 | −12.827 | 1.00 | 38.37 |
| ATOM | C | SER | L | 7 | 67.021 | 42.748 | −14.217 | 1.00 | 28.45 |
| ATOM | O | SER | L | 7 | 68.242 | 42.910 | −14.216 | 1.00 | 27.60 |
| ATOM | N | PRO | L | 8 | 66.348 | 42.341 | −15.308 | 1.00 | 28.70 |
| ATOM | CD | PRO | L | 8 | 66.881 | 42.417 | −16.681 | 1.00 | 28.01 |
| ATOM | CA | PRO | L | 8 | 64.922 | 41.991 | −15.316 | 1.00 | 28.37 |
| ATOM | CB | PRO | L | 8 | 64.554 | 42.151 | −16.783 | 1.00 | 29.19 |
| ATOM | CG | PRO | L | 8 | 65.817 | 41.747 | −17.482 | 1.00 | 29.51 |
| ATOM | C | PRO | L | 8 | 64.743 | 40.547 | −14.832 | 1.00 | 29.08 |
| ATOM | O | PRO | L | 8 | 65.667 | 39.752 | −14.932 | 1.00 | 30.35 |
| ATOM | N | SER | L | 9 | 63.575 | 40.212 | −14.294 | 1.00 | 28.83 |
| ATOM | CA | SER | L | 9 | 63.333 | 38.857 | −13.797 | 1.00 | 30.10 |
| ATOM | CB | SER | L | 9 | 61.986 | 38.773 | −13.061 | 1.00 | 31.53 |
| ATOM | OG | SER | L | 9 | 60.912 | 38.862 | −13.978 | 1.00 | 37.73 |
| ATOM | C | SER | L | 9 | 63.356 | 37.849 | −14.945 | 1.00 | 29.29 |
| ATOM | O | SER | L | 9 | 63.765 | 36.689 | −14.781 | 1.00 | 27.22 |
| ATOM | N | THR | L | 10 | 62.883 | 38.296 | −16.098 | 1.00 | 28.81 |
| ATOM | CA | THR | L | 10 | 62.839 | 37.468 | −17.292 | 1.00 | 31.44 |
| ATOM | CB | THR | L | 10 | 61.426 | 36.830 | −17.508 | 1.00 | 30.75 |
| ATOM | OG1 | THR | L | 10 | 60.415 | 37.843 | −17.438 | 1.00 | 34.36 |
| ATOM | CG2 | THR | L | 10 | 61.128 | 35.787 | −16.441 | 1.00 | 30.35 |
| ATOM | C | THR | L | 10 | 63.225 | 38.341 | −18.487 | 1.00 | 31.24 |
| ATOM | O | THR | L | 10 | 63.135 | 39.568 | −18.433 | 1.00 | 31.34 |
| ATOM | N | LEU | L | 11 | 63.737 | 37.712 | −19.528 | 1.00 | 32.55 |
| ATOM | CA | LEU | L | 11 | 64.132 | 38.432 | −20.717 | 1.00 | 33.50 |
| ATOM | CB | LEU | L | 11 | 65.473 | 39.126 | −20.500 | 1.00 | 35.64 |
| ATOM | CG | LEU | L | 11 | 65.986 | 39.917 | −21.709 | 1.00 | 39.37 |
| ATOM | CD1 | LEU | L | 11 | 65.040 | 41.089 | −22.003 | 1.00 | 39.67 |
| ATOM | CD2 | LEU | L | 11 | 67.387 | 40.421 | −21.437 | 1.00 | 39.27 |
| ATOM | C | LEU | L | 11 | 64.261 | 37.471 | −21.881 | 1.00 | 33.70 |
| ATOM | O | LEU | L | 11 | 64.755 | 36.361 | −21.723 | 1.00 | 32.16 |
| ATOM | N | SER | L | 12 | 63.751 | 37.881 | −23.031 | 1.00 | 33.08 |
| ATOM | CA | SER | L | 12 | 63.857 | 37.090 | −24.245 | 1.00 | 34.60 |
| ATOM | CB | SER | L | 12 | 62.479 | 36.805 | −24.827 | 1.00 | 34.91 |
| ATOM | OG | SER | L | 12 | 61.601 | 36.360 | −23.810 | 1.00 | 42.30 |
| ATOM | C | SER | L | 12 | 64.610 | 38.050 | −25.140 | 1.00 | 33.62 |
| ATOM | O | SER | L | 12 | 64.251 | 39.232 | −25.224 | 1.00 | 35.15 |
| ATOM | N | ALA | L | 13 | 65.691 | 37.583 | −25.742 | 1.00 | 30.90 |
| ATOM | CA | ALA | L | 13 | 66.482 | 38.439 | −26.599 | 1.00 | 30.58 |
| ATOM | CE | ALA | L | 13 | 67.607 | 39.084 | −25.801 | 1.00 | 30.23 |
| ATOM | C | ALA | L | 13 | 67.039 | 37.583 | −27.707 | 1.00 | 31.78 |
| ATOM | O | ALA | L | 13 | 67.214 | 36.380 | −27.544 | 1.00 | 31.55 |
| ATOM | N | SER | L | 14 | 67.289 | 38.204 | −28.851 | 1.00 | 33.80 |
| ATOM | CA | SER | L | 14 | 67.816 | 37.494 | −30.011 | 1.00 | 33.44 |
| ATOM | CB | SER | L | 14 | 67.526 | 38.294 | −31.277 | 1.00 | 33.43 |
| ATOM | OG | SER | L | 14 | 66.232 | 38.878 | −31.214 | 1.00 | 37.66 |
| ATOM | C | SER | L | 14 | 69.308 | 37.280 | −29.897 | 1.00 | 31.30 |
| ATOM | O | SER | L | 14 | 69.984 | 37.924 | −29.101 | 1.00 | 33.92 |
| ATOM | N | VAL | L | 15 | 69.820 | 36.367 | −30.698 | 1.00 | 31.26 |

TABLE 2-continued

| | | Atom A.A. Type | | | X | Y | Z | Occ | B |
|---|---|---|---|---|---|---|---|---|---|
| ATOM | CA | VAL | L | 15 | 71.239 | 36.100 | −30.720 | 1.00 | 29.90 |
| ATOM | CB | VAL | L | 15 | 71.525 | 34.913 | −31.632 | 1.00 | 26.09 |
| ATOM | CG1 | VAL | L | 15 | 72.997 | 34.762 | −31.859 | 1.00 | 27.20 |
| ATOM | CG2 | VAL | L | 15 | 70.977 | 33.662 | −31.014 | 1.00 | 25.79 |
| ATOM | C | VAL | L | 15 | 71.940 | 37.371 | −31.239 | 1.00 | 33.94 |
| ATOM | O | VAL | L | 15 | 71.432 | 38.085 | −32.122 | 1.00 | 33.32 |
| ATOM | N | GLY | L | 16 | 73.086 | 37.682 | −30.644 | 1.00 | 36.81 |
| ATOM | CA | GLY | L | 16 | 73.840 | 38.853 | −31.045 | 1.00 | 35.94 |
| ATOM | C | GLY | L | 16 | 73.498 | 40.058 | −30.212 | 1.00 | 35.51 |
| ATOM | O | GLY | L | 16 | 74.262 | 41.014 | −30.194 | 1.00 | 39.24 |
| ATOM | N | ASP | L | 17 | 72.366 | 40.016 | −29.520 | 1.00 | 34.04 |
| ATOM | CA | ASP | L | 17 | 71.946 | 41.121 | −28.672 | 1.00 | 34.26 |
| ATOM | CE | ASP | L | 17 | 70.547 | 40.856 | −28.113 | 1.00 | 34.85 |
| ATOM | CG | ASP | L | 17 | 69.447 | 41.156 | −29.110 | 1.00 | 37.86 |
| ATOM | OD1 | ASP | L | 17 | 68.303 | 41.380 | −28.658 | 1.00 | 37.46 |
| ATOM | OD2 | ASP | L | 17 | 69.717 | 41.172 | −30.332 | 1.00 | 38.37 |
| ATOM | C | ASP | L | 17 | 72.896 | 41.368 | −27.500 | 1.00 | 34.67 |
| ATOM | O | ASP | L | 17 | 73.665 | 40.484 | −27.112 | 1.00 | 33.04 |
| ATOM | N | ARG | L | 18 | 72.857 | 42.581 | −26.956 | 1.00 | 33.25 |
| ATOM | CA | ARG | L | 18 | 73.666 | 42.913 | −25.803 | 1.00 | 32.51 |
| ATOM | CE | ARG | L | 18 | 74.286 | 44.304 | −25.932 | 1.00 | 37.82 |
| ATOM | CG | ARG | L | 18 | 75.007 | 44.766 | −24.667 | 1.00 | 42.38 |
| ATOM | CD | ARG | L | 18 | 75.722 | 46.081 | −24.870 | 1.00 | 45.92 |
| ATOM | NE | ARG | L | 18 | 77.152 | 45.955 | −24.600 | 1.00 | 52.00 |
| ATOM | CZ | ARG | L | 18 | 78.042 | 45.463 | −25.459 | 1.00 | 55.43 |
| ATOM | NH1 | ARG | L | 18 | 77.660 | 45.038 | −26.661 | 1.00 | 56.79 |
| ATOM | NH2 | ARG | L | 18 | 79.324 | 45.401 | −25.119 | 1.00 | 57.64 |
| ATOM | C | ARG | L | 18 | 72.662 | 42.882 | −24.671 | 1.00 | 32.18 |
| ATOM | O | ARG | L | 18 | 71.569 | 43.443 | −24.793 | 1.00 | 32.94 |
| ATOM | N | VAL | L | 19 | 73.018 | 42.215 | −23.579 | 1.00 | 30.42 |
| ATOM | CA | VAL | L | 19 | 72.118 | 42.081 | −22.449 | 1.00 | 29.59 |
| ATOM | CB | VAL | L | 19 | 71.638 | 40.584 | −22.304 | 1.00 | 30.77 |
| ATOM | CG1 | VAL | L | 19 | 70.816 | 40.395 | −21.036 | 1.00 | 28.91 |
| ATOM | CG2 | VAL | L | 19 | 70.803 | 40.173 | −23.538 | 1.00 | 29.02 |
| ATOM | C | VAL | L | 19 | 72.795 | 42.561 | −21.173 | 1.00 | 28.10 |
| ATOM | O | VAL | L | 19 | 73.964 | 42.275 | −20.941 | 1.00 | 27.17 |
| ATOM | N | THR | L | 20 | 72.035 | 43.285 | −20.359 | 1.00 | 28.30 |
| ATOM | CA | THR | L | 20 | 72.508 | 43.827 | −19.100 | 1.00 | 31.45 |
| ATOM | CE | THR | L | 20 | 72.585 | 45.362 | −19.149 | 1.00 | 33.55 |
| ATOM | OG1 | THR | L | 20 | 73.469 | 45.771 | −20.204 | 1.00 | 33.44 |
| ATOM | CG2 | THR | L | 20 | 73.075 | 45.916 | −17.801 | 1.00 | 32.77 |
| ATOM | C | THR | L | 20 | 71.540 | 43.456 | −17.982 | 1.00 | 33.30 |
| ATOM | O | THR | L | 20 | 70.343 | 43.747 | −18.061 | 1.00 | 32.85 |
| ATOM | N | ILE | L | 21 | 72.082 | 42.840 | −16.935 | 1.00 | 34.18 |
| ATOM | CA | ILE | L | 21 | 71.324 | 42.415 | −15.763 | 1.00 | 31.59 |
| ATOM | CB | ILE | L | 21 | 71.602 | 40.918 | −15.467 | 1.00 | 31.26 |
| ATOM | CG2 | ILE | L | 21 | 70.863 | 40.470 | −14.234 | 1.00 | 31.18 |
| ATOM | CG1 | ILE | L | 21 | 71.200 | 40.073 | −16.680 | 1.00 | 32.87 |
| ATOM | CD1 | ILE | L | 21 | 71.639 | 38.629 | −16.607 | 1.00 | 32.99 |
| ATOM | C | ILE | L | 21 | 71.802 | 43.294 | −14.602 | 1.00 | 30.37 |
| ATOM | O | ILE | L | 21 | 73.000 | 43.557 | −14.468 | 1.00 | 26.47 |
| ATOM | N | THR | L | 22 | 70.872 | 43.721 | −13.756 | 1.00 | 29.86 |
| ATOM | CA | THR | L | 22 | 71.206 | 44.592 | −12.643 | 1.00 | 31.35 |
| ATOM | CB | THR | L | 22 | 70.612 | 46.032 | −12.903 | 1.00 | 30.91 |
| ATOM | OG1 | THR | L | 22 | 71.159 | 46.574 | −14.117 | 1.00 | 29.08 |
| ATOM | CG2 | THR | L | 22 | 70.925 | 46.988 | −11.743 | 1.00 | 31.26 |
| ATOM | C | THR | L | 22 | 70.765 | 44.090 | −11.253 | 1.00 | 31.33 |
| ATOM | O | THR | L | 22 | 69.677 | 43.530 | −11.093 | 1.00 | 31.64 |
| ATOM | N | CYS | L | 23 | 71.648 | 44.245 | −10.268 | 1.00 | 32.19 |
| ATOM | CA | CYS | L | 23 | 71.351 | 43.899 | −8.877 | 1.00 | 32.45 |
| ATOM | C | CYS | L | 23 | 71.574 | 45.153 | −8.040 | 1.00 | 33.34 |
| ATOM | O | CYS | L | 23 | 72.639 | 45.759 | −8.090 | 1.00 | 30.85 |
| ATOM | CB | CYS | L | 23 | 72.213 | 42.738 | −8.358 | 1.00 | 31.61 |
| ATOM | SG | CYS | L | 23 | 71.545 | 41.112 | −8.839 | 1.00 | 32.93 |
| ATOM | N | LYS | L | 24 | 70.513 | 45.586 | −7.370 | 1.00 | 37.25 |
| ATOM | CA | LYS | L | 24 | 70.523 | 46.764 | −6.518 | 1.00 | 42.39 |
| ATOM | CB | LYS | L | 24 | 69.405 | 47.728 | −6.922 | 1.00 | 45.13 |
| ATOM | CG | LYS | L | 24 | 69.514 | 48.293 | −8.333 | 1.00 | 50.30 |
| ATOM | CD | LYS | L | 24 | 68.276 | 49.122 | −8.680 | 1.00 | 52.53 |
| ATOM | CE | LYS | L | 24 | 68.393 | 49.784 | −10.042 | 1.00 | 54.46 |
| ATOM | NZ | LYS | L | 24 | 67.154 | 50.539 | −10.379 | 1.00 | 56.06 |
| ATOM | C | LYS | L | 24 | 70.282 | 46.314 | −5.087 | 1.00 | 44.53 |
| ATOM | O | LYS | L | 24 | 69.300 | 45.614 | −4.792 | 1.00 | 45.31 |
| ATOM | N | CYS | L | 25 | 71.204 | 46.662 | −4.205 | 1.00 | 47.46 |
| ATOM | CA | CYS | L | 25 | 71.064 | 46.302 | −2.813 | 1.00 | 50.46 |
| ATOM | CB | CYS | L | 25 | 72.361 | 45.719 | −2.262 | 1.00 | 51.49 |

TABLE 2-continued

| | | Atom A.A. Type | | | X | Y | Z | Occ | B |
|---|---|---|---|---|---|---|---|---|---|
| ATOM | SG | CYS | L | 25 | 72.217 | 45.136 | −0.553 | 1.00 | 55.90 |
| ATOM | C | CYS | L | 25 | 70.726 | 47.576 | −2.084 | 1.00 | 52.05 |
| ATOM | O | CYS | L | 25 | 71.080 | 48.673 | −2.527 | 1.00 | 51.90 |
| ATOM | N | GLN | L | 26 | 70.002 | 47.434 | −0.985 | 1.00 | 55.05 |
| ATOM | CA | GLN | L | 26 | 69.611 | 48.584 | −0.177 | 1.00 | 58.36 |
| ATOM | CB | GLN | L | 26 | 68.491 | 48.207 | 0.811 | 1.00 | 60.14 |
| ATOM | CG | GLN | L | 26 | 68.266 | 46.704 | 1.019 | 1.00 | 63.23 |
| ATOM | CD | GLN | L | 26 | 67.641 | 46.023 | −0.200 | 1.00 | 66.56 |
| ATOM | OE1 | GLN | L | 26 | 68.181 | 45.039 | −0.729 | 1.00 | 67.74 |
| ATOM | NE2 | GLN | L | 26 | 66.508 | 46.551 | −0.656 | 1.00 | 67.30 |
| ATOM | C | GLN | L | 26 | 70.841 | 49.078 | 0.579 | 1.00 | 58.79 |
| ATOM | O | GLN | L | 26 | 70.977 | 50.263 | 0.891 | 1.00 | 59.68 |
| ATOM | N | LEU | L | 28 | 71.759 | 48.152 | 0.820 | 1.00 | 57.89 |
| ATOM | CA | LEU | L | 28 | 72.977 | 48.441 | 1.547 | 1.00 | 55.81 |
| ATOM | CB | LEU | L | 28 | 73.202 | 47.342 | 2.594 | 1.00 | 56.86 |
| ATOM | CG | LEU | L | 28 | 71.922 | 46.791 | 3.252 | 1.00 | 57.59 |
| ATOM | CD1 | LEU | L | 28 | 72.278 | 45.712 | 4.269 | 1.00 | 57.76 |
| ATOM | CD2 | LEU | L | 28 | 71.117 | 47.912 | 3.921 | 1.00 | 58.04 |
| ATOM | C | LEU | L | 28 | 74.139 | 48.487 | 0.568 | 1.00 | 53.54 |
| ATOM | O | LEU | L | 28 | 74.132 | 47.788 | −0.447 | 1.00 | 51.34 |
| ATOM | N | SER | L | 29 | 75.117 | 49.338 | 0.858 | 1.00 | 52.55 |
| ATOM | CA | SER | L | 29 | 76.292 | 49.456 | 0.007 | 1.00 | 50.75 |
| ATOM | CB | SER | L | 29 | 77.226 | 50.551 | 0.521 | 1.00 | 51.65 |
| ATOM | OG | SER | L | 29 | 77.860 | 51.233 | −0.547 | 1.00 | 52.04 |
| ATOM | C | SER | L | 29 | 76.979 | 48.093 | 0.021 | 1.00 | 48.93 |
| ATOM | O | SER | L | 29 | 76.977 | 47.387 | 1.035 | 1.00 | 50.11 |
| ATOM | N | VAL | L | 30 | 77.566 | 47.733 | −1.106 | 1.00 | 45.38 |
| ATOM | CA | VAL | L | 30 | 78.194 | 46.441 | −1.256 | 1.00 | 43.49 |
| ATOM | CB | VAL | L | 30 | 77.446 | 45.616 | −2.348 | 1.00 | 45.26 |
| ATOM | CG1 | VAL | L | 30 | 78.148 | 44.296 | −2.627 | 1.00 | 45.55 |
| ATOM | CG2 | VAL | L | 30 | 76.008 | 45.374 | −1.926 | 1.00 | 45.67 |
| ATOM | C | VAL | L | 30 | 79.633 | 46.609 | −1.662 | 1.00 | 40.20 |
| ATOM | O | VAL | L | 30 | 79.954 | 47.472 | −2.474 | 1.00 | 40.25 |
| ATOM | N | GLY | L | 31 | 80.496 | 45.770 | −1.104 | 1.00 | 37.47 |
| ATOM | CA | GLY | L | 31 | 81.902 | 45.830 | −1.442 | 1.00 | 36.78 |
| ATOM | C | GLY | L | 31 | 82.132 | 45.328 | −2.857 | 1.00 | 36.26 |
| ATOM | O | GLY | L | 31 | 82.562 | 46.082 | −3.725 | 1.00 | 36.41 |
| ATOM | N | TYR | L | 32 | 81.794 | 44.064 | −3.096 | 1.00 | 35.02 |
| ATOM | CA | TYR | L | 32 | 81.967 | 43.427 | −4.401 | 1.00 | 33.17 |
| ATOM | CB | TYR | L | 32 | 83.290 | 42.658 | −4.431 | 1.00 | 31.32 |
| ATOM | CG | TYR | L | 32 | 83.436 | 41.688 | −3.276 | 1.00 | 33.00 |
| ATOM | CD1 | TYR | L | 32 | 82.777 | 40.454 | −3.279 | 1.00 | 33.06 |
| ATOM | CE1 | TYR | L | 32 | 82.852 | 39.586 | −2.191 | 1.00 | 32.01 |
| ATOM | CD2 | TYR | L | 32 | 84.183 | 42.025 | −2.154 | 1.00 | 33.11 |
| ATOM | CE2 | TYR | L | 32 | 84.267 | 41.161 | −1.057 | 1.00 | 33.14 |
| ATOM | CZ | TYR | L | 32 | 83.595 | 39.945 | −1.085 | 1.00 | 32.91 |
| ATOM | OH | TYR | L | 32 | 83.651 | 39.107 | 0.002 | 1.00 | 30.28 |
| ATOM | C | TYR | L | 32 | 80.780 | 42.483 | −4.692 | 1.00 | 33.63 |
| ATOM | O | TYR | L | 32 | 80.035 | 42.099 | −3.771 | 1.00 | 33.48 |
| ATOM | N | MET | L | 33 | 80.632 | 42.082 | −5.954 | 1.00 | 31.62 |
| ATOM | CA | MET | L | 33 | 79.532 | 41.209 | −6.373 | 1.00 | 27.51 |
| ATOM | CB | MET | L | 33 | 78.556 | 42.016 | −7.245 | 1.00 | 27.25 |
| ATOM | CG | MET | L | 33 | 77.203 | 41.373 | −7.521 | 1.00 | 26.66 |
| ATOM | SD | MET | L | 33 | 76.102 | 41.202 | −6.088 | 1.00 | 31.44 |
| ATOM | CE | MET | L | 33 | 75.676 | 42.936 | −5.687 | 1.00 | 28.65 |
| ATOM | C | MET | L | 33 | 80.048 | 39.999 | −7.150 | 1.00 | 24.55 |
| ATOM | O | MET | L | 33 | 81.115 | 40.062 | −7.767 | 1.00 | 22.26 |
| ATOM | N | HIS | L | 34 | 79.342 | 38.875 | −7.029 | 1.00 | 22.23 |
| ATOM | CA | HIS | L | 34 | 79.684 | 37.641 | −7.754 | 1.00 | 21.25 |
| ATOM | CB | HIS | L | 34 | 79.853 | 36.452 | −6.789 | 1.00 | 19.84 |
| ATOM | CG | HIS | L | 34 | 81.229 | 36.312 | −6.199 | 1.00 | 19.58 |
| ATOM | CD2 | HIS | L | 34 | 82.214 | 35.415 | −6.443 | 1.00 | 16.56 |
| ATOM | ND1 | HIS | L | 34 | 81.702 | 37.133 | −5.195 | 1.00 | 17.59 |
| ATOM | CE1 | HIS | L | 34 | 82.917 | 36.747 | −4.847 | 1.00 | 17.33 |
| ATOM | NE2 | HIS | L | 34 | 83.251 | 35.709 | −5.591 | 1.00 | 16.19 |
| ATOM | C | HIS | L | 34 | 78.489 | 37.349 | −8.662 | 1.00 | 21.03 |
| ATOM | O | HIS | L | 34 | 77.356 | 37.702 | −8.323 | 1.00 | 22.35 |
| ATOM | N | TRP | L | 35 | 78.726 | 36.736 | −9.816 | 1.00 | 22.50 |
| ATOM | CA | TRP | L | 35 | 77.634 | 36.390 | −10.738 | 1.00 | 20.38 |
| ATOM | CB | TRP | L | 35 | 77.665 | 37.258 | −12.003 | 1.00 | 20.95 |
| ATOM | CG | TRP | L | 35 | 77.300 | 38.704 | −11.763 | 1.00 | 20.91 |
| ATOM | CD2 | TRP | L | 35 | 75.977 | 39.281 | −11.759 | 1.00 | 19.43 |
| ATOM | CE2 | TRP | L | 35 | 76.123 | 40.660 | −11.473 | 1.00 | 19.35 |
| ATOM | CE3 | TRP | L | 35 | 74.689 | 38.768 | −11.966 | 1.00 | 19.03 |
| ATOM | CD | TRP | L | 35 | 78.165 | 39.730 | −11.495 | 1.00 | 18.32 |
| ATOM | NE1 | TRP | L | 35 | 77.465 | 40.904 | −11.323 | 1.00 | 17.92 |

TABLE 2-continued

| | | Atom A.A. Type | | | X | Y | Z | Occ | B |
|---|---|---|---|---|---|---|---|---|---|
| ATOM | CZ2 | TRP | L | 35 | 75.026 | 41.534 | −11.382 | 1.00 | 18.46 |
| ATOM | CZ3 | TRP | L | 35 | 73.593 | 39.644 | −11.877 | 1.00 | 18.57 |
| ATOM | CH2 | TRP | L | 35 | 73.777 | 41.010 | −11.584 | 1.00 | 20.31 |
| ATOM | C | TRP | L | 35 | 77.747 | 34.922 | −11.115 | 1.00 | 19.11 |
| ATOM | O | TRP | L | 35 | 78.856 | 34.411 | −11.342 | 1.00 | 17.52 |
| ATOM | N | TYR | L | 36 | 76.607 | 34.243 | −11.151 | 1.00 | 17.89 |
| ATOM | CA | TYR | L | 36 | 76.554 | 32.824 | −11.496 | 1.00 | 18.67 |
| ATOM | CE | TYR | L | 36 | 76.157 | 31.973 | −10.277 | 1.00 | 16.85 |
| ATOM | CG | TYR | L | 36 | 77.103 | 32.151 | −9.112 | 1.00 | 18.90 |
| ATOM | CD1 | TYR | L | 36 | 78.206 | 31.301 | −8.943 | 1.00 | 17.35 |
| ATOM | CE1 | TYR | L | 36 | 79.138 | 31.515 | −7.925 | 1.00 | 15.46 |
| ATOM | CD2 | TYR | L | 36 | 76.948 | 33.215 | −8.225 | 1.00 | 16.62 |
| ATOM | CE2 | TYR | L | 36 | 77.870 | 33.435 | −7.210 | 1.00 | 18.33 |
| ATOM | CZ | TYR | L | 36 | 78.959 | 32.586 | −7.072 | 1.00 | 16.23 |
| ATOM | OH | TYR | L | 36 | 79.879 | 32.834 | −6.101 | 1.00 | 16.90 |
| ATOM | C | TYR | L | 36 | 75.586 | 32.547 | −12.640 | 1.00 | 18.87 |
| ATOM | O | TYR | L | 36 | 74.598 | 33.266 | −12.833 | 1.00 | 16.77 |
| ATOM | N | GLN | L | 37 | 75.912 | 31.511 | −13.406 | 1.00 | 20.01 |
| ATOM | CA | GLN | L | 37 | 75.099 | 31.069 | −14.524 | 1.00 | 20.83 |
| ATOM | CE | GLN | L | 37 | 75.938 | 31.002 | −15.791 | 1.00 | 19.79 |
| ATOM | CG | GLN | L | 37 | 75.133 | 30.614 | −17.009 | 1.00 | 21.34 |
| ATOM | CD | GLN | L | 37 | 76.012 | 30.207 | −18.156 | 1.00 | 21.69 |
| ATOM | OE1 | GLN | L | 37 | 76.829 | 29.295 | −18.022 | 1.00 | 20.70 |
| ATOM | NE2 | GLN | L | 37 | 75.862 | 30.880 | −19.293 | 1.00 | 22.45 |
| ATOM | C | GLN | L | 37 | 74.565 | 29.677 | −14.217 | 1.00 | 17.81 |
| ATOM | O | GLN | L | 37 | 75.338 | 28.763 | −13.982 | 1.00 | 16.05 |
| ATOM | N | GLN | L | 38 | 73.251 | 29.508 | −14.231 | 1.00 | 19.04 |
| ATOM | CA | GLN | L | 38 | 72.697 | 28.199 | −13.952 | 1.00 | 19.08 |
| ATOM | CB | GLN | L | 38 | 71.947 | 28.200 | −12.625 | 1.00 | 18.05 |
| ATOM | CG | GLN | L | 38 | 71.425 | 26.836 | −12.231 | 1.00 | 16.18 |
| ATOM | CD | GLN | L | 38 | 70.504 | 26.879 | −11.020 | 1.00 | 19.78 |
| ATOM | OE1 | GLN | L | 38 | 70.437 | 25.910 | −10.242 | 1.00 | 20.20 |
| ATOM | NE2 | GLN | L | 38 | 69.780 | 27.986 | −10.854 | 1.00 | 13.17 |
| ATOM | C | GLN | L | 38 | 71.799 | 27.644 | −15.043 | 1.00 | 21.27 |
| ATOM | O | GLN | L | 38 | 70.754 | 28.206 | −15.345 | 1.00 | 19.19 |
| ATOM | N | LYS | L | 39 | 72.238 | 26.545 | −15.648 | 1.00 | 26.27 |
| ATOM | CA | LYS | L | 39 | 71.463 | 25.856 | −16.671 | 1.00 | 30.24 |
| ATOM | CB | LYS | L | 39 | 72.360 | 24.926 | −17.482 | 1.00 | 31.09 |
| ATOM | CG | LYS | L | 39 | 73.184 | 25.657 | −18.549 | 1.00 | 31.78 |
| ATOM | CD | LYS | L | 39 | 72.269 | 26.309 | −19.569 | 1.00 | 36.19 |
| ATOM | CE | LYS | L | 39 | 73.016 | 26.722 | −20.839 | 1.00 | 38.15 |
| ATOM | NZ | LYS | L | 39 | 72.095 | 27.028 | −22.005 | 1.00 | 33.68 |
| ATOM | C | LYS | L | 39 | 70.411 | 25.081 | −15.886 | 1.00 | 34.01 |
| ATOM | O | LYS | L | 39 | 70.687 | 24.575 | −14.793 | 1.00 | 31.70 |
| ATOM | N | PRO | L | 40 | 69.185 | 24.995 | −16.422 | 1.00 | 38.94 |
| ATOM | CD | PRO | L | 40 | 68.854 | 25.278 | −17.829 | 1.00 | 41.35 |
| ATOM | CA | PRO | L | 40 | 68.073 | 24.296 | −15.770 | 1.00 | 39.98 |
| ATOM | CB | PRO | L | 40 | 67.076 | 24.070 | −16.919 | 1.00 | 42.33 |
| ATOM | CG | PRO | L | 40 | 67.934 | 24.119 | −18.165 | 1.00 | 43.50 |
| ATOM | C | PRO | L | 40 | 68.406 | 23.007 | −15.020 | 1.00 | 40.98 |
| ATOM | O | PRO | L | 40 | 69.001 | 22.066 | −15.576 | 1.00 | 39.72 |
| ATOM | N | GLY | L | 41 | 68.063 | 23.017 | −13.730 | 1.00 | 41.78 |
| ATOM | CA | GLY | L | 41 | 68.267 | 21.872 | −12.861 | 1.00 | 41.84 |
| ATOM | C | GLY | L | 41 | 69.698 | 21.410 | −12.703 | 1.00 | 42.49 |
| ATOM | O | GLY | L | 41 | 69.927 | 20.346 | −12.125 | 1.00 | 45.08 |
| ATOM | N | LYS | L | 42 | 70.648 | 22.195 | −13.215 | 1.00 | 39.68 |
| ATOM | CA | LYS | L | 42 | 72.073 | 21.891 | −13.136 | 1.00 | 33.25 |
| ATOM | CB | LYS | L | 42 | 72.723 | 22.072 | −14.513 | 1.00 | 37.87 |
| ATOM | CG | LYS | L | 42 | 74.156 | 21.538 | −14.609 | 1.00 | 45.96 |
| ATOM | CD | LYS | L | 42 | 75.019 | 22.270 | −15.667 | 1.00 | 47.70 |
| ATOM | CE | LYS | L | 42 | 75.041 | 21.551 | −17.009 | 1.00 | 51.25 |
| ATOM | NZ | LYS | L | 42 | 75.556 | 20.145 | −16.892 | 1.00 | 53.52 |
| ATOM | C | LYS | L | 42 | 72.667 | 22.867 | −12.115 | 1.00 | 27.28 |
| ATOM | O | LYS | L | 42 | 72.048 | 23.868 | −11.785 | 1.00 | 22.25 |
| ATOM | N | ALA | L | 43 | 73.842 | 22.555 | −11.584 | 1.00 | 25.53 |
| ATOM | CA | ALA | L | 43 | 74.485 | 23.416 | −10.591 | 1.00 | 23.99 |
| ATOM | CB | ALA | L | 43 | 75.633 | 22.685 | −9.919 | 1.00 | 24.09 |
| ATOM | C | ALA | L | 43 | 74.976 | 24.738 | −11.178 | 1.00 | 21.59 |
| ATOM | O | ALA | L | 43 | 75.360 | 24.796 | −12.353 | 1.00 | 20.16 |
| ATOM | N | PRO | L | 44 | 74.928 | 25.829 | −10.377 | 1.00 | 18.22 |
| ATOM | CD | PRO | L | 44 | 74.263 | 25.938 | −9.068 | 1.00 | 14.64 |
| ATOM | CA | PRO | L | 44 | 75.379 | 27.152 | −10.834 | 1.00 | 18.30 |
| ATOM | CB | PRO | L | 44 | 75.067 | 28.053 | −9.637 | 1.00 | 16.73 |
| ATOM | CG | PRO | L | 44 | 73.859 | 27.389 | −9.035 | 1.00 | 15.24 |
| ATOM | C | PRO | L | 44 | 76.872 | 27.159 | −11.169 | 1.00 | 19.43 |
| ATOM | O | PRO | L | 44 | 77.649 | 26.404 | −10.573 | 1.00 | 18.33 |

TABLE 2-continued

| | | Atom A.A. Type | | | X | Y | Z | Occ | B |
|---|---|---|---|---|---|---|---|---|---|
| ATOM | N | LYS | L | 45 | 77.238 | 27.955 | −12.174 | 1.00 | 18.18 |
| ATOM | CA | LYS | L | 45 | 78.621 | 28.103 | −12.620 | 1.00 | 18.06 |
| ATOM | CB | LYS | L | 45 | 78.747 | 27.822 | −14.125 | 1.00 | 20.32 |
| ATOM | CG | LYS | L | 45 | 80.192 | 27.912 | −14.647 | 1.00 | 25.63 |
| ATOM | CD | LYS | L | 45 | 80.284 | 27.852 | −16.169 | 1.00 | 28.87 |
| ATOM | CE | LYS | L | 45 | 79.679 | 29.096 | −16.801 | 1.00 | 36.26 |
| ATOM | NZ | LYS | L | 45 | 79.705 | 29.101 | −18.297 | 1.00 | 37.77 |
| ATOM | C | LYS | L | 45 | 79.091 | 29.525 | −12.346 | 1.00 | 15.28 |
| ATOM | O | LYS | L | 45 | 78.433 | 30.493 | −12.719 | 1.00 | 13.64 |
| ATOM | N | LEU | L | 46 | 80.222 | 29.646 | −11.676 | 1.00 | 16.78 |
| ATOM | CA | LEU | L | 46 | 80.781 | 30.950 | −11.375 | 1.00 | 18.03 |
| ATOM | CB | LEU | L | 46 | 81.979 | 30.795 | −10.430 | 1.00 | 17.46 |
| ATOM | CG | LEU | L | 46 | 82.748 | 32.077 | −10.079 | 1.00 | 18.46 |
| ATOM | CD1 | LEU | L | 46 | 81.862 | 33.118 | −9.387 | 1.00 | 15.94 |
| ATOM | CD2 | LEU | L | 46 | 83.924 | 31.719 | −9.199 | 1.00 | 21.70 |
| ATOM | C | LEU | L | 46 | 81.208 | 31.666 | −12.662 | 1.00 | 17.99 |
| ATOM | O | LEU | L | 46 | 81.974 | 31.122 | −13.446 | 1.00 | 16.91 |
| ATOM | N | LEU | L | 47 | 80.703 | 32.877 | −12.880 | 1.00 | 19.12 |
| ATOM | CA | LEU | L | 47 | 81.066 | 33.661 | −14.068 | 1.00 | 21.92 |
| ATOM | CB | LEU | L | 47 | 79.830 | 34.286 | −14.736 | 1.00 | 23.03 |
| ATOM | CG | LEU | L | 47 | 78.726 | 33.442 | −15.371 | 1.00 | 24.65 |
| ATOM | CD1 | LEU | L | 47 | 77.572 | 34.351 | −15.770 | 1.00 | 23.61 |
| ATOM | CD2 | LEU | L | 47 | 79.261 | 32.674 | −16.578 | 1.00 | 22.42 |
| ATOM | C | LEU | L | 47 | 82.008 | 34.816 | −13.729 | 1.00 | 23.45 |
| ATOM | O | LEU | L | 47 | 83.011 | 35.034 | −14.404 | 1.00 | 24.27 |
| ATOM | N | ILE | L | 48 | 81.644 | 35.572 | −12.697 | 1.00 | 24.75 |
| ATOM | CA | ILE | L | 48 | 82.388 | 36.748 | −12.287 | 1.00 | 24.56 |
| ATOM | CB | ILE | L | 48 | 81.603 | 38.041 | −12.743 | 1.00 | 26.86 |
| ATOM | CG2 | ILE | L | 48 | 82.215 | 39.316 | −12.148 | 1.00 | 23.10 |
| ATOM | CG1 | ILE | L | 48 | 81.460 | 38.105 | −14.276 | 1.00 | 27.21 |
| ATOM | CD1 | ILE | L | 48 | 82.758 | 38.266 | −15.051 | 1.00 | 29.72 |
| ATOM | C | ILE | L | 48 | 82.540 | 36.814 | −10.763 | 1.00 | 27.68 |
| ATOM | O | ILE | L | 48 | 81.572 | 36.581 | −10.016 | 1.00 | 28.36 |
| ATOM | N | TYR | L | 49 | 83.749 | 37.130 | −10.304 | 1.00 | 27.66 |
| ATOM | CA | TYR | L | 49 | 84.010 | 37.313 | −8.879 | 1.00 | 26.50 |
| ATOM | CB | TYR | L | 49 | 84.961 | 36.242 | −8.338 | 1.00 | 25.78 |
| ATOM | CG | TYR | L | 49 | 86.345 | 36.242 | −8.942 | 1.00 | 27.79 |
| ATOM | CD1 | TYR | L | 49 | 87.318 | 37.147 | −8.510 | 1.00 | 27.87 |
| ATOM | CE1 | TYR | L | 49 | 88.610 | 37.122 | −9.023 | 1.00 | 26.39 |
| ATOM | CD2 | TYR | L | 49 | 86.702 | 35.308 | −9.913 | 1.00 | 28.91 |
| ATOM | CE2 | TYR | L | 49 | 87.995 | 35.275 | −10.437 | 1.00 | 29.68 |
| ATOM | CZ | TYR | L | 49 | 88.939 | 36.189 | −9.982 | 1.00 | 28.14 |
| ATOM | OH | TYR | L | 49 | 90.205 | 36.178 | −10.499 | 1.00 | 27.11 |
| ATOM | C | TYR | L | 49 | 84.608 | 38.715 | −8.710 | 1.00 | 28.04 |
| ATOM | O | TYR | L | 49 | 84.987 | 39.351 | −9.701 | 1.00 | 26.90 |
| ATOM | N | ASP | L | 50 | 84.668 | 39.203 | −7.471 | 1.00 | 27.93 |
| ATOM | CA | ASP | L | 50 | 85.228 | 40.526 | −7.166 | 1.00 | 30.07 |
| ATOM | CB | ASP | L | 50 | 86.764 | 40.450 | −7.231 | 1.00 | 32.48 |
| ATOM | OG | ASP | L | 50 | 87.455 | 41.699 | −6.684 | 1.00 | 34.53 |
| ATOM | OD1 | ASP | L | 50 | 86.809 | 42.526 | −5.994 | 1.00 | 33.00 |
| ATOM | OD2 | ASP | L | 50 | 88.669 | 41.836 | −6.955 | 1.00 | 34.56 |
| ATOM | C | ASP | L | 50 | 84.670 | 41.625 | −8.093 | 1.00 | 29.48 |
| ATOM | O | ASP | L | 50 | 85.408 | 42.469 | −8.621 | 1.00 | 28.02 |
| ATOM | N | THR | L | 51 | 83.360 | 41.563 | −8.312 | 1.00 | 28.37 |
| ATOM | CA | THR | L | 51 | 82.637 | 42.514 | −9.150 | 1.00 | 29.26 |
| ATOM | CB | THR | L | 51 | 82.819 | 43.979 | −8.642 | 1.00 | 29.35 |
| ATOM | OG1 | THR | L | 51 | 82.378 | 44.070 | −7.281 | 1.00 | 29.46 |
| ATOM | CG2 | THR | L | 51 | 82.007 | 44.957 | −9.474 | 1.00 | 26.57 |
| ATOM | C | THR | L | 51 | 82.901 | 42.458 | −10.657 | 1.00 | 29.27 |
| ATOM | O | THR | L | 51 | 81.950 | 42.407 | −11.448 | 1.00 | 28.35 |
| ATOM | N | SER | L | 52 | 84.167 | 42.388 | −11.057 | 1.00 | 29.47 |
| ATOM | CA | SER | L | 52 | 84.492 | 42.413 | −12.475 | 1.00 | 29.99 |
| ATOM | CB | SER | L | 52 | 84.959 | 43.829 | −12.841 | 1.00 | 32.61 |
| ATOM | OG | SER | L | 52 | 85.836 | 44.382 | −11.852 | 1.00 | 34.91 |
| ATOM | C | SER | L | 52 | 85.492 | 41.397 | −12.999 | 1.00 | 30.37 |
| ATOM | O | SER | L | 52 | 85.854 | 41.431 | −14.172 | 1.00 | 30.49 |
| ATOM | N | LYS | L | 53 | 85.923 | 40.472 | −12.159 | 1.00 | 30.92 |
| ATOM | CA | LYS | L | 53 | 86.898 | 39.488 | −12.603 | 1.00 | 33.14 |
| ATOM | CB | LYS | L | 53 | 87.752 | 39.014 | −11.427 | 1.00 | 35.84 |
| ATOM | CG | LYS | L | 53 | 88.815 | 40.005 | −10.988 | 1.00 | 37.91 |
| ATOM | CD | LYS | L | 53 | 89.913 | 40.093 | −12.024 | 1.00 | 41.62 |
| ATOM | CE | LYS | L | 53 | 90.774 | 41.308 | −11.779 | 1.00 | 45.49 |
| ATOM | NZ | LYS | L | 53 | 89.949 | 42.558 | −11.856 | 1.00 | 50.35 |
| ATOM | C | LYS | L | 53 | 86.273 | 38.290 | −13.281 | 2.00 | 33.94 |
| ATOM | O | LYS | L | 53 | 85.488 | 37.568 | −12.666 | 1.00 | 35.02 |
| ATOM | N | LEU | L | 54 | 86.624 | 38.076 | −14.544 | 1.00 | 33.95 |

TABLE 2-continued

| | | Atom A.A. Type | | | X | Y | Z | Occ | B |
|---|---|---|---|---|---|---|---|---|---|
| ATOM | CA | LEU | L | 54 | 86.112 | 36.934 | −15.287 | 1.00 | 35.46 |
| ATOM | CB | LEU | L | 54 | 86.500 | 37.029 | −16.770 | 1.00 | 36.70 |
| ATOM | CG | LEU | L | 54 | 85.401 | 37.137 | −17.837 | 1.00 | 37.08 |
| ATOM | CD1 | LEU | L | 54 | 85.948 | 36.771 | −19.210 | 1.00 | 33.57 |
| ATOM | CD2 | LEU | L | 54 | 84.264 | 36.216 | −17.493 | 1.00 | 36.74 |
| ATOM | C | LEU | L | 54 | 86.715 | 35.664 | −14.687 | 1.00 | 35.69 |
| ATOM | O | LEU | L | 54 | 87.932 | 35.555 | −14.545 | 1.00 | 35.01 |
| ATOM | N | ALA | L | 55 | 85.860 | 34.714 | −14.324 | 1.00 | 36.81 |
| ATOM | CA | ALA | L | 55 | 86.317 | 33.451 | −13.753 | 1.00 | 37.12 |
| ATOM | CB | ALA | L | 55 | 85.154 | 32.709 | −13.126 | 1.00 | 34.93 |
| ATOM | C | ALA | L | 55 | 86.968 | 32.609 | −14.849 | 1.00 | 38.49 |
| ATOM | O | ALA | L | 55 | 86.818 | 32.903 | −16.034 | 1.00 | 39.16 |
| ATOM | N | SER | L | 56 | 87.687 | 31.561 | −14.468 | 1.00 | 40.87 |
| ATOM | CA | SER | L | 56 | 88.356 | 30.728 | −15.461 | 1.00 | 43.84 |
| ATOM | CB | SER | L | 56 | 89.365 | 29.779 | −14.795 | 1.00 | 46.40 |
| ATOM | OG | SER | L | 56 | 88.718 | 28.774 | −14.024 | 1.00 | 50.55 |
| ATOM | C | SER | L | 56 | 87.352 | 29.937 | −16.282 | 1.00 | 44.04 |
| ATOM | O | SER | L | 56 | 86.409 | 29.359 | −15.735 | 1.00 | 44.83 |
| ATOM | N | GLY | L | 57 | 87.567 | 29.903 | −17.594 | 1.00 | 44.28 |
| ATOM | CA | GLY | L | 57 | 86.666 | 29.176 | −18.475 | 1.00 | 43.67 |
| ATOM | C | GLY | L | 57 | 85.361 | 29.904 | −18.758 | 1.00 | 42.62 |
| ATOM | O | GLY | L | 57 | 84.320 | 29.277 | −18.963 | 1.00 | 43.63 |
| ATOM | N | VAL | L | 58 | 85.405 | 31.229 | −18.758 | 1.00 | 39.62 |
| ATOM | CA | VAL | L | 58 | 84.210 | 32.012 | −19.014 | 1.00 | 38.57 |
| ATOM | CB | VAL | L | 58 | 83.758 | 32.788 | −17.742 | 1.00 | 35.08 |
| ATOM | CG1 | VAL | L | 58 | 82.474 | 33.549 | −18.020 | 1.00 | 34.33 |
| ATOM | CG2 | VAL | L | 58 | 83.553 | 31.826 | −16.585 | 1.00 | 28.89 |
| ATOM | C | VAL | L | 58 | 84.481 | 32.972 | −20.174 | 1.00 | 40.23 |
| ATOM | O | VAL | L | 58 | 85.455 | 33.716 | −20.158 | 1.00 | 40.10 |
| ATOM | N | PRO | L | 59 | 83.656 | 32.910 | −21.230 | 1.00 | 42.12 |
| ATOM | CD | PRO | L | 59 | 82.539 | 31.958 | −21.393 | 1.00 | 42.64 |
| ATOM | CA | PRO | L | 59 | 83.791 | 33.767 | −22.414 | 1.00 | 41.98 |
| ATOM | CB | PRO | L | 59 | 82.505 | 33.470 | −23.186 | 1.00 | 42.48 |
| ATOM | CG | PRO | L | 59 | 82.260 | 32.023 | −22.872 | 1.00 | 41.91 |
| ATOM | C | PRO | L | 59 | 83.896 | 35.255 | −22.083 | 1.00 | 42.11 |
| ATOM | O | PRO | L | 59 | 83.106 | 35.782 | −21.290 | 1.00 | 40.98 |
| ATOM | N | SER | L | 60 | 84.818 | 35.942 | −22.760 | 1.00 | 42.19 |
| ATOM | CA | SER | L | 60 | 85.031 | 37.376 | −22.566 | 1.00 | 42.32 |
| ATOM | CB | SER | L | 60 | 86.131 | 37.869 | −23.493 | 1.00 | 44.75 |
| ATOM | CG | SER | L | 60 | 85.777 | 37.637 | −24.846 | 1.00 | 48.53 |
| ATOM | C | SER | L | 60 | 83.756 | 38.145 | −22.867 | 1.00 | 41.50 |
| ATOM | O | SER | L | 60 | 83.689 | 39.363 | −22.684 | 1.00 | 41.56 |
| ATOM | N | ARG | L | 61 | 82.772 | 37.411 | −23.385 | 1.00 | 41.32 |
| ATOM | CA | ARG | L | 61 | 81.446 | 37.907 | −23.745 | 1.00 | 40.02 |
| ATOM | CB | ARG | L | 61 | 80.649 | 36.727 | −24.312 | 1.00 | 41.65 |
| ATOM | CG | ARG | L | 61 | 79.520 | 37.058 | −25.262 | 1.00 | 44.33 |
| ATOM | CD | ARG | L | 61 | 78.721 | 35.782 | −25.563 | 1.00 | 45.07 |
| ATOM | NE | ARG | L | 61 | 79.586 | 34.654 | −25.902 | 1.00 | 42.81 |
| ATOM | CZ | ARG | L | 61 | 79.368 | 33.400 | −25.523 | 1.00 | 41.29 |
| ATOM | NH1 | ARG | L | 61 | 78.314 | 33.096 | −24.790 | 1.00 | 39.59 |
| ATOM | NH2 | ARG | L | 61 | 80.205 | 32.442 | −25.887 | 1.00 | 42.30 |
| ATOM | C | ARG | L | 61 | 80.738 | 38.458 | −22.499 | 1.00 | 38.03 |
| ATOM | O | ARG | L | 61 | 79.912 | 39.367 | −22.583 | 1.00 | 37.15 |
| ATOM | N | PHE | L | 62 | 81.052 | 37.876 | −21.347 | 1.00 | 36.07 |
| ATOM | CA | PHE | L | 62 | 80.451 | 38.293 | −20.092 | 1.00 | 34.13 |
| ATOM | CB | PHE | L | 62 | 80.242 | 37.079 | −19.191 | 1.00 | 32.20 |
| ATOM | CG | PHE | L | 62 | 79.316 | 36.040 | −19.753 | 1.00 | 30.05 |
| ATOM | CD1 | PHE | L | 62 | 79.813 | 34.969 | −20.475 | 1.00 | 28.20 |
| ATOM | CD2 | PHE | L | 62 | 77.950 | 36.097 | −19.498 | 1.00 | 29.72 |
| ATOM | CE1 | PHE | L | 62 | 78.963 | 33.970 | −20.928 | 1.00 | 28.11 |
| ATOM | CE2 | PHE | L | 62 | 77.092 | 35.099 | −19.950 | 1.00 | 27.00 |
| ATOM | CZ | PHE | L | 62 | 77.597 | 34.038 | −20.662 | 1.00 | 24.59 |
| ATOM | C | PHE | L | 62 | 81.363 | 39.263 | −19.354 | 1.00 | 32.87 |
| ATOM | O | PHE | L | 62 | 82.579 | 39.113 | −19.382 | 1.00 | 32.64 |
| ATOM | N | SER | L | 63 | 80.782 | 40.235 | −18.670 | 1.00 | 32.15 |
| ATOM | CA | SER | L | 63 | 81.572 | 41.176 | −17.890 | 1.00 | 32.65 |
| ATOM | CB | SER | L | 63 | 82.113 | 42.318 | −18.757 | 1.00 | 32.01 |
| ATOM | OG | SER | L | 63 | 81.080 | 43.183 | −19.173 | 1.00 | 32.88 |
| ATOM | C | SER | L | 63 | 80.718 | 41.731 | −16.759 | 1.00 | 33.28 |
| ATOM | O | SER | L | 63 | 79.486 | 41.746 | −16.850 | 1.00 | 34.08 |
| ATOM | N | GLY | L | 64 | 81.377 | 42.150 | −15.682 | 1.00 | 33.66 |
| ATOM | CA | GLY | L | 64 | 80.678 | 42.695 | −14.541 | 1.00 | 30.72 |
| ATOM | C | GLY | L | 64 | 81.233 | 44.058 | −14.191 | 1.00 | 31.74 |
| ATOM | O | GLY | L | 64 | 82.415 | 44.338 | −14.403 | 1.00 | 29.96 |
| ATOM | N | SER | L | 65 | 80.368 | 44.908 | −13.653 | 1.00 | 31.35 |
| ATOM | CA | SER | L | 65 | 80.743 | 46.249 | −13.250 | 1.00 | 32.13 |

TABLE 2-continued

| | | Atom A.A. Type | | | X | Y | Z | Occ | B |
|---|---|---|---|---|---|---|---|---|---|
| ATOM | CB | SER | L | 65 | 80.579 | 47.198 | −14.427 | 1.00 | 33.39 |
| ATOM | OG | SER | L | 65 | 81.199 | 48.432 | −14.145 | 1.00 | 38.02 |
| ATOM | C | SER | L | 65 | 79.836 | 46.687 | −12.107 | 1.00 | 32.01 |
| ATOM | O | SER | L | 65 | 78.958 | 45.936 | −11.670 | 1.00 | 32.14 |
| ATOM | N | GLY | L | 66 | 80.069 | 47.883 | −11.587 | 1.00 | 32.03 |
| ATOM | CA | GLY | L | 66 | 79.229 | 48.367 | −10.514 | 1.00 | 31.82 |
| ATOM | C | GLY | L | 66 | 79.988 | 48.757 | −9.268 | 1.00 | 32.34 |
| ATOM | O | GLY | L | 66 | 81.187 | 48.499 | −9.149 | 1.00 | 33.45 |
| ATOM | N | SER | L | 67 | 79.275 | 49.387 | −8.342 | 1.00 | 33.28 |
| ATOM | CA | SER | L | 67 | 79.829 | 49.819 | −7.070 | 1.00 | 33.09 |
| ATOM | CB | SER | L | 67 | 80.853 | 50.946 | −7.281 | 1.00 | 34.89 |
| ATOM | OG | SER | L | 67 | 80.222 | 52.176 | −7.613 | 1.00 | 36.97 |
| ATOM | C | SER | L | 67 | 78.673 | 50.308 | −6.203 | 1.00 | 33.38 |
| ATOM | O | SER | L | 67 | 77.529 | 50.430 | −6.665 | 1.00 | 32.21 |
| ATOM | N | GLY | L | 68 | 78.967 | 50.573 | −4.939 | 1.00 | 34.02 |
| ATOM | CA | GLY | L | 68 | 77.946 | 51.067 | −4.043 | 1.00 | 35.08 |
| ATOM | C | GLY | L | 68 | 76.785 | 50.114 | −3.895 | 1.00 | 36.51 |
| ATOM | O | GLY | L | 68 | 76.953 | 49.014 | −3.381 | 1.00 | 37.01 |
| ATOM | N | THR | L | 69 | 75.614 | 50.526 | −4.362 | 1.00 | 38.06 |
| ATOM | CA | THR | L | 69 | 74.413 | 49.706 | −4.257 | 1.00 | 39.69 |
| ATOM | CB | THR | L | 69 | 73.238 | 50.539 | −3.709 | 1.00 | 41.73 |
| ATOM | OG1 | THR | L | 69 | 73.143 | 51.764 | −4.451 | 1.00 | 44.69 |
| ATOM | CG2 | THR | L | 69 | 73.435 | 50.853 | −2.226 | 1.00 | 43.12 |
| ATOM | C | THR | L | 69 | 73.959 | 49.053 | −5.568 | 1.00 | 39.10 |
| ATOM | O | THR | L | 69 | 73.035 | 48.239 | −5.559 | 1.00 | 40.25 |
| ATOM | N | GLU | L | 70 | 74.596 | 49.393 | −6.686 | 1.00 | 36.36 |
| ATOM | CA | GLU | L | 70 | 74.190 | 48.823 | −7.963 | 1.00 | 33.95 |
| ATOM | CB | GLU | L | 70 | 73.480 | 49.869 | −8.803 | 1.00 | 35.14 |
| ATOM | C | GLU | L | 70 | 75.331 | 48.192 | −8.749 | 1.00 | 32.26 |
| ATOM | O | GLU | L | 70 | 76.366 | 48.816 | −8.994 | 1.00 | 31.16 |
| ATOM | N | PHE | L | 71 | 75.129 | 46.939 | −9.141 | 1.00 | 30.51 |
| ATOM | CA | PHE | L | 71 | 76.125 | 46.192 | −9.885 | 1.00 | 29.00 |
| ATOM | CB | PHE | L | 71 | 76.713 | 45.102 | −8.983 | 1.00 | 25.95 |
| ATOM | CG | PHE | L | 71 | 77.425 | 45.644 | −7.766 | 1.00 | 26.50 |
| ATOM | CD1 | PHE | L | 71 | 78.818 | 45.695 | −7.718 | 1.00 | 23.83 |
| ATOM | CD2 | PHE | L | 71 | 76.704 | 46.140 | −6.681 | 1.00 | 23.86 |
| ATOM | CE1 | PHE | L | 71 | 79.472 | 46.231 | −6.615 | 1.00 | 23.12 |
| ATOM | CE2 | PHE | L | 71 | 77.360 | 46.682 | −5.574 | 1.00 | 25.02 |
| ATOM | CZ | PHE | L | 71 | 78.743 | 46.726 | −5.543 | 1.00 | 19.89 |
| ATOM | C | PHE | L | 71 | 75.440 | 45.591 | −11.103 | 1.00 | 31.37 |
| ATOM | O | PHE | L | 71 | 74.215 | 45.385 | −11.089 | 1.00 | 32.37 |
| ATOM | N | THR | L | 72 | 76.213 | 45.319 | −12.154 | 1.00 | 31.74 |
| ATOM | CA | THR | L | 72 | 75.660 | 44.756 | −13.381 | 1.00 | 31.21 |
| ATOM | CB | THR | L | 72 | 75.437 | 45.846 | −14.458 | 1.00 | 33.86 |
| ATOM | OG1 | THR | L | 72 | 76.680 | 46.488 | −14.753 | 1.00 | 34.13 |
| ATOM | CG2 | THR | L | 72 | 74.408 | 46.887 | −13.991 | 1.00 | 33.49 |
| ATOM | C | THR | L | 72 | 76.460 | 43.632 | −14.038 | 1.00 | 31.02 |
| ATOM | O | THR | L | 72 | 77.683 | 43.518 | −13.867 | 1.00 | 27.20 |
| ATOM | N | LEU | L | 73 | 75.730 | 42.792 | −14.768 | 1.00 | 29.35 |
| ATOM | CA | LEU | L | 73 | 76.297 | 41.685 | −15.521 | 1.00 | 30.38 |
| ATOM | CB | LEU | L | 73 | 75.674 | 40.341 | −15.120 | 1.00 | 28.33 |
| ATOM | CG | LEU | L | 73 | 76.122 | 39.098 | −15.913 | 1.00 | 28.85 |
| ATOM | CG1 | LEU | L | 73 | 77.598 | 38.759 | −15.662 | 1.00 | 26.27 |
| ATOM | CD2 | LEU | L | 73 | 75.221 | 37.917 | −15.559 | 1.00 | 26.75 |
| ATOM | C | LEU | L | 73 | 75.939 | 41.994 | −16.971 | 1.00 | 30.49 |
| ATOM | O | LEU | L | 73 | 74.778 | 42.295 | −17.282 | 1.00 | 29.18 |
| ATOM | N | THR | L | 74 | 76.922 | 41.896 | −17.855 | 1.00 | 30.05 |
| ATOM | CA | THR | L | 74 | 76.682 | 42.181 | −19.253 | 1.00 | 31.19 |
| ATOM | CB | THR | L | 74 | 77.270 | 43.566 | −19.662 | 1.00 | 31.37 |
| ATOM | OG1 | THR | L | 74 | 76.667 | 44.597 | −18.868 | 1.00 | 28.24 |
| ATOM | CG2 | THR | L | 74 | 77.014 | 43.849 | −21.158 | 1.00 | 30.50 |
| ATOM | C | THR | L | 74 | 77.222 | 41.106 | −20.172 | 1.00 | 29.92 |
| ATOM | O | THR | L | 74 | 78.336 | 40.621 | −20.002 | 1.00 | 28.40 |
| ATOM | N | ILE | L | 75 | 76.373 | 40.714 | −21.114 | 1.00 | 33.76 |
| ATOM | CA | ILE | L | 75 | 76.679 | 39.712 | −22.140 | 1.00 | 38.02 |
| ATOM | CB | ILE | L | 75 | 75.587 | 38.579 | −22.177 | 1.00 | 38.72 |
| ATOM | CG2 | ILE | L | 75 | 76.058 | 37.421 | −23.055 | 1.00 | 37.88 |
| ATOM | CG1 | ILE | L | 75 | 75.312 | 38.071 | −20.744 | 1.00 | 39.78 |
| ATOM | CD1 | ILE | L | 75 | 74.105 | 37.164 | −20.583 | 1.00 | 37.31 |
| ATOM | C | ILE | L | 75 | 76.635 | 40.580 | −23.406 | 1.00 | 38.55 |
| ATOM | O | ILE | L | 75 | 75.579 | 41.106 | −23.771 | 1.00 | 38.37 |
| ATOM | N | SER | L | 76 | 77.802 | 40.787 | −24.008 | 1.00 | 40.06 |
| ATOM | CA | SER | L | 76 | 77.944 | 41.651 | −25.170 | 1.00 | 42.95 |
| ATOM | CB | SER | L | 76 | 79.420 | 41.847 | −25.484 | 1.00 | 42.51 |
| ATOM | OG | SER | L | 76 | 80.107 | 40.607 | −25.441 | 1.00 | 47.98 |
| ATOM | C | SER | L | 76 | 77.173 | 41.258 | −26.418 | 1.00 | 44.99 |

TABLE 2-continued

| | | Atom A.A. Type | | | X | Y | Z | Occ | B |
|---|---|---|---|---|---|---|---|---|---|
| ATOM | O | SER | L | 76 | 76.675 | 42.128 | −27.141 | 1.00 | 47.12 |
| ATOM | N | SER | L | 77 | 77.078 | 39.961 | −26.677 | 1.00 | 43.59 |
| ATOM | CA | SER | L | 77 | 76.346 | 39.475 | −27.834 | 1.00 | 44.13 |
| ATOM | CB | SER | L | 77 | 77.226 | 39.498 | −29.075 | 1.00 | 45.12 |
| ATOM | OG | SER | L | 77 | 78.508 | 38.981 | −28.772 | 1.00 | 51.53 |
| ATOM | C | SER | L | 77 | 75.870 | 38.069 | −27.523 | 1.00 | 43.98 |
| ATOM | O | SER | L | 77 | 76.590 | 37.086 | −27.689 | 1.00 | 42.87 |
| ATOM | N | LEU | L | 78 | 74.664 | 38.012 | −26.991 | 1.00 | 43.76 |
| ATOM | CA | LEU | L | 78 | 74.010 | 36.786 | −26.591 | 1.00 | 44.13 |
| ATOM | CB | LEU | L | 78 | 72.550 | 37.110 | −26.295 | 1.00 | 45.19 |
| ATOM | CG | LEU | L | 78 | 71.735 | 36.161 | −25.433 | 1.00 | 45.72 |
| ATOM | CD1 | LEU | L | 78 | 72.357 | 36.067 | −24.054 | 1.00 | 44.08 |
| ATOM | CD2 | LEU | L | 78 | 70.315 | 36.697 | −25.359 | 1.00 | 46.47 |
| ATOM | C | LEU | L | 78 | 74.076 | 35.704 | −27.654 | 1.00 | 43.75 |
| ATOM | O | LEU | L | 78 | 74.230 | 35.988 | −28.834 | 1.00 | 45.19 |
| ATOM | N | GLN | L | 79 | 74.002 | 34.455 | −27.226 | 1.00 | 43.45 |
| ATOM | CA | GLN | L | 79 | 73.989 | 33.350 | −28.162 | 1.00 | 44.42 |
| ATOM | CB | GLN | L | 79 | 75.384 | 32.990 | −28.648 | 1.00 | 46.01 |
| ATOM | CG | GLN | L | 79 | 76.334 | 32.491 | −27.653 | 1.00 | 53.13 |
| ATOM | CD | GLN | L | 79 | 77.643 | 32.175 | −28.330 | 1.00 | 60.30 |
| ATOM | OE1 | GLN | L | 79 | 78.434 | 33.077 | −28.630 | 1.00 | 63.72 |
| ATOM | NE2 | GLN | L | 79 | 77.860 | 30.898 | −28.635 | 1.00 | 62.41 |
| ATOM | C | GLN | L | 79 | 73.229 | 32.184 | −27.551 | 1.00 | 42.80 |
| ATOM | O | GLN | L | 79 | 73.019 | 32.155 | −26.343 | 1.00 | 42.45 |
| ATOM | N | PRO | L | 80 | 72.754 | 31.238 | −28.382 | 1.00 | 42.66 |
| ATOM | CD | PRO | L | 80 | 73.022 | 31.156 | −29.831 | 1.00 | 41.71 |
| ATOM | CA | PRO | L | 80 | 71.989 | 30.064 | −27.942 | 1.00 | 40.32 |
| ATOM | CB | PRO | L | 80 | 72.141 | 29.113 | −29.123 | 1.00 | 42.49 |
| ATOM | CG | PRO | L | 80 | 72.095 | 30.051 | −30.277 | 1.00 | 42.33 |
| ATOM | C | PRO | L | 80 | 72.347 | 29.406 | −26.604 | 1.00 | 37.21 |
| ATOM | O | PRO | L | 80 | 71.466 | 29.170 | −25.774 | 1.00 | 34.11 |
| ATOM | N | ASP | L | 81 | 73.631 | 29.153 | −26.369 | 1.00 | 36.25 |
| ATOM | CA | ASP | L | 81 | 74.053 | 28.513 | −25.121 | 1.00 | 35.32 |
| ATOM | CB | ASP | L | 81 | 75.428 | 27.880 | −25.283 | 1.00 | 37.14 |
| ATOM | CG | ASP | L | 81 | 75.785 | 26.986 | −24.115 | 1.00 | 41.90 |
| ATOM | OD1 | ASP | L | 81 | 76.936 | 27.061 | −23.634 | 1.00 | 48.22 |
| ATOM | OD2 | ASP | L | 81 | 74.908 | 26.221 | −23.661 | 1.00 | 41.44 |
| ATOM | C | ASP | L | 81 | 74.031 | 29.405 | −23.879 | 1.00 | 30.85 |
| ATOM | O | ASP | L | 81 | 74.419 | 28.986 | −22.791 | 1.00 | 28.33 |
| ATOM | N | ASP | L | 82 | 73.571 | 30.636 | −24.046 | 1.00 | 30.80 |
| ATOM | CA | ASP | L | 82 | 73.497 | 31.587 | −22.943 | 1.00 | 29.65 |
| ATOM | CB | ASP | L | 82 | 73.750 | 33.011 | −23.438 | 1.00 | 29.14 |
| ATOM | CG | ASP | L | 82 | 75.183 | 33.230 | −23.872 | 1.00 | 29.25 |
| ATOM | OD1 | ASP | L | 82 | 75.430 | 34.180 | −24.636 | 1.00 | 31.44 |
| ATOM | OD2 | ASP | L | 82 | 76.067 | 32.463 | −23.438 | 1.00 | 29.20 |
| ATOM | C | ASP | L | 82 | 72.151 | 31.494 | −22.260 | 1.00 | 27.63 |
| ATOM | O | ASP | L | 82 | 71.843 | 32.270 | −21.359 | 1.00 | 27.38 |
| ATOM | N | PHE | L | 83 | 71.324 | 30.570 | −22.730 | 1.00 | 24.99 |
| ATOM | CA | PHE | L | 83 | 70.025 | 30.371 | −22.116 | 1.00 | 23.55 |
| ATOM | CB | PHE | L | 83 | 69.218 | 29.325 | −22.901 | 1.00 | 20.70 |
| ATOM | CG | PHE | L | 83 | 68.164 | 28.651 | −22.088 | 1.00 | 19.09 |
| ATOM | CG1 | PHE | L | 83 | 67.068 | 29.359 | −21.634 | 1.00 | 16.96 |
| ATOM | CD2 | PHE | L | 83 | 68.306 | 27.313 | −21.720 | 1.00 | 20.10 |
| ATOM | CE1 | PHE | L | 83 | 66.133 | 28.753 | −20.823 | 1.00 | 18.32 |
| ATOM | CE2 | PHE | L | 83 | 67.368 | 26.694 | −20.905 | 1.00 | 19.05 |
| ATOM | CZ | PHE | L | 83 | 66.282 | 27.412 | −20.455 | 1.00 | 19.06 |
| ATOM | C | PHE | L | 83 | 70.368 | 29.850 | −20.727 | 1.00 | 20.93 |
| ATOM | O | PHE | L | 83 | 71.155 | 28.921 | −20.618 | 1.00 | 22.26 |
| ATOM | N | ALA | L | 84 | 69.843 | 30.485 | −19.684 | 1.00 | 19.63 |
| ATOM | CA | ALA | L | 84 | 70.095 | 30.070 | −18.304 | 1.00 | 19.18 |
| ATOM | CB | ALA | L | 84 | 71.600 | 29.995 | −18.039 | 1.00 | 17.02 |
| ATOM | C | ALA | L | 84 | 69.483 | 31.081 | −17.357 | 1.00 | 18.18 |
| ATOM | O | ALA | L | 84 | 68.926 | 32.085 | −17.786 | 1.00 | 20.57 |
| ATOM | N | THR | L | 85 | 69.513 | 30.778 | −16.070 | 1.00 | 18.27 |
| ATOM | CA | THR | L | 85 | 69.046 | 31.733 | −15.078 | 1.00 | 18.66 |
| ATOM | CB | THR | L | 85 | 68.138 | 31.090 | −14.007 | 1.00 | 16.55 |
| ATOM | OG1 | THR | L | 85 | 66.921 | 30.664 | −14.625 | 1.00 | 19.88 |
| ATOM | CG2 | THR | L | 85 | 67.776 | 32.102 | −12.943 | 1.00 | 12.55 |
| ATOM | C | THR | L | 85 | 70.328 | 32.298 | −14.449 | 1.00 | 18.52 |
| ATOM | O | THR | L | 85 | 71.240 | 31.533 | −14.081 | 1.00 | 16.60 |
| ATOM | N | TYR | L | 86 | 70.440 | 33.625 | −14.453 | 1.00 | 17.64 |
| ATOM | CA | TYR | L | 86 | 71.598 | 34.311 | −13.895 | 1.00 | 19.24 |
| ATOM | CB | TYR | L | 86 | 72.066 | 35.426 | −14.817 | 1.00 | 18.33 |
| ATOM | CG | TYR | L | 86 | 72.555 | 34.865 | −16.118 | 1.00 | 18.76 |
| ATOM | CD1 | TYR | L | 86 | 71.673 | 34.633 | −17.172 | 1.00 | 21.98 |
| ATOM | CE1 | TYR | L | 86 | 72.111 | 34.050 | −18.360 | 1.00 | 21.65 |

TABLE 2-continued

| | | Atom A.A. Type | | | X | Y | Z | Occ | B |
|---|---|---|---|---|---|---|---|---|---|
| ATOM | CD2 | TYR | L | 86 | 73.890 | 34.502 | −16.283 | 1.00 | 15.25 |
| ATOM | CE2 | TYR | L | 86 | 74.335 | 33.923 | −17.456 | 1.00 | 18.24 |
| ATOM | CZ | TYR | L | 86 | 73.441 | 33.700 | −18.492 | 1.00 | 18.78 |
| ATOM | OH | TYR | L | 86 | 73.879 | 33.135 | −19.663 | 1.00 | 21.03 |
| ATOM | C | TYR | L | 86 | 71.303 | 34.847 | −12.519 | 1.00 | 19.80 |
| ATOM | O | TYR | L | 86 | 70.173 | 35.270 | −12.237 | 1.00 | 19.56 |
| ATOM | N | TYR | L | 87 | 72.309 | 34.760 | −11.645 | 1.00 | 19.65 |
| ATOM | CA | TYR | L | 87 | 72.180 | 35.201 | −10.259 | 1.00 | 19.63 |
| ATOM | CB | TYR | L | 87 | 72.042 | 33.995 | −9.324 | 1.00 | 17.97 |
| ATOM | CG | TYR | L | 87 | 70.802 | 33.165 | −9.522 | 1.00 | 15.59 |
| ATOM | CD1 | TYR | L | 87 | 70.854 | 31.964 | −10.233 | 1.00 | 14.99 |
| ATOM | CE1 | TYR | L | 87 | 69.746 | 31.158 | −10.356 | 1.00 | 14.07 |
| ATOM | CD2 | TYR | L | 87 | 69.596 | 33.538 | −8.945 | 1.00 | 15.68 |
| ATOM | CE2 | TYR | L | 87 | 68.466 | 32.731 | −9.058 | 1.00 | 16.41 |
| ATOM | CZ | TYR | L | 87 | 68.548 | 31.542 | −9.767 | 1.00 | 15.92 |
| ATOM | OH | TYR | L | 87 | 67.444 | 30.735 | −9.911 | 1.00 | 16.14 |
| ATOM | C | TYR | L | 87 | 73.376 | 35.984 | −9.773 | 1.00 | 19.98 |
| ATOM | O | TYR | L | 87 | 74.518 | 35.626 | −10.061 | 1.00 | 21.18 |
| ATOM | N | CYS | L | 88 | 73.117 | 37.049 | −9.030 | 1.00 | 19.62 |
| ATOM | CA | CYS | L | 88 | 742.96 | 37.811 | −8.445 | 1.00 | 20.76 |
| ATOM | C | CYS | L | 88 | 74.219 | 37.345 | −6.995 | 1.00 | 22.45 |
| ATOM | O | CYS | L | 88 | 732.87 | 36.914 | −6.448 | 1.00 | 22.65 |
| ATOM | CB | CYS | L | 88 | 73.915 | 39.305 | −8.494 | 1.00 | 20.25 |
| ATOM | SG | CYS | L | 88 | 72.419 | 39.779 | −7.595 | 1.00 | 23.98 |
| ATOM | N | PHE | L | 89 | 75.399 | 37.375 | −6.392 | 1.00 | 21.08 |
| ATOM | CA | PHE | L | 89 | 75.556 | 36.982 | −5.011 | 1.00 | 20.36 |
| ATOM | CB | PHE | L | 89 | 76.258 | 35.622 | −4.910 | 1.00 | 19.78 |
| ATOM | CG | PHE | L | 89 | 76.577 | 35.202 | −3.488 | 1.00 | 21.53 |
| ATOM | CD1 | PHE | L | 89 | 77.898 | 35.078 | −3.060 | 1.00 | 21.75 |
| ATOM | CD2 | PHE | L | 89 | 75.553 | 34.945 | −2.573 | 1.00 | 21.04 |
| ATOM | CE1 | PHE | L | 89 | 782.89 | 34.709 | −1.747 | 1.00 | 22.24 |
| ATOM | CE2 | PHE | L | 89 | 75.838 | 34.577 | −1.264 | 1.00 | 22.75 |
| ATOM | CZ | PHE | L | 89 | 77.160 | 34.459 | −0.849 | 1.00 | 22.39 |
| ATOM | C | PHE | L | 89 | 76.387 | 38.044 | −4.295 | 1.00 | 21.40 |
| ATOM | O | PHE | L | 89 | 77.455 | 38.454 | −4.784 | 1.00 | 19.17 |
| ATOM | N | GLN | L | 90 | 75.878 | 38.497 | −3.155 | 1.00 | 22.20 |
| ATOM | CA | GLN | L | 90 | 76.567 | 39.480 | −2.337 | 1.00 | 25.57 |
| ATOM | CB | GLN | L | 90 | 75.629 | 40.659 | −1.999 | 1.00 | 27.68 |
| ATOM | CG | GLN | L | 90 | 75.673 | 41.205 | −0.555 | 1.00 | 34.37 |
| ATOM | CD | GLN | L | 90 | 76.975 | 41.908 | −0.185 | 1.00 | 36.51 |
| ATOM | OE1 | GLN | L | 90 | 78.050 | 41.538 | −0.647 | 1.00 | 37.64 |
| ATOM | NE2 | GLN | L | 90 | 76.879 | 42.923 | 0.666 | 1.00 | 42.09 |
| ATOM | C | GLN | L | 90 | 77.091 | 38.771 | −1.084 | 1.00 | 24.62 |
| ATOM | O | GLN | L | 90 | 76.316 | 38.362 | −0.220 | 1.00 | 24.09 |
| ATOM | N | GLY | L | 91 | 78.405 | 38.560 | −1.045 | 1.00 | 24.26 |
| ATOM | CA | GLY | L | 91 | 79.036 | 37.915 | 0.088 | 1.00 | 25.85 |
| ATOM | C | GLY | L | 91 | 80.073 | 38.818 | 0.743 | 1.00 | 27.80 |
| ATOM | O | GLY | L | 91 | 80.845 | 38.369 | 1.590 | 1.00 | 28.54 |
| ATOM | N | SER | L | 92 | 802.01 | 40.089 | 0.354 | 1.00 | 28.11 |
| ATOM | CA | SER | L | 92 | 81.052 | 41.037 | 0.922 | 1.00 | 29.42 |
| ATOM | CB | SER | L | 92 | 81.342 | 42.170 | −0.067 | 1.00 | 27.86 |
| ATOM | OG | SER | L | 92 | 80.L72 | 42.809 | −0.525 | 1.00 | 28.57 |
| ATOM | C | SER | L | 92 | 80.628 | 41.603 | 2.279 | 1.00 | 29.98 |
| ATOM | O | SER | L | 92 | 81.464 | 42.051 | 3.053 | 1.00 | 29.20 |
| ATOM | N | GLY | L | 93 | 79.334 | 41.554 | 2.571 | 1.00 | 31.33 |
| ATOM | CA | GLY | L | 93 | 78.825 | 42.063 | 3.833 | 1.00 | 32.06 |
| ATOM | C | GLY | L | 93 | 77.548 | 41.346 | 4.230 | 1.00 | 32.98 |
| ATOM | O | GLY | L | 93 | 76.951 | 40.646 | 3.412 | 1.00 | 31.29 |
| ATOM | N | TYR | L | 94 | 77.116 | 41.524 | 5.474 | 1.00 | 34.98 |
| ATOM | CA | TYR | L | 94 | 75.907 | 40.862 | 5.956 | 1.00 | 39.24 |
| ATOM | CB | TYR | L | 94 | 76.044 | 40.534 | 7.438 | 1.00 | 41.36 |
| ATOM | CG | TYR | L | 94 | 77.141 | 39.539 | 7.743 | 1.00 | 45.93 |
| ATOM | CD1 | TYR | L | 94 | 78.125 | 39.829 | 8.691 | 1.00 | 47.27 |
| ATOM | CE1 | TYR | L | 94 | 79.121 | 38.916 | 8.996 | 1.00 | 48.93 |
| ATOM | CD2 | TYR | L | 94 | 772.87 | 38.299 | 7.102 | 1.00 | 45.87 |
| ATOM | CR2 | TYR | L | 94 | 78.183 | 37.377 | 7.400 | 1.00 | 47.29 |
| ATOM | CZ | TYR | L | 94 | 79.147 | 37.692 | 8.348 | 1.00 | 48.81 |
| ATOM | OH | TYR | L | 94 | 80.149 | 36.795 | 8.645 | 1.00 | 51.35 |
| ATOM | C | TYR | L | 94 | 74.390 | 41.606 | 5.696 | 1.00 | 39.68 |
| ATOM | O | TYR | L | 94 | 74.534 | 42.837 | 5.735 | 1.00 | 40.70 |
| ATOM | N | PRO | L | 95 | 73.516 | 40.859 | 5.375 | 1.00 | 39.57 |
| ATOM | CG | PRO | L | 95 | 72.146 | 41.409 | 5.309 | 1.00 | 40.15 |
| ATOM | CA | PRO | L | 95 | 73.503 | 39.395 | 5.249 | 1.00 | 36.54 |
| ATOM | CB | PRO | L | 95 | 72.055 | 39.050 | 5.573 | 1.00 | 36.84 |
| ATOM | CG | PRO | L | 95 | 71.308 | 40.192 | 4.948 | 1.00 | 38.59 |
| ATOM | C | PRO | L | 95 | 73.877 | 38.944 | 3.835 | 1.00 | 33.17 |

TABLE 2-continued

|  |  | Atom A.A. Type |  |  | X | Y | Z | Occ | B |
|---|---|---|---|---|---|---|---|---|---|
| ATOM | O | PRO | L | 95 | 73.645 | 39.662 | 2.863 | 1.00 | 32.32 |
| ATOM | N | PHE | L | 96 | 74.469 | 37.762 | 3.726 | 1.00 | 32.39 |
| ATOM | CA | PHE | L | 96 | 74.850 | 37.231 | 2.421 | 1.00 | 33.60 |
| ATOM | CB | PHE | L | 96 | 75.661 | 35.947 | 2.576 | 1.00 | 30.98 |
| ATOM | CG | PHE | L | 96 | 76.991 | 36.139 | 3.242 | 1.00 | 33.91 |
| ATOM | CD1 | PHE | L | 96 | 77.518 | 37.416 | 3.432 | 1.00 | 33.81 |
| ATOM | CD2 | PHE | L | 96 | 77.733 | 35.033 | 3.662 | 1.00 | 36.87 |
| ATOM | CE1 | PHE | L | 96 | 78.759 | 37.595 | 4.027 | 1.00 | 36.46 |
| ATOM | CE2 | PHE | L | 96 | 78.987 | 35.196 | 4.266 | 1.00 | 38.28 |
| ATOM | CZ | PHE | L | 96 | 79.500 | 36.481 | 4.447 | 1.00 | 37.60 |
| ATOM | C | PHE | L | 96 | 73.558 | 36.938 | 1.685 | 1.00 | 29.65 |
| ATOM | O | PHE | L | 96 | 72.661 | 36.310 | 2.241 | 1.00 | 29.87 |
| ATOM | N | THR | L | 97 | 73.447 | 37.377 | 0.442 | 1.00 | 27.80 |
| ATOM | CA | THR | L | 97 | 72.217 | 37.154 | −0.294 | 1.00 | 27.85 |
| ATOM | CB | THR | L | 97 | 71.252 | 38.356 | −0.119 | 1.00 | 31.07 |
| ATOM | OG1 | THR | L | 97 | 71.957 | 39.581 | −0.373 | 1.00 | 34.91 |
| ATOM | CG2 | THR | L | 97 | 70.670 | 38.394 | 1.283 | 1.00 | 34.02 |
| ATOM | C | THR | L | 97 | 72.421 | 36.964 | −1.780 | 1.00 | 25.56 |
| ATOM | O | THR | L | 97 | 73.385 | 37.468 | −2.354 | 1.00 | 25.97 |
| ATOM | N | PHE | L | 98 | 71.493 | 36.243 | −2.395 | 1.00 | 23.93 |
| ATOM | CA | PHE | L | 98 | 71.494 | 36.003 | −3.837 | 1.00 | 22.96 |
| ATOM | CB | PHE | L | 98 | 71.203 | 34.545 | −4.157 | 1.00 | 20.08 |
| ATOM | CG | PHE | L | 98 | 72.257 | 33.586 | −4.165 | 1.00 | 17.47 |
| ATOM | CD1 | PHE | L | 98 | 72.517 | 32.782 | −3.068 | 1.00 | 18.73 |
| ATOM | CD2 | PHE | L | 98 | 73.109 | 33.517 | −5.252 | 1.00 | 15.42 |
| ATOM | CE1 | PHE | L | 98 | 73.616 | 31.930 | −3.053 | 1.00 | 18.52 |
| ATOM | CE2 | PHE | L | 98 | 74.207 | 32.664 | −5.239 | 1.00 | 17.15 |
| ATOM | CZ | PHE | L | 98 | 74.159 | 31.874 | −4.138 | 1.00 | 16.08 |
| ATOM | C | PHE | L | 98 | 70.424 | 36.910 | −4.436 | 1.00 | 23.92 |
| ATOM | O | PHE | L | 98 | 69.522 | 37.385 | −3.734 | 1.00 | 26.57 |
| ATOM | N | GLY | L | 99 | 70.537 | 37.190 | −5.723 | 1.00 | 24.88 |
| ATOM | CA | GLY | L | 99 | 69.512 | 37.977 | −6.370 | 1.00 | 24.29 |
| ATOM | C | GLY | L | 99 | 68.379 | 37.008 | −6.685 | 1.00 | 24.25 |
| ATOM | O | GLY | L | 99 | 68.569 | 35.778 | −6.622 | 1.00 | 22.05 |
| ATOM | N | GLY | L | 100 | 67.213 | 37.553 | −7.032 | 1.00 | 22.89 |
| ATOM | CA | GLY | L | 100 | 66.059 | 36.732 | −7.357 | 1.00 | 19.67 |
| ATOM | C | GLY | L | 100 | 66.275 | 35.998 | −8.683 | 1.00 | 20.73 |
| ATOM | O | GLY | L | 100 | 65.395 | 35.082 | −8.959 | 1.00 | 18.00 |
| ATOM | N | GLY | L | 101 | 67.116 | 36.420 | −9.521 | 1.00 | 19.87 |
| ATOM | CA | GLY | L | 101 | 67.306 | 35.765 | −10.797 | 1.00 | 19.54 |
| ATOM | C | GLY | L | 101 | 66.184 | 36.508 | −12.017 | 1.00 | 20.81 |
| ATOM | O | GLY | L | 101 | 65.922 | 37.391 | −11.930 | 1.00 | 20.98 |
| ATOM | N | THR | L | 102 | 67.389 | 36.176 | −13.151 | 1.00 | 21.18 |
| ATOM | CA | THR | L | 102 | 67.038 | 36.707 | −14.459 | 1.00 | 22.07 |
| ATOM | CD | THR | L | 102 | 68.080 | 37.735 | −14.978 | 1.00 | 22.40 |
| ATOM | OG1 | THR | L | 102 | 68.114 | 38.880 | −14.116 | 1.00 | 23.14 |
| ATOM | CG2 | THR | L | 102 | 67.721 | 38.190 | −16.378 | 1.00 | 22.44 |
| ATOM | C | THR | L | 102 | 67.085 | 35.483 | −15.379 | 1.00 | 22.40 |
| ATOM | O | THR | L | 102 | 68.170 | 34.937 | −15.636 | 1.00 | 20.43 |
| ATOM | N | LYS | L | 103 | 65.913 | 34.990 | −15.782 | 1.00 | 22.47 |
| ATOM | CA | LYS | L | 103 | 65.851 | 33.843 | −16.684 | 1.00 | 23.31 |
| ATOM | CB | LYS | L | 103 | 64.583 | 33.021 | −16.478 | 1.00 | 21.12 |
| ATOM | CG | LYS | L | 103 | 64.550 | 31.824 | −17.392 | 1.00 | 22.43 |
| ATOM | CD | LYS | L | 103 | 63.660 | 30.711 | −16.876 | 1.00 | 24.88 |
| ATOM | CE | LYS | L | 103 | 63.733 | 29.481 | −17.797 | 1.00 | 23.83 |
| ATOM | NZ | LYS | L | 103 | 63.023 | 28.313 | −17.241 | 1.00 | 21.06 |
| ATOM | G | LYS | L | 103 | 65.908 | 34.396 | −18.093 | 1.00 | 25.31 |
| ATOM | O | LYS | L | 103 | 65.044 | 35.172 | −18.512 | 1.00 | 26.75 |
| ATOM | N | LEU | L | 104 | 66.930 | 33.987 | −18.824 | 1.00 | 25.69 |
| ATOM | CA | LEU | L | 104 | 67.161 | 34.469 | −20.168 | 1.00 | 27.01 |
| ATOM | CD | LEU | L | 104 | 68.650 | 34.808 | −20.298 | 1.00 | 27.67 |
| ATOM | CG | LEU | L | 104 | 69.152 | 35.661 | −21.448 | 1.00 | 27.93 |
| ATOM | CD1 | LEU | L | 104 | 68.423 | 36.985 | −21.446 | 1.00 | 29.85 |
| ATOM | CD2 | LEU | L | 104 | 70.630 | 35.881 | −21.265 | 1.00 | 29.69 |
| ATOM | C | LEU | L | 104 | 66.754 | 33.473 | −21.244 | 1.00 | 28.40 |
| ATOM | O | LEU | L | 104 | 67.285 | 32.364 | −21.301 | 1.00 | 30.35 |
| ATOM | N | GLU | L | 105 | 65.813 | 33.874 | −22.092 | 1.00 | 28.05 |
| ATOM | CA | GLU | L | 105 | 65.343 | 33.039 | −23.191 | 1.00 | 29.59 |
| ATOM | CB | GLU | L | 105 | 63.823 | 33.113 | −23.325 | 1.00 | 32.46 |
| ATOM | CG | GLU | L | 105 | 63.264 | 32.079 | −24.291 | 1.00 | 39.22 |
| ATOM | CD | GLU | L | 105 | 62.213 | 32.632 | −25.237 | 1.00 | 41.09 |
| ATOM | OE1 | GLU | L | 105 | 62.584 | 33.444 | −26.101 | 1.00 | 43.86 |
| ATOM | OE2 | GLU | L | 105 | 61.028 | 32.240 | −25.138 | 1.00 | 39.88 |
| ATOM | C | GLU | L | 105 | 65.965 | 33.593 | −24.456 | 1.00 | 28.60 |
| ATOM | O | GLU | L | 105 | 66.142 | 34.797 | −24.581 | 1.00 | 28.67 |
| ATOM | N | ILE | L | 106 | 66.272 | 32.716 | −25.399 | 1.00 | 29.12 |

TABLE 2-continued

| | | Atom A.A. Type | | | X | Y | Z | Occ | B |
|---|---|---|---|---|---|---|---|---|---|
| ATOM | CA | ILE | L | 106 | 66.870 | 33.111 | −26.670 | 1.00 | 30.41 |
| ATOM | CB | ILE | L | 106 | 68.039 | 32.149 | −27.066 | 1.00 | 30.16 |
| ATOM | CG2 | ILE | L | 106 | 68.710 | 32.616 | −28.340 | 1.00 | 32.05 |
| ATOM | CG1 | ILE | L | 106 | 69.056 | 32.011 | −25.928 | 1.00 | 29.52 |
| ATOM | CD1 | ILE | L | 106 | 69.615 | 33.317 | −25.418 | 1.00 | 30.24 |
| ATOM | C | ILE | L | 106 | 65.792 | 33.091 | −27.773 | 1.00 | 31.27 |
| ATOM | O | ILE | L | 106 | 65.043 | 32.116 | −27.916 | 1.00 | 32.16 |
| ATOM | N | LYS | L | 107 | 65.676 | 34.187 | −28.514 | 1.00 | 30.72 |
| ATOM | CA | LYS | L | 107 | 64.69B | 34.265 | −29.585 | 1.00 | 32.13 |
| ATOM | CB | LYS | L | 107 | 64.400 | 35.716 | −29.968 | 1.00 | 32.27 |
| ATOM | CG | LYS | L | 107 | 63.701 | 36.569 | −28.945 | 1.00 | 34.00 |
| ATOM | CD | LYS | L | 107 | 63.503 | 37.967 | −29.540 | 1.00 | 34.55 |
| ATOM | CE | LYS | L | 107 | 62.918 | 38.935 | −28.536 | 1.00 | 37.68 |
| ATOM | NZ | LYS | L | 107 | 61.661 | 38.391 | −27.962 | 1.00 | 40.96 |
| ATOM | C | LYS | L | 107 | 65.270 | 33.593 | −30.817 | 1.00 | 31.68 |
| ATOM | O | LYS | L | 107 | 66.462 | 33.684 | −31.074 | 1.00 | 32.74 |
| ATOM | N | ARG | L | 108 | 64.413 | 32.937 | −31.586 | 1.00 | 31.51 |
| ATOM | CA | ARG | L | 108 | 64.821 | 32.295 | −32.824 | 1.00 | 29.52 |
| ATOM | CB | ARG | L | 108 | 65.265 | 30.861 | −32.591 | 1.00 | 29.77 |
| ATOM | CG | ARG | L | 108 | 64.243 | 29.994 | −31.905 | 1.00 | 30.89 |
| ATOM | CD | ARG | L | 108 | 64.344 | 28.565 | −32.408 | 1.00 | 30.81 |
| ATOM | NE | ARG | L | 108 | 64.038 | 28.496 | −33.829 | 1.00 | 30.96 |
| ATOM | CZ | ARG | L | 108 | 64.564 | 27.618 | −34.674 | 1.00 | 31.44 |
| ATOM | NH1 | ARG | L | 108 | 65.440 | 26.716 | −34.250 | 1.00 | 27.52 |
| ATOM | NH2 | ARG | L | 108 | 64.205 | 27.646 | −35.952 | 1.00 | 29.16 |
| ATOM | C | ARG | L | 108 | 63.636 | 32.342 | −33.771 | 1.00 | 28.69 |
| ATOM | O | ARG | L | 108 | 62.572 | 32.852 | −33.421 | 1.00 | 28.53 |
| ATOM | N | THR | L | 109 | 63.832 | 31.858 | −34.985 | 1.00 | 29.11 |
| ATOM | CA | THR | L | 109 | 62.168 | 31.858 | −35.976 | 1.00 | 30.78 |
| ATOM | CB | THR | L | 109 | 63.315 | 31.518 | −37.370 | 1.00 | 32.45 |
| ATOM | OG1 | THR | L | 109 | 64.064 | 30.299 | −37.309 | 1.00 | 35.48 |
| ATOM | CG2 | THR | L | 109 | 64.223 | 32.635 | −37.874 | 1.00 | 30.66 |
| ATOM | C | THR | L | 109 | 61.693 | 30.850 | −35.595 | 1.00 | 31.46 |
| ATOM | O | THR | L | 109 | 61.937 | 29.954 | −34.795 | 1.00 | 31.24 |
| ATOM | N | VAL | L | 110 | 60.496 | 31.009 | −36.146 | 1.00 | 31.64 |
| ATOM | CA | VAL | L | 110 | 59.417 | 30.086 | −35.836 | 1.00 | 31.60 |
| ATOM | CB | VAL | L | 110 | 58.057 | 30.560 | −36.394 | 1.00 | 32.31 |
| ATOM | CG1 | VAL | L | 110 | 56.964 | 29.541 | −36.066 | 1.00 | 31.80 |
| ATOM | CG2 | VAL | L | 110 | 57.692 | 31.919 | −35.807 | 1.00 | 31.73 |
| ATOM | C | VAL | L | 110 | 59.760 | 28.722 | −36.400 | 1.00 | 30.86 |
| ATOM | O | VAL | L | 110 | 60.394 | 28.614 | −37.451 | 1.00 | 30.96 |
| ATOM | N | ALA | L | 111 | 59.434 | 27.693 | −35.634 | 1.00 | 29.60 |
| ATOM | CA | ALA | L | 111 | 59.680 | 26.318 | −36.032 | 1.00 | 28.26 |
| ATOM | CB | ALA | L | 111 | 60.901 | 25.755 | −35.316 | 1.00 | 26.88 |
| ATOM | C | ALA | L | 111 | 58.431 | 25.567 | −35.618 | 1.00 | 27.23 |
| ATOM | O | ALA | L | 111 | 57.993 | 25.646 | −34.466 | 1.00 | 25.20 |
| ATOM | N | ALA | L | 112 | 57.807 | 24.910 | −36.581 | 1.00 | 26.83 |
| ATOM | CA | ALA | L | 112 | 56.602 | 24.153 | −36.308 | 1.00 | 26.48 |
| ATOM | CB | ALA | L | 112 | 55.840 | 23.880 | −37.610 | 1.00 | 27.20 |
| ATOM | C | ALA | L | 112 | 56.943 | 22.843 | −35.606 | 1.00 | 23.94 |
| ATOM | O | ALA | L | 112 | 57.988 | 22.244 | −35.855 | 1.00 | 23.22 |
| ATOM | N | PRO | L | 113 | 56.075 | 22.409 | −34.691 | 1.00 | 22.26 |
| ATOM | CD | PRO | L | 113 | 54.924 | 23.154 | −34.147 | 1.00 | 20.36 |
| ATOM | CA | PRO | L | 113 | 56.286 | 21.161 | −33.957 | 1.00 | 23.79 |
| ATOM | CB | PRO | L | 113 | 55.244 | 21.249 | −32.838 | 1.00 | 22.36 |
| ATOM | CG | PRO | L | 113 | 54.149 | 22.066 | −33.453 | 1.00 | 23.79 |
| ATOM | C | PRO | L | 113 | 56.013 | 19.922 | −34.794 | 1.00 | 23.47 |
| ATOM | O | PRO | L | 113 | 55.136 | 19.931 | −35.655 | 1.00 | 25.95 |
| ATOM | N | SER | L | 114 | 56.769 | 18.863 | −34.535 | 1.00 | 21.45 |
| ATOM | CA | SER | L | 114 | 56.557 | 17.580 | −35.194 | 1.00 | 21.91 |
| ATOM | CB | SER | L | 114 | 57.871 | 16.823 | −35.335 | 1.00 | 24.05 |
| ATOM | OG | SER | L | 114 | 58.789 | 17.547 | −36.137 | 1.00 | 28.55 |
| ATOM | C | SER | L | 114 | 55.670 | 16.904 | −34.157 | 1.00 | 20.29 |
| ATOM | O | SER | L | 114 | 56.077 | 16.777 | −32.997 | 1.00 | 21.52 |
| ATOM | N | VAL | L | 115 | 54.463 | 16.509 | −34.552 | 1.00 | 17.56 |
| ATOM | CA | VAL | L | 115 | 53.500 | 15.914 | −33.621 | 1.00 | 17.02 |
| ATOM | CB | VAL | L | 115 | 52.110 | 16.578 | −33.810 | 1.00 | 16.79 |
| ATOM | CG1 | VAL | L | 115 | 51.120 | 16.067 | −32.800 | 1.00 | 14.41 |
| ATOM | CG2 | VAL | L | 115 | 52.244 | 18.092 | −33.709 | 1.00 | 16.01 |
| ATOM | C | VAL | L | 115 | 53.379 | 14.394 | −33.693 | 1.00 | 17.60 |
| ATOM | O | VAL | L | 115 | 53.355 | 13.818 | −34.786 | 1.00 | 20.11 |
| ATOM | N | PHE | L | 116 | 53.347 | 13.746 | −32.528 | 1.00 | 15.99 |
| ATOM | CA | PHE | L | 116 | 53.226 | 12.289 | −32.439 | 1.00 | 17.49 |
| ATOM | CB | PHE | L | 116 | 54.562 | 11.646 | −32.059 | 1.00 | 15.67 |
| ATOM | CG | PHE | L | 116 | 55.701 | 12.057 | −32.926 | 1.00 | 16.56 |
| ATOM | CD1 | PHE | L | 116 | 56.376 | 13.258 | −32.687 | 1.00 | 15.63 |

TABLE 2-continued

| | | Atom A.A. Type | | | X | Y | Z | Occ | B |
|---|---|---|---|---|---|---|---|---|---|
| ATOM | CD2 | PHE | L | 116 | 56.115 | 11.246 | −33.984 | 1.00 | 17.82 |
| ATOM | CE1 | PHE | L | 116 | 57.452 | 13.652 | −33.489 | 1.00 | 18.32 |
| ATOM | CE2 | PHE | L | 116 | 57.186 | 11.627 | −34.792 | 1.00 | 18.08 |
| ATOM | CZ | PHE | L | 116 | 57.860 | 12.839 | −34.542 | 1.00 | 17.81 |
| ATOM | C | PHE | L | 116 | 52.219 | 11.915 | −31.355 | 1.00 | 19.64 |
| ATOM | O | PHE | L | 116 | 52.139 | 12.586 | −30.321 | 1.00 | 20.26 |
| ATOM | N | ILE | L | 117 | 51.447 | 10.858 | −31.585 | 1.00 | 18.75 |
| ATOM | CA | ILE | L | 117 | 50.490 | 10.392 | −30.585 | 1.00 | 19.77 |
| ATOM | CB | ILE | L | 117 | 49.029 | 10.490 | −31.075 | 1.00 | 20.51 |
| ATOM | CG2 | ILE | L | 117 | 48.815 | 9.610 | −32.295 | 1.00 | 18.97 |
| ATOM | CG1 | ILE | L | 117 | 48.071 | 10.086 | −29.946 | 1.00 | 18.35 |
| ATOM | CG1 | ILE | L | 117 | 45.635 | 10.459 | −30.206 | 1.00 | 17.73 |
| ATOM | C | ILE | L | 117 | 50.833 | 8.941 | −30.213 | 1.00 | 20.69 |
| ATOM | O | ILE | L | 117 | 51.222 | 8.143 | −31.076 | 1.00 | 20.52 |
| ATOM | N | PHE | L | 118 | 50.741 | 8.611 | −28.929 | 1.00 | 19.61 |
| ATOM | CA | PHE | L | 118 | 51.047 | 7.262 | −28.477 | 1.00 | 17.90 |
| ATOM | CB | PHE | L | 118 | 52.268 | 7.252 | −27.557 | 1.00 | 16.09 |
| ATOM | CG | PHE | L | 118 | 53.491 | 7.832 | −28.175 | 1.00 | 18.71 |
| ATOM | CD1 | PHE | L | 118 | 53.868 | 9.141 | −27.902 | 1.00 | 18.19 |
| ATOM | CD2 | PHE | L | 118 | 54.283 | 7.069 | −29.034 | 1.00 | 17.56 |
| ATOM | CE1 | PHE | L | 118 | 55.014 | 9.686 | −28.471 | 1.00 | 19.36 |
| ATOM | CE2 | PHE | L | 118 | 55.436 | 7.613 | −29.608 | 1.00 | 20.45 |
| ATOM | CZ | PHE | L | 118 | 55.799 | 8.917 | −29.328 | 1.00 | 18.79 |
| ATOM | C | PHE | L | 118 | 49.883 | 6.662 | −27.714 | 1.00 | 18.98 |
| ATOM | O | PHE | L | 118 | 49.391 | 7.261 | −26.759 | 1.00 | 18.51 |
| ATOM | N | PRO | L | 119 | 49.363 | 5.519 | −28.193 | 1.00 | 19.68 |
| ATOM | CD | PRO | L | 119 | 49.626 | 4.897 | −29.503 | 1.00 | 19.95 |
| ATOM | CA | PRO | L | 119 | 48.254 | 4.839 | −27.527 | 1.00 | 19.86 |
| ATOM | CB | PRO | L | 119 | 47.843 | 3.789 | −28.562 | 1.00 | 16.77 |
| ATOM | CG | PRO | L | 119 | 49.099 | 3.521 | −29.297 | 1.00 | 19.18 |
| ATOM | C | PRO | L | 119 | 48.778 | 4.176 | −26.243 | 1.00 | 18.58 |
| ATOM | O | PRO | L | 119 | 49.997 | 4.040 | −26.050 | 1.00 | 15.88 |
| ATOM | N | PRO | L | 120 | 47.872 | 3.839 | −25.312 | 1.00 | 20.20 |
| ATOM | CD | PRO | L | 120 | 46.416 | 4.079 | −25.288 | 1.00 | 19.97 |
| ATOM | CA | PRO | L | 120 | 48.314 | 3.193 | −24.073 | 1.00 | 20.19 |
| ATOM | CB | PRO | L | 120 | 47.030 | 3.132 | −23.245 | 1.00 | 19.86 |
| ATOM | CG | PRO | L | 120 | 45.958 | 3.059 | −24.282 | 1.00 | 19.24 |
| ATOM | C | PRO | L | 120 | 48.826 | 1.788 | −24.393 | 1.00 | 23.23 |
| ATOM | O | PRO | L | 120 | 48.385 | 1.155 | −25.371 | 1.00 | 23.12 |
| ATOM | N | SER | L | 121 | 49.770 | 1.309 | −23.593 | 1.00 | 23.42 |
| ATOM | CA | SER | L | 121 | 50.327 | −0.018 | −23.803 | 1.00 | 21.02 |
| ATOM | CB | SER | L | 121 | 51.678 | −0.139 | −23.087 | 1.00 | 21.17 |
| ATOM | OG | SER | L | 121 | 51.545 | 0.081 | −21.687 | 1.00 | 21.28 |
| ATOM | C | SER | L | 121 | 49.346 | −1.019 | −23.229 | 1.00 | 20.91 |
| ATOM | O | SER | L | 121 | 48.540 | −0.664 | −22.356 | 1.00 | 17.96 |
| ATOM | N | ASP | L | 122 | 49.380 | −2.251 | −23.734 | 1.00 | 20.98 |
| ATOM | CA | ASP | L | 122 | 48.493 | −3.292 | −23.213 | 1.00 | 23.86 |
| ATOM | CB | ASP | L | 122 | 48.631 | −4.578 | −24.018 | 1.00 | 24.89 |
| ATOM | CG | ASP | L | 122 | 48.131 | −4.424 | −25.433 | 1.00 | 27.96 |
| ATOM | OD1 | ASP | L | 122 | 47.303 | −3.524 | −25.681 | 1.00 | 27.84 |
| ATOM | OD2 | ASP | L | 122 | 48.576 | −5.193 | −26.305 | 1.00 | 32.19 |
| ATOM | C | ASP | L | 122 | 48.845 | −3.544 | −21.757 | 1.00 | 23.60 |
| ATOM | O | ASP | L | 122 | 47.977 | −3.813 | −20.932 | 1.00 | 21.88 |
| ATOM | N | GLU | L | 123 | 50.130 | −3.411 | −21.454 | 1.00 | 23.93 |
| ATOM | CA | GLU | L | 123 | 50.642 | −3.585 | −20.109 | 1.00 | 27.91 |
| ATOM | CD | GLU | L | 123 | 52.163 | −3.426 | −20.122 | 1.00 | 32.19 |
| ATOM | CG | GLU | L | 123 | 52.830 | −3.698 | −18.791 | 1.00 | 40.41 |
| ATOM | CD | GLU | L | 123 | 54.258 | −3.194 | −18.748 | 1.00 | 47.82 |
| ATOM | OE1 | GLU | L | 123 | 55.115 | −3.894 | −18.169 | 1.00 | 53.21 |
| ATOM | OE2 | GLU | L | 123 | 54.527 | −2.092 | −19.280 | 1.00 | 51.56 |
| ATOM | C | GLU | L | 123 | 50.001 | −2.588 | −19.117 | 1.00 | 27.85 |
| ATOM | O | GLU | L | 123 | 49.575 | −2.977 | −18.019 | 1.00 | 27.68 |
| ATOM | N | GLN | L | 124 | 49.938 | −1.308 | −19.480 | 1.00 | 24.64 |
| ATOM | CA | GLN | L | 124 | 49.332 | −0.337 | −18.578 | 1.00 | 23.22 |
| ATOM | CB | GLN | L | 124 | 49.514 | 1.088 | −19.072 | 1.00 | 20.28 |
| ATOM | CG | GLN | L | 124 | 49.008 | 2.087 | −18.064 | 1.00 | 14.77 |
| ATOM | CD | GLN | L | 124 | 48.953 | 3.485 | −18.578 | 1.00 | 14.59 |
| ATOM | OE1 | GLN | L | 124 | 48.958 | 3.730 | −19.780 | 1.00 | 17.10 |
| ATOM | NE2 | GLN | L | 124 | 48.861 | 4.424 | −17.665 | 1.00 | 15.03 |
| ATOM | C | GLN | L | 124 | 47.842 | −0.597 | −18.400 | 1.00 | 25.72 |
| ATOM | O | GLN | L | 124 | 47.315 | −0.529 | −17.285 | 1.00 | 26.05 |
| ATOM | N | LEU | L | 125 | 47.155 | −0.864 | −19.504 | 1.00 | 27.91 |
| ATOM | CA | LEU | L | 125 | 45.723 | −1.132 | −19.467 | 1.00 | 30.96 |
| ATOM | CB | LEU | L | 125 | 45.219 | −1.558 | −20.847 | 1.00 | 28.53 |
| ATOM | CG | LEU | L | 125 | 45.112 | −0.447 | −21.887 | 1.00 | 27.48 |
| ATOM | CE1 | LEU | L | 125 | 44.392 | −0.998 | −23.088 | 1.00 | 28.97 |

TABLE 2-continued

| | | Atom A.A. Type | | | X | Y | Z | Occ | B |
|---|---|---|---|---|---|---|---|---|---|
| ATOM | CD2 | LEU | L | 125 | 44.352 | 0.738 | −21.318 | 1.00 | 27.09 |
| ATOM | C | LEU | L | 125 | 45.416 | −2.208 | −18.439 | 1.00 | 33.69 |
| ATOM | O | LEU | L | 125 | 44.440 | −2.107 | −17.698 | 1.00 | 34.97 |
| ATOM | N | LYS | L | 126 | 46.286 | −3.207 | −18.357 | 1.00 | 36.13 |
| ATOM | CA | LYS | L | 126 | 46.107 | −4.282 | −17.401 | 1.00 | 39.52 |
| ATOM | CB | LYS | L | 126 | 47.296 | −5.246 | −17.441 | 1.00 | 45.42 |
| ATOM | CG | LYS | L | 126 | 46.968 | −6.615 | −16.849 | 1.00 | 52.87 |
| ATOM | CD | LYS | L | 126 | 48.168 | −7.301 | −16.193 | 1.00 | 55.14 |
| ATOM | CE | LYS | L | 126 | 47.770 | −8.667 | −15.616 | 1.00 | 56.30 |
| ATOM | NZ | LYS | L | 126 | 46.588 | −8.603 | −14.695 | 1.00 | 56.59 |
| ATOM | C | LYS | L | 126 | 45.958 | −3.715 | −15.989 | 1.00 | 39.37 |
| ATOM | O | LYS | L | 126 | 45.105 | −4.170 | −15.232 | 1.00 | 40.56 |
| ATOM | N | SER | L | 127 | 46.745 | −2.686 | −15.667 | 1.00 | 38.46 |
| ATOM | CA | SER | L | 127 | 46.730 | −2.052 | −14.343 | 1.00 | 36.08 |
| ATOM | CB | SER | L | 127 | 47.994 | −1.191 | −14.125 | 1.00 | 36.59 |
| ATOM | OG | SER | L | 127 | 47.895 | 0.119 | −14.693 | 1.00 | 38.49 |
| ATOM | C | SER | L | 127 | 45.478 | −1.227 | −14.072 | 1.00 | 33.85 |
| ATOM | O | SER | L | 127 | 45.333 | −0.633 | −13.000 | 1.00 | 36.40 |
| ATOM | N | GLY | L | 128 | 44.583 | −1.166 | −15.048 | 1.00 | 31.83 |
| ATOM | CA | GLY | L | 128 | 43.354 | −0.414 | −14.865 | 1.00 | 28.09 |
| ATOM | C | GLY | L | 128 | 43.336 | 1.015 | −15.374 | 1.00 | 28.23 |
| ATOM | O | GLY | L | 128 | 42.290 | 1.666 | −15.312 | 1.00 | 27.58 |
| ATOM | N | THR | L | 129 | 44.454 | 1.513 | −15.894 | 1.00 | 26.97 |
| ATOM | CA | THR | L | 129 | 44.486 | 2.883 | −16.390 | 1.00 | 26.43 |
| ATOM | CB | THR | L | 129 | 45.222 | 3.804 | −15.424 | 1.00 | 28.39 |
| ATOM | OG1 | THR | L | 129 | 44.466 | 3.862 | −14.194 | 1.00 | 32.69 |
| ATOM | OG2 | THR | L | 129 | 45.325 | 5.214 | −15.997 | 1.00 | 29.42 |
| ATOM | C | THR | L | 129 | 45.071 | 3.015 | −17.774 | 1.00 | 23.68 |
| ATOM | O | THR | L | 129 | 45.875 | 2.192 | −18.194 | 1.00 | 25.37 |
| ATOM | N | ALA | L | 130 | 44.625 | 4.044 | −18.487 | 1.00 | 20.97 |
| ATOM | CA | ALA | L | 130 | 45.069 | 4.323 | −19.639 | 1.00 | 19.62 |
| ATOM | CB | ALA | L | 130 | 43.909 | 4.148 | −20.807 | 1.00 | 18.49 |
| ATOM | C | ALA | L | 130 | 45.637 | 5.739 | −19.961 | 1.00 | 19.53 |
| ATOM | O | ALA | L | 130 | 44.955 | 6.718 | −19.646 | 1.00 | 19.42 |
| ATOM | N | SER | L | 131 | 46.909 | 5.832 | −20.347 | 1.00 | 16.98 |
| ATOM | CA | SER | L | 131 | 47.656 | 7.114 | −20.553 | 1.00 | 16.02 |
| ATOM | CB | SER | L | 131 | 48.899 | 7.186 | −19.834 | 1.00 | 14.60 |
| ATOM | OG | SER | L | 131 | 48.729 | 7.094 | −18.434 | 1.00 | 16.28 |
| ATOM | C | SER | L | 131 | 47.760 | 7.262 | −22.048 | 1.00 | 15.07 |
| ATOM | O | SER | L | 131 | 48.211 | 6.333 | −22.708 | 1.00 | 15.64 |
| ATOM | N | VAL | L | 132 | 47.325 | 8.389 | −22.593 | 1.00 | 15.03 |
| ATOM | CA | VAL | L | 132 | 47.475 | 8.667 | −24.010 | 1.00 | 16.30 |
| ATOM | CB | VAL | L | 132 | 46.116 | 9.021 | −24.691 | 1.00 | 15.74 |
| ATOM | CG1 | VAL | L | 132 | 46.291 | 9.031 | −26.210 | 1.00 | 14.83 |
| ATOM | CG2 | VAL | L | 132 | 45.014 | 8.034 | −24.255 | 1.00 | 12.79 |
| ATOM | C | VAL | L | 132 | 48.420 | 9.861 | −24.039 | 1.00 | 16.78 |
| ATOM | O | VAL | L | 132 | 48.193 | 10.852 | −23.349 | 1.00 | 15.30 |
| ATOM | N | VAL | L | 133 | 49.601 | 9.736 | −24.796 | 1.00 | 14.90 |
| ATOM | CA | VAL | L | 133 | 50.497 | 10.786 | −24.853 | 1.00 | 16.13 |
| ATOM | CB | VAL | L | 133 | 51.901 | 10.246 | −24.396 | 1.00 | 15.26 |
| ATOM | CG1 | VAL | L | 133 | 52.953 | 11.362 | −24.412 | 1.00 | 14.56 |
| ATOM | CG2 | VAL | L | 133 | 51.794 | 9.620 | −23.018 | 1.00 | 13.03 |
| ATOM | C | VAL | L | 133 | 50.622 | 11.409 | −26.226 | 1.00 | 14.37 |
| ATOM | O | VAL | L | 133 | 50.629 | 10.721 | −27.251 | 1.00 | 13.58 |
| ATOM | N | CYS | L | 134 | 50.734 | 12.727 | −26.222 | 1.00 | 16.21 |
| ATOM | CA | CYS | L | 134 | 50.906 | 13.508 | −27.433 | 1.00 | 16.73 |
| ATOM | C | CYS | L | 134 | 52.188 | 14.309 | −27.250 | 1.00 | 17.07 |
| ATOM | O | CYS | L | 134 | 52.391 | 14.974 | −26.229 | 1.00 | 16.97 |
| ATOM | CB | CYS | L | 134 | 49.727 | 14.456 | −27.645 | 1.00 | 18.80 |
| ATOM | SG | CYS | L | 134 | 49.723 | 15.237 | −29.291 | 1.00 | 24.75 |
| ATOM | N | LEU | L | 135 | 53.075 | 14.186 | −28.216 | 1.00 | 16.87 |
| ATOM | CA | LEU | L | 135 | 54.339 | 14.872 | −28.187 | 1.00 | 17.83 |
| ATOM | CB | LEU | L | 135 | 55.458 | 13.849 | −28.433 | 1.00 | 14.08 |
| ATOM | CG | LEU | L | 135 | 56.857 | 14.414 | −28.734 | 1.00 | 16.16 |
| ATOM | CD1 | LEU | L | 135 | 57.424 | 15.070 | −27.488 | 1.00 | 13.93 |
| ATOM | CD2 | LEU | L | 135 | 57.794 | 13.329 | −29.223 | 1.00 | 14.15 |
| ATOM | C | LEU | L | 135 | 54.364 | 15.922 | −29.294 | 1.00 | 19.16 |
| ATOM | O | LEU | L | 135 | 53.898 | 15.648 | −30.401 | 1.00 | 18.16 |
| ATOM | N | LEU | L | 136 | 54.826 | 17.136 | −28.974 | 1.00 | 19.85 |
| ATOM | CA | LEU | L | 136 | 55.005 | 18.200 | −29.973 | 1.00 | 18.72 |
| ATOM | CB | LEU | L | 136 | 54.371 | 19.523 | −29.578 | 1.00 | 16.93 |
| ATOM | CG | LEU | L | 136 | 53.008 | 19.601 | −28.922 | 1.00 | 22.19 |
| ATOM | CD1 | LEU | L | 136 | 52.444 | 20.977 | −29.261 | 1.00 | 20.90 |
| ATOM | CD2 | LEU | L | 136 | 52.077 | 18.504 | −29.370 | 1.00 | 16.66 |
| ATOM | C | LEU | L | 136 | 56.494 | 18.330 | −29.821 | 1.00 | 18.78 |
| ATOM | O | LEU | L | 136 | 56.968 | 18.683 | −28.745 | 1.00 | 19.77 |

TABLE 2-continued

| | | Atom A.A. Type | | | X | Y | Z | Occ | B |
|---|---|---|---|---|---|---|---|---|---|
| ATOM | N | ASN | L | 137 | 57.231 | 18.044 | −30.878 | 1.00 | 17.88 |
| ATOM | CA | ASN | L | 137 | 58.677 | 18.051 | −30.811 | 1.00 | 17.03 |
| ATOM | CB | ASN | L | 137 | 59.198 | 16.728 | −31.408 | 1.00 | 18.02 |
| ATOM | CG | ASN | L | 137 | 60.452 | 16.198 | −30.714 | 1.00 | 19.89 |
| ATOM | OD1 | ASN | L | 137 | 60.761 | 16.559 | −29.569 | 1.00 | 21.01 |
| ATOM | ND2 | ASN | L | 137 | 61.160 | 15.309 | −31.396 | 1.00 | 17.37 |
| ATOM | C | ASN | L | 137 | 59.382 | 19.211 | −31.487 | 1.00 | 17.90 |
| ATOM | O | ASN | L | 137 | 59.030 | 19.624 | −32.601 | 1.00 | 19.36 |
| ATOM | N | ASN | L | 138 | 60.371 | 19.745 | −30.786 | 1.00 | 18.41 |
| ATOM | CA | ASN | L | 138 | 61.225 | 20.806 | −31.298 | 1.00 | 19.22 |
| ATOM | CB | ASN | L | 138 | 62.269 | 20.191 | −32.234 | 1.00 | 19.52 |
| ATOM | CG | ASN | L | 138 | 63.097 | 19.099 | −31.563 | 1.00 | 19.73 |
| ATOM | OD1 | ASN | L | 138 | 63.268 | 19.078 | −30.340 | 1.00 | 19.78 |
| ATOM | ND2 | ASN | L | 138 | 63.612 | 18.186 | −32.364 | 1.00 | 23.67 |
| ATOM | C | ASN | L | 138 | 60.576 | 21.998 | −31.987 | 1.00 | 20.58 |
| ATOM | O | ASN | L | 138 | 60.845 | 22.240 | −33.153 | 1.00 | 22.46 |
| ATOM | N | PHE | L | 139 | 59.841 | 22.811 | −31.232 | 1.00 | 21.42 |
| ATOM | CA | PHE | L | 139 | 59.142 | 23.976 | −31.777 | 1.00 | 21.68 |
| ATOM | CB | PHE | L | 139 | 57.630 | 23.775 | −31.654 | 1.00 | 18.86 |
| ATOM | CG | PHE | L | 139 | 57.128 | 23.694 | −30.227 | 1.00 | 17.94 |
| ATOM | CD1 | PHE | L | 139 | 56.634 | 24.822 | −29.582 | 1.00 | 17.65 |
| ATOM | CD2 | PHE | L | 139 | 57.081 | 22.478 | −29.556 | 1.00 | 17.82 |
| ATOM | CE1 | PHE | L | 139 | 56.091 | 24.744 | −28.299 | 1.00 | 15.73 |
| ATOM | CE2 | PHE | L | 139 | 56.540 | 22.399 | −28.272 | 1.00 | 18.39 |
| ATOM | CZ | PHE | L | 139 | 56.042 | 23.541 | −27.646 | 1.00 | 15.75 |
| ATOM | C | PHE | L | 139 | 59.902 | 25.314 | −31.137 | 1.00 | 20.62 |
| ATOM | O | PHE | L | 139 | 60.190 | 25.369 | −30.129 | 1.00 | 20.00 |
| ATOM | N | TYR | L | 140 | 59.018 | 26.390 | −31.738 | 1.00 | 21.80 |
| ATOM | CA | TYR | L | 140 | 59.239 | 27.746 | −31.232 | 1.00 | 25.88 |
| ATOM | CB | TYR | L | 140 | 60.712 | 28.166 | −31.365 | 1.00 | 28.61 |
| ATOM | CG | TYR | L | 140 | 61.014 | 29.491 | −30.677 | 1.00 | 32.85 |
| ATOM | CG1 | TYR | L | 140 | 60.690 | 30.704 | −31.285 | 1.00 | 32.88 |
| ATOM | CE1 | TYR | L | 140 | 60.943 | 31.915 | −30.648 | 1.00 | 33.51 |
| ATOM | CD2 | TYR | L | 140 | 61.607 | 29.532 | −29.408 | 1.00 | 31.57 |
| ATOM | CE2 | TYR | L | 140 | 61.866 | 30.740 | −28.772 | 1.00 | 29.63 |
| ATOM | CE | TYR | L | 140 | 61.530 | 31.922 | −29.394 | 1.00 | 31.58 |
| ATOM | OH | TYR | L | 140 | 61.766 | 33.127 | −28.777 | 1.00 | 32.96 |
| ATOM | C | TYR | L | 140 | 58.344 | 28.729 | −31.992 | 1.00 | 25.00 |
| ATOM | O | TYR | L | 140 | 58.228 | 28.649 | −33.216 | 1.00 | 26.01 |
| ATOM | N | PRO | L | 141 | 57.716 | 29.682 | −31.290 | 1.00 | 25.66 |
| ATOM | CD | PRO | L | 141 | 56.823 | 30.618 | −31.995 | 1.00 | 26.17 |
| ATOM | CA | PRO | L | 141 | 57.729 | 29.979 | −29.855 | 1.00 | 26.74 |
| ATOM | CB | PRO | L | 141 | 56.894 | 31.257 | −29.772 | 1.00 | 26.54 |
| ATOM | CG | PRO | L | 141 | 55.924 | 31.091 | −30.885 | 1.00 | 25.01 |
| ATOM | C | PRO | L | 141 | 57.149 | 28.887 | −28.972 | 1.00 | 27.91 |
| ATOM | O | PRO | L | 141 | 56.590 | 27.910 | −29.468 | 1.00 | 27.79 |
| ATOM | N | ARG | L | 142 | 57.267 | 29.086 | −27.661 | 1.00 | 28.05 |
| ATOM | CA | ARG | L | 142 | 56.781 | 28.140 | −26.660 | 1.00 | 29.58 |
| ATOM | CB | ARG | L | 142 | 57.336 | 28.500 | −25.282 | 1.00 | 32.03 |
| ATOM | CG | ARG | L | 142 | 57.042 | 27.480 | −24.205 | 1.00 | 36.16 |
| ATOM | CD | ARG | L | 142 | 57.579 | 27.937 | −22.862 | 1.00 | 43.89 |
| ATOM | NE | ARG | L | 142 | 56.887 | 27.256 | −21.769 | 1.00 | 52.50 |
| ATOM | CZ | ARG | L | 142 | 55.698 | 27.622 | −21.285 | 1.00 | 56.42 |
| ATOM | NH1 | ARG | L | 142 | 55.061 | 28.684 | −21.787 | 1.00 | 57.72 |
| ATOM | NH2 | ARG | L | 142 | 55.115 | 26.889 | −20.337 | 1.00 | 56.76 |
| ATOM | C | ARG | L | 142 | 55.264 | 27.995 | −26.579 | 1.00 | 29.52 |
| ATOM | O | ARG | L | 142 | 54.771 | 26.935 | −26.189 | 1.00 | 31.05 |
| ATOM | N | GLU | L | 143 | 54.523 | 29.044 | −26.925 | 1.00 | 27.77 |
| ATOM | CA | GLU | L | 143 | 53.064 | 28.994 | −26.878 | 1.00 | 29.28 |
| ATOM | CB | GLU | L | 143 | 52.461 | 30.381 | −27.143 | 1.00 | 33.40 |
| ATOM | CG | GLU | L | 143 | 51.192 | 30.739 | −26.316 | 1.00 | 43.31 |
| ATOM | CD | GLU | L | 143 | 49.989 | 29.789 | −26.518 | 1.00 | 49.45 |
| ATOM | OE1 | GLU | L | 143 | 49.242 | 29.944 | −27.521 | 1.00 | 5L.48 |
| ATOM | OE2 | GLU | L | 143 | 49.767 | 28.909 | −25.643 | 1.00 | 51.44 |
| ATOM | CG | GLU | L | 143 | 52.529 | 27.985 | −27.900 | 1.00 | 28.06 |
| ATOM | O | GLU | L | 143 | 52.854 | 28.036 | −29.094 | 1.00 | 27.27 |
| ATOM | N | ALA | L | 144 | 51.722 | 27.054 | −27.419 | 1.00 | 26.94 |
| ATOM | CA | ALA | L | 144 | 51.138 | 26.036 | −28.272 | 1.00 | 28.67 |
| ATOM | CB | ALA | L | 144 | 52.129 | 24.898 | −28.509 | 1.00 | 25.66 |
| ATOM | C | ALA | L | 144 | 49.514 | 25.527 | −27.546 | 1.00 | 29.63 |
| ATOM | O | ALA | L | 144 | 49.903 | 25.442 | −26.311 | 1.00 | 30.81 |
| ATOM | N | LYS | L | 145 | 48.860 | 25.259 | −28.307 | 1.00 | 30.65 |
| ATOM | CA | LYS | L | 145 | 47.623 | 24.756 | −27.734 | 1.00 | 30.11 |
| ATOM | CB | LYS | L | 145 | 46.446 | 25.673 | −28.075 | 1.00 | 33.51 |
| ATOM | CG | LYS | L | 145 | 45.168 | 25.314 | −27.333 | 1.00 | 38.19 |
| ATOM | CD | LYS | L | 145 | 44.013 | 25.039 | −28.287 | 1.00 | 44.45 |

TABLE 2-continued

| | | Atom A.A. Type | | | X | Y | Z | Occ | B |
|---|---|---|---|---|---|---|---|---|---|
| ATOM | CE | LYS | L | 145 | 43.662 | 26.272 | −29.116 | 1.00 | 45.04 |
| ATOM | NZ | LYS | L | 145 | 42.426 | 26.059 | −29.917 | 1.00 | 45.43 |
| ATOM | C | LYS | L | 145 | 47.362 | 23.357 | −28.251 | 1.00 | 28.14 |
| ATOM | O | LYS | L | 145 | 47.377 | 23.103 | −29.461 | 1.00 | 26.62 |
| ATOM | N | VAL | L | 146 | 47.171 | 22.437 | −27.325 | 1.00 | 28.70 |
| ATOM | CA | VAL | L | 146 | 46.907 | 21.065 | −27.690 | 1.00 | 30.08 |
| ATOM | CB | VAL | L | 146 | 48.104 | 20.097 | −27.325 | 1.00 | 30.21 |
| ATOM | CG1 | VAL | L | 146 | 49.130 | 20.784 | −26.451 | 1.00 | 30.48 |
| ATOM | CG2 | VAL | L | 146 | 47.606 | 18.807 | −26.701 | 1.00 | 29.81 |
| ATOM | C | VAL | L | 146 | 45.593 | 20.657 | −27.057 | 1.00 | 29.32 |
| ATOM | O | VAL | L | 146 | 45.391 | 20.831 | −25.860 | 1.00 | 29.58 |
| ATOM | N | GLN | L | 147 | 44.661 | 20.233 | −27.902 | 1.00 | 30.06 |
| ATOM | CA | GLN | L | 147 | 43.346 | 19.802 | −27.455 | 1.00 | 30.42 |
| ATOM | CB | GLN | L | 147 | 42.236 | 20.636 | −28.113 | 1.00 | 35.67 |
| ATOM | CG | GLN | L | 147 | 42.091 | 22.049 | −27.550 | 1.00 | 40.36 |
| ATOM | CD | GLN | L | 147 | 40.817 | 22.745 | −28.005 | 1.00 | 43.14 |
| ATOM | CE1 | GLN | L | 147 | 39.992 | 23.141 | −27.186 | 1.00 | 43.76 |
| ATOM | NE2 | GLN | L | 147 | 40.856 | 22.903 | −29.314 | 1.00 | 43.31 |
| ATOM | C | GLN | L | 147 | 43.117 | 18.330 | −27.745 | 1.00 | 28.02 |
| ATOM | O | GLN | L | 147 | 43.417 | 17.837 | −28.838 | 1.00 | 25.81 |
| ATOM | N | TRP | L | 148 | 42.622 | 17.624 | −26.742 | 1.00 | 25.59 |
| ATOM | CA | TRP | L | 148 | 42.333 | 16.213 | −26.882 | 1.00 | 25.12 |
| ATOM | CB | TRP | L | 148 | 42.574 | 15.493 | −25.573 | 1.00 | 23.52 |
| ATOM | CG | TRP | L | 148 | 44.015 | 15.322 | −25.266 | 1.00 | 22.59 |
| ATOM | CD2 | TRP | L | 148 | 44.870 | 14.282 | −25.753 | 1.00 | 21.52 |
| ATOM | CE2 | TRP | L | 148 | 46.114 | 14.439 | −25.122 | 1.00 | 17.40 |
| ATOM | CE3 | TRP | L | 148 | 44.898 | 13.226 | −26.660 | 1.00 | 21.73 |
| ATOM | CD1 | TRP | L | 148 | 44.760 | 16.063 | −24.401 | 1.00 | 19.92 |
| ATOM | NE1 | TRP | L | 148 | 46.020 | 15.532 | −24.304 | 1.00 | 18.98 |
| ATOM | CZ2 | TRP | L | 148 | 47.185 | 13.579 | −25.359 | 1.00 | 19.15 |
| ATOM | CZ3 | TRP | L | 148 | 45.767 | 12.372 | −26.900 | 1.00 | 19.55 |
| ATOM | CH2 | TRP | L | 148 | 46.993 | 12.555 | −26.249 | 1.00 | 17.26 |
| ATOM | C | TRP | L | 148 | 40.897 | 16.050 | −27.267 | 1.00 | 27.24 |
| ATOM | O | TRP | L | 148 | 40.021 | 16.706 | −26.704 | 1.00 | 29.09 |
| ATOM | N | LYS | L | 149 | 40.842 | 15.170 | −28.218 | 1.00 | 27.78 |
| ATOM | CA | LYS | L | 149 | 39.286 | 14.927 | −28.655 | 1.00 | 28.56 |
| ATOM | CB | LYS | L | 149 | 39.065 | 15.540 | −30.043 | 1.00 | 33.33 |
| ATOM | CG | LYS | L | 149 | 39.014 | 17.083 | −30.049 | 1.00 | 40.99 |
| ATOM | CD | LYS | L | 149 | 39.056 | 17.665 | −31.460 | 1.00 | 45.80 |
| ATOM | CE | LYS | L | 149 | 40.413 | 17.409 | −32.118 | 1.00 | 50.94 |
| ATOM | NZ | LYS | L | 149 | 40.478 | 17.798 | −33.568 | 1.00 | 52.55 |
| ATOM | C | LYS | L | 149 | 39.064 | 13.431 | −28.673 | 1.00 | 27.65 |
| ATOM | O | LYS | L | 149 | 39.836 | 12.686 | −29.274 | 1.00 | 26.68 |
| ATOM | N | VAL | L | 150 | 38.064 | 12.979 | −27.932 | 1.00 | 28.55 |
| ATOM | CA | VAL | L | 150 | 37.736 | 11.555 | −27.890 | 1.00 | 30.17 |
| ATOM | CB | VAL | L | 150 | 37.694 | 11.019 | −26.437 | 1.00 | 29.56 |
| ATOM | CG1 | VAL | L | 150 | 37.346 | 9.542 | −26.446 | 1.00 | 31.46 |
| ATOM | CG2 | VAL | L | 150 | 39.049 | 11.233 | −25.747 | 1.00 | 28.62 |
| ATOM | C | VAL | L | 150 | 36.376 | 11.403 | −28.584 | 1.00 | 32.05 |
| ATOM | O | VAL | L | 150 | 35.356 | 11.919 | −28.106 | 1.00 | 31.85 |
| ATOM | N | ASP | L | 151 | 36.380 | 10.737 | −29.736 | 1.00 | 33.92 |
| ATOM | CA | ASP | L | 151 | 35.177 | 10.553 | −30.555 | 1.00 | 34.55 |
| ATOM | CB | ASP | L | 151 | 34.146 | 9.661 | −29.863 | 1.00 | 34.11 |
| ATOM | CG | ASP | L | 151 | 34.488 | 8.190 | −29.982 | 1.00 | 35.60 |
| ATOM | OD1 | ASP | L | 151 | 35.120 | 7.820 | −30.992 | 1.00 | 34.60 |
| ATOM | OD2 | ASP | L | 151 | 34.129 | 7.405 | −29.076 | 1.00 | 38.15 |
| ATOM | C | ASP | L | 151 | 34.601 | 11.916 | −30.912 | 1.00 | 34.81 |
| ATOM | O | ASP | L | 151 | 33.396 | 12.141 | −30.887 | 1.00 | 35.02 |
| ATOM | N | ASN | L | 152 | 35.513 | 12.837 | −31.189 | 1.00 | 34.49 |
| ATOM | CA | ASN | L | 152 | 35.190 | 14.191 | −31.574 | 1.00 | 35.32 |
| ATOM | CB | ASN | L | 152 | 34.202 | 14.168 | −32.734 | 1.00 | 39.44 |
| ATOM | CG | ASN | L | 152 | 34.735 | 13.365 | −33.910 | 1.00 | 44.85 |
| ATOM | OD1 | ASN | L | 152 | 34.762 | 12.136 | −33.877 | 1.00 | 46.35 |
| ATOM | ND2 | ASN | L | 152 | 35.233 | 14.059 | −34.922 | 1.00 | 48.06 |
| ATOM | C | ASN | L | 152 | 34.729 | 15.076 | −30.435 | 1.00 | 33.57 |
| ATOM | O | ASN | L | 152 | 34.545 | 16.275 | −30.619 | 1.00 | 36.79 |
| ATOM | N | ALA | L | 153 | 34.614 | 14.506 | −29.243 | 1.00 | 31.08 |
| ATOM | CA | ALA | L | 153 | 34.207 | 15.266 | −28.073 | 1.00 | 28.26 |
| ATOM | CB | ALA | L | 153 | 33.481 | 14.371 | −27.116 | 1.00 | 28.75 |
| ATOM | C | ALA | L | 153 | 35.439 | 15.875 | −27.403 | 1.00 | 28.92 |
| ATOM | O | ALA | L | 153 | 36.384 | 15.155 | −27.053 | 1.00 | 26.45 |
| ATOM | N | LEU | L | 154 | 35.422 | 17.195 | −27.221 | 1.00 | 29.49 |
| ATOM | CA | LEU | L | 154 | 36.532 | 17.924 | −26.606 | 1.00 | 30.90 |
| ATOM | CB | LEU | L | 154 | 36.386 | 19.416 | −26.835 | 1.00 | 33.24 |
| ATOM | CG | LEU | L | 154 | 37.433 | 20.289 | −26.146 | 1.00 | 36.75 |
| ATOM | CD1 | LEU | L | 154 | 38.831 | 19.982 | −26.665 | 1.00 | 38.15 |

TABLE 2-continued

|  | Atom | A.A. Type |  |  | X | Y | Z | Occ | B |
|---|---|---|---|---|---|---|---|---|---|
| ATOM | CD2 | LEU | L | 154 | 37.086 | 21.748 | −26.380 | 1.00 | 39.59 |
| ATOM | C | LEU | L | 154 | 36.645 | 17.642 | −25.117 | 1.00 | 31.55 |
| ATOM | O | LEU | L | 154 | 35.690 | 17.838 | −24.362 | 1.00 | 31.00 |
| ATOM | N | GLN | L | 155 | 37.840 | 17.209 | −24.713 | 1.00 | 31.11 |
| ATOM | CA | GLN | L | 155 | 38.151 | 16.846 | −23.336 | 1.00 | 28.18 |
| ATOM | CB | GLN | L | 155 | 39.328 | 15.878 | −23.317 | 1.00 | 25.72 |
| ATOM | CG | GLN | L | 155 | 39.079 | 14.638 | −24.112 | 1.00 | 23.68 |
| ATOM | CD | GLN | L | 155 | 37.881 | 13.888 | −23.604 | 1.00 | 25.63 |
| ATOM | OE1 | GLN | L | 155 | 37.975 | 13.140 | −22.639 | 1.00 | 26.96 |
| ATOM | NE2 | GLN | L | 155 | 36.737 | 14.094 | −24.237 | 1.00 | 25.22 |
| ATOM | C | GLN | L | 155 | 38.485 | 18.050 | −22.492 | 1.00 | 29.16 |
| ATOM | O | GLN | L | 155 | 39.007 | 19.047 | −22.995 | 1.00 | 28.96 |
| ATOM | N | SER | L | 156 | 38.231 | 17.931 | −21.196 | 1.00 | 29.53 |
| ATOM | CA | SER | L | 156 | 38.498 | 19.015 | −20.273 | 1.00 | 30.80 |
| ATOM | CB | SER | L | 156 | 37.260 | 19.914 | −20.143 | 1.00 | 34.66 |
| ATOM | OG | SER | L | 156 | 36.60 | 20.429 | −21.409 | 1.00 | 43.01 |
| ATOM | C | SER | L | 156 | 38.838 | 18.467 | −18.907 | 1.00 | 29.08 |
| ATOM | O | SER | L | 156 | 38.103 | 17.641 | −18.368 | 1.00 | 29.54 |
| ATOM | N | GLY | L | 157 | 39.972 | 18.901 | −18.368 | 1.00 | 28.54 |
| ATOM | CA | GLY | L | 157 | 40.372 | 18.490 | −17.038 | 1.00 | 26.39 |
| ATOM | C | GLY | L | 157 | 40.936 | 17.101 | −16.850 | 1.00 | 26.37 |
| ATOM | O | GLY | L | 157 | 41.120 | 16.671 | −15.715 | 1.00 | 29.38 |
| ATOM | N | ASN | L | 158 | 41.216 | 16.385 | −17.928 | 1.00 | 23.45 |
| ATOM | CA | ASN | L | 158 | 41.770 | 15.049 | −17.777 | 1.00 | 21.09 |
| ATOM | CB | ASN | L | 158 | 40.764 | 13.989 | −18.244 | 1.00 | 19.33 |
| ATOM | CG | ASN | L | 158 | 40.216 | 14.252 | −19.630 | 1.00 | 17.19 |
| ATOM | OG1 | ASN | L | 158 | 40.588 | 15.213 | −20.302 | 1.00 | 18.35 |
| ATOM | ND2 | ASN | L | 158 | 39.331 | 13.387 | −20.066 | 1.00 | 18.99 |
| ATOM | C | ASN | L | 158 | 43.136 | 14.867 | −18.440 | 1.00 | 19.26 |
| ATOM | O | ASN | L | 158 | 43.534 | 13.753 | −18.767 | 1.00 | 21.16 |
| ATOM | N | SER | L | 159 | 43.874 | 15.959 | −18.600 | 1.00 | 18.71 |
| ATOM | CA | SER | L | 159 | 45.187 | 15.890 | −19.218 | 1.00 | 20.76 |
| ATOM | CB | SER | L | 159 | 45.077 | 16.188 | −20.714 | 1.00 | 18.72 |
| ATOM | OG | SER | L | 159 | 44.532 | 17.477 | −20.945 | 1.00 | 20.62 |
| ATOM | C | SER | L | 159 | 46.131 | 16.882 | −18.553 | 1.00 | 23.10 |
| ATOM | O | SER | L | 159 | 45.685 | 17.868 | −17.957 | 1.00 | 24.15 |
| ATOM | N | GLN | L | 160 | 47.427 | 16.585 | −18.592 | 1.00 | 21.31 |
| ATOM | CA | GLN | L | 160 | 48.442 | 17.471 | −18.021 | 1.00 | 21.04 |
| ATOM | CB | GLN | L | 160 | 49.069 | 16.879 | −16.736 | 1.00 | 23.45 |
| ATOM | OG | GLN | L | 160 | 48.154 | 16.872 | −15.510 | 1.00 | 27.10 |
| ATOM | CD | GLN | L | 160 | 48.835 | 16.394 | −14.231 | 1.00 | 28.51 |
| ATOM | GE1 | GLN | L | 160 | 49.047 | 15.187 | −14.036 | 1.00 | 24.70 |
| ATOM | NE2 | GLN | L | 160 | 49.135 | 17.334 | −13.329 | 1.00 | 25.84 |
| ATOM | C | GLN | L | 160 | 49.532 | 17.659 | −19.066 | 1.00 | 20.99 |
| ATOM | O | GLN | L | 160 | 49.863 | 16.734 | −19.816 | 1.00 | 21.59 |
| ATOM | N | GLU | L | 161 | 50.098 | 18.853 | −19.124 | 1.00 | 20.61 |
| ATOM | CA | GLU | L | 161 | 51.172 | 19.106 | −20.072 | 1.00 | 20.46 |
| ATOM | CB | GLU | L | 161 | 50.901 | 20.359 | −20.890 | 1.00 | 20.91 |
| ATOM | CG | GLU | L | 161 | 49.611 | 20.349 | −21.674 | 1.00 | 24.55 |
| ATOM | CD | GLU | L | 161 | 49.542 | 21.528 | −22.619 | 1.00 | 26.26 |
| ATOM | OE1 | GLU | L | 161 | 50.300 | 22.486 | −22.485 | 1.00 | 29.28 |
| ATOM | OE2 | GLU | L | 161 | 48.648 | 21.497 | −23.507 | 1.00 | 28.66 |
| ATOM | C | GLU | L | 161 | 52.476 | 19.303 | −19.328 | 1.00 | 19.83 |
| ATOM | O | GLU | L | 161 | 52.493 | 19.602 | −18.134 | 1.00 | 20.07 |
| ATOM | N | SER | L | 162 | 53.569 | 19.107 | −20.036 | 1.00 | 17.23 |
| ATOM | CA | SER | L | 162 | 54.865 | 19.323 | −19.455 | 1.00 | 17.53 |
| ATOM | CB | SER | L | 162 | 55.447 | 18.035 | −18.889 | 1.00 | 14.42 |
| ATOM | OG | SER | L | 162 | 56.762 | 18.252 | −18.431 | 1.00 | 18.03 |
| ATOM | C | SER | L | 162 | 55.709 | 19.870 | −20.579 | 1.00 | 16.58 |
| ATOM | O | SER | L | 162 | 55.655 | 19.376 | −21.705 | 1.00 | 17.04 |
| ATOM | N | VAL | L | 163 | 56.386 | 20.975 | −20.311 | 1.00 | 19.21 |
| ATOM | CA | VAL | L | 163 | 57.226 | 21.568 | −21.323 | 1.00 | 18.37 |
| ATOM | CB | VAL | L | 163 | 56.819 | 23.039 | −21.669 | 1.00 | 18.75 |
| ATOM | CG1 | VAL | L | 163 | 56.923 | 23.931 | −20.442 | 2.00 | 20.07 |
| ATOM | CG2 | VAL | L | 163 | 57.696 | 23.590 | −22.802 | 1.00 | 13.07 |
| ATOM | C | VAL | L | 163 | 58.686 | 21.463 | −20.921 | 1.00 | 19.06 |
| ATOM | O | VAL | L | 163 | 59.071 | 21.541 | −19.744 | 1.00 | 16.78 |
| ATOM | N | THR | L | 164 | 59.484 | 21.211 | −21.936 | 1.00 | 18.83 |
| ATOM | CA | THR | L | 164 | 60.915 | 21.063 | −21.827 | 1.00 | 19.31 |
| ATOM | CE | THR | L | 164 | 61.331 | 20.278 | −23.114 | 1.00 | 19.43 |
| ATOM | OG1 | THR | L | 164 | 61.683 | 18.919 | −22.809 | 1.00 | 22.69 |
| ATOM | CG2 | THR | L | 164 | 62.355 | 20.966 | −23.872 | 1.00 | 16.60 |
| ATOM | C | THR | L | 164 | 61.579 | 22.474 | −21.698 | 1.00 | 19.84 |
| ATOM | O | THR | L | 164 | 60.976 | 23.506 | −22.053 | 1.00 | 17.28 |
| ATOM | N | GLU | L | 165 | 62.756 | 22.535 | −21.083 | 1.00 | 19.36 |

TABLE 2-continued

|  |  | Atom A.A. Type |  |  | X | Y | Z | Occ | B |
|---|---|---|---|---|---|---|---|---|---|
| ATOM | CA | GLU | L | 165 | 63.471 | 23.800 | −20.983 | 1.00 | 19.55 |
| ATOM | CB | GLU | L | 165 | 64.575 | 23.736 | −19.925 | 1.00 | 23.79 |
| ATOM | CG | GLU | L | 165 | 64.076 | 23.813 | −18.473 | 1.00 | 31.50 |
| ATOM | CD | GLU | L | 165 | 63.482 | 25.178 | −18.114 | 1.00 | 38.33 |
| ATOM | OE1 | GLU | L | 165 | 64.068 | 26.216 | −18.506 | 1.00 | 42.53 |
| ATOM | OE2 | GLU | L | 165 | 62.426 | 25.220 | −17.441 | 1.00 | 42.33 |
| ATOM | C | GLU | L | 165 | 64.063 | 24.052 | −22.364 | 1.00 | 17.91 |
| ATOM | O | GLU | L | 165 | 64.328 | 23.115 | −23.111 | 1.00 | 16.78 |
| ATOM | N | GLN | L | 166 | 64.261 | 25.311 | −22.715 | 1.00 | 19.48 |
| ATOM | CA | GLN | L | 166 | 64.794 | 25.653 | −24.030 | 1.00 | 22.17 |
| ATOM | CB | GLN | L | 166 | 65.000 | 27.162 | −24.135 | 1.00 | 23.76 |
| ATOM | CG | GLN | L | 166 | 65.302 | 27.660 | −25.525 | 1.00 | 22.40 |
| ATOM | CD | GLN | L | 166 | 65.300 | 29.163 | −25.585 | 1.00 | 24.53 |
| ATOM | OE1 | GLN | L | 166 | 65.665 | 29.834 | −24.615 | 1.00 | 23.40 |
| ATOM | NE2 | GLN | L | 166 | 64.862 | 29.710 | −26.710 | 1.00 | 22.79 |
| ATOM | C | GLN | L | 166 | 66.082 | 24.923 | −24.354 | 1.00 | 22.88 |
| ATOM | O | GLN | L | 166 | 66.968 | 24.829 | −23.514 | 1.00 | 23.51 |
| ATOM | N | ASP | L | 167 | 66.277 | 24.395 | −25.570 | 1.00 | 24.27 |
| ATOM | CA | ASP | L | 167 | 67.363 | 23.665 | −25.995 | 1.00 | 24.79 |
| ATOM | CB | ASP | L | 167 | 67.086 | 22.929 | −27.307 | 1.00 | 25.67 |
| ATOM | CG | ASP | L | 167 | 68.201 | 21.975 | −27.691 | 1.00 | 26.79 |
| ATOM | OD1 | ASP | L | 167 | 68.072 | 20.765 | −27.439 | 1.00 | 29.58 |
| ATOM | OD2 | ASP | L | 167 | 69.206 | 22.429 | −28.260 | 1.00 | 28.02 |
| ATOM | C | ASP | L | 167 | 68.528 | 24.647 | −26.147 | 1.00 | 25.55 |
| ATOM | O | ASP | L | 167 | 68.392 | 25.708 | −26.753 | 1.00 | 23.48 |
| ATOM | N | SER | L | 168 | 69.675 | 24.277 | −25.597 | 1.00 | 27.95 |
| ATOM | CA | SER | L | 168 | 70.860 | 25.120 | −25.625 | 1.00 | 29.28 |
| ATOM | CB | SER | L | 168 | 71.831 | 24.670 | −24.531 | 1.00 | 28.03 |
| ATOM | OG | SER | L | 168 | 71.341 | 24.844 | −23.243 | 1.00 | 28.54 |
| ATOM | C | SER | L | 168 | 71.554 | 25.200 | −26.987 | 1.00 | 31.24 |
| ATOM | O | SER | L | 168 | 72.477 | 25.993 | −27.164 | 1.00 | 33.45 |
| ATOM | N | LYS | L | 169 | 71.122 | 24.369 | −27.935 | 1.00 | 32.30 |
| ATOM | CA | LYS | L | 169 | 71.692 | 24.370 | −29.287 | 1.00 | 32.24 |
| ATOM | CB | LYS | L | 169 | 71.975 | 22.947 | −29.796 | 1.00 | 33.42 |
| ATOM | CG | LYS | L | 169 | 73.305 | 22.207 | −29.102 | 1.00 | 41.01 |
| ATOM | CD | LYS | L | 169 | 72.677 | 21.620 | −27.743 | 1.00 | 50.52 |
| ATOM | CE | LYS | L | 169 | 71.807 | 20.369 | −27.899 | 1.00 | 53.08 |
| ATOM | NZ | LYS | L | 169 | 70.996 | 20.036 | −26.688 | 1.00 | 53.75 |
| ATOM | C | LYS | L | 169 | 70.744 | 25.064 | −30.261 | 1.00 | 31.01 |
| ATOM | O | LYS | L | 169 | 71.098 | 26.081 | −30.867 | 1.00 | 30.68 |
| ATOM | N | ASP | L | 170 | 69.534 | 24.522 | −30.407 | 1.00 | 28.81 |
| ATOM | CA | ASP | L | 170 | 68.577 | 25.097 | −31.337 | 1.00 | 25.15 |
| ATOM | CB | ASP | L | 170 | 67.953 | 24.024 | −32.229 | 1.00 | 26.91 |
| ATOM | CG | ASP | L | 170 | 67.157 | 22.996 | −31.460 | 1.00 | 28.83 |
| ATOM | OD1 | ASP | L | 170 | 66.590 | 23.320 | −30.406 | 1.00 | 30.B3 |
| ATOM | OD2 | ASP | L | 170 | 67.082 | 21.846 | −31.927 | 1.00 | 33.97 |
| ATOM | C | ASP | L | 170 | 67.515 | 26.027 | −30.786 | 1.00 | 25.54 |
| ATOM | O | ASP | L | 170 | 66.600 | 26.397 | −31.512 | 1.00 | 25.89 |
| ATOM | N | SER | L | 171 | 67.607 | 26.368 | −29.504 | 1.00 | 24.11 |
| ATOM | CA | SER | L | 171 | 66.662 | 27.300 | −28.878 | 1.00 | 25.64 |
| ATOM | CB | SER | L | 171 | 66.966 | 28.712 | −29.391 | 1.00 | 25.56 |
| ATOM | OG | SER | L | 171 | 68.371 | 28.936 | −29.352 | 1.00 | 28.30 |
| ATOM | C | SER | L | 171 | 65.175 | 26.947 | −29.074 | 1.00 | 23.90 |
| ATOM | O | SER | L | 171 | 64.279 | 27.800 | −29.011 | 1.00 | 25.67 |
| ATOM | N | THR | L | 172 | 64.929 | 25.653 | −29.168 | 1.00 | 23.05 |
| ATOM | CA | THR | L | 172 | 63.609 | 25.103 | −29.394 | 1.00 | 22.83 |
| ATOM | CB | THR | L | 172 | 63.769 | 24.085 | −30.562 | 1.00 | 24.46 |
| ATOM | OG1 | THR | L | 172 | 62.989 | 24.482 | −31.695 | 1.00 | 28.40 |
| ATOM | CG2 | THR | L | 172 | 63.498 | 22.695 | −30.140 | 1.00 | 18.05 |
| ATOM | C | THR | L | 172 | 63.030 | 24.465 | −28.099 | 1.00 | 23.36 |
| ATOM | O | THR | L | 172 | 63.743 | 24.308 | −27.094 | 1.00 | 20.90 |
| ATOM | N | TYR | L | 173 | 61.735 | 24.141 | −28.123 | 1.00 | 23.45 |
| ATOM | CA | TYR | L | 173 | 61.033 | 23.508 | −26.999 | 1.00 | 21.92 |
| ATOM | CB | TYR | L | 173 | 59.935 | 24.431 | −26.453 | 1.00 | 22.23 |
| ATOM | CG | TYR | L | 173 | 60.430 | 25.740 | −25.917 | 1.00 | 24.83 |
| ATOM | CD1 | TYR | L | 173 | 61.023 | 25.808 | −24.664 | 1.00 | 25.38 |
| ATOM | CE1 | TYR | L | 173 | 61.483 | 26.991 | −24.161 | 1.00 | 24.43 |
| ATOM | CD2 | TYR | L | 173 | 60.311 | 26.912 | −26.659 | 1.00 | 25.09 |
| ATOM | CE2 | TYR | L | 173 | 60.774 | 28.115 | −26.160 | 1.00 | 26.35 |
| ATOM | CZ | TYR | L | 173 | 61.559 | 28.143 | −24.903 | 1.00 | 25.86 |
| ATOM | OH | TYR | L | 173 | 61.799 | 29.324 | −24.366 | 1.00 | 26.61 |
| ATOM | C | TYR | L | 173 | 60.325 | 22.231 | −27.463 | 1.00 | 20.70 |
| ATOM | O | TYR | L | 173 | 60.063 | 22.049 | −28.648 | 1.00 | 18.08 |
| ATOM | N | SER | L | 174 | 60.025 | 21.354 | −26.515 | 1.00 | 18.47 |
| ATOM | CA | SER | L | 174 | 59.275 | 20.134 | −26.785 | 1.00 | 17.88 |
| ATOM | CB | SER | L | 174 | 60.178 | 18.904 | −26.831 | 1.00 | 15.91 |

TABLE 2-continued

| | | Atom A.A. Type | | | X | Y | Z | Occ | B |
|---|---|---|---|---|---|---|---|---|---|
| ATOM | OG | SER | L | 174 | 60.833 | 18.848 | −28.095 | 1.00 | 17.19 |
| ATOM | C | SER | L | 174 | 58.212 | 20.047 | −25.692 | 1.00 | 17.46 |
| ATOM | O | SER | L | 174 | 58.445 | 20.462 | −24.555 | 1.00 | 16.26 |
| ATOM | N | LEU | L | 175 | 57.035 | 19.548 | −26.036 | 1.00 | 17.03 |
| ATOM | CA | LEU | L | 175 | 55.952 | 19.487 | −25.076 | 1.00 | 17.80 |
| ATOM | CB | LEU | L | 175 | 54.352 | 20.613 | −25.378 | 1.00 | 16.17 |
| ATOM | CG | LEU | L | 175 | 53.705 | 20.835 | −24.513 | 1.00 | 19.25 |
| ATOM | CD1 | LEU | L | 175 | 53.316 | 22.301 | −24.587 | 1.00 | 19.61 |
| ATOM | CD2 | LEU | L | 175 | 52.537 | 19.964 | −24.943 | 1.00 | 18.86 |
| ATOM | C | LEU | L | 175 | 55.233 | 18.154 | −25.138 | 1.00 | 18.23 |
| ATOM | O | LEU | L | 175 | 55.153 | 17.549 | −26.207 | 1.00 | 18.92 |
| ATOM | N | SER | L | 176 | 54.150 | 17.691 | −23.985 | 1.00 | 17.34 |
| ATOM | CA | SER | L | 176 | 53.983 | 16.460 | −23.912 | 1.00 | 16.51 |
| ATOM | CB | SER | L | 176 | 54.722 | 15.383 | −23.107 | 1.00 | 16.81 |
| ATOM | OG | SER | L | 176 | 54.108 | 15.643 | −21.710 | 1.00 | 18.80 |
| ATOM | C | SER | L | 176 | 52.648 | 16.785 | −23.236 | 1.00 | 18.21 |
| ATOM | O | SER | L | 176 | 52.599 | 17.593 | −22.291 | 1.00 | 17.16 |
| ATOM | N | SER | L | 177 | 51.563 | 16.269 | −23.804 | 1.00 | 16.60 |
| ATOM | CA | SER | L | 177 | 50.242 | 16.426 | −23.221 | 1.00 | 15.84 |
| ATOM | CB | SER | L | 177 | 49.266 | 17.107 | −24.170 | 1.00 | 17.29 |
| ATOM | OG | SER | L | 177 | 47.980 | 17.148 | −23.580 | 1.00 | 18.53 |
| ATOM | C | SER | L | 177 | 49.830 | 14.986 | −22.963 | 1.00 | 16.07 |
| ATOM | O | SER | L | 177 | 49.953 | 14.120 | −23.843 | 1.00 | 15.65 |
| ATOM | N | THR | L | 178 | 49.399 | 14.706 | −21.740 | 1.00 | 15.55 |
| ATOM | CA | THR | L | 178 | 49.039 | 13.355 | −21.395 | 1.00 | 14.30 |
| ATOM | CB | THR | L | 178 | 50.000 | 12.811 | −20.331 | 1.00 | 15.61 |
| ATOM | OG1 | THR | L | 178 | 51.350 | 12.944 | −20.813 | 1.00 | 15.71 |
| ATOM | CG2 | THR | L | 178 | 49.686 | 11.333 | −20.008 | 1.00 | 15.89 |
| ATOM | C | THR | L | 178 | 47.626 | 13.286 | −20.905 | 1.00 | 16.11 |
| ATOM | O | THR | L | 178 | 47.253 | 14.017 | −19.981 | 1.00 | 14.99 |
| ATOM | N | LEU | L | 179 | 46.843 | 12.431 | −21.562 | 1.00 | 16.21 |
| ATOM | CA | LEU | L | 179 | 45.428 | 12.195 | −21.247 | 1.00 | 17.85 |
| ATOM | CB | LEU | L | 179 | 44.639 | 12.046 | −22.551 | 1.00 | 16.22 |
| ATOM | CG | LEU | L | 179 | 43.152 | 11.701 | −22.489 | 1.00 | 16.81 |
| ATOM | CD1 | LEU | L | 179 | 42.374 | 12.854 | −21.907 | 1.00 | 15.95 |
| ATOM | CD2 | LEU | L | 179 | 42.664 | 11.397 | −23.890 | 1.00 | 17.04 |
| ATOM | C | LEU | L | 179 | 45.305 | 10.909 | −20.424 | 1.00 | 19.34 |
| ATOM | O | LEU | L | 179 | 45.805 | 9.862 | −20.843 | 1.00 | 19.74 |
| ATOM | N | THR | L | 180 | 44.686 | 10.984 | −19.245 | 1.00 | 19.39 |
| ATOM | CA | THR | L | 180 | 44.528 | 9.800 | −18.402 | 1.00 | 20.40 |
| ATOM | CB | THR | L | 180 | 45.074 | 10.010 | −16.980 | 1.00 | 21.84 |
| ATOM | OG1 | THR | L | 180 | 46.378 | 10.611 | −17.036 | 1.00 | 22.46 |
| ATOM | CG2 | THR | L | 180 | 45.181 | 8.668 | −16.261 | 1.00 | 20.50 |
| ATOM | C | THR | L | 180 | 43.061 | 9.406 | −18.294 | 1.00 | 23.01 |
| ATOM | O | THR | L | 180 | 42.192 | 10.237 | −17.975 | 1.00 | 21.76 |
| ATOM | N | LEU | L | 181 | 42.797 | 8.132 | −18.553 | 1.00 | 23.18 |
| ATOM | CA | LEU | L | 181 | 41.456 | 7.579 | −18.503 | 1.00 | 24.23 |
| ATOM | CB | LEU | L | 181 | 40.928 | 7.330 | −19.917 | 1.00 | 25.07 |
| ATOM | CG | LEU | L | 181 | 40.619 | 8.578 | −20.729 | 1.00 | 26.14 |
| ATOM | CD1 | LEU | L | 181 | 40.168 | 8.204 | −22.132 | 1.00 | 28.53 |
| ATOM | CD2 | LEU | L | 181 | 39.545 | 9.361 | −19.998 | 1.00 | 30.01 |
| ATOM | C | LEU | L | 181 | 41.504 | 6.256 | −17.784 | 1.00 | 24.92 |
| ATOM | O | LEU | L | 181 | 42.558 | 5.637 | −17.691 | 1.00 | 25.25 |
| ATOM | N | SER | L | 182 | 40.364 | 5.848 | −17.237 | 1.00 | 27.27 |
| ATOM | CA | SER | L | 182 | 40.250 | 4.567 | −16.563 | 1.00 | 25.98 |
| ATOM | CB | SER | L | 182 | 38.940 | 4.502 | −15.780 | 1.00 | 28.54 |
| ATOM | OG | SER | L | 182 | 37.810 | 4.674 | −16.630 | 1.00 | 27.58 |
| ATOM | C | SER | L | 182 | 40.176 | 3.594 | −17.715 | 1.00 | 26.31 |
| ATOM | O | SER | L | 182 | 39.793 | 3.991 | −18.826 | 1.00 | 25.06 |
| ATOM | N | LYS | L | 183 | 40.556 | 2.341 | −17.477 | 1.00 | 25.27 |
| ATOM | CA | LYS | L | 183 | 40.489 | 1.336 | −18.526 | 1.00 | 29.03 |
| ATOM | CB | LYS | L | 183 | 40.914 | −0.032 | −17.992 | 1.00 | 30.64 |
| ATOM | CG | LYS | L | 183 | 40.694 | −1.155 | −18.969 | 1.00 | 32.86 |
| ATOM | CD | LYS | L | 183 | 41.393 | −2.411 | −18.519 | 1.00 | 38.66 |
| ATOM | CE | LYS | L | 183 | 41.157 | −3.533 | −19.526 | 1.00 | 43.79 |
| ATOM | NZ | LYS | L | 183 | 42.049 | −4.722 | −19.316 | 1.00 | 50.95 |
| ATOM | C | LYS | L | 183 | 39.049 | 1.276 | −19.027 | 1.00 | 31.27 |
| ATOM | O | LYS | L | 183 | 38.800 | 1.120 | −20.227 | 1.00 | 32.73 |
| ATOM | N | ALA | L | 184 | 38.110 | 1.419 | −18.093 | 1.00 | 32.33 |
| ATOM | CA | ALA | L | 184 | 36.683 | 1.402 | −18.389 | 1.00 | 32.00 |
| ATOM | CB | ALA | L | 184 | 35.885 | 1.598 | −17.112 | 1.00 | 32.27 |
| ATOM | C | ALA | L | 184 | 36.316 | 2.476 | −19.395 | 1.00 | 31.78 |
| ATOM | O | ALA | L | 184 | 35.759 | 2.179 | −20.453 | 1.00 | 34.22 |
| ATOM | N | ASP | L | 185 | 36.660 | 3.719 | −19.086 | 1.00 | 31.26 |
| ATOM | CA | ASP | L | 185 | 36.335 | 4.827 | −19.976 | 1.00 | 33.90 |
| ATOM | CB | ASP | L | 185 | 36.558 | 6.151 | −19.268 | 1.00 | 38.89 |

TABLE 2-continued

| | | Atom A.A. Type | | | X | Y | Z | Occ | B |
|---|---|---|---|---|---|---|---|---|---|
| ATOM | CG | ASP | L | 185 | 35.528 | 6.392 | −18.184 | 1.00 | 45.46 |
| ATOM | OD1 | ASP | L | 185 | 34.316 | 6.444 | −18.507 | 1.00 | 48.98 |
| ATOM | OD2 | ASP | L | 185 | 35.919 | 6.493 | −17.006 | 1.00 | 50.41 |
| ATOM | C | ASP | L | 185 | 37.042 | 4.801 | −21.315 | 1.00 | 32.24 |
| ATOM | O | ASP | L | 185 | 36.468 | 5.185 | −22.333 | 1.00 | 31.83 |
| ATOM | N | TYR | L | 186 | 38.283 | 4.327 | −21.311 | 1.00 | 31.61 |
| ATOM | CA | TYR | L | 186 | 39.078 | 4.226 | −22.520 | 1.00 | 28.14 |
| ATOM | CB | TYR | L | 186 | 40.493 | 3.754 | −22.174 | 1.00 | 24.69 |
| ATOM | CG | TYR | L | 186 | 41.352 | 3.542 | −23.390 | 1.00 | 21.62 |
| ATOM | CD1 | TYR | L | 186 | 41.837 | 4.623 | −24.114 | 1.00 | 22.76 |
| ATOM | CE1 | TYR | L | 186 | 42.592 | 4.437 | −25.250 | 1.00 | 20.71 |
| ATOM | CD2 | TYR | L | 186 | 41.652 | 2.260 | −23.841 | 1.00 | 20.70 |
| ATOM | CE2 | TYR | L | 186 | 42.411 | 2.064 | −24.981 | 1.00 | 20.68 |
| ATOM | CZ | TYR | L | 186 | 42.874 | 3.164 | −25.673 | 1.00 | 20.70 |
| ATOM | OH | TYR | L | 186 | 43.646 | 2.996 | −26.787 | 1.00 | 26.48 |
| ATOM | C | TYR | L | 186 | 38.420 | 3.256 | −23.500 | 1.00 | 30.06 |
| ATOM | O | TYR | L | 186 | 38.380 | 3.506 | −24.708 | 1.00 | 27.70 |
| ATOM | N | GLU | L | 187 | 37.885 | 2.157 | −22.973 | 1.00 | 33.21 |
| ATOM | CA | GLU | L | 187 | 37.236 | 1.147 | −23.803 | 1.00 | 35.81 |
| ATOM | CB | GLU | L | 187 | 37.307 | −0.211 | −23.122 | 1.00 | 37.97 |
| ATOM | CG | GLU | L | 187 | 38.738 | −0.704 | −23.053 | 1.00 | 43.63 |
| ATOM | CD | GLU | L | 187 | 38.909 | −1.895 | −22.158 | 1.00 | 47.42 |
| ATOM | OE1 | GLU | L | 187 | 39.179 | −2.736 | −22.466 | 1.00 | 49.65 |
| ATOM | OE2 | GLU | L | 187 | 38.185 | −1.984 | −21.143 | 1.00 | 50.40 |
| ATOM | C | GLU | L | 187 | 35.816 | 1.495 | −24.207 | 1.00 | 35.32 |
| ATOM | O | GLU | L | 187 | 35.171 | 0.766 | −24.948 | 1.00 | 35.82 |
| ATOM | N | LYS | L | 188 | 35.361 | 2.650 | −23.747 | 1.00 | 36.88 |
| ATOM | CA | LYS | L | 188 | 34.034 | 3.159 | −24.049 | 1.00 | 36.72 |
| ATOM | CB | LYS | L | 188 | 33.581 | 4.028 | −22.867 | 1.00 | 40.35 |
| ATOM | CG | LYS | L | 188 | 32.390 | 4.606 | −22.957 | 1.00 | 48.51 |
| ATOM | CD | LYS | L | 188 | 31.859 | 5.399 | −21.684 | 1.00 | 55.80 |
| ATOM | CE | LYS | L | 188 | 30.375 | 5.811 | −21.620 | 1.00 | 58.80 |
| ATOM | NZ | LYS | L | 188 | 29.969 | 6.745 | −22.711 | 1.00 | 61.10 |
| ATOM | C | LYS | L | 188 | 34.121 | 4.004 | −25.333 | 1.00 | 35.19 |
| ATOM | O | LYS | L | 188 | 33.099 | 4.440 | −25.875 | 1.00 | 33.77 |
| ATOM | N | HIS | L | 189 | 35.338 | 4.222 | −25.832 | 1.00 | 31.64 |
| ATOM | CA | HIS | L | 189 | 35.517 | 5.062 | −27.014 | 1.00 | 30.51 |
| ATOM | CB | HIS | L | 189 | 35.936 | 6.465 | −26.585 | 1.00 | 31.61 |
| ATOM | CG | HIS | L | 189 | 35.092 | 7.012 | −25.479 | 1.00 | 33.55 |
| ATOM | CD2 | HIS | L | 189 | 35.356 | 7.192 | −24.162 | 1.00 | 34.11 |
| ATOM | ND1 | HIS | L | 189 | 33.766 | 7.340 | −25.652 | 1.00 | 33.12 |
| ATOM | CE1 | HIS | L | 189 | 33.246 | 7.690 | −24.489 | 1.00 | 34.25 |
| ATOM | NE2 | HIS | L | 189 | 34.190 | 7.608 | −23.570 | 1.00 | 35.58 |
| ATOM | C | HIS | L | 189 | 36.447 | 4.525 | −28.081 | 1.00 | 29.17 |
| ATOM | O | HIS | L | 189 | 37.263 | 3.650 | −27.821 | 1.00 | 26.39 |
| ATOM | N | LYS | L | 190 | 36.310 | 5.087 | −29.283 | 1.00 | 30.68 |
| ATOM | CA | LYS | L | 190 | 37.075 | 4.672 | −30.455 | 1.00 | 32.94 |
| ATOM | CB | LYS | L | 190 | 36.120 | 4.481 | −31.650 | 1.00 | 36.49 |
| ATOM | CG | LYS | L | 190 | 36.776 | 4.064 | −32.983 | 1.00 | 39.14 |
| ATOM | CD | LYS | L | 190 | 37.615 | 2.800 | −32.838 | 1.00 | 41.61 |
| ATOM | CE | LYS | L | 190 | 36.773 | 1.619 | −32.404 | 1.00 | 43.23 |
| ATOM | NZ | LYS | L | 190 | 37.611 | 0.436 | −32.111 | 1.00 | 44.23 |
| ATOM | C | LYS | L | 190 | 38.240 | 5.571 | −30.867 | 1.00 | 31.98 |
| ATOM | O | LYS | L | 190 | 39.395 | 5.159 | −30.759 | 1.00 | 32.68 |
| ATOM | N | VAL | L | 191 | 37.956 | 6.776 | −31.363 | 1.00 | 29.70 |
| ATOM | CA | VAL | L | 191 | 39.040 | 7.635 | −31.805 | 1.00 | 27.93 |
| ATOM | CB | VAL | L | 191 | 38.770 | 8.312 | −33.177 | 1.00 | 27.89 |
| ATOM | CG1 | VAL | L | 191 | 37.581 | 7.663 | −33.876 | 1.00 | 30.46 |
| ATOM | CG2 | VAL | L | 191 | 38.601 | 9.791 | −33.042 | 1.00 | 30.08 |
| ATOM | C | VAL | L | 191 | 39.569 | 8.620 | −30.783 | 1.00 | 25.97 |
| ATOM | O | VAL | L | 191 | 38.816 | 9.303 | −30.081 | 1.00 | 25.01 |
| ATOM | N | TYR | L | 192 | 40.891 | 8.605 | −30.668 | 1.00 | 25.08 |
| ATOM | CA | TYR | L | 192 | 41.644 | 9.461 | −29.756 | 1.00 | 21.91 |
| ATOM | CB | TYR | L | 192 | 42.505 | 8.596 | −28.825 | 1.00 | 19.53 |
| ATOM | CG | TYR | L | 192 | 41.653 | 7.806 | −27.853 | 1.00 | 20.50 |
| ATOM | CD1 | TYR | L | 192 | 41.307 | 8.349 | −26.619 | 1.00 | 21.28 |
| ATOM | CE1 | TYR | L | 192 | 40.415 | 7.714 | −25.773 | 1.00 | 20.30 |
| ATOM | CD2 | TYR | L | 192 | 41.082 | 6.575 | −28.211 | 1.00 | 22.35 |
| ATOM | CE2 | TYR | L | 192 | 40.176 | 5.930 | −27.359 | 1.00 | 21.21 |
| ATOM | CZ | TYR | L | 192 | 39.853 | 6.517 | −26.144 | 1.00 | 23.15 |
| ATOM | OH | TYR | L | 192 | 38.963 | 5.935 | −25.280 | 1.00 | 26.13 |
| ATOM | C | TYR | L | 192 | 42.478 | 10.352 | −30.665 | 1.00 | 19.39 |
| ATOM | O | TYR | L | 192 | 43.240 | 9.869 | −31.490 | 1.00 | 16.16 |
| ATOM | N | ALA | L | 193 | 42.243 | 11.652 | −30.574 | 1.00 | 17.37 |
| ATOM | CA | ALA | L | 193 | 42.925 | 12.609 | −31.416 | 1.00 | 1.38 |
| ATOM | CB | ALA | L | 193 | 41.951 | 13.200 | −32.422 | 1.00 | 14.68 |

TABLE 2-continued

|  |  | Atom | A.A. Type |  | X | Y | Z | Occ | B |
|---|---|---|---|---|---|---|---|---|---|
| ATOM | C | ALA | L | 193 | 43.546 | 13.714 | −30.591 | 1.00 | 19.81 |
| ATOM | O | ALA | L | 193 | 42.991 | 14.144 | −29.568 | 1.00 | 19.87 |
| ATOM | N | CYS | L | 194 | 44.721 | 14.143 | −31.029 | 1.00 | 19.00 |
| ATOM | CA | CYS | L | 194 | 45.446 | 15.212 | −30.390 | 1.00 | 20.02 |
| ATOM | C | CYS | L | 194 | 45.533 | 16.306 | −31.451 | 1.00 | 22.09 |
| ATOM | O | CYS | L | 194 | 46.104 | 16.099 | −32.526 | 1.00 | 23.10 |
| ATOM | CB | CYS | L | 194 | 46.836 | 14.736 | −29.982 | 1.00 | 20.62 |
| ATOM | SG | CYS | L | 194 | 47.887 | 16.076 | −29.359 | 1.00 | 27.82 |
| ATOM | N | GLU | L | 195 | 44.897 | 17.438 | −31.198 | 1.00 | 21.48 |
| ATOM | CA | GLU | L | 195 | 44.922 | 18.522 | −32.155 | 1.00 | 26.37 |
| ATOM | CB | GLU | L | 195 | 43.508 | 19.070 | −32.380 | 1.00 | 30.62 |
| ATOM | CG | GLU | L | 195 | 43.452 | 20.166 | −33.425 | 1.00 | 39.13 |
| ATOM | CD | GLU | L | 195 | 42.043 | 20.556 | −33.786 | 1.00 | 46.06 |
| ATOM | OE1 | GLU | L | 195 | 41.281 | 20.924 | −32.866 | 1.00 | 49.26 |
| ATOM | OE2 | GLU | L | 195 | 41.697 | 20.467 | −34.992 | 1.00 | 50.81 |
| ATOM | C | GLU | L | 195 | 45.870 | 19.607 | −31.669 | 1.00 | 25.13 |
| ATOM | O | GLU | L | 195 | 45.711 | 20.140 | −30.571 | 1.00 | 24.45 |
| ATOM | N | VAL | L | 196 | 46.825 | 19.965 | −32.519 | 1.00 | 24.78 |
| ATOM | CA | VAL | L | 196 | 47.839 | 20.960 | −32.187 | 1.00 | 26.26 |
| ATOM | CB | VAL | L | 196 | 49.255 | 20.369 | −32.373 | 1.00 | 23.55 |
| ATOM | CG1 | VAL | L | 196 | 50.325 | 21.443 | −32.160 | 1.00 | 23.61 |
| ATOM | CG2 | VAL | L | 196 | 49.454 | 19.172 | −31.429 | 1.00 | 20.96 |
| ATOM | C | VAL | L | 196 | 47.749 | 22.271 | −32.965 | 1.00 | 28.29 |
| ATOM | O | VAL | L | 196 | 47.776 | 22.287 | −34.200 | 1.00 | 28.62 |
| ATOM | N | THR | L | 197 | 47.664 | 23.369 | −32.225 | 1.00 | 28.72 |
| ATOM | CA | THR | L | 197 | 47.612 | 24.694 | −32.820 | 1.00 | 31.05 |
| ATOM | CB | THR | L | 197 | 46.441 | 25.524 | −32.232 | 1.00 | 30.50 |
| ATOM | OG1 | THR | L | 197 | 45.202 | 24.869 | −32.519 | 1.00 | 31.44 |
| ATOM | CG2 | THR | L | 197 | 46.399 | 26.909 | −32.834 | 1.00 | 30.89 |
| ATOM | C | THR | L | 197 | 48.952 | 25.356 | −32.472 | 1.00 | 32.18 |
| ATOM | O | THR | L | 197 | 49.396 | 25.309 | −31.313 | 1.00 | 31.68 |
| ATOM | N | HIS | L | 198 | 49.612 | 25.938 | −33.468 | 1.00 | 32.23 |
| ATOM | CA | HIS | L | 198 | 50.884 | 26.602 | −33.225 | 1.00 | 32.28 |
| ATOM | CB | HIS | L | 198 | 52.018 | 25.577 | −33.141 | 1.00 | 31.15 |
| ATOM | CG | HIS | L | 198 | 53.331 | 26.168 | −32.727 | 1.00 | 30.40 |
| ATOM | CD2 | HIS | L | 198 | 53.626 | 26.466 | −31.500 | 1.00 | 29.70 |
| ATOM | ND1 | HIS | L | 198 | 54.299 | 26.545 | −33.635 | 1.00 | 27.78 |
| ATOM | CE1 | HIS | L | 198 | 55.332 | 27.052 | −32.984 | 1.00 | 29.10 |
| ATOM | NE2 | HIS | L | 198 | 55.071 | 27.014 | −31.688 | 1.00 | 28.06 |
| ATOM | C | HIS | L | 198 | 51.186 | 27.622 | −34.313 | 1.00 | 33.18 |
| ATOM | O | HIS | L | 198 | 50.840 | 27.421 | −35.471 | 1.00 | 33.74 |
| ATOM | N | GLN | L | 199 | 51.877 | 28.691 | −33.933 | 1.00 | 35.27 |
| ATOM | CA | GLN | L | 199 | 52.247 | 29.767 | −34.846 | 1.00 | 36.38 |
| ATOM | CB | GLN | L | 199 | 53.225 | 30.727 | −34.156 | 1.00 | 37.34 |
| ATOM | CG | GLN | L | 199 | 53.508 | 31.989 | −34.964 | 1.00 | 43.51 |
| ATOM | CD | GLN | L | 199 | 54.222 | 33.074 | −34.174 | 1.00 | 45.57 |
| ATOM | OE1 | GLN | L | 199 | 54.997 | 33.848 | −34.733 | 1.00 | 47.22 |
| ATOM | NE2 | GLN | L | 199 | 53.943 | 33.153 | −32.879 | 1.00 | 46.45 |
| ATOM | C | GLN | L | 199 | 52.833 | 29.255 | −36.162 | 1.00 | 35.85 |
| ATOM | O | GLN | L | 199 | 52.477 | 29.725 | −37.233 | 1.00 | 36.61 |
| ATOM | N | GLY | L | 200 | 53.706 | 28.263 | −36.083 | 1.00 | 35.48 |
| ATOM | CA | GLY | L | 200 | 54.310 | 27.734 | −37.291 | 1.00 | 35.01 |
| ATOM | C | GLY | L | 200 | 53.403 | 26.833 | −38.102 | 1.00 | 35.20 |
| ATOM | O | GLY | L | 200 | 53.837 | 26.247 | −39.087 | 1.00 | 35.29 |
| ATOM | N | LEU | L | 201 | 52.152 | 26.699 | −37.682 | 1.00 | 35.81 |
| ATOM | CA | LEU | L | 201 | 51.198 | 25.857 | −38.393 | 1.00 | 36.05 |
| ATOM | CB | LEU | L | 201 | 50.543 | 24.862 | −37.433 | 1.00 | 33.90 |
| ATOM | CG | LEU | L | 201 | 51.478 | 23.925 | −36.668 | 1.00 | 33.97 |
| ATOM | CD1 | LEU | L | 201 | 50.674 | 23.147 | −35.641 | 1.00 | 32.30 |
| ATOM | CD2 | LEU | L | 201 | 52.204 | 22.978 | −37.632 | 1.00 | 31.98 |
| ATOM | C | LEU | L | 201 | 50.133 | 26.743 | −39.033 | 1.00 | 36.97 |
| ATOM | O | LEU | L | 201 | 49.499 | 27.558 | −38.346 | 1.00 | 36.27 |
| ATOM | N | SER | L | 202 | 49.968 | 26.609 | −40.349 | 1.00 | 38.32 |
| ATOM | CA | SER | L | 202 | 48.973 | 27.388 | −41.085 | 1.00 | 40.35 |
| ATOM | CB | SER | L | 202 | 49.179 | 27.229 | −42.588 | 1.00 | 39.68 |
| ATOM | OG | SER | L | 202 | 49.055 | 25.874 | −42.981 | 1.00 | 43.15 |
| ATOM | C | SER | L | 202 | 47.580 | 26.907 | −40.688 | 1.00 | 41.57 |
| ATOM | O | SER | L | 202 | 46.599 | 27.656 | −40.750 | 1.00 | 43.86 |
| ATOM | N | SER | L | 203 | 47.512 | 25.653 | −40.261 | 1.00 | 40.52 |
| ATOM | CA | SER | L | 203 | 46.269 | 25.049 | −39.824 | 1.00 | 40.76 |
| ATOM | CB | SER | L | 203 | 45.526 | 24.478 | −41.028 | 1.00 | 42.78 |
| ATOM | OG | SER | L | 203 | 46.420 | 23.731 | −41.838 | 1.00 | 50.38 |
| ATOM | C | SER | L | 203 | 46.623 | 23.942 | −38.834 | 1.00 | 39.15 |
| ATOM | O | SER | L | 203 | 47.654 | 23.273 | −38.992 | 1.00 | 38.36 |
| ATOM | N | PRO | L | 204 | 45.801 | 23.774 | −37.778 | 1.00 | 37.58 |
| ATOM | CD | PRO | L | 204 | 44.653 | 24.641 | −37.453 | 1.00 | 36.52 |

TABLE 2-continued

| | | Atom A.A. Type | | | X | Y | Z | Occ | B |
|---|---|---|---|---|---|---|---|---|---|
| ATOM | CA | PRO | L | 204 | 45.983 | 22.764 | −36.731 | 1.00 | 36.27 |
| ATOM | CB | PRO | L | 204 | 44.648 | 22.806 | −35.989 | 1.00 | 36.27 |
| ATOM | CG | PRO | L | 204 | 44.336 | 24.256 | −36.011 | 1.00 | 37.26 |
| ATOM | C | PRO | L | 204 | 46.274 | 21.379 | −37.270 | 1.00 | 34.75 |
| ATOM | O | PRO | L | 204 | 45.661 | 20.931 | −38.238 | 1.00 | 33.73 |
| ATOM | N | VAL | L | 205 | 47.260 | 20.733 | −36.663 | 1.00 | 34.45 |
| ATOM | CA | VAL | L | 205 | 47.652 | 19.390 | −37.047 | 1.00 | 31.64 |
| ATOM | CB | VAL | L | 205 | 49.170 | 19.203 | −36.935 | 1.00 | 29.36 |
| ATOM | CG1 | VAL | L | 205 | 49.545 | 17.778 | −37.215 | 1.00 | 28.96 |
| ATOM | CG2 | VAL | L | 205 | 49.855 | 20.097 | −37.919 | 1.00 | 31.43 |
| ATOM | C | VAL | L | 205 | 46.952 | 18.438 | −36.099 | 1.00 | 31.45 |
| ATOM | O | VAL | L | 205 | 46.809 | 18.732 | −34.919 | 1.00 | 31.91 |
| ATOM | N | THR | L | 206 | 46.480 | 17.315 | −36.618 | 1.00 | 30.31 |
| ATOM | CA | THR | L | 206 | 45.812 | 16.348 | −35.776 | 1.00 | 27.81 |
| ATOM | CB | THR | L | 206 | 44.286 | 16.304 | −36.030 | 1.00 | 28.22 |
| ATOM | OG1 | THR | L | 206 | 43.699 | 17.541 | −35.612 | 1.00 | 30.85 |
| ATOM | CG2 | THR | L | 206 | 43.639 | 15.180 | −35.227 | 1.00 | 25.07 |
| ATOM | C | THR | L | 206 | 46.403 | 14.969 | −35.954 | 1.00 | 26.65 |
| ATOM | O | THR | L | 206 | 46.585 | 14.49B | −37.075 | 1.00 | 26.93 |
| ATOM | N | LYS | L | 207 | 46.801 | 14.375 | −34.834 | 1.00 | 26.50 |
| ATOM | CA | LYS | L | 207 | 47.340 | 13.013 | −34.803 | 1.00 | 24.40 |
| ATOM | CB | LYS | L | 207 | 48.719 | 12.976 | −34.138 | 1.00 | 22.17 |
| ATOM | CG | LYS | L | 207 | 49.800 | 13.584 | −35.000 | 1.00 | 22.70 |
| ATOM | CD | LYS | L | 207 | 49.682 | 13.080 | −36.420 | 1.00 | 25.39 |
| ATOM | CE | LYS | L | 207 | 50.876 | 13.490 | −37.283 | 1.00 | 27.96 |
| ATOM | NZ | LYS | L | 207 | 50.979 | 14.962 | −37.448 | 1.00 | 32.56 |
| ATOM | C | LYS | L | 207 | 46.332 | 12.152 | −34.041 | 1.00 | 21.89 |
| ATOM | O | LYS | L | 207 | 45.836 | 12.552 | −32.990 | 1.00 | 29.91 |
| ATOM | N | SER | L | 208 | 46.002 | 10.986 | −34.573 | 1.00 | 20.67 |
| ATOM | CA | SER | L | 208 | 45.023 | 10.160 | −33.895 | 1.00 | 22.53 |
| ATOM | CB | SER | L | 208 | 43.607 | 10.641 | −34.229 | 1.00 | 23.05 |
| ATOM | OG | SER | L | 208 | 43.309 | 10.503 | −35.605 | 1.00 | 22.35 |
| ATOM | C | SER | L | 208 | 45.152 | 8.692 | −34.236 | 1.00 | 21.41 |
| ATOM | O | SER | L | 208 | 45.917 | 8.323 | −35.128 | 1.00 | 23.53 |
| ATOM | N | PHE | L | 209 | 44.414 | 7.867 | −33.503 | 1.00 | 20.17 |
| ATOM | CA | PHE | L | 209 | 44.384 | 6.428 | −33.709 | 1.00 | 19.98 |
| ATOM | CB | PHE | L | 209 | 45.499 | 5.733 | −32.917 | 1.00 | 27.21 |
| ATOM | CG | PHE | L | 209 | 45.340 | 5.830 | −31.421 | 1.00 | 17.15 |
| ATOM | CG1 | PHE | L | 209 | 45.980 | 6.838 | −30.705 | 1.00 | 15.87 |
| ATOM | CD2 | PHE | L | 209 | 44.544 | 4.926 | −30.735 | 1.00 | 14.47 |
| ATOM | CE1 | PHE | L | 209 | 45.826 | 6.945 | −29.335 | 1.00 | 13.72 |
| ATOM | CE2 | PHE | L | 209 | 44.379 | 5.024 | −29.363 | 1.00 | 15.39 |
| ATOM | CZ | PHE | L | 209 | 45.024 | 6.039 | −28.659 | 1.00 | 15.16 |
| ATOM | C | PHE | L | 209 | 43.027 | 5.919 | −33.241 | 1.00 | 20.93 |
| ATOM | O | PHE | L | 209 | 42.326 | 6.582 | −32.474 | 1.00 | 20.26 |
| ATOM | N | ASN | L | 210 | 42.643 | 4.745 | −33.709 | 1.00 | 23.29 |
| ATOM | CA | ASN | L | 210 | 41.384 | 4.167 | −33.285 | 1.00 | 25.15 |
| ATOM | CB | ASN | L | 210 | 40.588 | 3.627 | −34.469 | 1.00 | 27.36 |
| ATOM | CG | ASN | L | 210 | 40.138 | 4.709 | −35.406 | 1.00 | 28.83 |
| ATOM | OG1 | ASN | L | 210 | 39.666 | 5.761 | −34.986 | 1.00 | 30.55 |
| ATOM | ND2 | ASN | L | 210 | 40.284 | 4.459 | −36.691 | 1.00 | 32.86 |
| ATOM | C | ASN | L | 210 | 41.735 | 3.020 | −32.361 | 1.00 | 25.95 |
| ATOM | O | ASN | L | 210 | 42.595 | 2.177 | −32.691 | 1.00 | 23.37 |
| ATOM | N | ARG | L | 211 | 41.107 | 3.016 | −31.190 | 1.00 | 24.99 |
| ATOM | CA | ARG | L | 211 | 41.310 | 1.973 | −30.200 | 1.00 | 26.72 |
| ATOM | CB | ARG | L | 211 | 40.272 | 2.126 | −29.096 | 1.00 | 29.08 |
| ATOM | CG | ARG | L | 211 | 40.439 | 1.203 | −27.920 | 1.00 | 32.37 |
| ATOM | CD | ARG | L | 211 | 39.260 | 1.337 | −26.982 | 1.00 | 38.35 |
| ATOM | NE | ARG | L | 211 | 38.303 | 0.250 | −27.164 | 1.00 | 44.72 |
| ATOM | CZ | ARG | L | 211 | 37.227 | 0.300 | −27.942 | 1.00 | 47.51 |
| ATOM | NE1 | ARG | L | 211 | 36.934 | 1.387 | −28.635 | 1.00 | 50.78 |
| ATOM | NH2 | ARG | L | 211 | 36.460 | −0.770 | −28.060 | 1.00 | 52.10 |
| ATOM | C | ARG | L | 211 | 41.086 | 0.649 | −30.920 | 1.00 | 27.05 |
| ATOM | O | ARG | L | 211 | 40.070 | 0.488 | −31.598 | 1.00 | 25.38 |
| ATOM | N | GLY | L | 212 | 42.075 | −0.240 | −30.863 | 1.00 | 25.25 |
| ATOM | CA | GLY | L | 212 | 41.935 | −1.528 | −31.512 | 1.00 | 27.36 |
| ATOM | C | GLY | L | 212 | 42.467 | −1.669 | −32.931 | 1.00 | 28.73 |
| ATOM | O | GLY | L | 212 | 42.374 | −2.753 | −33.500 | 1.00 | 30.55 |
| ATOM | N | GLU | L | 213 | 43.013 | −0.603 | −33.519 | 1.00 | 28.63 |
| ATOM | CA | GLU | L | 213 | 43.559 | −0.706 | −34.878 | 1.00 | 28.38 |
| ATOM | CB | GLU | L | 213 | 43.809 | 0.676 | −35.485 | 1.00 | 27.47 |
| ATOM | CG | GLU | L | 213 | 44.767 | 1.547 | −34.702 | 1.00 | 30.90 |
| ATOM | CD | GLU | L | 213 | 45.140 | 2.811 | −35.442 | 1.00 | 32.32. |
| ATOM | OE1 | GLU | L | 213 | 44.256 | 3.660 | −35.697 | 1.00 | 28.43 |
| ATOM | OE2 | GLU | L | 213 | 46.337 | 2.951 | −35.777 | 1.00 | 38.75 |
| ATOM | C | GLU | L | 213 | 44.848 | −1.545 | −34.912 | 1.00 | 27.34 |

TABLE 2-continued

| | | Atom A.A. Type | | | X | Y | Z | Occ | B |
|---|---|---|---|---|---|---|---|---|---|
| ATOM | O | GLU | L | 213 | 45.340 | −1.905 | −35.984 | 1.00 | 27.73 |
| ATOM | N | CYS | L | 214 | 45.386 | −1.824 | −33.730 | 1.00 | 23.79 |
| ATOM | CA | CYS | L | 214 | 46.588 | −2.617 | −33.568 | 1.00 | 24.14 |
| ATOM | CB | CYS | L | 214 | 47.832 | −1.793 | −33.929 | 1.00 | 21.09 |
| ATOM | SG | CYS | L | 214 | 49.402 | −2.696 | −33.720 | 1.00 | 21.16 |
| ATOM | C | CYS | L | 214 | 46.655 | −3.098 | −32.113 | 1.00 | 25.60 |
| ATOM | O | CYS | L | 214 | 46.497 | −4.317 | −31.886 | 1.00 | 26.55 |
| ATOM | OXT | CYS | L | 214 | 46.812 | −2.250 | −31.208 | 1.00 | 25.04 |
| ATOM | CB | GLN | H | 1 | 89.041 | 17.551 | −11.026 | 1.00 | 38.73 |
| ATOM | CG | GLN | H | 1 | 89.504 | 16.894 | −12.327 | 1.00 | 43.69 |
| ATOM | CD | GLN | H | 1 | 90.587 | 17.700 | −13.054 | 1.00 | 47.34 |
| ATOM | OE1 | GLN | H | 1 | 91.700 | 17.172 | −13.322 | 1.00 | 49.92 |
| ATOM | NE2 | GLN | H | 1 | 90.284 | 18.983 | −13.367 | 1.00 | 44.36 |
| ATOM | C | GLN | H | 1 | 89.366 | 17.829 | −8.582 | 1.00 | 32.86 |
| ATOM | O | GLN | H | 1 | 89.282 | 16.917 | −7.752 | 1.00 | 32.27 |
| ATOM | N | GLN | H | 1 | 90.700 | 16.216 | −9.797 | 1.00 | 36.03 |
| ATOM | CA | GLN | H | 1 | 90.081 | 17.570 | −9.909 | 1.00 | 35.50 |
| ATOM | N | VAL | H | 2 | 88.863 | 19.049 | −8.385 | 1.00 | 31.14 |
| ATOM | CA | VAL | H | 2 | 88.124 | 19.398 | −7.168 | 1.00 | 27.15 |
| ATOM | CB | VAL | H | 2 | 88.139 | 20.922 | −6.901 | 1.00 | 28.34 |
| ATOM | CG1 | VAL | H | 2 | 87.231 | 21.267 | −5.723 | 1.00 | 25.54 |
| ATOM | CG2 | VAL | H | 2 | 89.545 | 21.385 | −6.600 | 1.00 | 31.24 |
| ATOM | C | VAL | H | 2 | 86.677 | 18.955 | −7.400 | 1.00 | 24.53 |
| ATOM | O | VAL | H | 2 | 86.089 | 19.295 | −8.435 | 1.00 | 23.94 |
| ATOM | N | THR | H | 3 | 86.120 | 18.198 | −6.452 | 1.00 | 20.44 |
| ATOM | CA | THR | H | 3 | 84.749 | 17.696 | −6.557 | 1.00 | 21.79 |
| ATOM | CB | THR | H | 3 | 84.695 | 16.180 | −7.087 | 1.00 | 21.21 |
| ATOM | OG1 | THR | H | 3 | 85.135 | 15.276 | −6.066 | 1.00 | 24.96 |
| ATOM | CG2 | THR | H | 3 | 85.595 | 15.968 | −8.301 | 1.00 | 19.19 |
| ATOM | C | THR | H | 3 | 84.047 | 17.771 | −5.198 | 1.00 | 19.89 |
| ATOM | O | THR | H | 3 | 84.687 | 17.698 | −4.146 | 1.00 | 20.44 |
| ATOM | N | LEU | H | 4 | 82.737 | 17.982 | −5.222 | 1.00 | 21.46 |
| ATOM | CA | LEU | H | 4 | 81.932 | 18.026 | −3.996 | 1.00 | 21.29 |
| ATOM | CB | LEU | H | 4 | 81.412 | 19.433 | −3.711 | 1.00 | 20.12 |
| ATOM | CG | LEU | H | 4 | 82.224 | 20.719 | −3.514 | 1.00 | 23.52 |
| ATOM | CD1 | LEU | H | 4 | 82.836 | 20.766 | −2.153 | 1.00 | 21.59 |
| ATOM | CD2 | LEU | H | 4 | 83.219 | 20.968 | −4.618 | 1.00 | 22.05 |
| ATOM | C | LEU | H | 4 | 80.726 | 17.137 | −4.299 | 1.00 | 20.12 |
| ATOM | O | LEU | H | 4 | 80.291 | 17.071 | −5.447 | 1.00 | 20.31 |
| ATOM | N | ARG | H | 5 | 80.207 | 16.432 | −3.299 | 1.00 | 19.84 |
| ATOM | CA | ARG | H | 5 | 79.032 | 15.574 | −3.504 | 1.00 | 19.68 |
| ATOM | CB | ARG | H | 5 | 79.57 | 14.128 | −3.746 | 1.00 | 25.17 |
| ATOM | CG | ARG | H | 5 | 78.424 | 13.305 | −4.463 | 1.00 | 29.51 |
| ATOM | CD | ARG | H | 5 | 78.626 | 11.812 | −4.206 | 1.00 | 38.74 |
| ATOM | NE | ARG | H | 5 | 78.217 | 11.422 | −2.851 | 1.00 | 46.80 |
| ATOM | CZ | ARG | H | 5 | 79.055 | 11.063 | −1.879 | 1.00 | 49.80 |
| ATOM | NH1 | ARG | H | 5 | 80.369 | 11.032 | −2.093 | 1.00 | 51.08 |
| ATOM | NH2 | ARG | H | 5 | 78.574 | 10.751 | −0.682 | 1.00 | 51.13 |
| ATOM | C | ARG | H | 5 | 78.100 | 15.618 | −2.301 | 1.00 | 15.95 |
| ATOM | O | ARG | H | 5 | 78.504 | 15.298 | −1.190 | 1.00 | 15.47 |
| ATOM | N | GLU | H | 6 | 76.842 | 15.968 | −2.533 | 1.00 | 16.47 |
| ATOM | CA | GLU | H | 6 | 75.860 | 16.042 | −1.450 | 1.00 | 15.47 |
| ATOM | CB | GLU | H | 6 | 74.865 | 17.196 | −1.654 | 1.00 | 15.61 |
| ATOM | CG | GLU | H | 6 | 75.459 | 18.549 | −1.986 | 1.00 | 13.15 |
| ATOM | CD | GLU | H | 6 | 75.769 | 18.732 | −3.474 | 1.00 | 14.34 |
| ATOM | OE1 | GLU | H | 6 | 75.679 | 17.763 | −4.264 | 1.00 | 14.15 |
| ATOM | OE2 | GLU | H | 6 | 76.100 | 19.869 | −3.860 | 1.00 | 16.39 |
| ATOM | C | GLU | H | 6 | 75.077 | 14.735 | −1.382 | 1.00 | 14.85 |
| ATOM | O | GLU | H | 6 | 74.811 | 14.095 | −2.405 | 1.00 | 13.49 |
| ATOM | N | SER | H | 7 | 74.730 | 14.335 | −0.169 | 1.00 | 16.74 |
| ATOM | CA | SER | H | 7 | 73.953 | 13.131 | 0.045 | 1.00 | 16.80 |
| ATOM | CB | SER | H | 7 | 74.876 | 11.897 | 0.097 | 1.00 | 18.29 |
| ATOM | OG | SER | H | 7 | 75.885 | 12.018 | 1.085 | 1.00 | 20.20 |
| ATOM | C | SER | H | 7 | 73.087 | 13.260 | 1.302 | 1.00 | 14.45 |
| ATOM | O | SER | H | 7 | 73.379 | 14.039 | 2.220 | 1.00 | 12.60 |
| ATOM | N | GLY | H | 8 | 71.972 | 12.556 | 1.292 | 1.00 | 13.11 |
| ATOM | CA | GLY | H | 8 | 71.061 | 12.581 | 2.411 | 1.00 | 13.45 |
| ATOM | C | GLY | H | 8 | 69.796 | 11.883 | 1.963 | 1.00 | 15.80 |
| ATOM | O | GLY | H | 8 | 69.751 | 11.362 | 0.840 | 1.00 | 16.91 |
| ATOM | N | PRO | H | 9 | 68.786 | 11.766 | 2.827 | 1.00 | 15.87 |
| ATOM | CD | PRO | H | 9 | 68.706 | 12.263 | 4.210 | 1.00 | 16.52 |
| ATOM | CA | PRO | H | 9 | 67.36 | 11.105 | 2.419 | 1.00 | 16.14 |
| ATOM | CB | PRO | H | 9 | 66.747 | 11.050 | 3.718 | 1.00 | 15.96 |
| ATOM | CG | PRO | H | 9 | 67.217 | 12.297 | 4.431 | 1.00 | 19.96 |
| ATOM | C | PRO | H | 9 | 66.820 | 11.970 | 1.378 | 1.00 | 16.98 |

TABLE 2-continued

| | | Atom A.A. Type | | | X | Y | Z | Occ | B |
|---|---|---|---|---|---|---|---|---|---|
| ATOM | O | PRO | H | 9 | 66.961 | 13.204 | 1.366 | 1.00 | 15.45 |
| ATOM | N | ALA | H | 10 | 66.069 | 11.337 | 0.491 | 1.00 | 16.97 |
| ATOM | CA | ALA | H | 10 | 65.359 | 12.091 | −0.536 | 1.00 | 17.03 |
| ATOM | CB | ALA | H | 10 | 65.148 | 11.232 | −1.762 | 1.00 | 17.55 |
| ATOM | C | ALA | H | 10 | 64.016 | 12.627 | −0.042 | 1.00 | 16.22 |
| ATOM | O | ALA | H | 10 | 63.475 | 13.574 | −0.607 | 1.00 | 14.92 |
| ATOM | N | LEU | H | 11 | 63.517 | 12.059 | 1.049 | 1.00 | 16.76 |
| ATOM | CA | LEU | H | 11 | 62.231 | 12.444 | 1.590 | 1.00 | 17.28 |
| ATOM | CB | LEU | H | 11 | 61.224 | 11.333 | 1.282 | 1.00 | 20.63 |
| ATOM | CG | LEU | H | 11 | 59.722 | 11.535 | 1.042 | 1.00 | 23.90 |
| ATOM | CD1 | LEU | H | 11 | 59.037 | 10.144 | 1.116 | 1.00 | 17.36 |
| ATOM | CD2 | LEU | H | 11 | 59.111 | 12.498 | 2.054 | 1.00 | 26.18 |
| ATOM | C | LEU | H | 11 | 62.409 | 12.524 | 3.083 | 1.00 | 18.81 |
| ATOM | O | LEU | H | 11 | 63.081 | 11.682 | 3.670 | 1.00 | 20.70 |
| ATOM | N | VAL | H | 12 | 61.817 | 13.535 | 3.697 | 1.00 | 18.51 |
| ATOM | CA | VAL | H | 12 | 61.890 | 13.700 | 5.137 | 1.00 | 19.38 |
| ATOM | CB | VAL | H | 12 | 63.009 | 14.740 | 5.513 | 1.00 | 21.22 |
| ATOM | CG1 | VAL | H | 12 | 62.819 | 16.018 | 4.757 | 1.00 | 22.31 |
| ATOM | CG2 | VAL | H | 12 | 63.045 | 15.008 | 6.991 | 1.00 | 22.98 |
| ATOM | C | VAL | H | 12 | 60.472 | 14.120 | 5.559 | 1.00 | 17.45 |
| ATOM | O | VAL | H | 12 | 59.737 | 14.698 | 4.769 | 1.00 | 19.16 |
| ATOM | N | LYS | H | 13 | 60.044 | 13.757 | 6.753 | 1.00 | 16.45 |
| ATOM | CA | LYS | H | 13 | S8.70S | 14.125 | 7.193 | 1.00 | 19.16 |
| ATOM | CB | LYS | H | 13 | 58.119 | 13.002 | 8.045 | 1.00 | 19.92 |
| ATOM | CG | LYS | H | 13 | 57.944 | 11.718 | 7.279 | 1.00 | 21.38 |
| ATOM | CD | LYS | H | 13 | 57.493 | 10.592 | 8.168 | 1.00 | 23.63 |
| ATOM | CE | LYS | H | 13 | 57.213 | 9.342 | 7.3S0 | 1.00 | 26.68 |
| ATOM | NZ | LYS | H | 13 | 55.952 | 9.380 | 6.548 | 1.00 | 29.7S |
| ATOM | C | LYS | H | 13 | 58.678 | 15.447 | 7.959 | 1.00 | 21.82 |
| ATOM | O | LYS | H | 13 | 59.659 | 15.813 | 8.630 | 1.00 | 23.05 |
| ATOM | N | PRO | H | 14 | 57.564 | 16.202 | 7.852 | 1.00 | 20.98 |
| ATOM | CD | PRO | H | 14 | 56.341 | 15.940 | 7.068 | 1.00 | 20.16 |
| ATOM | CA | PRO | H | 14 | 57.468 | 17.480 | 8.564 | 1.00 | 20.48 |
| ATOM | CB | PRO | H | 14 | 55.980 | 17.813 | 8.457 | 1.00 | 20.21 |
| ATOM | CG | PRO | H | 14 | 55.622 | 17.275 | 7.117 | 1.00 | 19.19 |
| ATOM | C | PRO | H | 14 | 57.908 | 17.318 | 10.020 | 1.00 | 19.76 |
| ATOM | O | PRO | H | 14 | 57.703 | 16.263 | 10.616 | 1.00 | 19.05 |
| ATOM | N | THR | H | 15 | 58.572 | 18.345 | 10.543 | 1.00 | 22.03 |
| ATOM | CA | THR | H | 15 | 59.089 | 18.410 | 11.917 | 1.00 | 22.23 |
| ATOM | CB | THR | H | 15 | 58.010 | 18.048 | 13.007 | 1.00 | 22.84 |
| ATOM | OG1 | THR | H | 15 | 57.795 | 16.628 | 13.049 | 1.00 | 21.55 |
| ATOM | CG2 | THR | H | 15 | 56.672 | 18.786 | 12.719 | 1.00 | 23.91 |
| ATOM | C | THR | H | 15 | 60.356 | 17.613 | 12.182 | 1.00 | 22.65 |
| ATOM | O | THR | H | 15 | 61.010 | 17.825 | 13.208 | 1.00 | 21.92 |
| ATOM | N | GLN | H | 16 | 60.695 | 16.687 | 11.284 | 1.00 | 22.77 |
| ATOM | CA | GLN | H | 16 | 61.911 | 15.889 | 11.442 | 1.00 | 20.54 |
| ATOM | CB | GLN | H | 16 | 61.865 | 14.639 | 10.571 | 1.00 | 22.36 |
| ATOM | CG | GLN | H | 16 | 60.807 | 13.651 | 11.000 | 1.00 | 25.78 |
| ATOM | CD | GLN | H | 16 | 60.906 | 12.346 | 10.260 | 1.00 | 26.82 |
| ATOM | OE1 | GLN | H | 16 | 61.223 | 12.305 | 9.063 | 1.00 | 26.33 |
| ATOM | NE2 | GLN | H | 16 | 60.636 | 11.262 | 10.962 | 1.00 | 27.32 |
| ATOM | C | GLN | H | 16 | 63.178 | 16.681 | 11.141 | 1.00 | 18.94 |
| ATOM | O | GLN | H | 16 | 63.131 | 17.828 | 10.702 | 1.00 | 16.50 |
| ATOM | N | THR | H | 17 | 64.318 | 16.077 | 11.435 | 1.00 | 19.96 |
| ATOM | CA | THR | H | 17 | 65.582 | 16.737 | 11.197 | 1.00 | 20.38 |
| ATOM | CB | THR | H | 17 | 66.533 | 16.591 | 12.400 | 1.00 | 22.26 |
| ATOM | OG1 | THR | H | 17 | 65.940 | 17.211 | 13.549 | 1.00 | 24.95 |
| ATOM | CG2 | THR | H | 17 | 67.886 | 17.266 | 12.106 | 1.00 | 24.40 |
| ATOM | C | THR | H | 17 | 66.244 | 16.162 | 9.969 | 1.00 | 19.47 |
| ATOM | O | THR | H | 17 | 66.210 | 14.940 | 9.746 | 1.00 | 21.06 |
| ATOM | N | LEU | H | 18 | 66.776 | 17.056 | 9.141 | 1.00 | 17.08 |
| ATOM | CA | LEU | H | 18 | 67.481 | 16.660 | 7.934 | 1.00 | 18.72 |
| ATOM | CB | LEU | H | 18 | 67.118 | 17.590 | 6.771 | 1.00 | 16.71 |
| ATOM | CG | LEU | H | 18 | 67.911 | 17.343 | 5.481 | 1.00 | 17.37 |
| ATOM | CD1 | LEU | H | 18 | 67.516 | 16.008 | 4.874 | 1.00 | 17.23 |
| ATOM | CD2 | LEU | H | 18 | 67.684 | 18.478 | 4.489 | 1.00 | 16.91 |
| ATOM | C | LEU | H | 18 | 68.993 | 16.734 | 8.176 | 1.00 | 17.32 |
| ATOM | O | LEU | H | 18 | 69.488 | 17.704 | 8.724 | 1.00 | 16.61 |
| ATOM | N | THR | H | 19 | 69.707 | 15.683 | 7.803 | 1.00 | 18.33 |
| ATOM | CA | THR | H | 19 | 71.157 | 15.663 | 7.923 | 1.00 | 17.82 |
| ATOM | CB | THR | H | 19 | 71.628 | 14.541 | 8.862 | 1.00 | 18.17 |
| ATOM | OG1 | THR | H | 19 | 71.181 | 14.838 | 10.188 | 1.00 | 19.18 |
| ATOM | CG2 | THR | H | 19 | 73.162 | 14.394 | 8.833 | 1.00 | 16.07 |
| ATOM | C | THR | H | 19 | 71.728 | 15.472 | 6.511 | 1.00 | 17.19 |
| ATOM | O | THR | H | 19 | 71.464 | 14.460 | 5.846 | 1.00 | 17.03 |
| ATOM | N | LEU | H | 20 | 72.412 | 16.503 | 6.023 | 1.00 | 15.96 |

TABLE 2-continued

|  |  | Atom | A.A. Type |  | X | Y | Z | Occ | B |
|---|---|---|---|---|---|---|---|---|---|
| ATOM | CA | LEU | H | 20 | 73.021 | 16.477 | 4.705 | 1.00 | 16.02 |
| ATOM | CB | LEU | H | 20 | 72.693 | 17.760 | 3.935 | 1.00 | 12.09 |
| ATOM | CG | LEU | H | 20 | 71.242 | 17.974 | 3.533 | 1.00 | 14.01 |
| ATOM | CG1 | LEU | H | 20 | 71.021 | 19.422 | 3.324 | 1.00 | 15.03 |
| ATOM | CG2 | LEU | H | 20 | 70.877 | 17.173 | 2.312 | 1.00 | 14.28 |
| ATOM | C | LEU | H | 20 | 74.531 | 16.353 | 4.858 | 1.00 | 16.97 |
| ATOM | O | LEU | H | 20 | 75.122 | 16.960 | 5.754 | 1.00 | 17.31 |
| ATOM | N | THR | H | 21 | 75.151 | 15.586 | 3.972 | 1.00 | 15.60 |
| ATOM | CA | THR | H | 21 | 76.587 | 15.414 | 4.024 | 1.00 | 16.81 |
| ATOM | CB | THR | H | 21 | 76.941 | 13.958 | 4.332 | 1.00 | 15.79 |
| ATOM | OG1 | THR | H | 21 | 76.304 | 13.571 | 5.561 | 1.00 | 14.35 |
| ATOM | OG2 | THR | H | 21 | 78.458 | 13.798 | 4.472 | 1.00 | 14.58 |
| ATOM | C | THR | H | 21 | 77.219 | 15.863 | 2.714 | 1.00 | 15.76 |
| ATOM | O | THR | H | 21 | 76.689 | 15.595 | 1.646 | 1.00 | 15.65 |
| ATOM | N | CYS | H | 22 | 78.292 | 16.635 | 2.806 | 1.00 | 15.22 |
| ATOM | CA | CYS | H | 22 | 79.007 | 17.100 | 1.624 | 1.00 | 16.61 |
| ATOM | C | CYS | H | 22 | 80.386 | 16.462 | 1.661 | 1.00 | 17.70 |
| ATOM | O | CYS | H | 22 | 81.212 | 16.808 | 2.509 | 1.00 | 17.86 |
| ATOM | CB | CYS | H | 22 | 79.164 | 18.622 | 1.624 | 1.00 | 16.86 |
| ATOM | SG | CYS | H | 22 | 80.150 | 19.286 | 0.243 | 1.00 | 14.84 |
| ATOM | N | THR | H | 23 | 80.609 | 15.512 | 0.760 | 1.00 | 18.33 |
| ATOM | CA | THR | H | 23 | 81.879 | 14.812 | 0.670 | 1.00 | 19.26 |
| ATOM | CB | THR | H | 23 | 81.662 | 13.312 | 0.509 | 1.00 | 19.33 |
| ATOM | OG1 | THR | H | 23 | 80.879 | 12.853 | 1.613 | 1.00 | 22.21 |
| ATOM | CG2 | THR | H | 23 | 82.974 | 12.586 | 0.528 | 1.00 | 22.05 |
| ATOM | C | THR | H | 23 | 82.640 | 15.389 | −0.495 | 1.00 | 18.33 |
| ATOM | O | THR | H | 23 | 82.122 | 15.497 | −1.610 | 1.00 | 17.83 |
| ATOM | N | PHE | H | 24 | 83.875 | 15.782 | −0.236 | 1.00 | 19.13 |
| ATOM | CA | PHE | H | 24 | 84.656 | 16.408 | −1.288 | 1.00 | 22.34 |
| ATOM | CB | PHE | H | 24 | 84.806 | 17.918 | −0.994 | 1.00 | 21.75 |
| ATOM | CG | PHE | H | 24 | 85.421 | 18.218 | 0.347 | 1.00 | 20.43 |
| ATOM | CD1 | PHE | H | 24 | 86.808 | 18.263 | 0.496 | 1.00 | 22.58 |
| ATOM | CD2 | PHE | H | 24 | 84.623 | 18.387 | 1.467 | 1.00 | 19.58 |
| ATOM | CE1 | PHE | H | 24 | 87.383 | 18.462 | 1.743 | 1.00 | 21.78 |
| ATOM | CE2 | PHE | H | 24 | 85.182 | 18.585 | 2.713 | 1.00 | 18.19 |
| ATOM | CZ | PHE | H | 24 | 86.564 | 18.621 | 2.859 | 1.00 | 21.55 |
| ATOM | C | PHE | H | 24 | 86.020 | 15.778 | −1.498 | 1.00 | 23.38 |
| ATOM | O | PHE | H | 24 | 86.434 | 14.911 | −0.743 | 1.00 | 24.19 |
| ATOM | N | SER | H | 25 | 86.685 | 16.209 | −2.559 | 1.00 | 25.12 |
| ATOM | CA | SER | H | 25 | 88.021 | 15.754 | −2.885 | 1.00 | 27.58 |
| ATOM | CB | SER | H | 25 | 88.004 | 14.355 | −3.510 | 1.00 | 25.80 |
| ATOM | OG | SER | H | 25 | 87.469 | 14.384 | −4.822 | 1.00 | 28.75 |
| ATOM | C | SER | H | 25 | 88.628 | 16.788 | −3.837 | 1.00 | 28.21 |
| ATOM | O | SER | H | 25 | 87.931 | 17.666 | −4.365 | 1.00 | 26.90 |
| ATOM | NH | GLY | H | 26 | 89.936 | 16.692 | −4.035 | 1.00 | 30.76 |
| ATOM | CA | GLY | H | 26 | 90.625 | 17.627 | −4.900 | 1.00 | 27.87 |
| ATOM | C | GLY | H | 26 | 91.146 | 18.782 | −4.070 | 1.00 | 29.61 |
| ATOM | O | GLY | H | 26 | 91.781 | 19.678 | −4.611 | 1.00 | 30.97 |
| ATOM | N | PHE | H | 27 | 90.888 | 18.761 | −2.761 | 1.00 | 26.72 |
| ATOM | CA | PHE | H | 27 | 91.332 | 19.830 | −1.884 | 1.00 | 27.11 |
| ATOM | CB | PHE | H | 27 | 90.600 | 21.166 | −2.190 | 1.00 | 27.71 |
| ATOM | CG | PHE | H | 27 | 89.159 | 21.233 | −1.700 | 1.00 | 26.87 |
| ATOM | CD1 | PHE | H | 27 | 88.858 | 21.733 | −0.431 | 1.00 | 24.48 |
| ATOM | CD2 | PHE | H | 27 | 88.110 | 20.820 | −2.513 | 1.00 | 27.17 |
| ATOM | CE1 | PHE | H | 27 | 87.537 | 21.817 | 0.020 | 1.00 | 25.75 |
| ATOM | CE2 | PHE | H | 27 | 86.787 | 20.905 | −2.067 | 1.00 | 25.89 |
| ATOM | CZ | PHE | H | 27 | 86.506 | 21.402 | −0.801 | 1.00 | 24.60 |
| ATOM | C | PHE | H | 27 | 91.133 | 19.435 | −0.438 | 1.00 | 26.87 |
| ATOM | O | PHE | H | 27 | 90.467 | 18.439 | −0.150 | 1.00 | 27.66 |
| ATOM | N | SER | H | 28 | 91.714 | 20.223 | 0.464 | 1.00 | 26.42 |
| ATOM | CA | SER | H | 28 | 91.612 | 19.970 | 1.890 | 1.00 | 24.77 |
| ATOM | CB | SER | H | 28 | 92.976 | 19.626 | 2.481 | 1.00 | 21.30 |
| ATOM | OG | SER | H | 28 | 92.934 | 19.678 | 3.901 | 1.00 | 22.82 |
| ATOM | C | SER | H | 28 | 91.053 | 21.162 | 2.625 | 1.00 | 25.66 |
| ATOM | O | SER | H | 28 | 91.508 | 22.292 | 2.433 | 1.00 | 27.14 |
| ATOM | N | LEU | H | 29 | 90.131 | 20.888 | 3.540 | 1.00 | 26.30 |
| ATOM | CA | LEU | H | 29 | 89.508 | 21.926 | 4.334 | 1.00 | 26.90 |
| ATOM | CB | LEU | H | 29 | 88.237 | 21.399 | 5.013 | 1.00 | 27.65 |
| ATOM | CG | LEU | H | 29 | 86.958 | 22.199 | 4.723 | 1.00 | 27.49 |
| ATOM | CD1 | LEU | H | 29 | 85.790 | 21.609 | 5.467 | 1.00 | 25.56 |
| ATOM | CD2 | LEU | H | 29 | 87.123 | 23.664 | 5.097 | 1.00 | 26.24 |
| ATOM | C | LEU | H | 29 | 90.478 | 22.442 | 5.378 | 1.00 | 28.20 |
| ATOM | O | LEU | H | 29 | 90.104 | 23.243 | 6.225 | 1.00 | 30.84 |
| ATOM | N | SER | H | 30 | 91.699 | 21.917 | 5.381 | 1.00 | 29.52 |
| ATOM | CA | SER | H | 30 | 92.696 | 22.371 | 6.336 | 1.00 | 30.23 |
| ATOM | CB | SER | H | 30 | 93.591 | 21.223 | 6.779 | 1.00 | 32.80 |

TABLE 2-continued

| | | Atom A.A. Type | | | X | Y | Z | Occ | B |
|---|---|---|---|---|---|---|---|---|---|
| ATOM | OG | SER | H | 30 | 92.878 | 20.324 | 7.605 | 1.00 | 40.53 |
| ATOM | C | SER | H | 30 | 93.533 | 23.473 | 5.719 | 1.00 | 28.60 |
| ATOM | O | SER | H | 30 | 94.197 | 24.228 | 6.426 | 1.00 | 30.68 |
| ATOM | N | THR | H | 31 | 93.507 | 23.553 | 4.399 | 1.00 | 25.79 |
| ATOM | CA | THR | H | 31 | 94.251 | 24.574 | 3.689 | 1.00 | 25.17 |
| ATOM | CB | THR | H | 31 | 94.168 | 24.342 | 2.185 | 1.00 | 22.82 |
| ATOM | OG1 | THR | H | 31 | 94.642 | 23.026 | 1.884 | 1.00 | 21.22 |
| ATOM | CG2 | THR | H | 31 | 94.992 | 25.387 | 1.430 | 1.00 | 25.49 |
| ATOM | C | THR | H | 31 | 93.706 | 25.975 | 4.008 | 1.00 | 26.42 |
| ATOM | O | THR | H | 31 | 92.515 | 26.265 | 3.804 | 1.00 | 25.36 |
| ATOM | N | SER | H | 32 | 94.586 | 26.835 | 4.510 | 1.00 | 25.43 |
| ATOM | CA | SER | H | 32 | 94.243 | 28.204 | 4.846 | 1.00 | 22.79 |
| ATOM | CB | SER | H | 32 | 95.532 | 29.001 | 5.032 | 1.00 | 25.70 |
| ATOM | OG | SER | H | 32 | 95.273 | 30.390 | 5.103 | 1.00 | 28.76 |
| ATOM | C | SER | H | 32 | 93.391 | 28.837 | 3.744 | 1.00 | 21.57 |
| ATOM | O | SER | H | 32 | 93.675 | 28.691 | 2.548 | 1.00 | 17.71 |
| ATOM | N | GLY | H | 33 | 92.324 | 29.510 | 4.160 | 1.00 | 20.10 |
| ATOM | CA | GLY | H | 33 | 91.419 | 30.167 | 3.225 | 1.00 | 18.48 |
| ATOM | C | GLY | H | 33 | 90.306 | 29.308 | 2.637 | 1.00 | 18.96 |
| ATOM | O | GLY | H | 33 | 89.391 | 29.840 | 1.992 | 1.00 | 17.36 |
| ATOM | N | MET | H | 34 | 90.367 | 27.993 | 2.846 | 1.00 | 18.43 |
| ATOM | CA | MET | H | 34 | 89.353 | 27.091 | 2.301 | 1.00 | 21.06 |
| ATOM | CB | MET | H | 34 | 89.896 | 25.660 | 2.232 | 1.00 | 23.04 |
| ATOM | CG | MET | H | 34 | 89.583 | 24.932 | 0.932 | 1.00 | 24.08 |
| ATOM | SD | MET | H | 34 | 90.321 | 25.677 | −0.522 | 1.00 | 29.23 |
| ATOM | CE | MET | H | 34 | 91.809 | 24.779 | −0.645 | 1.00 | 28.50 |
| ATOM | C | MET | H | 34 | 88.032 | 27.140 | 3.088 | 1.00 | 20.35 |
| ATOM | O | MET | H | 34 | 88.023 | 27.277 | 4.321 | 1.00 | 20.61 |
| ATOM | N | SER | H | 35 | 86.921 | 27.022 | 2.367 | 1.00 | 18.89 |
| ATOM | CA | SER | H | 35 | 85.595 | 27.082 | 2.970 | 1.00 | 17.02 |
| ATOM | CB | SER | H | 35 | 85.119 | 28.554 | 2.963 | 1.00 | 16.91 |
| ATOM | OG | SER | H | 35 | 83.744 | 28.731 | 3.303 | 1.00 | 15.81 |
| ATOM | C | SER | H | 35 | 84.630 | 26.226 | 2.148 | 1.00 | 16.42 |
| ATOM | O | SER | H | 35 | 84.839 | 26.014 | 0.954 | 1.00 | 13.99 |
| ATOM | N | VAL | H | 35A | 83.609 | 25.695 | 2.813 | 1.00 | 17.17 |
| ATOM | CA | VAL | H | 35A | 82.561 | 24.928 | 2.145 | 1.00 | 18.21 |
| ATOM | CB | VAL | H | 35A | 82.627 | 23.410 | 2.457 | 1.00 | 10.71 |
| ATOM | CG1 | VAL | H | 35A | 81.375 | 22.712 | 1.965 | 1.00 | 19.97 |
| ATOM | CG2 | VAL | H | 35A | 83.834 | 22.791 | 1.780 | 1.00 | 19.38 |
| ATOM | C | VAL | H | 35A | 81.230 | 25.524 | 2.621 | 1.00 | 17.91 |
| ATOM | O | VAL | H | 35A | 81.013 | 25.716 | 3.821 | 1.00 | 17.18 |
| ATOM | N | GLY | H | 35B | 80.400 | 25.934 | 1.668 | 1.00 | 19.58 |
| ATOM | CA | GLY | H | 35B | 79.101 | 26.501 | 1.997 | 1.00 | 17.30 |
| ATOM | C | GLY | H | 35B | 77.953 | 25.659 | 1.464 | 1.00 | 13.26 |
| ATOM | O | GLY | H | 35B | 78.140 | 24.770 | 0.641 | 1.00 | 7.81 |
| ATOM | N | TRP | H | 36 | 76.760 | 25.939 | 1.961 | 1.00 | 16.00 |
| ATOM | CA | TRP | H | 36 | 75.554 | 25.254 | 1.546 | 1.00 | 14.93 |
| ATOM | CB | TRP | H | 36 | 74.910 | 24.504 | 2.711 | 1.00 | 12.98 |
| ATOM | CG | TRP | H | 36 | 75.636 | 23.264 | 3.120 | 1.00 | 14.47 |
| ATOM | CD2 | TRP | H | 36 | 75.431 | 21.931 | 2.608 | 1.00 | 14.01 |
| ATOM | CE2 | TRP | H | 36 | 76.264 | 21.066 | 3.353 | 1.00 | 12.94 |
| ATOM | CE3 | TRP | H | 36 | 74.619 | 21.388 | 1.598 | 1.00 | 11.52 |
| ATOM | CD1 | TRP | H | 36 | 76.574 | 23.150 | 4.115 | 1.00 | 14.35 |
| ATOM | NE1 | TRP | H | 36 | 76.945 | 21.834 | 4.262 | 1.00 | 15.17 |
| ATOM | CZ2 | TRP | H | 36 | 76.311 | 19.687 | 3.123 | 1.00 | 13.17 |
| ATOM | CZ3 | TRP | H | 36 | 74.666 | 20.008 | 1.367 | 1.00 | 14.14 |
| ATOM | CH2 | TRP | H | 36 | 75.508 | 19.176 | 2.130 | 1.00 | 13.90 |
| ATOM | C | TRP | H | 36 | 74.587 | 26.298 | 0.998 | 1.00 | 15.07 |
| ATOM | O | TRP | H | 36 | 74.433 | 27.393 | 1.569 | 1.00 | 14.43 |
| ATOM | N | ILE | H | 37 | 73.999 | 25.957 | −0.145 | 1.00 | 14.15 |
| ATOM | CA | ILE | H | 37 | 73.028 | 26.769 | −0.862 | 1.00 | 14.19 |
| ATOM | CB | ILE | H | 37 | 73.644 | 27.357 | −2.191 | 1.00 | 13.79 |
| ATOM | CG2 | ILE | H | 37 | 72.623 | 28.239 | −2.912 | 1.00 | 10.80 |
| ATOM | CG1 | ILE | H | 37 | 74.924 | 28.157 | −1.906 | 1.00 | 12.98 |
| ATOM | CD1 | ILE | H | 37 | 76.391 | 27.361 | −2.001 | 1.00 | 9.84 |
| ATOM | C | ILE | H | 37 | 71.857 | 25.834 | −1.255 | 1.00 | 14.48 |
| ATOM | O | ILE | H | 37 | 72.059 | 24.660 | −1.573 | 1.00 | 14.48 |
| ATOM | N | ARG | H | 38 | 70.632 | 26.337 | −1.187 | 1.00 | 15.05 |
| ATOM | CA | ARG | H | 38 | 69.490 | 25.537 | −1.594 | 1.00 | 13.99 |
| ATOM | CB | ARG | H | 38 | 68.654 | 25.107 | −0.400 | 1.00 | 12.72 |
| ATOM | CG | ARG | H | 38 | 67.837 | 26.195 | 0.206 | 1.00 | 11.35 |
| ATOM | CD | ARG | H | 38 | 66.955 | 25.629 | 1.271 | 1.00 | 12.76 |
| ATOM | NE | ARG | H | 38 | 66.226 | 26.687 | 1.942 | 1.00 | 17.72 |
| ATOM | CZ | ARG | H | 38 | 65.375 | 26.498 | 2.942 | 1.00 | 16.18 |
| ATOM | NH1 | ARG | H | 38 | 65.136 | 25.280 | 3.392 | 1.00 | 9.66 |
| ATOM | NH2 | ARG | H | 38 | 64.786 | 27.544 | 3.501 | 1.00 | 14.95 |

TABLE 2-continued

| | | Atom A.A. Type | | | X | Y | Z | Occ | B |
|---|---|---|---|---|---|---|---|---|---|
| ATOM | C | ARG | H | 38 | 68.622 | 26.289 | −2.601 | 1.00 | 13.81 |
| ATOM | O | ARG | H | 38 | 68.718 | 27.514 | −2.765 | 1.00 | 11.23 |
| ATOM | N | GLN | H | 39 | 67.776 | 25.544 | −3.285 | 1.00 | 12.87 |
| ATOM | CA | GLN | H | 39 | 66.919 | 26.147 | −4.265 | 1.00 | 14.66 |
| ATOM | CB | GLN | H | 39 | 67.527 | 26.167 | −5.612 | 1.00 | 16.19 |
| ATOM | CG | GLN | H | 39 | 66.876 | 26.910 | −6.694 | 1.00 | 15.68 |
| ATOM | CD | GLN | H | 39 | 67.681 | 27.024 | −7.956 | 1.00 | 15.98 |
| ATOM | OE1 | GLN | H | 39 | 67.798 | 28.106 | −8.538 | 1.00 | 17.80 |
| ATOM | NE2 | GLN | H | 39 | 68.259 | 25.910 | −8.390 | 1.00 | 16.85 |
| ATOM | C | GLN | H | 39 | 65.600 | 25.396 | −4.367 | 1.00 | 15.76 |
| ATOM | O | GLN | H | 39 | 65.556 | 24.249 | −4.835 | 1.00 | 14.34 |
| ATOM | N | PRO | H | 40 | 64.512 | 26.015 | −3.868 | 1.00 | 17.06 |
| ATOM | CD | PRO | H | 40 | 64.495 | 27.302 | −3.152 | 1.00 | 15.97 |
| ATOM | CA | PRO | H | 40 | 63.173 | 25.436 | −3.899 | 1.00 | 15.94 |
| ATOM | CB | PRO | H | 40 | 62.335 | 26.497 | −3.198 | 1.00 | 16.60 |
| ATOM | CG | PRO | H | 40 | 63.286 | 27.140 | −2.272 | 1.00 | 17.11 |
| ATOM | C | PRO | H | 40 | 62.768 | 25.339 | −5.350 | 1.00 | 17.70 |
| ATOM | O | PRO | H | 40 | 63.214 | 26.134 | −6.162 | 1.00 | 16.65 |
| ATOM | N | PRO | H | 41 | 61.958 | 24.334 | −5.710 | 1.00 | 20.76 |
| ATOM | CD | PRO | H | 41 | 61.398 | 23.245 | −4.889 | 1.00 | 22.23 |
| ATOM | CA | PRO | H | 41 | 61.336 | 24.210 | −7.108 | 1.00 | 20.87 |
| ATOM | CB | PRO | H | 41 | 60.416 | 23.185 | −7.025 | 1.00 | 22.27 |
| ATOM | CG | PRO | H | 41 | 60.893 | 22.279 | −5.936 | 1.00 | 23.84 |
| ATOM | C | PRO | H | 41 | 61.017 | 25.555 | −7.609 | 1.00 | 20.24 |
| ATOM | O | PRO | H | 41 | 60.256 | 26.225 | −6.917 | 1.00 | 22.84 |
| ATOM | N | GLY | H | 42 | 61.540 | 25.993 | −8.744 | 1.00 | 21.26 |
| ATOM | CA | GLY | H | 42 | 61.119 | 27.248 | −9.331 | 1.00 | 20.76 |
| ATOM | C | GLY | H | 42 | 61.459 | 28.521 | −8.583 | 1.00 | 21.38 |
| ATOM | O | GLY | H | 42 | 60.877 | 29.562 | −8.877 | 1.00 | 23.41 |
| ATOM | N | LYS | H | 43 | 62.367 | 28.474 | −7.614 | 1.00 | 21.11 |
| ATOM | CA | LYS | H | 43 | 62.721 | 29.693 | −6.885 | 1.00 | 21.46 |
| ATOM | CB | LYS | H | 43 | 62.341 | 29.597 | −5.402 | 1.00 | 24.52 |
| ATOM | CG | LYS | H | 43 | 60.863 | 29.358 | −5.133 | 1.00 | 26.93 |
| ATOM | CD | LYS | H | 43 | 60.568 | 29.524 | −3.660 | 1.00 | 33.74 |
| ATOM | CE | LYS | H | 43 | 59.089 | 29.328 | −3.340 | 1.00 | 38.50 |
| ATOM | NZ | LYS | H | 43 | 58.826 | 29.556 | −1.884 | 1.00 | 39.74 |
| ATOM | C | LYS | H | 43 | 64.210 | 29.976 | −7.021 | 1.00 | 20.27 |
| ATOM | O | LYS | H | 43 | 64.348 | 29.184 | −7.599 | 1.00 | 20.32 |
| ATOM | N | ALA | H | 44 | 64.646 | 31.106 | −6.487 | 1.00 | 19.41 |
| ATOM | CA | ALA | H | 44 | 66.051 | 31.491 | −6.557 | 1.00 | 19.41 |
| ATOM | CB | ALA | H | 44 | 66.189 | 32.990 | −6.372 | 1.00 | 19.26 |
| ATOM | C | ALA | H | 44 | 66.925 | 30.764 | −5.538 | 1.00 | 19.34 |
| ATOM | O | ALA | H | 44 | 66.435 | 30.088 | −4.620 | 1.00 | 19.44 |
| ATOM | N | LEU | H | 45 | 68.232 | 30.901 | −5.717 | 1.00 | 17.25 |
| ATOM | CA | LEU | H | 45 | 69.196 | 30.299 | −4.815 | 1.00 | 15.89 |
| ATOM | CB | LEU | H | 45 | 70.620 | 30.447 | −5.373 | 1.00 | 10.63 |
| ATOM | CD | LEU | H | 45 | 70.953 | 29.865 | −6.735 | 1.00 | 12.90 |
| ATOM | CD1 | LEU | H | 45 | 72.289 | 30.431 | −7.221 | 1.00 | 8.13 |
| ATOM | CD2 | LEU | H | 45 | 71.013 | 28.351 | −6.645 | 1.00 | 10.96 |
| ATOM | C | LEU | H | 45 | 69.105 | 31.048 | −3.488 | 1.00 | 24.70 |
| ATOM | O | LEU | H | 45 | 68.854 | 32.254 | −3.465 | 1.00 | 17.03 |
| ATOM | N | GLU | H | 46 | 69.320 | 30.326 | −2.398 | 1.00 | 15.19 |
| ATOM | CA | GLU | H | 46 | 69.317 | 30.877 | −1.058 | 1.00 | 14.24 |
| ATOM | CB | GLU | H | 46 | 68.054 | 30.488 | −0.307 | 1.00 | 13.44 |
| ATOM | CG | GLU | H | 46 | 68.093 | 30.929 | 1.136 | 1.00 | 14.99 |
| ATOM | CD | GLU | H | 46 | 66.813 | 30.604 | 1.879 | 1.00 | 20.34 |
| ATOM | OE1 | GLU | H | 46 | 66.322 | 29.460 | 1.784 | 1.00 | 20.65 |
| ATOM | OE2 | GLU | H | 46 | 66.295 | 31.499 | 2.563 | 1.00 | 22.75 |
| ATOM | C | GLU | H | 46 | 70.504 | 30.332 | −0.300 | 1.00 | 13.87 |
| ATOM | O | GLU | H | 46 | 70.608 | 29.121 | −0.094 | 1.00 | 14.81 |
| ATOM | N | TRP | H | 47 | 71.368 | 31.228 | 0.161 | 1.00 | 15.80 |
| ATOM | CA | TRP | H | 47 | 72.548 | 30.846 | 0.923 | 1.00 | 15.32 |
| ATOM | CB | TRP | H | 47 | 73.496 | 32.034 | 1.070 | 1.00 | 15.93 |
| ATOM | CG | TRP | H | 47 | 74.728 | 31.714 | 1.868 | 1.00 | 18.77 |
| ATOM | CD2 | TRP | H | 47 | 74.966 | 32.053 | 3.238 | 1.00 | 18.77 |
| ATOM | CE2 | TRP | H | 47 | 76.256 | 31.564 | 3.575 | 1.00 | 19.72 |
| ATOM | CE3 | TRP | H | 47 | 74.221 | 32.729 | 4.215 | 1.00 | 16.45 |
| ATOM | CG1 | TRP | H | 47 | 75.848 | 31.041 | 1.435 | 1.00 | 17.15 |
| ATOM | NE1 | TRP | H | 47 | 76.767 | 30.952 | 2.459 | 1.00 | 19.64 |
| ATOM | CZ2 | TRP | H | 47 | 76.814 | 31.733 | 4.846 | 1.00 | 16.17 |
| ATOM | CZ3 | TRP | H | 47 | 74.783 | 32.895 | 5.476 | 1.00 | 18.48 |
| ATOM | CH2 | TRP | H | 47 | 76.067 | 32.398 | 5.777 | 1.00 | 17.28 |
| ATOM | C | TRP | H | 47 | 72.095 | 30.349 | 2.293 | 1.00 | 15.44 |
| ATOM | O | TRP | H | 47 | 71.236 | 30.960 | 2.922 | 1.00 | 14.94 |
| ATOM | N | LEU | H | 48 | 72.674 | 29.240 | 2.742 | 1.00 | 13.88 |
| ATOM | CA | LEU | H | 48 | 72.311 | 28.639 | 4.021 | 1.00 | 14.64 |

TABLE 2-continued

| | | Atom A.A. Type | | | X | Y | Z | Occ | B |
|---|---|---|---|---|---|---|---|---|---|
| ATOM | CB | LEU | H | 48 | 72.057 | 27.151 | 3.829 | 1.00 | 15.18 |
| ATOM | CG | LEU | H | 48 | 70.642 | 26.595 | 3.685 | 1.00 | 19.59 |
| ATOM | CD1 | LEU | H | 48 | 69.668 | 27.639 | 3.236 | 1.00 | 19.86 |
| ATOM | CD2 | LEU | H | 48 | 70.658 | 25.396 | 2.779 | 1.00 | 14.67 |
| ATOM | C | LEU | H | 48 | 73.348 | 28.813 | 5.122 | 1.00 | 16.42 |
| ATOM | O | LEU | H | 48 | 73.030 | 29.297 | 6.217 | 1.00 | 16.87 |
| ATOM | N | ALA | H | 49 | 74.588 | 28.416 | 4.834 | 1.00 | 17.65 |
| ATOM | CA | ALA | H | 49 | 75.660 | 28.485 | 5.819 | 1.00 | 15.42 |
| ATOM | CB | ALA | H | 49 | 75.326 | 27.536 | 7.008 | 1.00 | 10.92 |
| ATOM | C | ALA | H | 49 | 77.000 | 28.083 | 5.197 | 1.00 | 15.85 |
| ATOM | O | ALA | H | 49 | 77.051 | 27.654 | 4.046 | 1.00 | 11.51 |
| ATOM | N | ASP | H | 50 | 78.085 | 28.311 | 5.941 | 1.00 | 17.23 |
| ATOM | CA | ASP | H | 50 | 79.427 | 27.915 | 5.526 | 1.00 | 19.09 |
| ATOM | CB | ASP | H | 50 | 80.068 | 28.898 | 4.515 | 1.00 | 21.53 |
| ATOM | CG | ASP | H | 50 | 80.480 | 30.247 | 5.125 | 1.00 | 28.53 |
| ATOM | OD1 | ASP | H | 50 | 80.865 | 30.328 | 6.307 | 1.00 | 32.68 |
| ATOM | OD2 | ASP | H | 50 | 80.448 | 31.257 | 4.392 | 1.00 | 31.09 |
| ATOM | C | ASP | H | 50 | 80.315 | 27.663 | 6.746 | 1.00 | 18.22 |
| ATOM | O | ASP | H | 50 | 79.981 | 28.049 | 7.867 | 1.00 | 17.40 |
| ATOM | N | ILE | H | 51 | 81.426 | 26.982 | 6.525 | 1.00 | 18.70 |
| ATOM | CA | ILE | H | 51 | 82.3,6 | 126.68 | 37.588 | 1.00 | 18.57 |
| ATOM | CB | ILE | H | 51 | 82.191 | 25.214 | 8.098 | 1.00 | 16.66 |
| ATOM | CG2 | ILE | H | 51 | 82.568 | 24.215 | 6.992 | 1.00 | 15.80 |
| ATOM | CG1 | ILE | H | 51 | 83.005 | 24.994 | 9.387 | 1.00 | 14.81 |
| ATOM | CD1 | ILE | H | 51 | 82.725 | 23.688 | 10.108 | 1.00 | 10.85 |
| ATOM | C | ILE | H | 51 | 83.757 | 26.900 | 6.994 | 1.00 | 20.10 |
| ATOM | O | ILE | H | 51 | 84.028 | 26.479 | 5.850 | 1.00 | 20.16 |
| ATOM | N | TRP | H | 52 | 84.613 | 27.592 | 7.750 | 1.00 | 17.80 |
| ATOM | CA | TRP | H | 52 | 85.976 | 27.885 | 7.322 | 1.00 | 18.52 |
| ATOM | CB | TRP | H | 52 | 86.438 | 29.230 | 7.882 | 1.00 | 17.60 |
| ATOM | CG | TRP | H | 52 | 85.852 | 30.427 | 7.186 | 1.00 | 18.48 |
| ATOM | CD2 | TRP | H | 52 | 86.315 | 31.773 | 7.275 | 1.00 | 18.83 |
| ATOM | CE2 | TRP | H | 52 | 85.460 | 32.568 | 6.470 | 1.00 | 17.83 |
| ATOM | CE3 | TRP | H | 52 | 87.372 | 32.393 | 7.960 | 1.00 | 20.10 |
| ATOM | CD1 | TRP | H | 52 | 84.765 | 30.454 | 6.346 | 1.00 | 18.77 |
| ATOM | NE1 | TRP | H | 52 | 84.525 | 31.739 | 5.915 | 1.00 | 19.18 |
| ATOM | CZ2 | TRP | H | 52 | 85.628 | 33.943 | 6.336 | 1.00 | 17.47 |
| ATOM | CZ3 | TRP | H | 52 | 87.536 | 33.759 | 7.823 | 1.00 | 16.79 |
| ATOM | CH2 | TRP | H | 52 | 86.668 | 34.520 | 7.018 | 1.00 | 17.22 |
| ATOM | C | TRP | H | 52 | 86.951 | 26.806 | 7.758 | 1.00 | 20.38 |
| ATOM | O | TRP | H | 52 | 86.658 | 26.004 | 8.640 | 1.00 | 18.84 |
| ATOM | N | TRP | H | 52A | 88.135 | 26.830 | 7.159 | 1.00 | 23.43 |
| ATOM | CA | TRP | H | 52A | 89.203 | 25.877 | 7.463 | 1.00 | 24.45 |
| ATOM | CB | TRP | H | 52A | 90.459 | 26.230 | 6.661 | 1.00 | 23.73 |
| ATOM | CG | TRP | H | 52A | 91.148 | 27.485 | 7.136 | 1.00 | 23.91 |
| ATOM | CD2 | TRP | H | 52A | 90.769 | 28.845 | 6.861 | 1.00 | 22.37 |
| ATOM | CE2 | TRP | H | 52A | 91.713 | 29.677 | 7.500 | 1.00 | 24.65 |
| ATOM | CE3 | TRP | H | 52A | 89.731 | 29.437 | 6.132 | 1.00 | 21.82 |
| ATOM | CG1 | TRP | H | 52A | 92.266 | 27.551 | 7.912 | 1.00 | 25.27 |
| ATOM | NE1 | TRP | H | 52A | 92.612 | 28.863 | 8.134 | 1.00 | 26.22 |
| ATOM | CZ2 | TRP | H | 52A | 91.652 | 31.068 | 7.435 | 1.00 | 21.13 |
| ATOM | CZ3 | TRP | H | 52A | 89.669 | 30.822 | 6.066 | 1.00 | 22.40 |
| ATOM | CH2 | TRP | H | 52A | 90.627 | 31.622 | 6.716 | 1.00 | 24.82 |
| ATOM | C | TRP | H | 52A | 89.537 | 25.895 | 8.952 | 1.00 | 25.32 |
| ATOM | O | TRP | H | 52A | 89.974 | 24.886 | 9.509 | 1.00 | 27.89 |
| ATOM | N | ASP | H | 52B | 89.338 | 27.046 | 9.584 | 1.00 | 24.77 |
| ATOM | CA | ASP | H | 52B | 89.624 | 27.204 | 10.998 | 1.00 | 26.84 |
| ATOM | CB | ASP | H | 52B | 90.186 | 28.606 | 11.274 | 1.00 | 27.51 |
| ATOM | CG | ASP | H | 52B | 89.193 | 29.722 | 10.979 | 1.00 | 31.35 |
| ATOM | OG1 | ASP | H | 52B | 87.991 | 29.447 | 10.793 | 1.00 | 31.83 |
| ATOM | OG2 | ASP | H | 52B | 89.619 | 30.898 | 10.942 | 1.00 | 33.88 |
| ATOM | C | ASP | H | 52B | 88.418 | 26.911 | 11.893 | 1.00 | 27.40 |
| ATOM | O | ASP | H | 52B | 88.410 | 27.245 | 13.072 | 1.00 | 26.88 |
| ATOM | N | ASP | H | 52C | 87.392 | 26.313 | 11.305 | 1.00 | 28.03 |
| ATOM | CA | ASP | H | 52C | 86.163 | 25.955 | 11.998 | 1.00 | 26.36 |
| ATOM | CB | ASP | H | 52C | 86.446 | 25.160 | 13.274 | 1.00 | 28.42 |
| ATOM | CG | ASP | H | 52C | 85.327 | 24.180 | 13.603 | 1.00 | 33.76 |
| ATOM | OD1 | ASP | H | 52C | 84.868 | 24.153 | 14.764 | 1.00 | 36.60 |
| ATOM | OD2 | ASP | H | 52C | 84.902 | 23.430 | 12.697 | 1.00 | 34.49 |
| ATOM | C | ASP | H | 52C | 85.184 | 27.093 | 12.269 | 1.00 | 25.03 |
| ATOM | O | ASP | H | 52C | 84.178 | 26.896 | 12.958 | 1.00 | 26.18 |
| ATOM | N | LYS | H | 53 | 85.440 | 28.274 | 11.713 | 1.00 | 23.11 |
| ATOM | CA | LYS | H | 53 | 84.492 | 29.376 | 11.893 | 1.00 | 24.05 |
| ATOM | CB | LYS | H | 53 | 85.050 | 30.712 | 11.388 | 1.00 | 25.09 |
| ATOM | CG | LYS | H | 53 | 84.286 | 31.929 | 11.912 | 1.00 | 24.49 |
| ATOM | CD | LYS | H | 53 | 84.751 | 33.225 | 11.245 | 1.00 | 25.32 |

TABLE 2-continued

| | | Atom A.A. Type | | | X | Y | Z | Occ | B |
|---|---|---|---|---|---|---|---|---|---|
| ATOM | CE | LYS | H | 53 | 84.428 | 33.243 | 9.741 | 1.00 | 27.10 |
| ATOM | NZ | LYS | H | 53 | 82.961 | 33.405 | 9.382 | 1.00 | 25.06 |
| ATOM | C | LYS | H | 53 | 83.237 | 29.016 | 11.078 | 1.00 | 24.81 |
| ATOM | O | LYS | H | 53 | 83.328 | 28.634 | 9.900 | 1.00 | 22.11 |
| ATOM | N | LYS | H | 54 | 82.076 | 29.153 | 11.706 | 1.00 | 24.62 |
| ATOM | CA | LYS | H | 54 | 80.798 | 28.831 | 11.085 | 1.00 | 23.21 |
| ATOM | CB | LYS | H | 54 | 80.045 | 27.879 | 11.995 | 1.00 | 20.83 |
| ATOM | CG | LYS | H | 54 | 80.861 | 26.659 | 12.357 | 1.00 | 20.72 |
| ATOM | CG | LYS | H | 54 | 80.211 | 25.853 | 13.454 | 1.00 | 20.64 |
| ATOM | CE | LYS | H | 54 | 81.055 | 24.631 | 13.802 | 1.00 | 22.89 |
| ATOM | NZ | LYS | H | 54 | 82.409 | 25.036 | 14.297 | 1.00 | 23.84 |
| ATOM | C | LYS | H | 54 | 79.975 | 30.090 | 10.870 | 1.00 | 23.07 |
| ATOM | O | LYS | H | 54 | 79.984 | 30.988 | 11.704 | 1.00 | 24.80 |
| ATOM | N | ASP | H | 55 | 79.286 | 30.171 | 9.740 | 1.00 | 23.45 |
| ATOM | CA | ASP | H | 55 | 78.452 | 31.331 | 9.448 | 1.00 | 23.61 |
| ATOM | CB | ASP | H | 55 | 79.083 | 32.190 | 8.358 | 1.00 | 29.01 |
| ATOM | CG | ASP | H | 55 | 78.710 | 33.653 | 8.481 | 1.00 | 33.21 |
| ATOM | OD1 | ASP | H | 55 | 79.219 | 34.452 | 7.674 | 1.00 | 36.92 |
| ATOM | OD2 | ASP | H | 55 | 77.911 | 34.015 | 9.375 | 1.00 | 37.49 |
| ATOM | C | ASP | H | 55 | 77.085 | 30.801 | 9.028 | 1.00 | 22.55 |
| ATOM | O | ASP | H | 55 | 77.000 | 29.775 | 8.357 | 1.00 | 22.79 |
| ATOM | N | TYR | H | 56 | 76.023 | 31.495 | 9.418 | 1.00 | 21.97 |
| ATOM | CA | TYR | H | 56 | 74.675 | 31.022 | 9.154 | 1.00 | 22.29 |
| ATOM | CB | TYR | H | 56 | 74.051 | 30.491 | 10.449 | 1.00 | 19.74 |
| ATOM | CG | TYR | H | 56 | 74.749 | 29.308 | 11.084 | 1.00 | 18.86 |
| ATOM | CG1 | TYR | H | 56 | 74.608 | 28.034 | 10.554 | 1.00 | 19.13 |
| ATOM | CE1 | TYR | H | 56 | 75.211 | 26.947 | 11.141 | 1.00 | 19.36 |
| ATOM | CD2 | TYR | H | 56 | 75.522 | 29.462 | 12.227 | 1.00 | 14.87 |
| ATOM | CE2 | TYR | H | 56 | 76.127 | 28.379 | 12.821 | 1.00 | 15.48 |
| ATOM | CZ | TYR | H | 56 | 75.971 | 27.126 | 12.281 | 1.00 | 17.68 |
| ATOM | OH | TYR | H | 56 | 76.565 | 26.031 | 12.868 | 1.00 | 20.54 |
| ATOM | C | TYR | H | 56 | 73.736 | 32.071 | 8.662 | 1.00 | 22.36 |
| ATOM | O | TYR | H | 56 | 73.833 | 33.228 | 9.047 | 1.00 | 22.95 |
| ATOM | N | ASN | H | 57 | 72.780 | 31.643 | 7.849 | 1.00 | 24.93 |
| ATOM | CA | ASN | H | 57 | 71.742 | 32.543 | 7.357 | 1.00 | 27.64 |
| ATOM | CB | ASN | H | 57 | 70.862 | 31.833 | 6.315 | 1.00 | 28.33 |
| ATOM | CG | ASN | H | 57 | 69.825 | 32.756 | 5.693 | 1.00 | 29.14 |
| ATOM | OD1 | ASN | H | 57 | 68.986 | 33.312 | 6.385 | 1.00 | 31.07 |
| ATOM | ND2 | ASN | H | 57 | 69.874 | 32.909 | 4.386 | 1.00 | 29.86 |
| ATOM | C | ASN | H | 57 | 70.929 | 32.879 | 8.617 | 1.00 | 27.04 |
| ATOM | O | ASN | H | 57 | 70.524 | 31.981 | 9.357 | 1.00 | 23.79 |
| ATOM | N | PRO | H | 58 | 70.762 | 34.176 | 8.921 | 1.00 | 28.56 |
| ATOM | CD | PRO | H | 58 | 71.297 | 35.280 | 8.113 | 1.00 | 28.44 |
| ATOM | CA | PRO | H | 58 | 70.025 | 34.708 | 10.077 | 1.00 | 29.68 |
| ATOM | CB | PRO | H | 58 | 70.043 | 36.205 | 9.816 | 1.00 | 31.68 |
| ATOM | CG | PRO | H | 58 | 71.336 | 36.388 | 9.102 | 1.00 | 32.72 |
| ATOM | C | PRO | H | 58 | 68.595 | 34.207 | 10.165 | 1.00 | 30.03 |
| ATOM | O | PRO | H | 58 | 68.138 | 33.842 | 11.241 | 1.00 | 32.06 |
| ATOM | N | SER | H | 59 | 67.902 | 34.203 | 9.028 | 1.00 | 30.81 |
| ATOM | CA | SER | H | 59 | 66.521 | 33.739 | 8.924 | 1.00 | 33.61 |
| ATOM | CB | SER | H | 59 | 66.045 | 33.796 | 7.464 | 1.00 | 33.98 |
| ATOM | OG | SER | H | 59 | 66.414 | 35.012 | 6.825 | 1.00 | 42.18 |
| ATOM | C | SER | H | 59 | 66.398 | 32.292 | 9.371 | 1.00 | 34.64 |
| ATOM | O | SER | H | 59 | 65.354 | 31.878 | 9.882 | 1.00 | 37.21 |
| ATOM | N | LEU | H | 60 | 67.461 | 31.521 | 9.142 | 1.00 | 34.74 |
| ATOM | CA | LEU | H | 60 | 67.485 | 30.100 | 9.463 | 1.00 | 33.58 |
| ATOM | CB | LEU | H | 60 | 67.896 | 29.314 | 8.205 | 1.00 | 32.72 |
| ATOM | CG | LEU | H | 60 | 66.922 | 28.895 | 7.093 | 1.00 | 34.81 |
| ATOM | CD1 | LEU | H | 60 | 65.565 | 29.513 | 7.313 | 1.00 | 36.52 |
| ATOM | CD2 | LEU | H | 60 | 67.479 | 29.259 | 5.716 | 1.00 | 30.66 |
| ATOM | C | LEU | H | 60 | 68.406 | 29.661 | 10.606 | 1.00 | 34.55 |
| ATOM | O | LEU | H | 60 | 68.276 | 28.523 | 11.082 | 1.00 | 32.36 |
| ATOM | N | LYS | H | 61 | 69.321 | 30.539 | 11.062 | 1.00 | 35.17 |
| ATOM | CA | LYS | H | 61 | 70.2 2 | 30.163 | 12.092 | 1.00 | 35.08 |
| ATOM | CB | LYS | H | 61 | 70.959 | 31.376 | 12.750 | 1.00 | 36.66 |
| ATOM | CG | LYS | H | 61 | 72.030 | 30.921 | 13.748 | 1.00 | 42.58 |
| ATOM | CD | LYS | H | 61 | 72.964 | 32.023 | 14.233 | 1.00 | 47.58 |
| ATOM | CE | LYS | H | 61 | 74.154 | 31.417 | 15.007 | 1.00 | 48.86 |
| ATOM | NZ | LYS | H | 61 | 75.157 | 32.426 | 15.480 | 1.00 | 51.14 |
| ATOM | C | LYS | H | 61 | 69.830 | 29.172 | 13.163 | 1.00 | 34.17 |
| ATOM | O | LYS | H | 61 | 70.520 | 28.174 | 13.423 | 1.00 | 29.94 |
| ATOM | N | SER | H | 62 | 68.646 | 29.426 | 13.726 | 1.00 | 30.94 |
| ATOM | CA | SER | H | 62 | 68.051 | 28.597 | 14.770 | 1.00 | 28.25 |
| ATOM | CB | SER | H | 62 | 66.650 | 29.117 | 15.072 | 1.00 | 30.62 |
| ATOM | CG | SER | H | 62 | 65.918 | 29.317 | 13.866 | 1.00 | 33.57 |

TABLE 2-continued

| | | Atom A.A. Type | | | X | Y | Z | Occ | B |
|---|---|---|---|---|---|---|---|---|---|
| ATOM | C | SER | H | 62 | 67.946 | 27.110 | 14.440 | 1.00 | 28.84 |
| ATOM | O | SER | H | 62 | 68.078 | 26.252 | 15.317 | 1.00 | 28.71 |
| ATOM | N | ARG | H | 63 | 67.708 | 26.807 | 13.171 | 1.00 | 26.01 |
| ATOM | CA | ARG | H | 63 | 67.528 | 25.432 | 12.743 | 1.00 | 23.24 |
| ATOM | CB | ARG | H | 63 | 66.394 | 25.407 | 11.739 | 1.00 | 24.03 |
| ATOM | CG | ARG | H | 63 | 65.149 | 26.109 | 12.252 | 1.00 | 27.07 |
| ATOM | CD | ARG | H | 63 | 64.142 | 26.336 | 11.146 | 1.00 | 30.24 |
| ATOM | NE | ARG | H | 63 | 63.910 | 25.102 | 10.417 | 1.00 | 29.49 |
| ATOM | CZ | ARG | H | 63 | 63.630 | 25.049 | 9.127 | 1.00 | 24.96 |
| ATOM | NH1 | ARG | H | 63 | 63.535 | 26.166 | 8.415 | 1.00 | 23.27 |
| ATOM | ND2 | ARG | H | 63 | 63.471 | 23.873 | 8.556 | 1.00 | 24.48 |
| ATOM | C | ARG | H | 63 | 68.741 | 24.751 | 12.145 | 1.00 | 22.40 |
| ATOM | O | ARG | H | 63 | 68.731 | 23.546 | 11.929 | 1.00 | 21.50 |
| ATOM | N | LEU | H | 64 | 69.804 | 25.518 | 11.941 | 1.00 | 22.16 |
| ATOM | CA | LEU | H | 64 | 71.023 | 25.034 | 11.296 | 1.00 | 21.65 |
| ATOM | CB | LEU | H | 64 | 71.466 | 26.058 | 10.243 | 1.00 | 19.30 |
| ATOM | CG | LEU | H | 64 | 70.890 | 26.155 | 8.832 | 1.00 | 20.78 |
| ATOM | CD1 | LEU | H | 64 | 69.545 | 25.524 | 8.719 | 1.00 | 20.71 |
| ATOM | CD2 | LEU | H | 64 | 70.879 | 27.617 | 8.396 | 1.00 | 15.66 |
| ATOM | C | LEU | H | 64 | 72.234 | 24.732 | 12.156 | 1.00 | 19.31 |
| ATOM | O | LEU | H | 64 | 72.564 | 25.472 | 13.070 | 1.00 | 20.05 |
| ATOM | N | THR | H | 65 | 72.941 | 23.676 | 11.785 | 1.00 | 19.59 |
| ATOM | CA | THR | H | 65 | 74.185 | 23.294 | 12.442 | 1.00 | 20.65 |
| ATOM | CB | THR | H | 65 | 73.998 | 22.193 | 13.493 | 1.00 | 20.20 |
| ATOM | OG1 | THR | H | 65 | 72.990 | 22.595 | 14.428 | 1.00 | 24.09 |
| ATOM | CG2 | THR | H | 65 | 75.315 | 21.946 | 14.225 | 1.00 | 19.32 |
| ATOM | C | THR | H | 65 | 75.144 | 22.768 | 11.378 | 1.00 | 19.21 |
| ATOM | O | THR | H | 65 | 74.857 | 21.778 | 10.702 | 1.00 | 21.02 |
| ATOM | N | ILE | H | 66 | 76.262 | 23.452 | 11.204 | 1.00 | 19.16 |
| ATOM | CA | ILE | H | 66 | 77.254 | 23.021 | 10.240 | 1.00 | 17.30 |
| ATOM | CB | ILE | H | 66 | 77.546 | 24.145 | 9.217 | 1.00 | 16.44 |
| ATOM | CG2 | ILE | H | 66 | 78.223 | 25.316 | 9.884 | 1.00 | 17.96 |
| ATOM | CG1 | ILE | H | 66 | 78.367 | 23.611 | 8.048 | 1.00 | 16.66 |
| ATOM | CD1 | ILE | H | 66 | 78.283 | 24.492 | 6.803 | 1.00 | 16.98 |
| ATOM | C | ILE | H | 66 | 78.509 | 22.541 | 10.984 | 1.00 | 17.84 |
| ATOM | O | ILE | H | 66 | 78.856 | 23.062 | 12.040 | 1.00 | 18.17 |
| ATOM | N | SER | H | 67 | 79.131 | 21.486 | 10.482 | 1.00 | 18.11 |
| ATOM | CA | SER | H | 67 | 80.321 | 20.948 | 11.105 | 1.00 | 20.14 |
| ATOM | CB | SER | H | 67 | 79.934 | 19.982 | 12.222 | 1.00 | 19.34 |
| ATOM | OG | SER | H | 67 | 79.148 | 18.916 | 11.722 | 1.00 | 22.34 |
| ATOM | C | SER | H | 67 | 81.129 | 20.235 | 10.042 | 1.00 | 21.51 |
| ATOM | O | SER | H | 67 | 80.617 | 19.939 | 8.963 | 1.00 | 23.77 |
| ATOM | N | LYS | H | 68 | 82.389 | 19.945 | 10.326 | 1.00 | 22.37 |
| ATOM | CA | LYS | H | 68 | 83.220 | 19.276 | 9.337 | 1.00 | 24.76 |
| ATOM | CB | LYS | H | 68 | 84.170 | 20.268 | 8.653 | 1.00 | 24.88 |
| ATOM | CG | LYS | H | 68 | 85.243 | 20.860 | 9.600 | 1.00 | 26.98 |
| ATOM | CD | LYS | H | 68 | 86.178 | 21.863 | 8.913 | 1.00 | 24.59 |
| ATOM | CE | LYS | H | 68 | 87.077 | 22.575 | 9.923 | 1.00 | 25.04 |
| ATOM | NZ | LYS | H | 68 | 87.950 | 21.660 | 10.691 | 1.00 | 22.91 |
| ATOM | C | LYS | H | 68 | 84.065 | 18.220 | 9.995 | 1.00 | 2.60 |
| ATOM | O | LYS | H | 68 | 84.222 | 18.194 | 11.211 | 1.00 | 26.90 |
| ATOM | N | ASP | H | 69 | 84.609 | 17.350 | 9.162 | 1.00 | 30.57 |
| ATOM | CA | ASP | H | 69 | 85.497 | 16.301 | 9.603 | 1.00 | 32.63 |
| ATOM | CB | ASP | H | 69 | 84.751 | 14.987 | 9.808 | 1.00 | 32.99 |
| ATOM | CG | ASP | H | 69 | 85.630 | 13.919 | 10.414 | 1.00 | 34.81 |
| ATOM | OD1 | ASP | H | 69 | 85.157 | 13.155 | 11.274 | 1.00 | 36.75 |
| ATOM | OD2 | ASP | H | 69 | 86.800 | 13.839 | 10.027 | 1.00 | 31.40 |
| ATOM | C | ASP | H | 69 | 86.530 | 16.184 | 8.487 | 1.00 | 34.03 |
| ATOM | O | ASP | H | 69 | 86.370 | 15.392 | 7.547 | 1.00 | 32.76 |
| ATOM | N | THR | H | 70 | 87.571 | 17.008 | 8.594 | 1.00 | 36.91 |
| ATOM | CA | THR | H | 70 | 88.660 | 17.047 | 7.624 | 1.00 | 38.63 |
| ATOM | CB | THR | H | 70 | 89.797 | 17.966 | 8.100 | 1.00 | 37.90 |
| ATOM | OG1 | THR | H | 70 | 89.244 | 19.134 | 8.721 | 1.00 | 40.53 |
| ATOM | CG2 | THR | H | 70 | 90.630 | 18.400 | 6.924 | 1.00 | 41.19 |
| ATOM | C | THR | H | 70 | 89.193 | 15.640 | 7.441 | 1.00 | 39.84 |
| ATOM | O | THR | H | 70 | 89.470 | 15.209 | 6.323 | 1.00 | 40.13 |
| ATOM | N | SER | H | 71 | 89.243 | 14.904 | 8.546 | 1.00 | 40.90 |
| ATOM | CA | SER | H | 71 | 89.711 | 13.526 | 8.543 | 1.00 | 42.40 |
| ATOM | CB | SER | H | 71 | 89.550 | 12.917 | 9.938 | 1.00 | 42.28 |
| ATOM | OG | SER | H | 71 | 89.247 | 13.928 | 10.895 | 1.00 | 46.77 |
| ATOM | C | SER | H | 71 | 88.900 | 12.714 | 7.539 | 1.00 | 42.54 |
| ATOM | O | SER | H | 71 | 89.441 | 11.844 | 6.858 | 1.00 | 45.17 |
| ATOM | N | LYS | H | 72 | 87.610 | 13.028 | 7.429 | 1.00 | 39.45 |
| ATOM | CA | LYS | H | 72 | 86.728 | 12.317 | 6.517 | 1.00 | 36.17 |
| ATOM | CB | LYS | H | 72 | 85.4.5 | 411.88 | 67.253 | 1.00 | 35.09 |
| ATOM | C | LYS | H | 72 | 86.394 | 13.122 | 5.253 | 1.00 | 34.32 |

TABLE 2-continued

| | | Atom A.A. Type | | | X | Y | Z | Occ | B |
|---|---|---|---|---|---|---|---|---|---|
| ATOM | O | LYS | H | 72 | 85.624 | 12.670 | 4.404 | 1.00 | 36.05 |
| ATOM | N | ASN | H | 73 | 86.985 | 14.303 | 5.110 | 1.00 | 30.90 |
| ATOM | CA | ASN | H | 73 | 86.725 | 15.122 | 3.935 | 1.00 | 28.57 |
| ATOM | CB | ASN | H | 73 | 87.339 | 14.479 | 2.698 | 1.00 | 30.95 |
| ATOM | CG | ASN | H | 73 | 88.753 | 14.930 | 2.459 | 1.00 | 32.43 |
| ATOM | OD1 | ASN | H | 73 | 89.410 | 15.448 | 3.356 | 1.00 | 33.76 |
| ATOM | ND2 | ASN | H | 73 | 89.217 | 14.781 | 1.231 | 1.00 | 33.57 |
| ATOM | C | ASN | H | 73 | 85.235 | 15.368 | 3.706 | 1.00 | 27.51 |
| ATOM | O | ASN | H | 73 | 84.723 | 15.252 | 2.581 | 1.00 | 24.45 |
| ATOM | N | GLN | H | 74 | 84.535 | 15.700 | 4.783 | 1.00 | 26.55 |
| ATOM | CA | GLN | H | 74 | 83.120 | 15.977 | 4.680 | 1.00 | 25.83 |
| ATOM | CB | GLN | H | 74 | 82.305 | 14.693 | 4.841 | 1.00 | 27.06 |
| ATOM | CG | GLN | H | 74 | 82.244 | 14.191 | 6.232 | 1.00 | 29.34 |
| ATOM | CD | GLN | H | 74 | 81.624 | 12.830 | 6.295 | 1.00 | 32.28 |
| ATOM | OE1 | GLN | H | 74 | 81.764 | 12.043 | 5.367 | 1.00 | 29.45 |
| ATOM | NE2 | GLN | H | 74 | 80.935 | 12.535 | 7.398 | 1.00 | 32.68 |
| ATOM | C | GLN | H | 74 | 82.649 | 17.068 | 5.638 | 1.00 | 23.47 |
| ATOM | O | GLN | H | 74 | 83.254 | 17.328 | 6.684 | 1.00 | 19.87 |
| ATOM | N | VAL | H | 75 | 81.633 | 17.784 | 5.185 | 1.00 | 20.78 |
| ATOM | CA | VAL | H | 75 | 81.016 | 18.858 | 5.934 | 1.00 | 18.65 |
| ATOM | CB | VAL | H | 75 | 81.073 | 20.188 | 5.119 | 1.00 | 19.56 |
| ATOM | CG1 | VAL | H | 75 | 80.267 | 21.297 | 5.808 | 1.00 | 17.72 |
| ATOM | CG2 | VAL | H | 75 | 82.528 | 20.639 | 4.948 | 1.00 | 16.40 |
| ATOM | C | VAL | H | 75 | 79.583 | 18.378 | 6.069 | 1.00 | 17.42 |
| ATOM | O | VAL | H | 75 | 79.042 | 17.751 | 5.185 | 1.00 | 18.13 |
| ATOM | N | VAL | H | 76 | 78.982 | 18.619 | 7.242 | 1.00 | 17.43 |
| ATOM | CA | VAL | H | 76 | 77.615 | 18.177 | 7.491 | 1.00 | 17.51 |
| ATOM | CB | VAL | H | 76 | 77.579 | 17.122 | 8.652 | 1.00 | 18.76 |
| ATOM | CG1 | VAL | H | 76 | 76.140 | 16.849 | 9.115 | 1.00 | 16.58 |
| ATOM | CG2 | VAL | H | 76 | 78.239 | 15.822 | 8.202 | 1.00 | 16.10 |
| ATOM | C | VAL | H | 76 | 76.753 | 19.363 | 7.872 | 1.00 | 16.23 |
| ATOM | O | VAL | H | 76 | 77.217 | 20.261 | 8.559 | 1.00 | 16.73 |
| ATOM | N | LEU | H | 77 | 75.523 | 19.387 | 7.375 | 1.00 | 15.92 |
| ATOM | CA | LEU | H | 77 | 74.573 | 20.441 | 7.701 | 1.00 | 17.74 |
| ATOM | CB | LEU | H | 77 | 74.182 | 21.259 | 6.454 | 1.00 | 17.08 |
| ATOM | CG | LEU | H | 77 | 73.669 | 22.718 | 6.499 | 1.00 | 18.21 |
| ATOM | CD1 | LEU | H | 77 | 72.305 | 22.832 | 5.904 | 1.00 | 18.50 |
| ATOM | CD2 | LEU | H | 77 | 73.717 | 23.340 | 7.886 | 1.00 | 20.05 |
| ATOM | C | LEU | H | 77 | 73.347 | 19.700 | 8.233 | 1.00 | 19.52 |
| ATOM | O | LEU | H | 77 | 72.890 | 18.745 | 7.606 | 1.00 | 18.14 |
| ATOM | N | LYS | H | 78 | 72.894 | 20.072 | 9.432 | 1.00 | 19.66 |
| ATOM | CA | LYS | H | 78 | 71.709 | 19.478 | 10.039 | 1.00 | 21.64 |
| ATOM | CB | LYS | H | 78 | 72.019 | 18.898 | 11.420 | 1.00 | 24.63 |
| ATOM | CG | LYS | H | 78 | 72.773 | 17.585 | 11.372 | 1.00 | 29.51 |
| ATOM | CD | LYS | H | 78 | 72.910 | 17.009 | 12.771 | 1.00 | 35.12 |
| ATOM | CE | LYS | H | 78 | 73.805 | 15.761 | 12.808 | 1.00 | 38.85 |
| ATOM | NZ | LYS | H | 78 | 73.139 | 14.504 | 12.308 | 1.00 | 43.57 |
| ATOM | C | LYS | H | 78 | 70.667 | 20.580 | 10.147 | 1.00 | 18.69 |
| ATOM | O | LYS | H | 78 | 70.941 | 21.647 | 10.687 | 1.00 | 21.34 |
| ATOM | N | VAL | H | 79 | 69.498 | 20.338 | 9.573 | 1.00 | 18.22 |
| ATOM | CA | VAL | H | 79 | 68.408 | 21.305 | 9.561 | 1.00 | 17.88 |
| ATOM | CB | VAL | H | 79 | 67.869 | 21.543 | 8.126 | 1.00 | 15.85 |
| ATOM | CG1 | VAL | H | 79 | 66.903 | 22.712 | 8.117 | 1.00 | 18.65 |
| ATOM | CG2 | VAL | H | 79 | 69.058 | 21.782 | 7.149 | 1.00 | 13.37 |
| ATOM | C | VAL | H | 79 | 67.288 | 20.688 | 10.373 | 1.00 | 19.10 |
| ATOM | O | VAL | H | 79 | 66.766 | 19.628 | 10.020 | 1.00 | 19.43 |
| ATOM | N | THR | H | 80 | 66.910 | 21.343 | 11.455 | 1.00 | 20.81 |
| ATOM | CA | THR | H | 80 | 65.866 | 20.808 | 12.315 | 1.00 | 21.37 |
| ATOM | CB | THR | H | 80 | 66.162 | 21.141 | 13.782 | 1.00 | 17.57 |
| ATOM | OG1 | THR | H | 80 | 66.408 | 22.543 | 13.898 | 1.00 | 20.71 |
| ATOM | CG2 | THR | H | 80 | 67.380 | 20.380 | 14.248 | 1.00 | 21.24 |
| ATOM | C | THR | H | 80 | 64.476 | 21.295 | 11.945 | 1.00 | 18.46 |
| ATOM | O | THR | H | 80 | 64.323 | 22.234 | 11.161 | 1.00 | 18.70 |
| ATOM | N | ASN | H | 81 | 63.480 | 20.594 | 12.471 | 1.00 | 19.47 |
| ATOM | CA | ASN | H | 81 | 62.081 | 20.917 | 12.263 | 1.00 | 20.71 |
| ATOM | CB | ASN | H | 81 | 61.693 | 22.053 | 13.203 | 1.00 | 23.15 |
| ATOM | CG | ASN | H | 81 | 60.208 | 22.296 | 13.243 | 1.00 | 26.34 |
| ATOM | OD1 | ASN | H | 81 | 59.409 | 21.384 | 13.099 | 1.00 | 28.57 |
| ATOM | ND2 | ASN | H | 81 | 59.830 | 23.541 | 13.429 | 1.00 | 28.83 |
| ATOM | C | ASN | H | 81 | 61.728 | 21.235 | 10.800 | 1.00 | 20.55 |
| ATOM | O | ASN | H | 81 | 61.222 | 22.316 | 10.475 | 1.00 | 18.95 |
| ATOM | N | MET | H | 82 | 61.995 | 20.268 | 9.925 | 1.00 | 19.37 |
| ATOM | CA | MET | H | 82 | 61.731 | 20.396 | 8.500 | 1.00 | 19.90 |
| ATOM | CB | MET | H | 82 | 62.119 | 19.104 | 7.775 | 1.00 | 20.79 |
| ATOM | CG | MET | H | 82 | 63.643 | 18.886 | 7.651 | 1.00 | 19.47 |
| ATOM | SD | MET | H | 82 | 64.499 | 20.227 | 6.746 | 1.00 | 21.79 |

TABLE 2-continued

| | | Atom A.A. Type | | | X | Y | Z | Occ | B |
|---|---|---|---|---|---|---|---|---|---|
| ATOM | CE | MET | H | 82 | 64.228 | 19.776 | 5.039 | 1.00 | 15.01 |
| ATOM | C | MET | H | 82 | 60.276 | 20.755 | 8.216 | 1.00 | 22.71 |
| ATOM | O | MET | H | 82 | 59.360 | 20.168 | 8.793 | 1.00 | 24.24 |
| ATOM | N | ASP | H | 83 | 60.080 | 21.683 | 7.284 | 1.00 | 22.76 |
| ATOM | CA | ASP | H | 83 | 58.759 | 22.184 | 6.888 | 1.00 | 23.77 |
| ATOM | CB | ASP | H | 83 | 58.714 | 23.696 | 7.144 | 1.00 | 25.06 |
| ATOM | CG | ASP | H | 83 | 57.367 | 24.298 | 6.842 | 1.00 | 28.59 |
| ATOM | OD1 | ASP | H | 83 | 56.478 | 24.190 | 7.701 | 1.00 | 32.41 |
| ATOM | OD2 | ASP | H | 83 | 57.178 | 24.852 | 5.742 | 1.00 | 29.90 |
| ATOM | C | ASP | H | 83 | 58.596 | 21.944 | 5.395 | 1.00 | 22.22 |
| ATOM | O | ASP | H | 83 | 59.590 | 21.841 | 4.699 | 1.00 | 23.36 |
| ATOM | N | PRO | H | 84 | 57.350 | 21.834 | 4.882 | 1.00 | 20.50 |
| ATOM | CD | PRO | H | 84 | 56.066 | 21.715 | 5.600 | 1.00 | 20.73 |
| ATOM | CA | PRO | H | 84 | 57.143 | 21.619 | 3.446 | 1.00 | 18.92 |
| ATOM | CB | PRO | H | 84 | 55.641 | 21.822 | 3.305 | 1.00 | 18.31 |
| ATOM | CG | PRO | H | 84 | 55.129 | 21.194 | 4.526 | 1.00 | 18.56 |
| ATOM | C | PRO | H | 84 | 57.916 | 22.652 | 2.619 | 1.00 | 19.61 |
| ATOM | O | PRO | H | 84 | 58.437 | 22.349 | 1.553 | 1.00 | 20.74 |
| ATOM | N | ALA | H | 85 | 58.004 | 23.872 | 3.132 | 1.00 | 19.68 |
| ATOM | CA | ALA | H | 85 | 58.720 | 24.946 | 2.465 | 1.00 | 21.18 |
| ATOM | CB | ALA | H | 85 | 58.457 | 26.256 | 3.166 | 1.00 | 22.00 |
| ATOM | C | ALA | H | 85 | 60.235 | 24.709 | 2.362 | 1.00 | 22.08 |
| ATOM | O | ALA | H | 85 | 60.949 | 25.498 | 1.735 | 1.00 | 24.05 |
| ATOM | N | ASP | H | 86 | 60.740 | 23.682 | 3.032 | 1.00 | 18.30 |
| ATOM | CA | ASP | H | 86 | 62.152 | 23.379 | 2.952 | 1.00 | 17.61 |
| ATOM | CB | ASP | H | 86 | 62.664 | 22.784 | 4.262 | 1.00 | 16.88 |
| ATOM | CG | ASP | H | 86 | 62.547 | 23.752 | 5.417 | 1.00 | 22.66 |
| ATOM | OD1 | ASP | H | 86 | 62.032 | 23.343 | 6.483 | 1.00 | 19.55 |
| ATOM | OD2 | ASP | H | 86 | 62.954 | 24.932 | 5.257 | 1.00 | 24.22 |
| ATOM | C | ASP | H | 86 | 62.415 | 22.421 | 1.791 | 1.00 | 17.63 |
| ATOM | O | ASP | H | 86 | 63.568 | 22.018 | 1.574 | 1.00 | 17.70 |
| ATOM | N | THR | H | 87 | 61.360 | 22.018 | 1.074 | 1.00 | 15.36 |
| ATOM | CA | THR | H | 87 | 61.526 | 21.122 | −0.066 | 1.00 | 14.35 |
| ATOM | CB | THR | H | 87 | 60.183 | 20.740 | −0.680 | 1.00 | 13.84 |
| ATOM | OG1 | THR | H | 87 | 59.454 | 19.945 | 0.257 | 1.00 | 15.44 |
| ATOM | CG2 | THR | H | 87 | 60.387 | 19.913 | −1.948 | 1.00 | 15.26 |
| ATOM | C | THR | H | 87 | 62.370 | 21.895 | −1.069 | 1.00 | 15.26 |
| ATOM | O | THR | H | 87 | 62.031 | 23.023 | −1.444 | 1.00 | 12.69 |
| ATOM | N | ALA | H | 88 | 63.507 | 21.317 | −1.446 | 1.00 | 16.68 |
| ATOM | CA | ALA | H | 88 | 64.422 | 21.994 | −2.352 | 1.00 | 16.96 |
| ATOM | CB | ALA | H | 88 | 64.946 | 23.281 | −1.663 | 1.00 | 15.82 |
| ATOM | C | ALA | H | 88 | 65.01 | 21.115 | −2.711 | 1.00 | 15.92 |
| ATOM | O | ALA | H | 88 | 65.736 | 19.998 | −2.218 | 1.00 | 15.04 |
| ATOM | N | THR | H | 89 | 66.429 | 21.627 | −3.610 | 1.00 | 14.79 |
| ATOM | CA | THR | H | 89 | 67.655 | 20.971 | −4.010 | 1.00 | 14.63 |
| ATOM | CB | THR | H | 89 | 67.923 | 21.180 | −5.485 | 1.00 | 15.26 |
| ATOM | OG1 | THR | H | 89 | 66.989 | 20.403 | −6.232 | 1.00 | 17.61 |
| ATOM | CG2 | THR | H | 89 | 69.360 | 20.774 | −5.854 | 1.00 | 13.56 |
| ATOM | C | THR | H | 89 | 68.738 | 21.675 | −3.190 | 1.00 | 14.21 |
| ATOM | O | THR | H | 89 | 68.802 | 22.907 | −3.156 | 1.00 | 14.78 |
| ATOM | N | TYR | H | 90 | 69.651 | 20.894 | −2.494 | 1.00 | 15.66 |
| ATOM | CA | TYR | H | 90 | 70.605 | 21.418 | −1.638 | 1.00 | 13.86 |
| ATOM | CB | TYR | H | 90 | 70.527 | 20.751 | −0.254 | 1.00 | 12.67 |
| ATOM | CG | TYR | H | 90 | 69.304 | 21.132 | 0.547 | 1.00 | 11.49 |
| ATOM | CD1 | TYR | H | 90 | 68.Q35 | 20.632 | 0.227 | 1.00 | 12.32 |
| ATOM | CE1 | TYR | H | 90 | 66.907 | 21.050 | 0.926 | 1.00 | 12.25 |
| ATOM | CD2 | TYR | H | 90 | 69.405 | 22.037 | 1.585 | 1.00 | 8.94 |
| ATOM | CE2 | TYR | H | 90 | 68.293 | 22.458 | 2.286 | 1.00 | 13.05 |
| ATOM | CZ | TYR | H | 90 | 67.053 | 21.967 | 1.951 | 1.00 | 13.38 |
| ATOM | OH | TYR | H | 90 | 65.981 | 22.433 | 2.651 | 1.00 | 16.83 |
| ATOM | C | TYR | H | 90 | 71.966 | 21.156 | −2.262 | 1.00 | 14.93 |
| ATOM | O | TYR | H | 90 | 72.273 | 20.023 | −2.664 | 1.00 | 12.21 |
| ATOM | N | TYR | H | 91 | 72.778 | 22.211 | −2.319 | 1.00 | 14.42 |
| ATOM | CA | TYR | H | 91 | 74.122 | 22.158 | −2.893 | 1.00 | 13.29 |
| ATOM | CB | TYR | H | 91 | 74.260 | 23.169 | −4.047 | 1.00 | 13.73 |
| ATOM | CG | TYR | H | 91 | 73.312 | 23.032 | −5.214 | 1.00 | 15.62 |
| ATOM | CD1 | TYR | H | 91 | 72.169 | 23.826 | −5.309 | 1.00 | 17.17 |
| ATOM | CE1 | TYR | H | 91 | 71.343 | 23.766 | −6.438 | 1.00 | 17.39 |
| ATOM | CD2 | TYR | H | 91 | 73.600 | 22.168 | −6.271 | 1.00 | 14.12 |
| ATOM | CE2 | TYR | H | 91 | 72.774 | 22.102 | −7.402 | 1.00 | 14.64 |
| ATOM | CZ | TYR | H | 91 | 71.662 | 22.899 | −7.471 | 1.00 | 17.01 |
| ATOM | OH | TYR | H | 91 | 70.867 | 22.826 | −8.572 | 1.00 | 19.82 |
| ATOM | C | TYR | H | 91 | 75.189 | 22.562 | −1.881 | 1.00 | 11.93 |
| ATOM | O | TYR | H | 91 | 74.949 | 23.392 | −1.016 | 1.00 | 11.94 |
| ATOM | N | CYS | H | 92 | 76.375 | 21.990 | −1.989 | 1.00 | 12.26 |

TABLE 2-continued

| | | Atom A.A. Type | | | X | Y | Z | Occ | B |
|---|---|---|---|---|---|---|---|---|---|
| ATOM | CA | CYS | H | 92 | 77.470 | 22.439 | −1.144 | 1.00 | 12.39 |
| ATOM | C | CYS | H | 92 | 78.467 | 22.930 | −2.191 | 1.00 | 13.50 |
| ATOM | O | CYS | H | 92 | 78.452 | 22.480 | −3.358 | 1.00 | 11.63 |
| ATOM | CB | CYS | H | 92 | 78.043 | 21.338 | −0.249 | 1.00 | 12.10 |
| ATOM | SG | CYS | H | 92 | 78.729 | 19.877 | −1.079 | 1.00 | 15.31 |
| ATOM | N | ALA | H | 93 | 79.242 | 23.935 | −1.826 | 1.00 | 14.24 |
| ATOM | CA | ALA | H | 93 | 80.178 | 24.503 | −2.755 | 1.00 | 15.22 |
| ATOM | CB | ALA | H | 93 | 79.506 | 25.690 | −3.505 | 1.00 | 12.31 |
| ATOM | C | ALA | H | 93 | 81.456 | 24.952 | −2.051 | 1.00 | 15.72 |
| ATOM | O | ALA | H | 93 | 81.436 | 25.311 | −0.872 | 1.00 | 14.75 |
| ATOM | N | ARG | H | 94 | 82.559 | 24.936 | −2.795 | 1.00 | 16.63 |
| ATOM | CA | ARG | H | 94 | 83.849 | 25.353 | −2.268 | 1.00 | 15.90 |
| ATOM | CB | ARG | H | 94 | 84.963 | 24.513 | −2.909 | 1.00 | 15.45 |
| ATOM | CG | ARG | H | 94 | 86.371 | 24.681 | −2.281 | 1.00 | 13.98 |
| ATOM | CD | ARG | H | 94 | 87.148 | 25.873 | −2.794 | 1.00 | 13.40 |
| ATOM | NE | ARG | H | 94 | 87.492 | 25.804 | −4.213 | 1.00 | 16.03 |
| ATOM | CZ | ARG | H | 94 | 88.506 | 25.108 | −4.717 | 1.00 | 18.37 |
| ATOM | NH1 | ARG | H | 94 | 89.289 | 24.390 | −3.932 | 1.00 | 18.16 |
| ATOM | NH2 | ARG | H | 94 | 88.783 | 25.180 | −6.006 | 1.00 | 18.51 |
| ATOM | C | ARG | H | 94 | 84.089 | 26.850 | −2.519 | 1.00 | 13.99 |
| ATOM | O | ARG | H | 94 | 83.743 | 27.379 | −3.576 | 1.00 | 13.67 |
| ATOM | N | SER | H | 95 | 84.679 | 27.521 | −1.536 | 1.00 | 16.14 |
| ATOM | CA | SER | H | 95 | 85.011 | 28.939 | −1.639 | 1.00 | 15.68 |
| ATOM | CB | SER | H | 95 | 84.065 | 29.810 | −0.780 | 1.00 | 15.30 |
| ATOM | OG | SER | H | 95 | 82.715 | 29.760 | −1.213 | 1.00 | 13.60 |
| ATOM | C | SER | H | 95 | 86.451 | 29.119 | −1.144 | 1.00 | 15.90 |
| ATOM | O | SER | H | 95 | 86.965 | 28.290 | −0.372 | 1.00 | 15.38 |
| ATOM | N | MET | H | 96 | 87.095 | 30.191 | −1.599 | 1.00 | 17.08 |
| ATOM | CA | MET | H | 96 | 88.465 | 30.527 | −1.201 | 1.00 | 19.15 |
| ATOM | CB | MET | H | 96 | 89.439 | 30.332 | −2.370 | 1.00 | 19.64 |
| ATOM | CG | MET | H | 96 | 89.701 | 28.849 | −2.678 | 1.00 | 25.79 |
| ATOM | SD | MET | H | 96 | 90.549 | 28.511 | −4.238 | 1.00 | 29.25 |
| ATOM | CE | MET | H | 96 | 91.543 | 27.150 | −3.780 | 1.00 | 30.33 |
| ATOM | C | MET | H | 96 | 88.418 | 31.977 | −0.727 | 1.00 | 16.53 |
| ATOM | O | MET | H | 96 | 88.319 | 32.907 | −1.522 | 1.00 | 17.07 |
| ATOM | N | ILE | H | 97 | 88.419 | 32.128 | 0.593 | 1.00 | 16.76 |
| ATOM | CA | ILE | H | 97 | 88.320 | 33.415 | 1.268 | 1.00 | 14.34 |
| ATOM | CB | ILE | H | 97 | 88.410 | 33.245 | 2.802 | 1.00 | 13.83 |
| ATOM | CG2 | ILE | H | 97 | 88.001 | 34.513 | 3.491 | 1.00 | 10.54 |
| ATOM | CG1 | ILE | H | 97 | 87.524 | 32.085 | 3.272 | 1.00 | 16.40 |
| ATOM | CD1 | ILE | H | 97 | 86.055 | 32.197 | 2.875 | 1.00 | 16.82 |
| ATOM | C | ILE | H | 97 | 89.381 | 34.388 | 0.774 | 1.00 | 15.53 |
| ATOM | O | ILE | H | 97 | 90.555 | 34.047 | 0.695 | 1.00 | :6.36 |
| ATOM | N | THR | H | 98 | 88.917 | 35.599 | 0.466 | 1.00 | 14.74 |
| ATOM | CA | THR | H | 98 | 89.661 | 36.739 | −0.068 | 1.00 | 12.35 |
| ATOM | CB | THR | H | 98 | 90.976 | 37.091 | 0.680 | 1.00 | 10.22 |
| ATOM | OG1 | THR | H | 98 | 92.000 | 36.156 | 0.326 | 1.00 | 10.30 |
| ATOM | CG2 | THR | H | 98 | 90.766 | 37.122 | 2.191 | 1.00 | 7.62 |
| ATOM | C | THR | H | 98 | 89.923 | 36.565 | −1.556 | 1.00 | 13.74 |
| ATOM | O | THR | H | 98 | 90.549 | 37.415 | −2.187 | 1.00 | 17.87 |
| ATOM | N | ASN | H | 99 | 89.402 | 35.481 | −2.124 | 1.00 | 14.64 |
| ATOM | CA | ASN | H | 99 | 89.551 | 35.205 | −3.541 | 1.00 | 15.20 |
| ATOM | CB | ASN | H | 99 | 90.448 | 33.998 | −3.760 | 1.00 | 16.40 |
| ATOM | CG | ASN | H | 99 | 91.902 | 34.344 | −3.591 | 1.00 | 17.20 |
| ATOM | OD1 | ASN | H | 99 | 92.388 | 35.290 | −4.214 | 1.00 | 15.38 |
| ATOM | ND2 | ASN | H | 99 | 92.594 | 33.626 | −2.720 | 1.00 | 15.23 |
| ATOM | C | ASN | H | 99 | 88.213 | 35.049 | −4.259 | 1.00 | 17.88 |
| ATOM | O | ASN | H | 99 | 87.855 | 35.899 | −5.083 | 1.00 | 18.92 |
| ATOM | N | TRP | H | 100 | 87.441 | 34.017 | −3.928 | 1.00 | 17.14 |
| ATOM | CA | TRP | H | 100 | 86.145 | 33.834 | −4.591 | 1.00 | 18.19 |
| ATOM | CB | TRP | H | 100 | 86.341 | 33.387 | −6.047 | 1.00 | 19.31 |
| ATOM | CG | TRP | H | 100 | 87.406 | 32.345 | −6.185 | 1.00 | 19.32 |
| ATOM | CD2 | TRP | H | 100 | 88.710 | 32.538 | −6.722 | 1.00 | 19.62 |
| ATOM | CE2 | TRP | H | 100 | 89.396 | 31.306 | −6.597 | 1.00 | 22.56 |
| ATOM | CE3 | TRP | H | 100 | 89.373 | 33.635 | −7.294 | 1.00 | 17.80 |
| ATOM | CD1 | TRP | H | 100 | 87.343 | 31.044 | −5.773 | 1.00 | 19.51 |
| ATOM | NE1 | TRP | H | 100 | 88.531 | 30.415 | −6.011 | 1.00 | 21.48 |
| ATOM | CZ2 | TRP | H | 100 | 90.729 | 31.131 | −7.027 | 1.00 | 21.08 |
| ATOM | CZ3 | TRP | H | 100 | 90.690 | 33.470 | −7.722 | 1.00 | 20.58 |
| ATOM | CH2 | TRP | H | 100 | 91.356 | 32.218 | −7.583 | 1.00 | 23.10 |
| ATOM | C | TRP | H | 100 | 85.183 | 32.874 | −3.908 | 1.00 | 16.39 |
| ATOM | O | TRP | H | 100 | 85.584 | 31.928 | −3.245 | 1.00 | 15.36 |
| ATOM | N | TYR | H | 100A | 83.901 | 33.129 | −4.105 | 1.00 | 15.37 |
| ATOM | CA | TYR | H | 100 | 82.862 | 32.289 | −3.555 | 1.00 | 16.59 |
| ATOM | CB | TYR | H | 100 | 81.656 | 33.136 | −3.135 | 1.00 | 16.72 |
| ATOM | CG | TYR | H | 100 | 81.746 | 33.717 | −1.749 | 1.00 | 22.50 |

TABLE 2-continued

| | | Atom A.A. Type | | | X | Y | Z | Occ | B |
|---|---|---|---|---|---|---|---|---|---|
| ATOM | CD1 | TYR | H | 100 | 81.600 | 35.098 | −1.553 | 1.00 | 23.43 |
| ATOM | CE1 | TYR | H | 100 | 81.645 | 35.637 | −0.273 | 1.00 | 22.21 |
| ATOM | CD2 | TYR | H | 100 | 81.744 | 32.883 | −0.626 | 1.00 | 24.26 |
| ATOM | CE2 | TYR | H | 100 | 81.793 | 33.405 | 0.659 | 1.00 | 27.56 |
| ATOM | CZ | TYR | H | 100 | 81.840 | 34.783 | 0.829 | 1.00 | 29.81 |
| ATOM | OH | TYR | H | 100 | 81.860 | 35.292 | 2.103 | 1.00 | 34.18 |
| ATOM | C | TYR | H | 100 | 82.385 | 31.279 | −4.587 | 1.00 | 14.72 |
| ATOM | O | TYR | H | 100 | 82.272 | 31.596 | −5.772 | 1.00 | 14.44 |
| ATOM | N | PHE | H | 100B | 82.115 | 30.070 | −4.118 | 1.00 | 14.18 |
| ATOM | CA | PHE | H | 100 | 81.552 | 28.985 | −4.923 | 1.00 | 15.04 |
| ATOM | CB | PHE | H | 100 | 80.018 | 29.135 | −4.968 | 1.00 | 11.93 |
| ATOM | CG | PHE | H | 100 | 79.433 | 29.732 | −3.719 | 1.00 | 10.44 |
| ATOM | CD1 | PHE | H | 100 | 78.547 | 30.789 | −3.798 | 1.00 | 12.27 |
| ATOM | CD2 | PHE | H | 100 | 79.803 | 29.258 | −2.469 | 1.00 | 10.01 |
| ATOM | CE1 | PHE | H | 100 | 78.027 | 31.378 | −2.647 | 1.00 | 14.34 |
| ATOM | CE2 | PHE | H | 100 | 79.304 | 29.823 | −1.308 | 1.00 | 10.04 |
| ATOM | CZ | PHE | H | 100 | 78.411 | 30.889 | −1.386 | 1.00 | 13.85 |
| ATOM | C | PHE | H | 100 | 82.095 | 28.814 | −6.341 | 1.00 | 16.03 |
| ATOM | O | PHE | H | 100 | 81.350 | 28.924 | −7.316 | 1.00 | 16.54 |
| ATOM | N | ASP | H | 101 | 83.381 | 28.510 | −6.459 | 1.00 | 15.78 |
| ATOM | CA | ASP | H | 101 | 83.966 | 28.305 | −7.776 | 1.00 | 17.03 |
| ATOM | CB | ASP | H | 101 | 85.467 | 28.643 | −7.788 | 1.00 | 16.29 |
| ATOM | CG | ASP | H | 101 | 86.280 | 27.761 | −6.876 | 1.00 | 17.74 |
| ATOM | OD1 | ASP | H | 101 | 87.419 | 27.421 | −7.233 | 1.00 | 23.19 |
| ATOM | OD2 | ASP | H | 101 | 85.815 | 27.429 | −5.782 | 1.00 | 18.97 |
| ATOM | C | ASP | H | 101 | 83.710 | 26.868 | −8.224 | 1.00 | 17.89 |
| ATOM | O | ASP | H | 101 | 83.770 | 26.569 | −9.414 | 1.00 | 18.15 |
| ATOM | N | VAL | H | 102 | 83.420 | 25.977 | −7.277 | 1.00 | 16.57 |
| ATOM | CA | VAL | H | 102 | 83.120 | 24.589 | −7.613 | 1.00 | 18.26 |
| ATOM | CB | VAL | H | 102 | 84.332 | 23.662 | −7.370 | 1.00 | 17.45 |
| ATOM | CG1 | VAL | H | 102 | 84.069 | 22.280 | −7.969 | 1.00 | 15.35 |
| ATOM | CG2 | VAL | H | 102 | 85.804 | 24.285 | −7.957 | 1.00 | 16.60 |
| ATOM | C | VAL | H | 102 | 81.940 | 24.118 | −6.753 | 1.00 | 18.17 |
| ATOM | O | VAL | H | 102 | 81.984 | 24.245 | −5.532 | 1.00 | 19.18 |
| ATOM | N | TRP | H | 103 | 80.908 | 23.565 | −7.392 | 1.00 | 17.66 |
| ATOM | CA | TRP | H | 103 | 79.695 | 23.070 | −6.714 | 1.00 | 16.97 |
| ATOM | CB | TRP | H | 103 | 78.450 | 23.733 | −7.307 | 1.00 | 14.66 |
| ATOM | CG | TRP | H | 103 | 78.402 | 25.206 | −7.217 | 1.00 | 13.16 |
| ATOM | CD2 | TRP | H | 103 | 77.335 | 25.990 | −6.683 | 1.00 | 13.16 |
| ATOM | CE2 | TRP | H | 103 | 77.674 | 27.346 | −6.885 | 1.00 | 11.97 |
| ATOM | CE3 | TRP | H | 103 | 76.116 | 25.680 | −6.053 | 1.00 | 14.23 |
| ATOM | CG1 | TRP | H | 103 | 79.327 | 26.091 | −7.698 | 1.00 | 12.35 |
| ATOM | NE1 | TRP | H | 103 | 78.897 | 27.374 | −7.503 | 1.00 | 10.43 |
| ATOM | CZ2 | TRP | H | 103 | 76.839 | 28.396 | −6.485 | 1.00 | 11.68 |
| ATOM | CZ3 | TRP | H | 103 | 75.287 | 26.723 | −5.652 | 1.00 | 12.59 |
| ATOM | CH2 | TRP | H | 103 | 75.652 | 28.066 | −5.870 | 1.00 | 12.82 |
| ATOM | C | TRP | H | 103 | 79.470 | 21.562 | −6.876 | 1.00 | 18.07 |
| ATOM | O | TRP | H | 103 | 79.944 | 20.953 | −7.839 | 1.00 | 19.15 |
| ATOM | N | GLY | H | 104 | 78.716 | 20.973 | −5.950 | 1.00 | 16.51 |
| ATOM | CA | GLY | H | 104 | 78.372 | 19.568 | −6.057 | 1.00 | 15.81 |
| ATOM | C | GLY | H | 104 | 77.235 | 19.521 | −7.080 | 1.00 | 17.22 |
| ATOM | O | GLY | H | 104 | 76.809 | 20.561 | −7.578 | 1.00 | 16.55 |
| ATOM | N | ALA | H | 105 | 76.699 | 18.340 | −7.373 | 1.00 | 18.21 |
| ATOM | CA | ALA | H | 105 | 75.623 | 18.238 | −8.359 | 1.00 | 15.09 |
| ATOM | CB | ALA | H | 105 | 75.555 | 16.842 | −8.906 | 1.00 | 17.38 |
| ATOM | C | ALA | H | 105 | 74.283 | 18.634 | −7.752 | 1.00 | 15.46 |
| ATOM | O | ALA | H | 105 | 73.356 | 19.008 | −8.470 | 1.00 | 15.25 |
| ATOM | N | GLY | H | 106 | 74.202 | 18.570 | −6.425 | 1.00 | 13.51 |
| ATOM | CA | GLY | H | 106 | 72.984 | 18.921 | −5.713 | 1.00 | 14.41 |
| ATOM | C | GLY | H | 106 | 72.153 | 17.692 | −5.417 | 1.00 | 14.89 |
| ATOM | O | GLY | H | 106 | 72.152 | 16.742 | −6.204 | 1.00 | 16.09 |
| ATOM | N | THR | H | 107 | 71.498 | 17.668 | −4.261 | 1.00 | 15.25 |
| ATOM | CA | THR | H | 107 | 70.647 | 16.531 | −3.907 | 1.00 | 12.89 |
| ATOM | CB | THR | H | 107 | 71.260 | 15.655 | −2.764 | 1.00 | 12.03 |
| ATOM | OG1 | THR | H | 107 | 70.529 | 14.434 | −2.627 | 1.00 | 14.85 |
| ATOM | CG2 | THR | H | 107 | 71.265 | 16.380 | −1.449 | 1.00 | 14.04 |
| ATOM | C | THR | H | 107 | 69.269 | 17.071 | −3.563 | 1.00 | 13.69 |
| ATOM | O | THR | H | 107 | 69.136 | 18.102 | −2.898 | 1.00 | 12.77 |
| ATOM | N | THR | H | 108 | 68.251 | 16.402 | −4.094 | 1.00 | 14.91 |
| ATOM | CA | THR | H | 108 | 66.861 | 16.767 | −3.896 | 1.00 | 14.31 |
| ATOM | CB | THR | H | 108 | 65.998 | 16.259 | −5.054 | 1.00 | 16.49 |
| ATOM | OG1 | THR | H | 108 | 66.604 | 16.644 | −6.288 | 1.00 | 23.43 |
| ATOM | CG2 | THR | H | 108 | 64.614 | 16.876 | −5.002 | 1.00 | 18.43 |
| ATOM | C | THR | H | 108 | 66.287 | 16.220 | −2.598 | 1.00 | 13.70 |
| ATOM | O | THR | H | 108 | 66.414 | 15.027 | −2.291 | 1.00 | 11.70 |
| ATOM | N | VAL | H | 109 | 65.670 | 17.119 | −1.836 | 1.00 | 12.30 |

TABLE 2-continued

| | Atom | A.A. Type | | | X | Y | Z | Occ | B |
|---|---|---|---|---|---|---|---|---|---|
| ATOM | CA | VAL | H | 109 | 65.026 | 16.784 | −0.582 | 1.00 | 14.43 |
| ATOM | CB | VAL | H | 109 | 65.729 | 17.472 | 0.619 | 1.00 | 14.88 |
| ATOM | CG1 | VAL | H | 109 | 65.026 | 17.122 | 1.920 | 1.00 | 13.86 |
| ATOM | CG2 | VAL | H | 109 | 67.193 | 17.060 | 0.672 | 1.00 | 10.78 |
| ATOM | C | VAL | H | 109 | 63.568 | 17.258 | −0.672 | 1.00 | 16.33 |
| ATOM | O | VAL | H | 109 | 63.292 | 18.397 | −1.089 | 1.00 | 16.26 |
| ATOM | N | THR | H | 110 | 62.645 | 16.340 | −0.382 | 1.00 | 16.17 |
| ATOM | CA | THR | H | 110 | 61.216 | 16.641 | −0.371 | 1.00 | 14.13 |
| ATOM | CB | THR | H | 110 | 60.426 | 15.726 | −1.325 | 1.00 | 13.82 |
| ATOM | OG1 | THR | H | 110 | 60.771 | 16.028 | −2.678 | 1.00 | 10.99 |
| ATOM | CG2 | THR | H | 110 | 58.529 | 15.931 | −1.147 | 1.00 | 12.81 |
| ATOM | C | THR | H | 110 | 60.707 | 16.415 | 1.050 | 1.00 | 13.72 |
| ATOM | O | THR | H | 110 | 61.045 | 15.409 | 1.680 | 1.00 | 14.07 |
| ATOM | N | VAL | H | 111 | 59.395 | 17.404 | 1.585 | 1.00 | 14.52 |
| ATOM | CA | VAL | H | 111 | 59.414 | 17.308 | 2.913 | 1.00 | 22.91 |
| ATOM | CB | VAL | H | 111 | 59.539 | 18.632 | 3.659 | 1.00 | 13.54 |
| ATOM | CG1 | VAL | H | 111 | 59.004 | 18.481 | 5.091 | 1.00 | 12.26 |
| ATOM | CG2 | VAL | H | 111 | 61.003 | 19.060 | 3.675 | 1.00 | 12.73 |
| ATOM | C | VAL | H | 111 | 57.946 | 16.927 | 2.735 | 1.00 | 23.85 |
| ATOM | O | VAL | H | 111 | 57.115 | 17.748 | 2.328 | 1.00 | 12.86 |
| ATOM | N | SER | H | 112 | 57.635 | 15.664 | 3.000 | 1.00 | 13.52 |
| ATOM | CA | SER | H | 112 | 56.277 | 15.186 | 2.825 | 1.00 | 14.65 |
| ATOM | CB | SER | H | 112 | 56.067 | 14.741 | 1.369 | 1.00 | 13.71 |
| ATOM | OG | SER | H | 112 | 54.733 | 14.274 | 1.173 | 1.00 | 16.01 |
| ATOM | C | SER | H | 112 | 55.895 | 14.049 | 3.757 | 1.00 | 25.63 |
| ATOM | O | SER | H | 112 | 56.743 | 13.287 | 4.216 | 1.00 | 16.01 |
| ATOM | N | SER | H | 113 | 54.594 | 13.929 | 3.998 | 1.00 | 17.91 |
| ATOM | CA | SER | H | 113 | 54.044 | 12.883 | 4.851 | 1.00 | 19.30 |
| ATOM | CB | SER | H | 113 | 52.757 | 13.394 | 5.523 | 1.00 | 20.59 |
| ATOM | OG | SER | H | 113 | 52.993 | 14.594 | 6.251 | 1.00 | 22.75 |
| ATOM | C | SER | H | 113 | 53.763 | 11.611 | 4.016 | 1.00 | 18.16 |
| ATOM | O | SER | H | 113 | 53.570 | 10.527 | 4.555 | 1.00 | 19.67 |
| ATOM | N | ALA | H | 114 | 53.747 | 11.757 | 2.698 | 1.00 | 17.12 |
| ATOM | CA | ALA | H | 114 | 53.492 | 10.633 | 1.808 | 1.00 | 16.60 |
| ATOM | CB | ALA | H | 114 | 53.203 | 11.129 | 0.405 | 1.00 | 15.09 |
| ATOM | C | ALA | H | 114 | 54.709 | 9.708 | 1.809 | 1.00 | 17.50 |
| ATOM | O | ALA | H | 114 | 55.829 | 10.144 | 2.067 | 1.00 | 27.91 |
| ATOM | N | SER | H | 115 | 54.489 | 8.442 | 1.491 | 1.00 | 16.28 |
| ATOM | CA | SER | H | 115 | 55.570 | 7.478 | 1.489 | 1.00 | 19.52 |
| ATOM | CB | SER | H | 115 | 55.079 | 6.132 | 2.064 | 1.00 | 19.19 |
| ATOM | OG | SER | H | 115 | 54.606 | 5.275 | 1.047 | 1.00 | 27.19 |
| ATOM | C | SER | H | 115 | 56.242 | 7.290 | 0.127 | 1.00 | 18.16 |
| ATOM | O | SER | H | 115 | 55.718 | 7.698 | −0.910 | 1.00 | 17.69 |
| ATOM | N | THR | H | 116 | 57.435 | 6.711 | 0.158 | 1.00 | 18.51 |
| ATOM | CA | THR | H | 116 | 58.225 | 6.436 | −1.034 | 1.00 | 17.26 |
| ATOM | CB | THR | H | 116 | 59.628 | 5.914 | −0.630 | 1.00 | 15.24 |
| ATOM | OG1 | THR | H | 116 | 60.286 | 6.915 | 0.161 | 1.00 | 16.91 |
| ATOM | CG2 | THR | H | 116 | 60.471 | 5.593 | −1.848 | 1.00 | 10.10 |
| ATOM | C | THR | H | 116 | 57.514 | 5.381 | −1.880 | 1.00 | 18.11 |
| ATOM | O | THR | H | 116 | 56.921 | 4.448 | −1.334 | 1.00 | 17.85 |
| ATOM | N | LYS | H | 117 | 57.535 | 5.566 | −3.202 | 1.00 | 15.14 |
| ATOM | CA | LYS | H | 117 | 56.928 | 4.625 | −4.138 | 1.00 | 14.76 |
| ATOM | CB | LYS | H | 117 | 55.487 | 5.047 | −4.448 | 1.00 | 11.84 |
| ATOM | CG | LYS | H | 117 | 54.753 | 4.082 | −5.354 | 1.00 | 11.64 |
| ATOM | CG | LYS | H | 117 | 53.331 | 4.533 | −5.609 | 1.00 | 13.39 |
| ATOM | CE | LYS | H | 117 | 52.618 | 3.541 | −6.493 | 1.00 | 14.85 |
| ATOM | NZ | LYS | H | 117 | 52.517 | 2.187 | −5.850 | 1.00 | 19.06 |
| ATOM | C | LYS | H | 117 | 57.774 | 4.596 | −5.429 | 1.00 | 15.11 |
| ATOM | O | LYS | H | 117 | 58.127 | 5.650 | −5.977 | 1.00 | 16.09 |
| ATOM | N | GLY | H | 118 | 58.155 | 3.400 | −5.867 | 1.00 | 14.77 |
| ATOM | CA | GLY | H | 118 | 58.963 | 3.255 | −7.067 | 1.00 | 13.25 |
| ATOM | C | GLY | H | 118 | 58.079 | 3.364 | −8.279 | 1.00 | 13.95 |
| ATOM | O | GLY | H | 118 | 56.894 | 3.074 | −8.202 | 1.00 | 16.47 |
| ATOM | N | PRO | H | 119 | 58.625 | 3.759 | −9.426 | 1.00 | 15.62 |
| ATOM | CG | PRO | H | 119 | 60.035 | 4.122 | −9.637 | 1.00 | 19.10 |
| ATOM | CA | PRO | H | 119 | 57.860 | 3.915 | −10.664 | 1.00 | 15.67 |
| ATOM | CB | PRO | H | 119 | 58.772 | 4.812 | −11.495 | 1.00 | 15.38 |
| ATOM | CG | PRO | H | 119 | 60.120 | 4.281 | −11.169 | 1.00 | 16.10 |
| ATOM | C | PRO | H | 119 | 57.538 | 2.660 | −11.451 | 1.00 | 14.47 |
| ATOM | O | PRO | H | 119 | 58.185 | 1.611 | −11.304 | 1.00 | 14.94 |
| ATOM | N | SER | H | 120 | 56.558 | 2.791 | −12.328 | 1.00 | 13.35 |
| ATOM | CA | SER | H | 120 | 56.178 | 1.714 | −13.232 | 1.00 | 15.97 |
| ATOM | CB | SER | H | 120 | 54.668 | 1.481 | −13.221 | 1.00 | 18.07 |
| ATOM | OG | SER | H | 120 | 54.260 | 0.992 | −11.952 | 1.00 | 22.46 |
| ATOM | C | SER | H | 120 | 56.608 | 2.310 | −14.556 | 1.00 | 14.66 |
| ATOM | O | SER | H | 120 | 56.604 | 3.525 | −14.702 | 1.00 | 16.58 |

TABLE 2-continued

| | Atom | A.A. Type | | | X | Y | Z | Occ | B |
|---|---|---|---|---|---|---|---|---|---|
| ATOM | N | VAL | H | 121 | 57.044 | 1.486 | −15.497 | 1.00 | 14.09 |
| ATOM | CA | VAL | H | 121 | 57.502 | 2.004 | −16.775 | 1.00 | 15.16 |
| ATOM | CB | VAL | H | 121 | 59.038 | 1.826 | −16.919 | 1.00 | 13.34 |
| ATOM | CD1 | VAL | H | 121 | 59.524 | 2.468 | −18.215 | 1.00 | 14.30 |
| ATOM | CG2 | VAL | H | 121 | 59.755 | 2.411 | −15.710 | 1.00 | 11.15 |
| ATOM | C | VAL | H | 121 | 56.753 | 1.298 | −17.902 | 1.00 | 16.62 |
| ATOM | O | VAL | H | 121 | 56.621 | 0.064 | −17.905 | 1.00 | 18.28 |
| ATOM | N | PHE | H | 122 | 56.211 | 2.086 | −18.821 | 1.00 | 15.27 |
| ATOM | CA | PHE | H | 122 | 55.444 | 1.553 | −19.935 | 1.00 | 16.26 |
| ATOM | CB | PHE | H | 122 | 53.971 | 1.986 | −19.827 | 1.00 | 13.75 |
| ATOM | CG | PHE | H | 122 | 53.328 | 1.608 | −18.525 | 1.00 | 17.83 |
| ATOM | CD1 | PHE | H | 122 | 53.066 | 0.272 | −18.225 | 1.00 | 16.34 |
| ATOM | CD2 | PHE | H | 122 | 53.022 | 2.577 | −17.578 | 1.00 | 17.41 |
| ATOM | CE1 | PHE | H | 122 | 52.520 | −0.088 | −17.010 | 1.00 | 15.75 |
| ATOM | CE2 | PHE | H | 122 | 52.472 | 2.217 | −16.349 | 1.00 | 17.96 |
| ATOM | CZ | PHE | H | 122 | 52.224 | 0.883 | −16.071 | 1.00 | 16.23 |
| ATOM | C | PHE | H | 122 | 56.028 | 2.100 | −21.211 | 1.00 | 16.57 |
| ATOM | O | PHE | H | 122 | 56.629 | 3.222 | −21.244 | 1.00 | 18.33 |
| ATOM | N | PRO | H | 123 | 55.989 | 1.309 | −22.281 | 1.00 | 15.62 |
| ATOM | CD | PRO | H | 123 | 55.570 | −0.103 | −22.354 | 1.00 | 14.76 |
| ATOM | CA | PRO | H | 123 | 56.530 | 1.768 | −23.555 | 1.00 | 14.94 |
| ATOM | CB | PRO | H | 123 | 56.649 | 0.472 | −24.337 | 1.00 | 17.14 |
| ATOM | CG | PRO | H | 123 | 55.456 | −0.323 | −23.836 | 1.00 | 16.17 |
| ATOM | C | PRO | H | 123 | 55.648 | 2.735 | −24.319 | 1.00 | 16.60 |
| ATOM | O | PRO | H | 123 | 54.411 | 2.680 | −24.245 | 1.00 | 17.55 |
| ATOM | N | LEU | H | 124 | 56.286 | 3.650 | −25.031 | 1.00 | 13.37 |
| ATOM | CA | LEU | H | 124 | 55.561 | 4.556 | −25.890 | 1.00 | 14.24 |
| ATOM | CB | LEU | H | 124 | 55.994 | 6.013 | −25.655 | 1.00 | 15.79 |
| ATOM | CG | LEU | H | 124 | 55.665 | 6.606 | −24.265 | 1.00 | 17.62 |
| ATOM | CD1 | LEU | H | 124 | 56.269 | 7.985 | −24.102 | 1.00 | 13.09 |
| ATOM | CD2 | LEU | H | 124 | 54.153 | 6.660 | −24.041 | 1.00 | 18.38 |
| ATOM | C | LEU | H | 124 | 56.077 | 3.994 | −27.221 | 1.00 | 16.57 |
| ATOM | O | LEU | H | 124 | 57.307 | 4.426 | −27.742 | 1.00 | 15.81 |
| ATOM | N | ALA | H | 125 | 55.420 | 2.937 | −27.697 | 1.00 | 16.47 |
| ATOM | CA | ALA | H | 125 | 55.828 | 2.245 | −28.920 | 1.00 | 15.66 |
| ATOM | CB | ALA | H | 125 | 54.977 | 1.002 | −29.140 | 1.00 | 10.29 |
| ATOM | C | ALA | H | 125 | 55.819 | 3.109 | −30.154 | 1.00 | 17.52 |
| ATOM | O | ALA | H | 125 | 54.968 | 3.984 | −30.318 | 1.00 | 21.55 |
| ATOM | N | PRO | H | 126 | 56.789 | 2.892 | −31.042 | 1.00 | 20.30 |
| ATOM | CD | PRO | H | 126 | 57.897 | 1.929 | −30.946 | 1.00 | 20.63 |
| ATOM | CA | PRO | H | 126 | 56.878 | 3.667 | −32.279 | 1.00 | 22.95 |
| ATOM | CB | PRO | H | 126 | 58.198 | 3.188 | −32.886 | 1.00 | 21.13 |
| ATOM | CG | PRO | H | 126 | 58.302 | 1.785 | −32.395 | 1.00 | 22.39 |
| ATOM | C | PRO | H | 126 | 55.700 | 3.375 | −33.193 | 1.00 | 27.03 |
| ATOM | O | PRO | H | 126 | 55.427 | 2.226 | −33.504 | 1.00 | 27.46 |
| ATOM | N | SER | H | 127 | 54.992 | 4.430 | −33.577 | 1.00 | 34.03 |
| ATOM | CA | SER | H | 127 | 53.833 | 4.346 | −34.460 | 1.00 | 39.73 |
| ATOM | CB | SER | H | 127 | 53.179 | 5.724 | −34.629 | 1.00 | 43.44 |
| ATOM | OG | SER | H | 127 | 52.642 | 5.910 | −35.940 | 1.00 | 42.93 |
| ATOM | C | SER | H | 127 | 54.300 | 3.881 | −35.803 | 1.00 | 42.00 |
| ATOM | O | SER | H | 127 | 53.500 | 3.580 | −36.684 | 1.00 | 43.71 |
| ATOM | N | SER | H | 128 | 55.597 | 3.962 | −36.008 | 1.00 | 44.63 |
| ATOM | CA | SER | H | 128 | 56.137 | 3.532 | −37.262 | 1.00 | 48.81 |
| ATOM | CB | SER | H | 128 | 57.449 | 4.268 | −37.540 | 1.00 | 50.45 |
| ATOM | OG | SER | H | 128 | 57.252 | 5.678 | −37.548 | 1.00 | 48.06 |
| ATOM | C | SER | H | 128 | 56.315 | 2.023 | −37.164 | 1.00 | 50.25 |
| ATOM | O | SER | H | 128 | 55.845 | 1.393 | −36.207 | 1.00 | 49.98 |
| ATOM | N | LYS | H | 129 | 56.944 | 1.443 | −38.175 | 1.00 | 49.86 |
| ATOM | CA | LYS | H | 129 | 57.180 | 0.014 | −38.191 | 1.00 | 49.05 |
| ATOM | CB | LYS | H | 129 | 55.874 | −0.722 | −38.414 | 1.00 | 49.61 |
| ATOM | C | LYS | H | 129 | 58.151 | −0.266 | −39.320 | 1.00 | 48.36 |
| ATOM | O | LYS | H | 129 | 59.112 | −1.022 | −39.152 | 1.00 | 44.64 |
| ATOM | NZ | LYS | H | 129 | 51.040 | −1.190 | −37.021 | 0.00 | 0.00 |
| ATOM | CE | LYS | H | 129 | 52.290 | −0.431 | −36.870 | 0.00 | 0.00 |
| ATOM | CD | LYS | H | 129 | 53.427 | −0.974 | −37.734 | 0.00 | 0.00 |
| ATOM | CG | LYS | H | 129 | 54.730 | −0.196 | −37.554 | 0.00 | 0.00 |
| ATOM | N | SER | H | 130 | 57.862 | 0.364 | −40.464 | 1.00 | 48.61 |
| ATOM | CA | SER | H | 130 | 58.643 | 0.255 | −41.703 | 1.00 | 47.96 |
| ATOM | CB | SER | H | 130 | 57.736 | 0.583 | −42.898 | 1.00 | 47.61 |
| ATOM | C | SER | H | 130 | 59.875 | 1.176 | −41.704 | 1.00 | 48.17 |
| ATOM | O | SER | H | 130 | 60.004 | 2.065 | −40.830 | 1.00 | 48.15 |
| ATOM | N | THR | H | 131 | 60.739 | 0.991 | −42.701 | 0.01 | 47.53 |
| ATOM | CA | THR | H | 131 | 61.974 | 1.757 | −42.843 | 0.01 | 47.59 |
| ATOM | CB | THR | H | 131 | 63.005 | 0.935 | −43.613 | 0.01 | 46.60 |
| ATOM | C | THR | H | 131 | 61.827 | 3.143 | −43.476 | 0.01 | 47.59 |
| ATOM | O | THR | H | 131 | 62.023 | 4.157 | −42.811 | 0.01 | 47.36 |

TABLE 2-continued

| | | Atom A.A. Type | | | X | Y | Z | Occ | B |
|---|---|---|---|---|---|---|---|---|---|
| ATOM | N | SER | H | 132 | 61.563 | 3.181 | −44.778 | 0.01 | 48.07 |
| ATOM | CA | SER | H | 132 | 61.404 | 4.433 | −45.510 | 0.01 | 48.10 |
| ATOM | CB | SER | H | 132 | 61.123 | 4.153 | −46.979 | 0.01 | 48.72 |
| ATOM | C | SER | H | 132 | 60.313 | 5.324 | −44.927 | 0.01 | 47.75 |
| ATOM | O | SER | H | 132 | 59.137 | 5.192 | −45.270 | 0.01 | 48.15 |
| ATOM | N | GLY | H | 133 | 60.717 | 6.221 | −44.035 | 0.01 | 46.82 |
| ATOM | CA | GLY | H | 133 | 59.778 | 7.138 | −43.419 | 0.01 | 45.30 |
| ATOM | C | GLY | H | 133 | 60.485 | 8.243 | −42.661 | 0.01 | 43.62 |
| ATOM | O | GLY | H | 133 | 59.855 | 8.993 | −41.914 | 0.01 | 44.14 |
| ATOM | N | GLY | H | 134 | 61.792 | 8.371 | −42.878 | 1.00 | 42.62 |
| ATOM | CA | GLY | H | 134 | 62.547 | 9.392 | −42.187 | 1.00 | 37.35 |
| ATOM | C | GLY | H | 134 | 62.780 | 9.112 | −40.710 | 1.00 | 34.73 |
| ATOM | O | GLY | H | 134 | 63.626 | 8.277 | −40.355 | 1.00 | 32.41 |
| ATOM | N | THR | H | 135 | 61.982 | 9.751 | −39.859 | 1.00 | 33.59 |
| ATOM | CA | THR | H | 135 | 62.140 | 9.647 | −38.406 | 1.00 | 32.75 |
| ATOM | CB | THR | H | 135 | 62.648 | 11.011 | −37.859 | 1.00 | 34.16 |
| ATOM | OG1 | THR | H | 135 | 63.967 | 11.256 | −38.361 | 1.00 | 36.29 |
| ATOM | CG2 | THR | H | 135 | 62.691 | 11.031 | −36.355 | 1.00 | 37.02 |
| ATOM | C | THR | H | 135 | 60.920 | 9.202 | −37.598 | 1.00 | 29.09 |
| ATOM | O | THR | H | 135 | 59.800 | 9.638 | −37.832 | 1.00 | 31.07 |
| ATOM | N | ALA | H | 136 | 61.164 | 8.374 | −36.597 | 1.00 | 25.01 |
| ATOM | CA | ALA | H | 136 | 60.105 | 7.878 | −35.744 | 1.00 | 23.72 |
| ATOM | CB | ALA | H | 136 | 60.022 | 6.363 | −35.859 | 1.00 | 24.23 |
| ATOM | C | ALA | H | 136 | 60.388 | 8.260 | −34.297 | 1.00 | 22.99 |
| ATOM | O | ALA | H | 136 | 61.545 | 8.331 | −33.884 | 1.00 | 22.43 |
| ATOM | N | ALA | H | 137 | 59.338 | 8.518 | −33.529 | 1.00 | 21.07 |
| ATOM | CA | ALA | H | 137 | 59.520 | 8.836 | −32.125 | 1.00 | 19.57 |
| ATOM | CB | ALA | H | 137 | 58.811 | 10.101 | −31.763 | 1.00 | 18.29 |
| ATOM | C | ALA | H | 137 | 58.991 | 7.686 | −31.293 | 1.00 | 20.25 |
| ATOM | O | ALA | H | 137 | 58.015 | 7.025 | −31.664 | 1.00 | 20.92 |
| ATOM | N | LEU | H | 138 | 59.678 | 7.422 | −30.194 | 1.00 | 19.10 |
| ATOM | CA | LEU | H | 138 | 59.317 | 6.375 | −29.258 | 1.00 | 15.77 |
| ATOM | CB | LEU | H | 138 | 60.036 | 5.075 | −29.618 | 1.00 | 16.18 |
| ATOM | CG | LEU | H | 138 | 61.569 | 5.057 | −29.693 | 1.00 | 14.59 |
| ATOM | CD1 | LEU | H | 138 | 62.140 | 4.576 | −28.386 | 1.00 | 16.58 |
| ATOM | CD2 | LEU | H | 138 | 61.983 | 4.113 | −30.775 | 1.00 | 15.53 |
| ATOM | C | LEU | H | 138 | 59.760 | 6.897 | −27.899 | 1.00 | 15.97 |
| ATOM | O | LEU | H | 138 | 60.466 | 7.904 | −27.818 | 1.00 | 16.00 |
| ATOM | N | GLY | H | 139 | 59.338 | 6.252 | −26.827 | 1.00 | 15.65 |
| ATOM | CA | GLY | H | 139 | 59.737 | 6.721 | −25.523 | 1.00 | 14.54 |
| ATOM | C | GLY | H | 139 | 59.295 | 5.785 | −24.437 | 1.00 | 15.97 |
| ATOM | O | GLY | H | 139 | 58.892 | 4.647 | −24.709 | 1.00 | 16.46 |
| ATOM | N | CYS | H | 140 | 59.326 | 6.290 | −23.209 | 1.00 | 15.70 |
| ATOM | CA | CYS | H | 140 | 58.925 | 5.539 | −22.035 | 1.00 | 14.57 |
| ATOM | C | CYS | H | 140 | 58.121 | 6.419 | −21.085 | 1.00 | 13.88 |
| ATOM | O | CYS | H | 140 | 58.457 | 7.592 | −20.881 | 1.00 | 11.51 |
| ATOM | CB | CYS | H | 140 | 60.153 | 5.011 | −21.302 | 1.00 | 16.76 |
| ATOM | SO | CYS | H | 140 | 60.792 | 3.452 | −21.985 | 1.00 | 16.67 |
| ATOM | N | LEU | H | 141 | 57.003 | 5.873 | −20.604 | 1.00 | 14.15 |
| ATOM | CA | LEU | H | 141 | 56.138 | 6.532 | −19.637 | 1.00 | 11.75 |
| ATOM | CB | LEU | H | 141 | 54.664 | 6.189 | −19.886 | 1.00 | 12.89 |
| ATOM | CG | LEU | H | 141 | 53.621 | 6.757 | −18.916 | 1.00 | 11.36 |
| ATOM | CD1 | LEU | H | 141 | 53.620 | 8.316 | −18.934 | 1.00 | 9.80 |
| ATOM | CD2 | LEU | H | 141 | 52.248 | 6.198 | −19.277 | 1.00 | 10.76 |
| ATOM | C | LEU | H | 141 | 56.590 | 5.992 | −18.276 | 1.00 | 13.36 |
| ATOM | O | LEU | H | 141 | 56.578 | 4.788 | −18.037 | 1.00 | 13.78 |
| ATOM | N | VAL | H | 142 | 57.044 | 6.905 | −17.421 | 1.00 | 14.52 |
| ATOM | CA | VAL | H | 142 | 57.542 | 6.601 | −16.086 | 1.00 | 13.75 |
| ATOM | CB | VAL | H | 142 | 58.923 | 7.264 | −15.872 | 1.00 | 12.16 |
| ATOM | CG1 | VAL | H | 142 | 59.516 | 6.856 | −14.542 | 1.00 | 9.59 |
| ATOM | CG2 | VAL | H | 142 | 59.866 | 6.851 | −17.005 | 1.00 | 10.00 |
| ATOM | C | VAL | H | 142 | 56.527 | 7.183 | −15.125 | 1.00 | 15.66 |
| ATOM | O | VAL | H | 142 | 56.541 | 8.384 | −14.850 | 1.00 | 15.64 |
| ATOM | N | LYS | H | 143 | 55.616 | 6.348 | −14.630 | 1.00 | 17.91 |
| ATOM | CA | LYS | H | 143 | 54.600 | 6.875 | −13.752 | 1.00 | 17.78 |
| ATOM | CB | LYS | H | 143 | 53.271 | 7.025 | −14.502 | 1.00 | 22.02 |
| ATOM | CG | LYS | H | 143 | 52.450 | 5.788 | −14.689 | 1.00 | 23.22 |
| ATOM | CD | LYS | H | 143 | 51.228 | 6.108 | −15.557 | 1.00 | 27.56 |
| ATOM | CE | LYS | H | 143 | 50.239 | 7.105 | −14.929 | 1.00 | 28.88 |
| ATOM | NZ | LYS | H | 143 | 49.292 | 6.527 | −13.914 | 1.00 | 29.43 |
| ATOM | C | LYS | H | 143 | 54.384 | 6.264 | −12.390 | 1.00 | 15.32 |
| ATOM | O | LYS | H | 143 | 54.827 | 5.144 | −12.106 | 1.00 | 11.57 |
| ATOM | N | ASP | H | 144 | 53.786 | 7.102 | −11.538 | 1.00 | 15.37 |
| ATOM | CA | ASP | H | 144 | 53.392 | 6.800 | −10.166 | 1.00 | 15.38 |
| ATOM | CB | ASP | H | 144 | 52.338 | 5.686 | −10.153 | 1.00 | 18.41 |
| ATOM | CG | ASP | H | 144 | 51.111 | 6.029 | −10.984 | 1.00 | 19.01 |

TABLE 2-continued

| | | Atom A.A. Type | | | X | Y | Z | Occ | B |
|---|---|---|---|---|---|---|---|---|---|
| ATOM | OD1 | ASP | H | 144 | 50.851 | 7.224 | −11.190 | 1.00 | 18.51 |
| ATOM | OD2 | ASP | H | 144 | 50.409 | 5.101 | −11.444 | 1.00 | 22.72 |
| ATOM | C | ASP | H | 144 | 54.518 | 6.499 | −9.191 | 1.00 | 13.76 |
| ATOM | O | ASP | H | 144 | 54.548 | 5.453 | −8.542 | 1.00 | 12.14 |
| ATOM | N | TYR | H | 145 | 55.434 | 7.451 | −9.075 | 1.00 | 14.87 |
| ATOM | CA | TYR | H | 145 | 56.557 | 7.312 | −8.164 | 1.00 | 11.80 |
| ATOM | CB | TYR | H | 145 | 57.880 | 7.176 | −8.936 | 1.00 | 12.15 |
| ATOM | CG | TYR | H | 145 | 58.300 | 8.405 | −9.722 | 1.00 | 13.86 |
| ATOM | CD1 | TYR | H | 145 | 57.996 | 8.535 | −11.083 | 1.00 | 10.29 |
| ATOM | CE1 | TYR | H | 145 | 58.360 | 9.682 | −11.778 | 1.00 | 10.58 |
| ATOM | CD2 | TYR | H | 145 | 58.980 | 9.452 | −9.089 | 1.00 | 10.94 |
| ATOM | CE2 | TYR | H | 145 | 59.344 | 10.597 | −9.772 | 1.00 | 10.46 |
| ATOM | CZ | TYR | H | 145 | 59.036 | 10.709 | −11.104 | 1.00 | 10.53 |
| ATOM | OH | TYR | H | 145 | 59.414 | 11.855 | −11.742 | 1.00 | 12.24 |
| ATOM | C | TYR | H | 145 | 56.560 | 8.543 | −7.272 | 1.00 | 11.16 |
| ATOM | O | TYR | H | 145 | 55.919 | 9.561 | −7.591 | 1.00 | 9.37 |
| ATOM | N | PHE | H | 146 | 57.271 | 8.440 | −6.157 | 1.00 | 11.54 |
| ATOM | CA | PHE | H | 146 | 57.397 | 9.518 | −5.199 | 1.00 | 10.60 |
| ATOM | CB | PHE | H | 146 | 56.155 | 9.580 | −4.292 | 1.00 | 12.01 |
| ATOM | CG | PHE | H | 146 | 56.050 | 10.860 | −3.486 | 1.00 | 10.87 |
| ATOM | CD1 | PHE | H | 146 | 56.420 | 10.888 | −2.145 | 1.00 | 9.67 |
| ATOM | CD2 | PHE | H | 146 | 55.620 | 12.047 | −4.095 | 1.00 | 10.37 |
| ATOM | CE1 | PHE | H | 146 | 56.376 | 12.071 | −1.422 | 1.00 | 7.13 |
| ATOM | CE2 | PHE | H | 146 | 55.569 | 13.239 | −3.387 | 1.00 | 11.35 |
| ATOM | CZ | PHE | H | 146 | 55.950 | 13.259 | −2.045 | 1.00 | 10.49 |
| ATOM | C | PHE | H | 146 | 58.603 | 9.165 | −4.351 | 1.00 | 11.66 |
| ATOM | O | PHE | H | 146 | 58.849 | 7.993 | −4.102 | 1.00 | 13.17 |
| ATOM | N | PRO | H | 147 | 59.475 | 10.144 | −4.061 | 1.00 | 15.11 |
| ATOM | CD | PRO | H | 147 | 60.393 | 10.039 | −2.903 | 1.00 | 11.77 |
| ATOM | CA | PRO | H | 147 | 59.374 | 11.538 | −4.512 | 1.00 | 12.86 |
| ATOM | CD | PRO | H | 147 | 59.920 | 12.318 | −3.301 | 1.00 | 11.39 |
| ATOM | CG | PRO | H | 147 | 61.014 | 11.442 | −2.810 | 1.00 | 13.59 |
| ATOM | C | PRO | H | 147 | 60.293 | 11.691 | −5.721 | 1.00 | 11.82 |
| ATOM | O | PRO | H | 147 | 60.710 | 10.694 | −6.331 | 1.00 | 10.54 |
| ATOM | N | GLU | H | 148 | 60.563 | 12.933 | −6.100 | 1.00 | 13.23 |
| ATOM | CA | GLU | H | 148 | 61.502 | 13.210 | −7.172 | 1.00 | 12.55 |
| ATOM | CB | GLU | H | 148 | 61.467 | 14.700 | −7.516 | 1.00 | 13.76 |
| ATOM | CG | GLU | H | 148 | 60.350 | 15.097 | −8.443 | 1.00 | 16.65 |
| ATOM | CD | GLU | H | 148 | 60.705 | 14.890 | −9.894 | 1.00 | 18.85 |
| ATOM | OE1 | GLU | H | 148 | 60.868 | 15.905 | −10.600 | 1.00 | 20.04 |
| ATOM | OE2 | GLU | H | 148 | 60.816 | 13.720 | −10.333 | 1.00 | 20.68 |
| ATOM | C | GLU | H | 148 | 62.873 | 12.884 | −6.537 | 1.00 | 12.83 |
| ATOM | O | GLU | H | 148 | 63.027 | 12.967 | −5.306 | 1.00 | 13.72 |
| ATOM | N | PRO | H | 149 | 63.889 | 12.558 | −7.358 | 1.00 | 13.44 |
| ATOM | CD | PRO | H | 149 | 65.297 | 12.743 | −6.955 | 1.00 | 9.52 |
| ATOM | CA | PRO | H | 149 | 63.793 | 12.483 | −8.813 | 1.00 | 12.75 |
| ATOM | CB | PRO | H | 149 | 64.933 | 13.390 | −9.233 | 1.00 | 13.35 |
| ATOM | CG | PRO | H | 149 | 66.009 | 12.955 | −8.279 | 1.00 | 11.58 |
| ATOM | C | PRO | H | 149 | 64.003 | 11.072 | −9.379 | 1.00 | 11.79 |
| ATOM | O | PRO | H | 149 | 64.357 | 10.138 | −8.672 | 1.00 | 13.53 |
| ATOM | N | VAL | H | 150 | 63.802 | 10.957 | −10.677 | 1.00 | 11.06 |
| ATOM | CA | VAL | H | 150 | 64.017 | 9.726 | −11.415 | 1.00 | 16.43 |
| ATOM | CB | VAL | H | 150 | 62.641 | 9.208 | −12.035 | 1.00 | 17.41 |
| ATOM | CG1 | VAL | H | 150 | 62.438 | 9.689 | −13.470 | 1.00 | 15.21 |
| ATOM | CG2 | VAL | H | 150 | 62.540 | 7.717 | −11.953 | 1.00 | 19.94 |
| ATOM | C | VAL | H | 150 | 65.002 | 10.163 | −12.527 | 1.00 | 16.34 |
| ATOM | O | VAL | H | 150 | 65.097 | 11.351 | −12.825 | 1.00 | 16.73 |
| ATOM | N | THR | H | 151 | 65.834 | 9.262 | −13.031 | 1.00 | 16.34 |
| ATOM | CA | THR | H | 151 | 66.702 | 9.616 | −14.150 | 1.00 | 15.33 |
| ATOM | CB | THR | H | 151 | 68.214 | 9.492 | −13.860 | 1.00 | 16.67 |
| ATOM | OG1 | THR | H | 151 | 68.521 | 8.147 | −13.507 | 1.00 | 19.39 |
| ATOM | CG2 | THR | H | 151 | 68.638 | 10.415 | −12.762 | 1.00 | 18.99 |
| ATOM | C | THR | H | 151 | 66.364 | 8.607 | −15.232 | 1.00 | 15.33 |
| ATOM | O | THR | H | 151 | 65.975 | 7.474 | −14.927 | 1.00 | 15.10 |
| ATOM | N | VAL | H | 152 | 66.463 | 9.024 | −16.489 | 1.00 | 15.67 |
| ATOM | CA | VAL | H | 152 | 66.186 | 8.130 | −17.593 | 1.00 | 15.90 |
| ATOM | CB | VAL | H | 152 | 64.840 | 8.463 | −18.298 | 1.00 | 16.43 |
| ATOM | CG1 | VAL | H | 152 | 64.559 | 7.429 | −19.389 | 1.00 | 17.02 |
| ATOM | CG2 | VAL | H | 152 | 63.687 | 8.514 | −17.289 | 1.00 | 12.53 |
| ATOM | C | VAL | H | 152 | 67.304 | 8.188 | −18.631 | 1.00 | 15.46 |
| ATOM | O | VAL | H | 152 | 67.725 | 9.273 | −19.044 | 1.00 | 15.77 |
| ATOM | N | SER | H | 153 | 67.823 | 7.025 | −19.010 | 1.00 | 15.40 |
| ATOM | CA | SER | H | 153 | 68.846 | 6.961 | −20.048 | 1.00 | 17.96 |
| ATOM | CB | SER | H | 153 | 70.220 | 6.517 | −19.500 | 1.00 | 19.47 |
| ATOM | CG | SER | H | 153 | 70.209 | 5.207 | −18.971 | 1.00 | 19.50 |
| ATOM | C | SER | H | 153 | 68.321 | 5.993 | −21.100 | 1.00 | 17.07 |

TABLE 2-continued

| | Atom | A.A. Type | | | X | Y | Z | Occ | B |
|---|---|---|---|---|---|---|---|---|---|
| ATOM | O | SER | H | 153 | 67.328 | 5.298 | −20.857 | 1.00 | 16.03 |
| ATOM | N | TRP | H | 154 | 68.51 | | 5.983 | −22.271 | 1.00 16.08 |
| ATOM | CA | TRP | H | 154 | 68.550 | 5.122 | −23.369 | 1.00 | 16.39 |
| ATOM | CB | TRP | H | 154 | 68.061 | 5.975 | −24.556 | 1.00 | 15.81 |
| ATOM | CG | TRP | H | 154 | 66.678 | 6.533 | −24.338 | 1.00 | 16.04 |
| ATOM | CD2 | TRP | H | 154 | 65.446 | 5.855 | −24.584 | 1.00 | 15.49 |
| ATOM | CE2 | TRP | H | 154 | 64.406 | 6.704 | −24.147 | 1.00 | 15.24 |
| ATOM | CE3 | TRP | H | 154 | 65.117 | 4.606 | −25.127 | 1.00 | 13.01 |
| ATOM | CG1 | TRP | H | 154 | 66.343 | 7.750 | −23.788 | 1.00 | 16.52 |
| ATOM | NE1 | TRP | H | 154 | 64.980 | 7.852 | −23.666 | 1.00 | 14.13 |
| ATOM | CZ2 | TRP | H | 154 | 63.061 | 6.338 | −24.239 | 1.00 | 13.45 |
| ATOM | CZ3 | TRP | H | 154 | 63.781 | 4.250 | −25.215 | 1.00 | 11.20 |
| ATOM | CH2 | TRP | H | 154 | 62.773 | 5.110 | −24.774 | 1.00 | 11.53 |
| ATOM | C | TRP | H | 154 | 69.743 | 4.288 | −23.792 | 1.00 | 19.86 |
| ATOM | O | TRP | H | 154 | 70.850 | 4.819 | −23.995 | 1.00 | 18.11 |
| ATOM | N | ASN | H | 155 | 69.536 | 2.978 | −23.886 | 1.00 | 19.14 |
| ATOM | CA | ASN | H | 155 | 70.595 | 2.051 | −24.284 | 1.00 | 18.51 |
| ATOM | CB | ASN | H | 155 | 70.884 | 2.203 | −25.773 | 1.00 | 16.21 |
| ATOM | CG | ASN | H | 155 | 69.744 | 1.697 | −26.624 | 1.00 | 14.90 |
| ATOM | OD1 | ASN | H | 155 | 68.890 | 0.968 | −26.132 | 1.00 | 15.81 |
| ATOM | ND2 | ASN | H | 155 | 69.734 | 2.045 | −27.902 | 1.00 | 14.10 |
| ATOM | C | ASN | H | 155 | 71.854 | 2.231 | −23.424 | 1.00 | 21.54 |
| ATOM | O | ASN | H | 155 | 72.986 | 2.289 | −23.926 | 1.00 | 21.60 |
| ATOM | N | SER | H | 156 | 71.618 | 2.307 | −22.114 | 1.00 | 23.82 |
| ATOM | CA | SER | H | 156 | 72.657 | 2.477 | −21.097 | 1.00 | 25.32 |
| ATOM | CB | SER | H | 156 | 73.478 | 1.194 | −20.947 | 1.00 | 23.36 |
| ATOM | OG | SER | H | 156 | 72.655 | 0.122 | −20.528 | 1.00 | 23.97 |
| ATOM | C | SER | H | 156 | 73.569 | 3.678 | −21.339 | 1.00 | 26.35 |
| ATOM | O | SER | H | 156 | 74.757 | 3.628 | −21.021 | 1.00 | 26.24 |
| ATOM | N | GLY | H | 157 | 73.001 | 4.756 | −21.888 | 1.00 | 24.38 |
| ATOM | CA | GLY | H | 157 | 73.763 | 5.966 | −22.160 | 1.00 | 21.04 |
| ATOM | C | GLY | H | 157 | 74.256 | 6.104 | −23.590 | 1.00 | 23.32 |
| ATOM | O | GLY | H | 157 | 74.639 | 7.183 | −24.016 | 1.00 | 23.51 |
| ATOM | N | ALA | H | 158 | 74.194 | 5.020 | −24.352 | 1.00 | 23.69 |
| ATOM | CA | ALA | H | 158 | 74.666 | 5.015 | −25.727 | 1.00 | 17.48 |
| ATOM | CB | ALA | H | 158 | 74.790 | 3.588 | −26.228 | 1.00 | 17.39 |
| ATOM | C | ALA | H | 158 | 73.797 | 5.822 | −26.668 | 1.00 | 13.71 |
| ATOM | O | ALA | H | 158 | 74.243 | 6.195 | −27.753 | 1.00 | 13.65 |
| ATOM | N | LEU | H | 159 | 72.544 | 6.058 | −26.281 | 1.00 | 18.26 |
| ATOM | CA | LEU | H | 159 | 71.636 | 6.827 | −27.127 | 1.00 | 19.74 |
| ATOM | CB | LEU | H | 159 | 70.335 | 6.056 | −27.370 | 1.00 | 18.94 |
| ATOM | CG | LEU | H | 159 | 69.576 | 6.197 | −28.689 | 1.00 | 19.52 |
| ATOM | CD1 | LEU | H | 159 | 68.134 | 5.790 | −28.448 | 1.00 | 16.51 |
| ATOM | CD2 | LEU | H | 159 | 69.649 | 7.583 | −29.248 | 1.00 | 23.06 |
| ATOM | C | LEU | H | 159 | 71.322 | 8.107 | −26.384 | 1.00 | 18.47 |
| ATOM | O | LEU | H | 159 | 70.659 | 8.083 | −25.357 | 1.00 | 18.48 |
| ATOM | N | THR | H | 160 | 71.791 | 9.229 | −26.904 | 1.00 | 23.36 |
| ATOM | CA | THR | H | 160 | 71.554 | 10.499 | −26.250 | 1.00 | 23.65 |
| ATOM | CB | THR | H | 160 | 72.826 | 10.963 | −25.546 | 1.00 | 21.22 |
| ATOM | OG1 | THR | H | 160 | 73.915 | 10.925 | −26.475 | 1.00 | 22.67 |
| ATOM | CG2 | THR | H | 160 | 73.148 | 10.037 | −24.385 | 1.00 | 23.98 |
| ATOM | C | THR | H | 160 | 71.050 | 11.574 | −27.202 | 1.00 | 23.49 |
| ATOM | O | THR | H | 160 | 70.370 | 12.512 | −26.785 | 1.00 | 19.91 |
| ATOM | N | SER | H | 161 | 71.344 | 11.442 | −28.487 | 1.00 | 23.44 |
| ATOM | CA | SER | H | 161 | 70.887 | 12.454 | −29.421 | 1.00 | 24.43 |
| ATOM | CB | SER | H | 161 | 71.613 | 12.343 | −30.769 | 1.00 | 25.80 |
| ATOM | CG | SER | H | 161 | 71.513 | 11.035 | −31.312 | 1.00 | 36.45 |
| ATOM | C | SER | H | 161 | 69.385 | 12.371 | −29.615 | 1.00 | 23.52 |
| ATOM | O | SER | H | 161 | 68.837 | 11.284 | −29.794 | 1.00 | 26.83 |
| ATOM | N | GLY | H | 162 | 68.718 | 13.515 | −29.511 | 1.00 | 22.52 |
| ATOM | CA | GLY | H | 162 | 67.287 | 13.574 | −29.719 | 1.00 | 19.26 |
| ATOM | C | GLY | H | 162 | 66.453 | 13.105 | −28.558 | 1.00 | 18.67 |
| ATOM | O | GLY | H | 162 | 65.263 | 12.867 | −28.727 | 1.00 | 19.57 |
| ATOM | N | VAL | H | 163 | 67.069 | 12.956 | −27.392 | 1.00 | 18.18 |
| ATOM | CA | VAL | H | 163 | 66.344 | 12.514 | −26.209 | 1.00 | 18.28 |
| ATOM | CB | VAL | H | 163 | 67.252 | 11.766 | −25.184 | 1.00 | 16.13 |
| ATOM | CG1 | VAL | H | 163 | 66.465 | 11.412 | −23.930 | 1.00 | 15.25 |
| ATOM | CG2 | VAL | H | 163 | 67.799 | 10.503 | −25.794 | 1.00 | 16.95 |
| ATOM | C | VAL | H | 163 | 65.763 | 13.728 | −25.521 | 1.00 | 18.72 |
| ATOM | O | VAL | H | 163 | 66.399 | 14.777 | −25.452 | 1.00 | 21.28 |
| ATOM | N | HIS | H | 164 | 64.541 | 13.586 | −25.031 | 1.00 | 17.35 |
| ATOM | CA | HIS | H | 164 | 63.871 | 14.649 | −24.313 | 1.00 | 16.94 |
| ATOM | CB | HIS | H | 164 | 62.817 | 15.341 | −25.182 | 1.00 | 19.00 |
| ATOM | CG | HIS | H | 164 | 63.372 | 16.361 | −26.128 | 1.00 | 18.12 |
| ATOM | CG2 | HIS | H | 164 | 63.975 | 17.549 | −25.898 | 1.00 | 16.70 |

TABLE 2-continued

| | | Atom A.A. Type | | | X | Y | Z | Occ | B |
|---|---|---|---|---|---|---|---|---|---|
| ATOM | ND1 | HIS | H | 164 | 63.256 | 16.251 | −27.497 | 1.00 | 18.61 |
| ATOM | CE1 | HIS | H | 164 | 63.753 | 17.331 | −28.068 | 1.00 | 14.03 |
| ATOM | NE2 | HIS | H | 164 | 64.194 | 18.133 | −27.119 | 1.00 | 18.56 |
| ATOM | C | HIS | H | 164 | 63.175 | 13.985 | −23.152 | 1.00 | 17.34 |
| ATOM | O | HIS | H | 164 | 62.250 | 13.191 | −23.347 | 1.00 | 16.54 |
| ATOM | N | THR | H | 165 | 63.663 | 14.252 | −21.952 | 1.00 | 17.07 |
| ATOM | CA | THR | H | 165 | 63.049 | 13.703 | −20.752 | 1.00 | 16.08 |
| ATOM | CB | THR | H | 165 | 64.097 | 13.062 | −19.842 | 1.00 | 15.02 |
| ATOM | OG1 | THR | H | 165 | 64.689 | 11.978 | −20.559 | 1.00 | 14.53 |
| ATOM | CG2 | THR | H | 165 | 63.475 | 12.517 | −18.570 | 1.00 | 13.69 |
| ATOM | C | THR | H | 165 | 62.325 | 14.853 | −20.083 | 1.00 | 13.93 |
| ATOM | O | THR | H | 165 | 62.933 | 15.766 | −19.533 | 1.00 | 12.69 |
| ATOM | N | PHE | H | 166 | 61.011 | 14.828 | −20.218 | 1.00 | 13.31 |
| ATOM | CA | PHE | H | 166 | 60.151 | 15.860 | −19.676 | 1.00 | 11.35 |
| ATOM | CB | PHE | H | 166 | 58.715 | 15.647 | −20.176 | 1.00 | 11.84 |
| ATOM | CG | PHE | H | 166 | 58.554 | 15.834 | −21.666 | 1.00 | 13.49 |
| ATOM | CD1 | PHE | H | 166 | 58.575 | 14.738 | −22.528 | 1.00 | 16.51 |
| ATOM | CD2 | PHE | H | 166 | 58.389 | 17.106 | −22.205 | 1.00 | 14.83 |
| ATOM | CH1 | PHE | H | 166 | 58.437 | 14.903 | −23.904 | 1.00 | 15.29 |
| ATOM | CE2 | PHE | H | 166 | 58.251 | 17.283 | −23.576 | 1.00 | 14.45 |
| ATOM | CZ | PHE | H | 166 | 58.275 | 16.181 | −24.427 | 1.00 | 15.22 |
| ATOM | C | PHE | H | 166 | 60.172 | 15.945 | −18.154 | 1.00 | 12.15 |
| ATOM | O | PHE | H | 166 | 60.378 | 14.945 | −17.466 | 1.00 | 9.27 |
| ATOM | N | PRO | H | 167 | 60.059 | 17.175 | −17.619 | 1.00 | 13.86 |
| ATOM | CD | PRO | H | 167 | 60.046 | 18.419 | −18.415 | 1.00 | 15.57 |
| ATOM | CA | PRO | H | 167 | 60.040 | 17.482 | −16.190 | 1.00 | 11.73 |
| ATOM | CB | PRO | H | 167 | 59.691 | 18.962 | −16.170 | 1.00 | 12.97 |
| ATOM | CG | PRO | H | 167 | 60.362 | 19.470 | −17.371 | 1.00 | 17.36 |
| ATOM | C | PRO | H | 167 | 58.873 | 16.727 | −15.611 | 1.00 | 12.24 |
| ATOM | O | PRO | H | 167 | 57.799 | 16.701 | −16.234 | 1.00 | 13.95 |
| ATOM | N | ALA | H | 168 | 59.057 | 16.122 | −14.439 | 1.00 | 12.11 |
| ATOM | CA | ALA | H | 168 | 57.976 | 15.386 | −13.793 | 1.00 | 12.13 |
| ATOM | CB | ALA | H | 168 | 58.475 | 14.688 | −12.552 | 1.00 | 8.32 |
| ATOM | C | ALA | H | 168 | 56.858 | 16.345 | −13.423 | 1.00 | 13.78 |
| ATOM | O | ALA | H | 168 | 57.081 | 17.544 | −13.234 | 1.00 | 15.51 |
| ATOM | N | VAL | H | 169 | 55.645 | 15.831 | −13.371 | 1.00 | 12.89 |
| ATOM | CA | VAL | H | 169 | 54.506 | 16.635 | −12.988 | 1.00 | 15.57 |
| ATOM | CB | VAL | H | 169 | 53.612 | 16.990 | −14.232 | 1.00 | 16.84 |
| ATOM | CG1 | VAL | H | 169 | 52.333 | 17.668 | −13.794 | 1.00 | 19.49 |
| ATOM | CG2 | VAL | H | 169 | 54.368 | 17.932 | −15.193 | 1.00 | 17.39 |
| ATOM | C | VAL | H | 169 | 53.761 | 15.763 | −11.980 | 1.00 | 15.66 |
| ATOM | O | VAL | H | 169 | 53.637 | 14.553 | −12.179 | 1.00 | 17.42 |
| ATOM | N | LEU | H | 170 | 53.393 | 16.347 | −10.844 | 1.00 | 15.29 |
| ATOM | CA | LEU | H | 170 | 52.668 | 15.627 | −9.804 | 1.00 | 15.27 |
| ATOM | CB | LEU | H | 170 | 52.716 | 16.381 | −8.461 | 1.00 | 12.42 |
| ATOM | CG | LEU | H | 170 | 52.125 | 15.662 | −7.235 | 1.00 | 13.03 |
| ATOM | CD1 | LEU | H | 170 | 53.065 | 14.595 | −6.769 | 1.00 | 13.43 |
| ATOM | CD2 | LEU | H | 170 | 51.929 | 16.616 | −6.109 | 1.00 | 18.10 |
| ATOM | C | LEU | H | 170 | 51.220 | 15.507 | −10.249 | 1.00 | 18.26 |
| ATOM | O | LEU | H | 170 | 50.696 | 16.503 | −10.610 | 1.00 | 18.33 |
| ATOM | N | GLN | H | 171 | 50.721 | 14.276 | −10.277 | 1.00 | 19.12 |
| ATOM | CA | GLN | H | 171 | 49.349 | 13.976 | −10.672 | 1.00 | 18.69 |
| ATOM | CB | GLN | H | 171 | 49.243 | 12.496 | −11.041 | 1.00 | 15.23 |
| ATOM | CG | GLN | H | 171 | 50.154 | 12.095 | −12.186 | 1.00 | 18.70 |
| ATOM | CD | GLN | H | 171 | 50.341 | 10.594 | −12.300 | 1.00 | 21.99 |
| ATOM | OE1 | GLN | H | 171 | 50.953 | 9.969 | −11.436 | 1.00 | 22.59 |
| ATOM | NE2 | GLN | H | 171 | 49.852 | 10.011 | −13.385 | 1.00 | 21.12 |
| ATOM | C | GLN | H | 171 | 48.437 | 14.260 | −9.479 | 1.00 | 21.17 |
| ATOM | O | GLN | H | 171 | 48.901 | 14.416 | −8.335 | 1.00 | 18.05 |
| ATOM | N | SER | H | 172 | 47.131 | 14.270 | −9.730 | 1.00 | 24.36 |
| ATOM | CA | SER | H | 172 | 46.177 | 14.508 | −8.657 | 1.00 | 24.61 |
| ATOM | CB | SER | H | 172 | 44.760 | 14.628 | −9.222 | 1.00 | 28.12 |
| ATOM | OG | SER | H | 172 | 44.475 | 13.541 | −10.090 | 1.00 | 35.60 |
| ATOM | C | SER | H | 172 | 46.275 | 13.373 | −7.629 | 1.00 | 23.66 |
| ATOM | O | SER | H | 172 | 45.942 | 13.572 | −6.464 | 1.00 | 26.39 |
| ATOM | N | SER | H | 173 | 46.758 | 12.201 | −8.050 | 1.00 | 19.22 |
| ATOM | CA | SER | H | 173 | 46.938 | 11.055 | −7.151 | 1.00 | 18.61 |
| ATOM | CB | SER | H | 173 | 47.319 | 9.825 | −7.961 | 1.00 | 19.87 |
| ATOM | OG | SER | H | 173 | 48.551 | 10.027 | −8.630 | 1.00 | 23.71 |
| ATOM | C | SER | H | 173 | 48.027 | 11.307 | −6.101 | 1.00 | 17.92 |
| ATOM | O | SER | H | 173 | 48.162 | 10.562 | −5.125 | 1.00 | 18.89 |
| ATOM | N | GLY | H | 174 | 48.800 | 12.367 | −6.309 | 1.00 | 17.55 |
| ATOM | CA | GLY | H | 174 | 49.869 | 12.711 | −5.389 | 1.00 | 16.52 |
| ATOM | C | GLY | H | 174 | 51.158 | 12.016 | −5.774 | 1.00 | 15.28 |
| ATOM | O | GLY | H | 174 | 52.121 | 12.031 | −5.011 | 1.00 | 15.34 |
| ATOM | N | LEU | H | 175 | 51.189 | 11.425 | −6.966 | 1.00 | 12.52 |

TABLE 2-continued

| | Atom | A.A. Type | | | X | Y | Z | Occ | B |
|---|---|---|---|---|---|---|---|---|---|
| ATOM | CA | LEU | H | 175 | 52.373 | 10.715 | −7.436 | 1.00 | 12.10 |
| ATOM | CB | LEU | H | 175 | 52.034 | 9.252 | −7.725 | 1.00 | 11.95 |
| ATOM | CG | LEU | H | 175 | 51.598 | 8.371 | −6.561 | 1.00 | 13.01 |
| ATOM | CG1 | LEU | H | 175 | 51.038 | 7.035 | −7.062 | 1.00 | 12.11 |
| ATOM | CD2 | LEU | H | 175 | 52.778 | 8.189 | −5.608 | 1.00 | 15.83 |
| ATOM | C | LEU | H | 175 | 52.835 | 11.377 | −8.712 | 1.00 | 11.41 |
| ATOM | O | LEU | H | 175 | 52.012 | 11.899 | −9.452 | 1.00 | 12.88 |
| ATOM | N | TYR | H | 176 | 54.149 | 11.379 | −8.959 | 1.00 | 12.75 |
| ATOM | CA | TYR | H | 176 | 54.715 | 11.984 | −10.169 | 1.00 | 9.90 |
| ATOM | CB | TYR | H | 176 | 56.186 | 12.344 | −9.977 | 1.00 | 6.99 |
| ATOM | CG | TYR | H | 176 | 56.437 | 13.446 | −8.977 | 1.00 | 9.80 |
| ATOM | CD1 | TYR | H | 176 | 56.298 | 14.786 | −9.332 | 1.00 | 9.18 |
| ATOM | CE1 | TYR | H | 176 | 56.529 | 15.796 | −8.404 | 1.00 | 8.22 |
| ATOM | CD2 | TYR | H | 176 | 56.812 | 13.145 | −7.670 | 1.00 | 9.26 |
| ATOM | CE2 | TYR | H | 176 | 57.039 | 14.139 | −6.746 | 1.00 | 10.18 |
| ATOM | CZ | TYR | H | 176 | 56.900 | 15.461 | −7.115 | 1.00 | 8.46 |
| ATOM | OH | TYR | H | 176 | 57.141 | 16.439 | −6.181 | 1.00 | 9.44 |
| ATOM | C | TYR | H | 176 | 54.617 | 11.068 | −11.365 | 1.00 | 9.94 |
| ATOM | O | TYR | H | 176 | 54.491 | 9.855 | −11.230 | 1.00 | 13.21 |
| ATOM | N | SER | H | 177 | 54.755 | 11.661 | −12.536 | 1.00 | 10.40 |
| ATOM | CA | SER | H | 177 | 54.729 | 10.927 | −13.787 | 1.00 | 13.02 |
| ATOM | CB | SER | H | 177 | 53.276 | 10.688 | −14.232 | 1.00 | 12.24 |
| ATOM | OG | SER | H | 177 | 53.214 | 9.929 | −15.425 | 1.00 | 15.89 |
| ATOM | C | SER | H | 177 | 55.462 | 11.760 | −14.833 | 1.00 | 11.43 |
| ATOM | O | SER | H | 177 | 55.457 | 12.991 | −14.759 | 1.00 | 13.35 |
| ATOM | N | LEU | H | 178 | 56.133 | 11.085 | −15.761 | 1.00 | 10.36 |
| ATOM | CA | LEU | H | 178 | 56.826 | 11.750 | −16.849 | 1.00 | 12.46 |
| ATOM | CB | LEU | H | 178 | 58.150 | 12.364 | −16.371 | 1.00 | 11.05 |
| ATOM | CG | LEU | H | 178 | 59.297 | 11.492 | −15.880 | 1.00 | 7.67 |
| ATOM | CG1 | LEU | H | 178 | 60.068 | 10.867 | −17.044 | 1.00 | 8.40 |
| ATOM | CD2 | LEU | H | 178 | 60.216 | 12.376 | −15.113 | 1.00 | 8.48 |
| ATOM | C | LEU | H | 178 | 57.090 | 10.782 | −17.995 | 1.00 | 12.58 |
| ATOM | O | LEU | H | 178 | 56.963 | 9.584 | −17.827 | 1.00 | 13.76 |
| ATOM | N | SER | H | 179 | 57.403 | 11.325 | −19.167 | 1.00 | 14.34 |
| ATOM | CA | SER | H | 179 | 57.763 | 10.541 | −20.351 | 1.00 | 14.75 |
| ATOM | CB | SER | H | 179 | 56.769 | 10.762 | −21.504 | 1.00 | 14.23 |
| ATOM | OG | SER | H | 179 | 55.540 | 10.086 | −21.291 | 1.00 | 15.49 |
| ATOM | C | SER | H | 179 | 59.155 | 11.009 | −20.803 | 1.00 | 14.23 |
| ATOM | O | SER | H | 179 | 59.560 | 12.141 | −20.548 | 1.00 | 12.08 |
| ATOM | N | SER | H | 180 | 59.888 | 10.108 | −21.437 | 1.00 | 14.48 |
| ATOM | CA | SER | H | 180 | 61.219 | 10.376 | −21.985 | 1.00 | 13.43 |
| ATOM | CB | SER | H | 180 | 62.301 | 9.565 | −21.280 | 1.00 | 12.19 |
| ATOM | OG | SER | H | 180 | 63.564 | 9.759 | −21.901 | 1.00 | 14.67 |
| ATOM | C | SER | H | 180 | 61.046 | 9.835 | −23.383 | 1.00 | 13.99 |
| ATOM | O | SER | H | 180 | 60.680 | 8.671 | −23.571 | 1.00 | 15.36 |
| ATOM | N | VAL | H | 181 | 61.257 | 10.690 | −24.358 | 1.00 | 15.02 |
| ATOM | CA | VAL | H | 181 | 61.078 | 10.307 | −25.735 | 1.00 | 15.74 |
| ATOM | CB | VAL | H | 181 | 59.957 | 11.166 | −26.398 | 1.00 | 15.83 |
| ATOM | CG1 | VAL | H | 181 | 58.639 | 10.960 | −25.647 | 1.00 | 12.76 |
| ATOM | CG2 | VAL | H | 181 | 60.357 | 12.647 | −26.430 | 1.00 | 15.72 |
| ATOM | C | VAL | H | 181 | 62.377 | 10.488 | −26.475 | 1.00 | 17.47 |
| ATOM | O | VAL | H | 181 | 63.265 | 11.199 | −26.000 | 1.00 | 15.89 |
| ATOM | N | VAL | H | 182 | 62.496 | 9.801 | −27.607 | 1.00 | 17.14 |
| ATOM | CA | VAL | H | 182 | 63.679 | 9.890 | −28.453 | 1.00 | 13.84 |
| ATOM | CB | VAL | H | 182 | 64.781 | 8.846 | −28.048 | 1.00 | 16.69 |
| ATOM | CG1 | VAL | H | 182 | 64.312 | 7.417 | −28.260 | 1.00 | 14.43 |
| ATOM | CG2 | VAL | H | 182 | 66.050 | 9.117 | −28.818 | 1.00 | 17.22 |
| ATOM | C | VAL | H | 182 | 63.226 | 9.693 | −29.900 | 1.00 | 21.36 |
| ATOM | O | VAL | H | 182 | 62.267 | 8.963 | −30.161 | 1.00 | 23.83 |
| ATOM | N | THR | H | 183 | 63.805 | 10.447 | −30.823 | 1.00 | 13.93 |
| ATOM | CA | THR | H | 183 | 63.450 | 10.295 | −32.227 | 1.00 | 21.38 |
| ATOM | CB | THR | H | 183 | 63.218 | 11.664 | −32.950 | 1.00 | 21.63 |
| ATOM | OG1 | THR | H | 183 | 64.273 | 12.570 | −32.639 | 1.00 | 24.70 |
| ATOM | CG2 | THR | H | 183 | 61.890 | 12.294 | −32.534 | 1.00 | 23.70 |
| ATOM | C | THR | H | 183 | 64.595 | 9.514 | −32.857 | 1.00 | 21.52 |
| ATOM | O | THR | H | 183 | 65.764 | 9.774 | −32.565 | 1.00 | 23.10 |
| ATOM | N | VAL | H | 184 | 64.259 | 8.488 | −33.628 | 1.00 | 23.35 |
| ATOM | CA | VAL | H | 184 | 65.259 | 7.652 | −34.266 | 1.00 | 19.98 |
| ATOM | CB | VAL | H | 184 | 65.373 | 6.269 | −33.537 | 1.00 | 21.07 |
| ATOM | CG1 | VAL | H | 184 | 65.755 | 6.479 | −32.084 | 1.00 | 23.71 |
| ATOM | CG2 | VAL | H | 184 | 64.059 | 5.439 | −33.668 | 1.00 | 17.17 |
| ATOM | C | VAL | H | 184 | 64.959 | 7.437 | −35.756 | 1.00 | 22.10 |
| ATOM | O | VAL | H | 184 | 63.900 | 7.836 | −36.253 | 1.00 | 21.90 |
| ATOM | N | PRO | H | 185 | 65.898 | 6.821 | −36.495 | 1.00 | 22.12 |
| ATOM | CD | PRO | H | 185 | 67.247 | 6.371 | −36.096 | 1.00 | 23.90 |
| ATOM | CA | PRO | H | 185 | 65.669 | 6.580 | −37.923 | 1.00 | 23.15 |

TABLE 2-continued

| | | Atom A.A. Type | | | X | Y | Z | Occ | B |
|---|---|---|---|---|---|---|---|---|---|
| ATOM | CB | PRO | H | 185 | 66.988 | 5.933 | −38.365 | 1.00 | 22.25 |
| ATOM | CG | PRO | H | 185 | 67.988 | 6.449 | −37.377 | 1.00 | 21.22 |
| ATOM | C | PRO | H | 185 | 64.522 | 5.584 | −38.097 | 1.00 | 23.63 |
| ATOM | O | PRO | H | 185 | 64.509 | 4.542 | −37.439 | 1.00 | 24.96 |
| ATOM | N | SER | H | 186 | 63.579 | 5.864 | −38.992 | 1.00 | 24.50 |
| ATOM | CA | SER | H | 186 | 62.472 | 4.932 | −39.208 | 1.00 | 26.40 |
| ATOM | CB | SER | H | 186 | 61.556 | 5.427 | −40.309 | 1.00 | 23.78 |
| ATOM | OG | SER | H | 186 | 60.922 | 6.625 | −39.929 | 1.00 | 31.60 |
| ATOM | C | SER | H | 186 | 63.008 | 3.566 | −39.596 | 1.00 | 26.90 |
| ATOM | O | SER | H | 186 | 62.520 | 2.530 | −39.132 | 1.00 | 28.22 |
| ATOM | N | SER | H | 187 | 64.055 | 3.578 | −40.411 | 1.00 | 25.91 |
| ATOM | CA | SER | H | 187 | 64.671 | 2.352 | −40.884 | 1.00 | 24.43 |
| ATOM | CB | SER | H | 187 | 65.803 | 2.698 | −41.846 | 1.00 | 25.38 |
| ATOM | OG | SER | H | 187 | 66.663 | 3.674 | −41.269 | 1.00 | 32.83 |
| ATOM | C | SER | H | 187 | 65.387 | 1.464 | −39.764 | 1.00 | 22.75 |
| ATOM | O | SER | H | 187 | 65.330 | 0.257 | −39.942 | 1.00 | 23.52 |
| ATOM | N | SER | H | 188 | 65.441 | 2.048 | −38.600 | 1.00 | 22.42 |
| ATOM | CA | SER | H | 188 | 65.971 | 1.274 | −37.489 | 1.00 | 21.39 |
| ATOM | CB | SER | H | 188 | 66.727 | 2.186 | −36.518 | 1.00 | 24.28 |
| ATOM | OG | SER | H | 188 | 65.870 | 3.153 | −35.929 | 1.00 | 24.35 |
| ATOM | C | SER | H | 188 | 64.919 | 0.478 | −36.737 | 1.00 | 19.89 |
| ATOM | O | SER | H | 188 | 65.252 | −0.418 | −35.967 | 1.00 | 21.67 |
| ATOM | N | LEU | H | 189 | 63.656 | 0.819 | −36.931 | 1.00 | 19.37 |
| ATOM | CA | LEU | H | 189 | 62.572 | 0.120 | −36.250 | 1.00 | 21.16 |
| ATOM | CB | LEU | H | 189 | 61.215 | 0.740 | −36.620 | 1.00 | 22.65 |
| ATOM | CG | LEU | H | 189 | 60.574 | 1.843 | −35.769 | 1.00 | 24.15 |
| ATOM | CD1 | LEU | H | 189 | 61.486 | 2.396 | −34.677 | 1.00 | 21.90 |
| ATOM | CD2 | LEU | H | 189 | 60.117 | 2.929 | −36.689 | 1.00 | 20.64 |
| ATOM | C | LEU | H | 189 | 62.567 | −1.358 | −36.594 | 1.00 | 20.08 |
| ATOM | O | LEU | H | 189 | 62.342 | −1.726 | −37.741 | 1.00 | 21.74 |
| ATOM | N | GLY | H | 190 | 62.405 | −2.204 | −35.586 | 1.00 | 22.92 |
| ATOM | CA | GLY | H | 190 | 62.376 | −3.638 | −35.815 | 1.00 | 23.25 |
| ATOM | C | GLY | H | 190 | 63.359 | −4.270 | −35.860 | 1.00 | 25.44 |
| ATOM | O | GLY | H | 190 | 63.889 | −5.489 | −35.736 | 1.00 | 24.73 |
| ATOM | N | THR | H | 191 | 64.396 | −3.451 | −36.039 | 1.00 | 27.60 |
| ATOM | CA | THR | H | 191 | 66.159 | −3.958 | −36.098 | 1.00 | 28.13 |
| ATOM | CB | THR | H | 191 | 66.858 | −3.649 | −37.469 | 1.00 | 29.33 |
| ATOM | OG1 | THR | H | 191 | 66.835 | −2.246 | −37.749 | 1.00 | 34.09 |
| ATOM | CG2 | THR | H | 191 | 66.345 | −4.368 | −38.597 | 1.00 | 32.02 |
| ATOM | C | THR | H | 191 | 67.001 | −3.468 | −34.931 | 1.00 | 27.84 |
| ATOM | O | THR | H | 191 | 67.686 | −4.254 | −34.293 | 1.00 | 29.90 |
| ATOM | N | GLN | H | 192 | 66.937 | −2.183 | −34.620 | 1.00 | 26.52 |
| ATOM | CA | GLN | H | 192 | 67.721 | −1.670 | −33.505 | 1.00 | 26.83 |
| ATOM | CB | GLN | H | 192 | 68.092 | −0.204 | −33.751 | 1.00 | 27.16 |
| ATOM | CG | GLN | H | 192 | 69.541 | 0.149 | −33.391 | 1.00 | 36.31 |
| ATOM | CD | GLN | H | 192 | 69.792 | 0.041 | −31.908 | 1.00 | 38.23 |
| ATOM | OE1 | GLN | H | 192 | 70.777 | −0.544 | −31.457 | 1.00 | 36.83 |
| ATOM | NE2 | GLN | H | 192 | 68.870 | 0.584 | −31.132 | 1.00 | 44.67 |
| ATOM | C | GLN | H | 192 | 66.946 | −1.821 | −32.193 | 1.00 | 25.50 |
| ATOM | O | GLN | H | 192 | 65.771 | −1.483 | −32.121 | 1.00 | 26.11 |
| ATOM | N | THR | H | 193 | 67.585 | −2.373 | −31.173 | 1.00 | 23.13 |
| ATOM | CA | THR | H | 193 | 66.946 | −2.531 | −29.876 | 1.00 | 23.22 |
| ATOM | CB | THR | H | 193 | 67.600 | −3.679 | −29.086 | 1.00 | 25.71 |
| ATOM | OG1 | THR | H | 193 | 67.396 | −4.909 | −29.794 | 1.00 | 27.62 |
| ATOM | CG2 | THR | H | 193 | 67.012 | −3.794 | −27.692 | 1.00 | 27.67 |
| ATOM | C | THR | H | 193 | 67.023 | −1.216 | −29.080 | 1.00 | 23.94 |
| ATOM | O | THR | H | 193 | 68.081 | −0.588 | −28.981 | 1.00 | 23.16 |
| ATOM | N | TYR | H | 194 | 65.889 | −0.783 | −28.545 | 1.00 | 21.58 |
| ATOM | CA | TYR | H | 194 | 65.823 | 0.444 | −27.774 | 1.00 | 18.67 |
| ATOM | CB | TYR | H | 194 | 64.901 | 1.445 | −28.442 | 1.00 | 18.25 |
| ATOM | CG | TYR | H | 194 | 65.447 | 1.934 | −29.754 | 1.00 | 18.87 |
| ATOM | CD1 | TYR | H | 194 | 66.497 | 2.842 | −29.782 | 1.00 | 17.22 |
| ATOM | CE1 | TYR | H | 194 | 66.999 | 3.310 | −30.971 | 1.00 | 20.86 |
| ATOM | CD2 | TYR | H | 194 | 64.908 | 1.497 | −30.969 | 1.00 | 19.91 |
| ATOM | CE2 | TYR | H | 194 | 65.401 | 1.963 | −32.180 | 1.00 | 20.11 |
| ATOM | CZ | TYR | H | 194 | 66.450 | 2.875 | −32.176 | 1.00 | 22.81 |
| ATOM | OH | TYR | H | 194 | 66.949 | 3.387 | −33.355 | 1.00 | 21.52 |
| ATOM | C | TYR | H | 194 | 65.325 | 0.114 | −26.397 | 1.00 | 18.70 |
| ATOM | O | TYR | H | 194 | 64.280 | −0.533 | −26.231 | 1.00 | 18.91 |
| ATOM | N | ILE | H | 195 | 66.100 | 0.535 | −25.407 | 1.00 | 15.98 |
| ATOM | CA | ILE | H | 195 | 65.782 | 0.268 | −24.025 | 1.00 | 15.14 |
| ATOM | CB | ILE | H | 195 | 66.731 | −0.820 | −23.489 | 1.00 | 14.19 |
| ATOM | CG2 | ILE | H | 195 | 66.476 | −1.079 | −22.032 | 1.00 | 14.73 |
| ATOM | CG1 | ILE | H | 195 | 66.594 | −2.082 | −24.339 | 1.00 | 17.52 |
| ATOM | CD1 | ILE | H | 195 | 67.386 | −3.252 | −23.844 | 1.00 | 21.62 |
| ATOM | C | ILE | H | 195 | 65.932 | 1.533 | −23.183 | 1.00 | 16.46 |

TABLE 2-continued

| | Atom | A.A. Type | | | X | Y | Z | Occ | B |
|---|---|---|---|---|---|---|---|---|---|
| ATOM | O | ILE | H | 195 | 66.932 | 2.239 | −23.308 | 1.00 | 4.40 |
| ATOM | N | CYS | H | 196 | 64.910 | 1.866 | −22.392 | 1.00 | 5.74 |
| ATOM | CA | CYS | H | 196 | 65.020 | 3.026 | −21.504 | 1.00 | 5.04 |
| ATOM | C | CYS | H | 196 | 65.414 | 2.433 | −20.151 | 1.00 | 5.47 |
| ATOM | O | CYS | H | 196 | 64.961 | 1.344 | −19.799 | 1.00 | 7.09 |
| ATOM | CB | CYS | H | 196 | 63.720 | 3.839 | −21.418 | 1.00 | 11.99 |
| ATOM | SO | CYS | H | 196 | 62.289 | 2.978 | −20.709 | 1.00 | 15.97 |
| ATOM | N | ASN | H | 197 | 66.369 | 3.080 | −19.479 | 1.00 | 4.76 |
| ATOM | CA | ASN | H | 197 | 66.881 | 2.639 | −18.185 | 1.00 | 5.71 |
| ATOM | CB | ASN | H | 197 | 68.424 | 2.530 | −18.227 | 1.00 | 3.36 |
| ATOM | CG | ASN | H | 197 | 68.955 | 2.061 | −19.583 | 1.00 | 4.38 |
| ATOM | OD1 | ASN | H | 197 | 69.482 | 2.855 | −20.369 | 1.00 | 2.39 |
| ATOM | ND2 | ASN | H | 197 | 68.618 | 0.772 | −19.864 | 1.00 | 4.64 |
| ATOM | C | ASN | H | 197 | 66.436 | 3.704 | −17.173 | 1.00 | 7.43 |
| ATOM | O | ASN | H | 197 | 66.676 | 4.862 | −17.212 | 1.00 | 7.96 |
| ATOM | N | VAL | H | 198 | 65.532 | 3.314 | −16.294 | 1.00 | 5.31 |
| ATOM | CA | VAL | H | 198 | 64.973 | 4.220 | −15.318 | 1.00 | 5.22 |
| ATOM | CB | VAL | H | 198 | 63.412 | 4.109 | −15.323 | 1.00 | 6.02 |
| ATOM | CG1 | VAL | H | 198 | 62.776 | 5.110 | −14.359 | 1.00 | 5.86 |
| ATOM | CG2 | VAL | H | 198 | 62.866 | 4.306 | −16.761 | 1.00 | 2.38 |
| ATOM | C | VAL | H | 198 | 65.520 | 3.951 | −13.934 | 1.00 | 5.38 |
| ATOM | O | VAL | H | 198 | 65.449 | 2.831 | −13.425 | 1.00 | 8.68 |
| ATOM | N | ASN | H | 199 | 66.057 | 4.985 | −13.305 | 1.00 | 5.30 |
| ATOM | CA | ASN | H | 199 | 66.604 | 4.828 | −11.970 | 1.00 | 5.88 |
| ATOM | CB | ASN | H | 199 | 68.122 | 5.034 | −12.009 | 1.00 | 7.62 |
| ATOM | CG | ASN | H | 199 | 68.789 | 4.716 | −10.708 | 1.00 | 9.95 |
| ATOM | OD1 | ASN | H | 199 | 69.967 | 4.990 | −10.544 | 1.00 | 24.61 |
| ATOM | ND2 | ASN | H | 199 | 68.063 | 4.113 | −9.782 | 1.00 | 22.49 |
| ATOM | C | ASN | H | 199 | 65.925 | 5.821 | −11.029 | 1.00 | 5.25 |
| ATOM | O | ASN | H | 199 | 65.808 | 7.003 | −11.356 | 1.00 | 4.39 |
| ATOM | N | HIS | H | 200 | 65.353 | 5.293 | −9.947 | 1.00 | 2.48 |
| ATOM | CA | HIS | H | 200 | 64.670 | 6.081 | −8.921 | 1.00 | 5.53 |
| ATOM | CB | HIS | H | 200 | 63.185 | 5.663 | −8.790 | 1.00 | 4.60 |
| ATOM | CG | HIS | H | 200 | 62.378 | 6.502 | −7.830 | 1.00 | 5.76 |
| ATOM | CD2 | HIS | H | 200 | 62.211 | 7.843 | −7.734 | 1.00 | 4.93 |
| ATOM | ND1 | HIS | H | 200 | 61.591 | 5.954 | −6.835 | 1.00 | 6.92 |
| ATOM | CE1 | HIS | H | 200 | 60.976 | 6.919 | −6.171 | 1.00 | 4.09 |
| ATOM | NE2 | HIS | H | 200 | 61.339 | 8.074 | −6.696 | 1.00 | 3.32 |
| ATOM | C | HIS | H | 200 | 65.447 | 5.843 | −7.624 | 1.00 | 4.98 |
| ATOM | O | HIS | H | 200 | 65.119 | 4.978 | −6.805 | 1.00 | 3.34 |
| ATOM | N | LYS | H | 201 | 66.526 | 6.595 | −7.479 | 1.00 | 5.91 |
| ATOM | CA | LYS | H | 201 | 67.80 | 6.488 | −6.310 | 1.00 | 18.09 |
| ATOM | CB | LYS | H | 201 | 68.496 | 7.515 | −6.381 | 1.00 | 9.93 |
| ATOM | CG | LYS | H | 201 | 69.484 | 7.233 | −7.489 | 1.00 | 28.78 |
| ATOM | CD | LYS | H | 201 | 70.774 | 8.000 | −7.249 | 1.00 | 34.66 |
| ATOM | CE | LYS | H | 201 | 71.815 | 7.701 | −8.301 | 1.00 | 38.20 |
| ATOM | NZ | LYS | H | 201 | 73.115 | 8.340 | −7.925 | 1.00 | 43.65 |
| ATOM | G | LYS | H | 201 | 66.627 | 6.591 | −4.989 | 1.00 | 7.71 |
| ATOM | O | LYS | H | 201 | 66.927 | 5.840 | −4.053 | 1.00 | 6.20 |
| ATOM | N | PRO | H | 202 | 65.637 | 7.512 | −4.884 | 1.00 | 6.23 |
| ATOM | CD | PRO | H | 202 | 65.277 | 8.587 | −5.828 | 1.00 | 2.43 |
| ATOM | CA | PRO | H | 202 | 64.862 | 7.663 | −3.644 | 1.00 | 4.45 |
| ATOM | CB | PRO | H | 202 | 63.777 | 8.643 | −4.056 | 1.00 | 3.02 |
| ATOM | CG | PRO | H | 202 | 64.516 | 9.552 | −4.928 | 1.00 | 4.37 |
| ATOM | C | PRO | H | 202 | 64.261 | 6.357 | −3.091 | 1.00 | 4.39 |
| ATOM | O | PRO | H | 202 | 64.013 | 6.259 | −1.895 | 1.00 | 6.85 |
| ATOM | N | SER | H | 203 | 64.055 | 5.359 | −3.949 | 1.00 | 5.31 |
| ATOM | CA | SER | H | 203 | 63.502 | 4.057 | −3.545 | 1.00 | 7.23 |
| ATOM | CD | SER | H | 203 | 62.151 | 3.798 | −4.231 | 1.00 | 4.94 |
| ATOM | CG | SER | H | 203 | 62.302 | 3.553 | −5.635 | 1.00 | 5.74 |
| ATOM | C | SER | H | 203 | 64.444 | 2.909 | −3.920 | 1.00 | 8.91 |
| ATOM | O | SER | H | 203 | 64.077 | 1.735 | −3.796 | 1.00 | 9.89 |
| ATOM | N | ASN | H | 204 | 65.619 | 3.247 | −4.446 | 1.00 | 9.73 |
| ATOM | CA | ASN | H | 204 | 66.589 | 2.245 | −4.867 | 1.00 | 21.67 |
| ATOM | CD | ASN | H | 204 | 67.081 | 1.459 | −3.649 | 1.00 | 24.42 |
| ATOM | CG | ASN | H | 204 | 68.422 | 0.782 | −3.881 | 1.00 | 26.57 |
| ATOM | OD1 | ASN | H | 204 | 69.212 | 1.197 | −4.734 | 1.00 | 28.87 |
| ATOM | ND2 | ASN | H | 204 | 68.693 | −0.257 | −3.103 | 1.00 | 27.26 |
| ATOM | C | ASN | H | 204 | 66.004 | 1.293 | −5.927 | 1.00 | 23.47 |
| ATOM | O | ASN | H | 204 | 66.334 | 0.109 | −5.956 | 1.00 | 23.25 |
| ATOM | N | THR | H | 205 | 65.129 | 1.818 | −6.784 | 1.00 | 23.37 |
| ATOM | CA | THR | H | 205 | 64.492 | 1.037 | −7.845 | 1.00 | 24.11 |
| ATOM | CD | THR | H | 205 | 62.955 | 1.294 | −7.917 | 1.00 | 25.63 |
| ATOM | OG1 | THR | H | 205 | 62.321 | 0.840 | −6.717 | 1.00 | 28.17 |
| ATOM | CG2 | THR | H | 205 | 62.332 | 0.567 | −9.101 | 1.00 | 26.85 |

TABLE 2-continued

| | | Atom | A.A. Type | | X | Y | Z | Occ | B |
|---|---|---|---|---|---|---|---|---|---|
| ATOM | C | THR | H | 205 | 65.063 | 1.389 | −9.210 | 1.00 | 24.23 |
| ATOM | O | THR | H | 205 | 65.224 | 2.566 | −9.526 | 1.00 | 22.91 |
| ATOM | N | LYS | H | 206 | 65.340 | 0.362 | −10.016 | 1.00 | 23.89 |
| ATOM | CA | LYS | H | 206 | 65.866 | 0.510 | −11.374 | 1.00 | 24.37 |
| ATOM | CB | LYS | H | 206 | 67.286 | −0.037 | −11.478 | 1.00 | 29.60 |
| ATOM | CG | LYS | H | 206 | 68.294 | 0.567 | −10.528 | 1.00 | 33.86 |
| ATOM | CD | LYS | H | 206 | 69.653 | −0.045 | −10.797 | 1.00 | 41.22 |
| ATOM | CE | LYS | H | 206 | 70.686 | 0.392 | −9.786 | 1.00 | 45.98 |
| ATOM | NZ | LYS | H | 206 | 71.959 | −0.336 | −10.034 | 1.00 | 50.69 |
| ATOM | C | LYS | H | 206 | 64.988 | −0.341 | −12.266 | 1.00 | 23.86 |
| ATOM | O | LYS | H | 206 | 64.677 | −1.478 | −11.913 | 1.00 | 25.27 |
| ATOM | N | VAL | H | 207 | 64.627 | 0.175 | −13.434 | 1.00 | 21.70 |
| ATOM | CA | VAL | H | 207 | 63.771 | −0.552 | −14.363 | 1.00 | 18.59 |
| ATOM | CB | VAL | H | 207 | 62.285 | −0.056 | −14.268 | 1.00 | 18.43 |
| ATOM | CG1 | VAL | H | 207 | 61.415 | −0.781 | −15.279 | 1.00 | 17.97 |
| ATOM | CG2 | VAL | H | 207 | 61.727 | −0.264 | −12.878 | 1.00 | 16.57 |
| ATOM | C | VAL | H | 207 | 64.241 | −0.337 | −15.806 | 1.00 | 18.98 |
| ATOM | O | VAL | H | 207 | 64.441 | 0.797 | −16.224 | 1.00 | 17.46 |
| ATOM | N | ASP | H | 208 | 64.515 | −1.412 | −16.536 | 1.00 | 18.90 |
| ATOM | CA | ASP | H | 208 | 64.879 | −1.263 | −17.938 | 1.00 | 21.28 |
| ATOM | CB | ASP | H | 208 | 66.054 | −2.146 | −18.334 | 1.00 | 24.33 |
| ATOM | CG | ASP | H | 208 | 67.309 | −1.813 | −17.583 | 1.00 | 27.92 |
| ATOM | OD1 | ASP | H | 208 | 67.899 | −2.730 | −16.991 | 1.00 | 32.30 |
| ATOM | OD2 | ASP | H | 208 | 67.704 | −0.637 | −17.569 | 1.00 | 27.86 |
| ATOM | C | ASP | H | 208 | 63.642 | −1.722 | −18.671 | 1.00 | 20.84 |
| ATOM | O | ASP | H | 208 | 63.037 | −2.736 | −18.312 | 1.00 | 22.22 |
| ATOM | N | LYS | H | 209 | 63.230 | −0.960 | −19.668 | 1.00 | 20.63 |
| ATOM | CA | LYS | H | 209 | 62.047 | −1.305 | −20.429 | 1.00 | 19.95 |
| ATOM | CB | LYS | H | 209 | 60.912 | −0.320 | −20.125 | 1.00 | 20.48 |
| ATOM | CG | LYS | H | 209 | 59.709 | −0.423 | −21.045 | 1.00 | 22.51 |
| ATOM | CD | LYS | H | 209 | 59.031 | −1.791 | −20.990 | 1.00 | 23.59 |
| ATOM | CE | LYS | H | 209 | 58.585 | −2.147 | −19.585 | 1.00 | 24.09 |
| ATOM | NZ | LYS | H | 209 | 57.765 | −3.385 | −19.580 | 1.00 | 23.79 |
| ATOM | C | LYS | H | 209 | 62.371 | −1.277 | −21.899 | 1.00 | 21.05 |
| ATOM | O | LYS | H | 209 | 62.857 | −0.263 | −22.411 | 1.00 | 19.10 |
| ATOM | N | ARG | H | 210 | 62.159 | −2.409 | −22.565 | 1.00 | 22.99 |
| ATOM | CA | ARG | H | 210 | 62.407 | −2.490 | −23.996 | 1.00 | 23.52 |
| ATOM | CB | ARG | H | 210 | 62.569 | −3.951 | −24.432 | 1.00 | 25.36 |
| ATOM | CG | ARG | H | 210 | 63.135 | −4.115 | −25.838 | 1.00 | 34.19 |
| ATOM | CD | ARG | H | 210 | 63.578 | −5.558 | −26.136 | 1.00 | 41.11 |
| ATOM | NE | ARG | H | 210 | 64.549 | −6.110 | −25.172 | 1.00 | 45.70 |
| ATOM | CZ | ARG | H | 210 | 65.558 | −6.917 | −25.506 | 1.00 | 45.18 |
| ATOM | NH1 | ARG | H | 210 | 65.738 | −7.255 | −26.778 | 1.00 | 45.60 |
| ATOM | NH2 | ARG | H | 210 | 66.357 | −7.428 | −24.571 | 1.00 | 44.97 |
| ATOM | C | ARG | H | 210 | 61.225 | −1.822 | −24.715 | 1.00 | 22.56 |
| ATOM | O | ARG | H | 210 | 60.064 | −1.975 | −24.314 | 1.00 | 21.94 |
| ATOM | N | VAL | H | 211 | 61.523 | −1.042 | −25.745 | 1.00 | 20.28 |
| ATOM | CA | VAL | H | 211 | 60.488 | −0.355 | −26.506 | 1.00 | 19.78 |
| ATOM | CB | VAL | H | 211 | 60.659 | 1.195 | −26.412 | 1.00 | 16.83 |
| ATOM | CG1 | VAL | H | 211 | 59.537 | 1.891 | −27.110 | 1.00 | 11.98 |
| ATOM | CG2 | VAL | H | 211 | 60.714 | 1.628 | −24.960 | 1.00 | 14.99 |
| ATOM | C | VAL | H | 211 | 60.627 | −0.837 | −27.943 | 1.00 | 20.10 |
| ATOM | O | VAL | H | 211 | 61.671 | −0.677 | −28.561 | 1.00 | 22.07 |
| ATOM | N | GLU | H | 212 | 59.578 | −1.449 | −28.474 | 1.00 | 22.41 |
| ATOM | CA | GLU | H | 212 | 59.615 | −1.993 | −29.831 | 1.00 | 22.33 |
| ATOM | CB | GLU | H | 212 | 59.888 | −3.486 | −29.741 | 1.00 | 24.22 |
| ATOM | CG | GLU | H | 212 | 58.992 | −4.175 | −28.714 | 1.00 | 30.31 |
| ATOM | CD | GLU | H | 212 | 59.156 | −5.688 | −28.681 | 1.00 | 36.52 |
| ATOM | OE1 | GLU | H | 212 | 58.119 | −6.380 | −28.685 | 1.00 | 42.79 |
| ATOM | OE2 | GLU | H | 212 | 60.302 | −6.195 | −28.638 | 1.00 | 38.30 |
| ATOM | C | GLU | H | 212 | 58.278 | −1.780 | −30.509 | 1.00 | 21.74 |
| ATOM | O | GLU | H | 212 | 57.274 | −1.487 | −29.844 | 1.00 | 23.29 |
| ATOM | N | PRO | H | 213 | 58.239 | −1.885 | −31.844 | 1.00 | 20.03 |
| ATOM | CG | PRO | H | 213 | 59.332 | −2.079 | −32.808 | 1.00 | 19.08 |
| ATOM | CA | PRO | H | 213 | 56.966 | −1.695 | −32.536 | 1.00 | 18.93 |
| ATOM | CB | PRO | H | 213 | 57.345 | −1.935 | −34.001 | 1.00 | 18.96 |
| ATOM | CG | PRO | H | 213 | 58.748 | −1.473 | −34.068 | 1.00 | 17.26 |
| ATOM | C | PRO | H | 213 | 55.994 | −2.757 | −32.005 | 1.00 | 18.93 |
| ATOM | O | PRO | H | 213 | 56.412 | −3.857 | −31.628 | 1.00 | 18.24 |
| ATOM | N | LYS | H | 214 | 54.717 | −2.409 | −31.924 | 1.00 | 19.00 |
| ATOM | CA | LYS | H | 214 | 53.706 | −3.332 | −31.410 | 1.00 | 19.14 |
| ATOM | CB | LYS | H | 214 | 52.483 | −2.552 | −30.924 | 1.00 | 16.91 |
| ATOM | CG | LYS | H | 214 | 51.526 | −3.410 | −30.161 | 1.00 | 17.14 |
| ATOM | CD | LYS | H | 214 | 50.262 | −2.680 | −29.811 | 1.00 | 20.10 |
| ATOM | CE | LYS | H | 214 | 49.434 | −3.588 | −28.931 | 1.00 | 24.84 |
| ATOM | NZ | LYS | H | 214 | 48.149 | −2.977 | −28.549 | 1.00 | 28.31 |

TABLE 2-continued

| | Atom | A.A. Type | | | X | Y | Z | Occ | B |
|---|---|---|---|---|---|---|---|---|---|
| ATOM | C | LYS | H | 214 | 53.222 | −4.400 | −32.394 | 1.00 | 19.27 |
| ATOM | O | LYS | H | 214 | 53.060 | −4.132 | −33.577 | 1.00 | 20.70 |
| ATOM | N | SER | H | 215 | 52.998 | −5.614 | −31.902 | 1.00 | 21.20 |
| ATOM | CA | SER | H | 215 | 52.459 | −6.677 | −32.744 | 1.00 | 21.88 |
| ATOM | CB | SER | H | 215 | 52.848 | −8.059 | −32.209 | 1.00 | 21.65 |
| ATOM | OG | SER | H | 215 | 52.273 | −9.089 | −33.001 | 1.00 | 19.53 |
| ATOM | C | SER | H | 215 | 50.931 | −6.494 | −32.683 | 1.00 | 21.88 |
| ATOM | O | SER | H | 215 | 50.308 | −6.622 | −31.615 | 1.00 | 20.22 |
| ATOM | N | CYS | H | 216 | 50.340 | −6.142 | −33.813 | 1.00 | 21.67 |
| ATOM | CA | CYS | H | 216 | 48.902 | −5.919 | −33.871 | 1.00 | 23.98 |
| ATOM | C | CYS | H | 216 | 48.066 | −7.189 | −33.695 | 1.00 | 27.00 |
| ATOM | O | CYS | H | 216 | 48.470 | −8.289 | −34.111 | 1.00 | 26.45 |
| ATOM | CB | CYS | H | 216 | 48.538 | −5.216 | −35.174 | 1.00 | 18.31 |
| ATOM | SG | CYS | H | 216 | 49.561 | −3.741 | −35.453 | 1.00 | 18.30 |
| ATOM | N | ASP | H | 217 | 46.945 | −7.040 | −32.990 | 1.00 | 31.27 |
| ATOM | CA | ASP | H | 217 | 46.009 | −8.136 | −32.750 | 1.00 | 33.27 |
| ATOM | CB | ASP | H | 217 | 45.320 | −7.991 | −31.392 | 1.00 | 33.17 |
| ATOM | CG | ASP | H | 217 | 44.278 | −9.088 | −31.123 | 1.00 | 36.31 |
| ATOM | OD1 | ASP | H | 217 | 43.634 | −9.600 | −32.069 | 1.00 | 32.97 |
| ATOM | OD2 | ASP | H | 217 | 44.085 | −9.424 | −29.935 | 1.00 | 37.95 |
| ATOM | C | ASP | H | 217 | 44.977 | −8.004 | −33.849 | 1.00 | 36.08 |
| ATOM | O | ASP | H | 217 | 44.272 | −6.989 | −33.945 | 1.00 | 37.14 |
| ATOM | N | LYS | H | 218 | 44.896 | −9.035 | −34.679 | 1.00 | 36.90 |
| ATOM | CA | LYS | H | 218 | 43.951 | −9.047 | −35.772 | 1.00 | 37.91 |
| ATOM | CB | LYS | H | 218 | 44.203 | −7.863 | −36.721 | 1.00 | 41.24 |
| ATOM | CG | LYS | H | 218 | 45.634 | −7.710 | −37.172 | 1.00 | 41.93 |
| ATOM | CD | LYS | H | 218 | 45.801 | −6.602 | −38.194 | 1.00 | 45.62 |
| ATOM | CE | LYS | H | 218 | 45.758 | −5.216 | −37.587 | 1.00 | 45.59 |
| ATOM | NZ | LYS | H | 218 | 45.929 | −4.191 | −38.654 | 1.00 | 46.72 |
| ATOM | C | LYS | H | 218 | 44.039 | −10.359 | −36.519 | 1.00 | 37.04 |
| ATOM | O | LYS | H | 218 | 44.749 | −11.268 | −36.108 | 1.00 | 33.26 |
| ATOM | N | THR | H | 219 | 43.284 | −10.447 | −37.604 | 1.00 | 38.01 |
| ATOM | CA | THR | H | 219 | 43.248 | −11.628 | −38.450 | 1.00 | 39.39 |
| ATOM | CB | THR | H | 219 | 41.948 | −11.656 | −39.246 | 1.00 | 42.48 |
| ATOM | OG1 | THR | H | 219 | 41.822 | −10.426 | −39.989 | 1.00 | 47.38 |
| ATOM | CG2 | THR | H | 219 | 40.770 | −11.783 | −38.286 | 1.00 | 39.71 |
| ATOM | C | THR | H | 219 | 44.432 | −11.539 | −39.390 | 1.00 | 38.37 |
| ATOM | O | THR | H | 219 | 44.447 | −10.745 | −40.343 | 1.00 | 36.99 |
| ATOM | N | HIS | H | 220 | 45.435 | −12.349 | −39.089 | 1.00 | 36.18 |
| ATOM | CA | HIS | H | 220 | 46.672 | −12.372 | −39.862 | 1.00 | 34.59 |
| ATOM | CB | HIS | H | 220 | 47.858 | −12.471 | −38.889 | 1.00 | 33.40 |
| ATOM | CG | HIS | H | 220 | 47.890 | −11.347 | −37.893 | 1.00 | 32.87 |
| ATOM | CD2 | HIS | H | 220 | 47.558 | −11.302 | −36.580 | 1.00 | 30.42 |
| ATOM | ND1 | HIS | H | 220 | 48.Z80 | −10.067 | −38.231 | 1.00 | 31.96 |
| ATOM | CE1 | HIS | H | 220 | 48.196 | −9.282 | −37.170 | 1.00 | 27.03 |
| ATOM | NE2 | HIS | H | 220 | 47.759 | −10.006 | −36.156 | 1.00 | 29.87 |
| ATOM | C | HIS | H | 220 | 46.656 | −13.500 | −40.894 | 1.00 | 32.03 |
| ATOM | O | HIS | H | 220 | 46.005 | −13.277 | −41.939 | 1.00 | 33.00 |
| ATOM | OXT | HIS | H | 220 | 47.241 | −14.578 | −40.662 | 1.00 | 26.67 |

What is claimed is:

1. A method of identifying a Synagis binding compound, comprising the step of using a three-dimensional structural representation of Synagis, Synagis Fab, or a fragment thereof comprising a Synagis antigen binding site, to computationally screen a candidate compound for an ability to bind the Synagis antigen binding site.

2. The method of claim 1 further including the steps of: synthesizing the candidate compound; and screening the candidate compound for Synagis binding activity.

3. A method of identifying a Synagis binding compound, comprising the steps of (a) using a three-dimensional structural representation of Synagis, Synagis Fab, or a fragment thereof comprising a Synagis antigen binding site, to computationally screen a candidate compound for an ability to bind the Synagis antigen binding site, (b) synthesizing the candidate compound; and (c) screening the candidate compound for Synagis binding activity, wherein the structural information comprises the atomic structure coordinates of residues comprising a Synagis CDR.

4. The method of claim 3 in which the Synagis CDR is L1, L2, L3, H1, H2 or H3.

5. The method of claim 4 in which the structural information comprises the antigen binding site of Synagis.

6. The method of claim 5 in which the structural information comprises the Fv fragment of Synagis.

7. The method of claim 6 in which the structural information comprises the Fab fragment of Synagis.

8. A method of identifying a Synagis binding compound comprising the step of using a three-dimensional structural representation of Synagis, Synagis Fab, or a fragment thereof comprising a Synagis antigen binding site, to computationally design a synthesizable candidate compound that binds Synagis.

9. The method of claim 8 in which the computational design comprises the steps of: identifying chemical entities or fragments capable of associating with the Synagis binding site; and assembling the chemical entities or fragments into a single molecule to provide the structure of the candidate compound.

10. The method of claim 9 further including the steps of: synthesizing the candidate compound; and screening the candidate compound for Synagis binding activity.

11. A method of identifying a Synagis binding compound comprising the step of using a three-dimensional structural representation of Synagis, Synagis Fab, or a fragment thereof comprising a Synagis antigen binding site, to computationally design a synthesizable candidate compound that binds Synagis, wherein the structural information comprises the atomic structure coordinates of residues comprising a Synagis CDR.

12. The method of claim 11 in which the Synagis CDR is L1, L2, L3, H1, H2 or H3.

13. The method of claim 11 in which the structural information comprises the antigen binding site of Synagis.

14. The method of claim 11 in which the structural information comprises the Fv fragment of Synagis.

15. The method of claim 12 in which the structural information comprises the Fab fragment of Synagis.

16. The method of claim 11 in which the computational design comprises the steps of: identifying chemical entities or fragments capable of associating with the Synagis binding site; and assembling the chemical entities or fragments into a single molecule to provide the structure of the candidate compound.

17. The method of claim 16 further including the steps of: synthesizing the candidate compound; and screening the candidate compound for Synagis binding activity.

* * * * *

SEQUENCE LISTING

<160> NUMBER OF SEQ ID NOS: 11

<210> SEQ ID NO 1
<211> LENGTH: 450
<212> TYPE: PRT
<213> ORGANISM: Artificial sequence
<220> FEATURE:
<223> OTHER INFORMATION: Description of artificial sequence: N-terminal
      variable segment of Synagis heavy chain humanized antibody

<400> SEQUENCE: 1

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

-continued

```
Gly Met Ser Val Gly Trp Ile Arg Gln Pro Gly Lys Ala Leu Glu
        35                  40                  45

Trp Leu Ala Asp Ile Trp Trp Asp Asp Lys Lys Asp Tyr Asn Pro Ser
 50                  55                  60

Leu Lys Ser Arg Leu Thr Ile Ser Lys Asp Thr Ser Lys Asn Gln Val
65                   70                  75                  80

Val Leu Lys Val Thr Asn Met Asp Pro Ala Asp Thr Ala Thr Tyr Tyr
                 85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
```

-continued

```
                               450

<210> SEQ ID NO 2
<211> LENGTH: 227
<212> TYPE: PRT
<213> ORGANISM: Artificial sequence
<220> FEATURE:
<223> OTHER INFORMATION: Description of artificial sequence: N-terminal
      fragment of Synagis heavy chain humanized antibody

<400> SEQUENCE: 2

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Cys Thr Cys Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His
225

<210> SEQ ID NO 3
<211> LENGTH: 223
<212> TYPE: PRT
<213> ORGANISM: Artificial sequence
<220> FEATURE:
<223> OTHER INFORMATION: Description of artificial sequence: C-terminal
      fragment of heavy chain of Synagis humanized antibody

<400> SEQUENCE: 3

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
```

```
                50                  55                  60
Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                     85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 4
<211> LENGTH: 12
<212> TYPE: PRT
<213> ORGANISM: Artificial sequence
<220> FEATURE:
<223> OTHER INFORMATION: Description of artificial sequence:
      Complementary determining region H1  ("CDRs") of Synagis heavy
      chain humanized antibody

<400> SEQUENCE: 4

Gly Phe Ser Leu Ser Thr Ser Gly Met Ser Val Gly
 1               5                  10

<210> SEQ ID NO 5
<211> LENGTH: 16
<212> TYPE: PRT
<213> ORGANISM: Artificial sequence
<220> FEATURE:
<223> OTHER INFORMATION: Description of artificial sequence:
      Complementary determining region H2  ("CDRs") of Synagis heavy
      chain humanized antibody

<400> SEQUENCE: 5

Asp Ile Trp Trp Asp Asp Lys Lys Asp Tyr Asn Pro Ser Leu Lys Ser
 1               5                  10                  15

<210> SEQ ID NO 6
<211> LENGTH: 10
<212> TYPE: PRT
<213> ORGANISM: Artificial sequence
<220> FEATURE:
<223> OTHER INFORMATION: Description of artificial sequence:
      Complementary determining region H3  ("CDRs") of Synagis heavy
      chain humanized antibody

<400> SEQUENCE: 6

Ser Met Ile Thr Asn Trp Tyr Phe Asp Val
 1               5                  10

<210> SEQ ID NO 7
```

```
<211> LENGTH: 213
<212> TYPE: PRT
<213> ORGANISM: Artificial sequence
<220> FEATURE:
<223> OTHER INFORMATION: Description of artificial sequence: Light chain
      of Synagis humanized antibody

<400> SEQUENCE: 7

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 8
<211> LENGTH: 10
<212> TYPE: PRT
<213> ORGANISM: Artificial sequence
<220> FEATURE:
<223> OTHER INFORMATION: Description of artificial sequence:
      Complementary determining region L1  ("CDRs") of Synagis light
      chain humanized antibody

<400> SEQUENCE: 8

Lys Cys Gln Leu Ser Val Gly Tyr Met His
1               5                   10

<210> SEQ ID NO 9
<211> LENGTH: 7
<212> TYPE: PRT
<213> ORGANISM: Artificial sequence
<220> FEATURE:
<223> OTHER INFORMATION: Description of artificial sequence:
      Complementary determining region L2  ("CDRs") of Synagis light
      chain humanized antibody

<400> SEQUENCE: 9

Asp Thr Ser Lys Leu Ala Ser
```

-continued

```
<210> SEQ ID NO 10
<211> LENGTH: 9
<212> TYPE: PRT
<213> ORGANISM: Artificial sequence
<220> FEATURE:
<223> OTHER INFORMATION: Description of artificial sequence:
      Complementary determining region L3  ("CDRs") of Synagis light
      chain humanized antibody

<400> SEQUENCE: 10

Phe Gln Gly Ser Gly Tyr Pro Phe Thr
1               5

<210> SEQ ID NO 11
<211> LENGTH: 209
<212> TYPE: PRT
<213> ORGANISM: Artificial sequence
<220> FEATURE:
<223> OTHER INFORMATION: Description of artificial sequence: Synagis
      humanized antibody light chain fragment

<400> SEQUENCE: 11

Met Thr Gln Ser Pro Ser Thr Leu Ser Ala Ser Val Gly Asp Arg Val
1               5                   10                  15

Thr Ile Thr Cys Lys Cys Gln Leu Ser Val Gly Tyr Met His Trp Tyr
            20                  25                  30

Gln Gln Lys Pro Gly Lys Ala Pro Lys Leu Leu Ile Tyr Asp Thr Ser
        35                  40                  45

Lys Leu Ala Ser Gly Val Pro Ser Arg Phe Ser Gly Ser Gly Ser Gly
    50                  55                  60

Thr Glu Phe Thr Leu Thr Ile Ser Ser Leu Gln Pro Asp Asp Phe Ala
65                  70                  75                  80

Thr Tyr Tyr Cys Phe Gln Gly Ser Gly Tyr Pro Phe Thr Phe Gly Gly
                85                  90                  95

Gly Thr Lys Leu Glu Ile Lys Arg Thr Val Ala Ala Pro Ser Val Phe
            100                 105                 110

Ile Phe Pro Ser Asp Glu Gln Leu Lys Ser Gly Thr Ala Ser Val Val
        115                 120                 125

Cys Leu Leu Asn Asn Phe Tyr Pro Arg Glu Ala Lys Val Gln Trp Lys
    130                 135                 140

Val Asp Asn Ala Leu Gln Ser Gly Asn Ser Gln Glu Ser Val Thr Glu
145                 150                 155                 160

Gln Asp Ser Lys Asp Ser Thr Tyr Ser Leu Ser Ser Thr Leu Thr Leu
                165                 170                 175

Ser Lys Ala Asp Tyr Glu Lys His Lys Val Tyr Ala Cys Glu Val Thr
            180                 185                 190

His Gln Gly Leu Ser Ser Pro Val Thr Lys Ser Phe Asn Arg Gly Glu
        195                 200                 205

Cys
```